(12) United States Patent
Gillespie et al.

(10) Patent No.: US 7,405,219 B2
(45) Date of Patent: Jul. 29, 2008

(54) TRIAZOLO [4,5-D] PYRIMIDINE DERIVATIVES AND THEIR USE AS PURINERGIC RECEPTOR ANTAGONISTS

(75) Inventors: Roger John Gillespie, Wokingham (GB); Joanne Lerpiniere, Wokingham (GB); Suneel Gaur, Wokingham (GB); Samantha Jayne Bamford, Wokingham (GB); Gemma Caroline Stratton, Wokingham (GB); Stefania Leonardi, Wokingham (GB); Scott Murray Weiss, Wokingham (GB)

(73) Assignee: Vernalis Research Limited, Wokingham (GB)

( * ) Notice: Subject to any disclaimer, the term of this patent is extended or adjusted under 35 U.S.C. 154(b) by 0 days.

(21) Appl. No.: 11/507,625

(22) Filed: Aug. 22, 2006

(65) Prior Publication Data

US 2007/0049607 A1    Mar. 1, 2007

Related U.S. Application Data

(63) Continuation of application No. 10/250,942, filed as application No. PCT/GB02/00091 on Jan. 10, 2002, now Pat. No. 7,141,575.

(30) Foreign Application Priority Data

Jan. 10, 2001 (GB) .................................. 0100624.6

(51) Int. Cl.
*A61K 31/519* (2006.01)
*A61P 25/16* (2006.01)
*A61P 9/02* (2006.01)
*A61P 25/02* (2006.01)
*A61P 25/14* (2006.01)
*A61P 25/18* (2006.01)
*A61P 25/28* (2006.01)

(52) U.S. Cl. .................................. 514/261.1
(58) Field of Classification Search ................. 514/261.1
See application file for complete search history.

(56) References Cited

U.S. PATENT DOCUMENTS

| 4,739,053 A | 4/1988 | Albert et al. |
| 5,204,353 A | 4/1993 | Meier |
| 5,747,496 A | 5/1998 | Cox et al. |
| 6,107,301 A | 8/2000 | Aldrich et al. |
| 6,197,788 B1 | 3/2001 | Fletcher et al. |
| 6,583,156 B1 | 6/2003 | Gillespie et al. |
| 6,608,085 B1 | 8/2003 | Gillespie et al. |
| 6,787,541 B1 | 9/2004 | Gillespie et al. |

FOREIGN PATENT DOCUMENTS

| EP | 1 221 444 A1 | 7/2002 |
| EP | 1 300 147 A1 | 4/2003 |
| JP | 56/131586 | 10/1981 |
| JP | 56/131587 | 10/1981 |
| JP | 59/062595 | 4/1984 |
| JP | 60/140335 | 7/1985 |
| WO | WO 99/01439 A | 1/1999 |
| WO | WO 99/21617 A | 5/1999 |

OTHER PUBLICATIONS (Abstract only) Bailey et al., "Changes in spinal δ- and κ-opioid systems in mice deficient in the A2A receptor gene", *Journal of Neuroscience*, vol. 22, No. 21, 2002 (pp. 9210-9220).
(Abstract only) Bara-Jimenez et al., "Adenosine A2A receptor antagonist treatment of Parkinson's disease", *Neurology*, vol. 61, No. 3, 2003 (pp. 293-296).
Bastia et al., "Effects of $A_1$ and $A_{2A}$ adenosine receptor ligands in mouse acute models of pain", *Neuroscience Letters 328*, 2002 (pp. 241-244).

(Continued)

*Primary Examiner*—Brenda L. Coleman
*Assistant Examiner*—Susanna Moore
(74) *Attorney, Agent, or Firm*—Foley & Lardner LLP

(57) ABSTRACT

The use of a compound of formula (I):

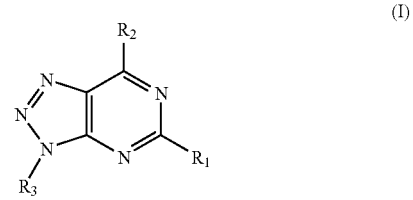

wherein
$R_1$ is selected from H, alkyl, aryl, alkoxy, aryloxy, alkylthio, arylthio, halogen, CN, $NR_5R_6$, $NR_4COR_5$, $NR_4CONR_5R_6$, $NR_4CO_2R_7$ and $NR_4SO_2R_7$;
$R_2$ is selected from aryl attached via an unsaturated carbon;
$R_3$ is selected from H, alkyl, $COR_5$, $CO_2R_7$, $CONR_5R_6$, $CONR_4NR_5R_6$ and $SO_2R_7$;
$R_4$, $R_5$ and $R_6$ are independently selected from H, alkyl and aryl or where $R_5$ and $R_6$ are in an $NR_5R_6$ group, $R_5$ and $R_6$ may be linked to form a heterocyclic group, or where $R_4$, $R_5$ and $R_6$ are in a ($CONR_4NR_5R_6$) group, $R_4$ and $R_5$ may be linked to form a heterocyclic group; and
$R_7$ is selected from alkyl and aryl,
or a pharmaceutically acceptable salt thereof or prodrug thereof, in the treatment or prevention of a disorder in which the blocking of purine receptors, particularly adenosine receptors and more particularly $A_{2A}$ receptors, may be beneficial, particularly wherein said disorder is a movement disorder such as Parkinson's disease or said disorder is depression, cognitive or memory impairment, acute or chronic pain, ADHD or narcolepsy, or for neuroprotection in a subject; compounds of formula (I) for use in therapy; and novel compounds of formula (I) per se.

26 Claims, No Drawings

OTHER PUBLICATIONS

Behan et al., "Enhanced neuronal damage by co-administration of quinolinic acid and free radicals, and protection by adenosine $A_{2A}$ receptor antagonists", *British Hournal of Pharmacology*, vol. 135, 2002 (pp. 1435-1442).
Bertorelli et al., "Effects of Selective Agonists and Antagonists for $A_1$ or $A_{2A}$ Adenosine Receptors on Sleep-Waking Patterns in Rats", *Drug Development Research*, vol. 37, 1996 (pp. 65-72).
(Abstract only) Chase et al., "Translating $A_{2A}$ antagonist KW6002 from animal models to parkinsonian patients", *Neurology*, vol. 61, (11, Suppl. 6), (pp. S107-S111).
Dall'Igna et al., "Neuroprotection of caffeine and adenosine $A_{2A}$ receptor blockade of β-amyloid neurotoxicity", *British Journal of Pharmacology*, vol. 138, 2003 (pp. 1207-1209).
Fredholm, et al., "Actions of Caffeine in the Brain with Special References to Factor That Contribute to Its widespread Use", *Pharmacological Reviews*, vol. 51, No. 1, 1999 (pp. 83-133).
Garfinkel, et al., "Responses to Methylphenidate and Varied Doses of Caffeine in Children with Attention Deficit Disorder", *Can. J. Psychiatry*, vol. 26, No. 6, Oct. 1981 (pp. 395-401).
González-Benitez et al., "Regulation of glycogen metabolism in hepatocytes through adenosine receptors. Role of $Ca^{2+}$ and cAMP", *European Journal of Pharmacology*, vol. 437, 2002 (pp. 105-111).
(Abstract only) Hauser et al., "Randomized trial of the adenosine A2A receptor antagonist istradefylline in advanced PD", *Neurology*, vol. 61, No. 3, 2003 (pp. 297-303).
Hess, "Recent advances in adenosine receptor antagonist research", *Review*, Monthly Focus: Central and Peripheral Nervous Systems, 2001 (pp. 1533-1561).
Ikeda et al., "Neuroprotection by adenosine $A_{2A}$ receptor blockade in experimental models of Parkinson's disease", *Journal of Neurochemistry*, vol. 80, No. 2, Jan. 2002 (pp. 262-270).
(Abstract only) Kase, "New aspects of physiological and pathophysiological functions of adenosine A2A receptor in basal ganglia", *Biochemistry*, vol. 65, No. 7, 2001 (pp. 1447-1457).
Kopf et al., "Adenosine and memory storage: effect of $A_1$ and $A_2$ receptor antagonists", *Psychopharmacology*, vol. 146, No. 2, Sep. 11, 1999 (pp. 214-219).
(Abstract only) Ledent et al., "Aggressiveness, hypoalgesia and high blood pressure in mice lacking the adenosine A2a receptor", *Nature*, vol. 388(6643), Aug. 14, 1997 (pp. 674-678).
Li et al., "Differing Roles of Adenosine Receptor Subtypes in Retinal Ischemia-Reperfusion Injury in the Rat", *Exp. Eye Res.*, vol. 68, 1999 (pp. 9-17).
Mally et al., "Potential of Adenosine $A_{2A}$ Receptor Antagonists in the Treatment of Movement Disorders", *CNS Drugs*, vol. 10, No. 5, Nov. 1998 (pp. 311-320).
Monopoli et al., "Blockade of adenosine $A_{2A}$ receptors by SCH 58261 results in neuroprotective effects in cerebral ischaemia in rats", *Neuropharmacology*, vol. 9, No. 17, Dec. 1, 1998 (pp. 3955-3959).
Monopoli et al., "Cardiovascular Pharmacology of the $A_{2A}$ Adenosine Receptor Antagonist, SCH 58261, in the Rat", *The Journal of Pharmacology and Experimental Therapeutics*, vol. 285, No. 1, 1998 (pp. 9-15).
Ongini et al., "Dual Actions of $A_{2A}$ Adenosine Receptor Antagonists on Motor Dysfunction and Neurodegenerative Processes", *Drug Development Research*, vol. 52, No. ½, 2001 (pp. 379-386).
Popoli et al., "Blockade of Striatal Adenosine $A_{2A}$ Receptor Reduces, through a Presynaptic Mechanism, Quinolinic Acid-Induced Excitotoxicity: Possible Relevance to Neuroprotective Interventions in Neurodegenerative Diseases of the Striatum", *The Journal of Neuroscience*, vol. 22, No. 5, Mar. 1, 2002 (pp. 1967-1975).
Satoh et al., "Involvement of adenosine $A_{2A}$ receptor in sleep promotion", *European Journal of Pharmacology*, vol. 351, 1998 (pp. 155-162).
Scammell et al., "An Adenosine A2a Agonist Increases Sleep and Induces FOS in Ventrolateral Preoptic Neurons", *Neuroscience*, vol. 107 No. 4, 2001 (pp. 653-663).
Schechter, M.D. et al., "Objectively Measured Hyperactivity—II. Caffeine and Amphetamine Effects", *J. Clin. Pharmacol.*, vol. 25, 1985 (pp. 276-280).

Stone et al., "Neuroprotection by $A_{2A}$ Receptor Antagonists", *Drug Development Research*, vol. 52 No. ½, 2001 (pp. 323-330).
Svenningsson, P. et al., "Distribution, Biochemistry and Function of Striatal Adenosine $A_{2A}$ Receptors", *Progress in Neurobiology*, vol. 59, 1999 (pp. 355-396).
(Abstract only) Urade et al., "Sleep regulation in adenosine $A_{2A}$ receptor-deficient mice", *Neurology*, vol. 61(11, Suppl. 6), 2003 (pp. S94-S96).
(Abstract only) Varani et al., "Aberrant $A_{2A}$ receptor function in peripheral blood cells in Huntington's disease", *FASEB Journal*, vol. 17, No. 14, 2003 (pp. 2148-2150).
Varani et al., "Adenosine $A_{2A}$ Antagonists and Huntington's disease", *Colloque Scientifique sur le Café*, 2001, $19^{th}$ (pp. 51-58).
Ei Yacoubi et al., "Adenosine $A_{2A}$ receptor antagonists are potential antidepressants: evidence based on pharmacology and $A_{2A}$ receptor knockout mice", *British Journal of Pharmacology*, vol. 134, No. 1, 2001 (pp. 68-77).
Betti, L. et al., "New amino derivatives of 1,2,3-triazolo'4,5-dlprimidines and their affinity towards A1 and A2A adenosine receptors," *European Journal of Medicinal Chemistry, Editions Scientifique* (Oct. 1999), vol. 34, No. 10, Elseiver, Paris, France, pp. 867-875, XP004202941, ISSN: 0223-5234.
Cocuzza, A.J. et al., "Use of the suzuki reaction for the synthesis of aryl-substituted heterocycles as corticotropin-releasing hormone (CRH) antagonists," *Bioorganic & Medicinal Chemistry Letters* (Apr. 1999), vol. 9, No. 7, Oxford, Great Britain, pp. 1063-1066, XP004162586, ISSN: 0960-894X.
Chorvat, et al., J. Med. Chem., 1999, pp. 833-848, 42.
Higashino, et al., Chem. Pharm. Bull, 1979, pp. 3176-3179, 27(12).
Higashino, et al., Chem. Pharm. Bull, 1979, pp. 2431-2436, 27(10).
Higashino, et al., Fukusokan Kagaku Toronkai Koen Yoshishu, 12th, 1979, 171-5 (Japanese Language Conference Report ; English language abstract supplied).
Miyashita, et al., Heterocycles, 1994, pp. 823-831, 37(2).
Higashino, et al., Chem. Pharm. Bull, 1985, pp. 950-961, 33(3).
Tanji, et al., Chem. Pharm. Bull. 1992, pp. 513-517, 40(2).
Tanji, et al., Chem. Pharm. Bull. 1989, pp. 1731-1734, 37(7).
Higashino, et al., Chem. Pharm. Bull, 1985, pp. 1395-1399, 33(4).
Higashino, et al., Chem. Pharm. Bull, 1980, pp. 255-261, 28(1).
Tanji, et al., Chem. Pharm. Bull, 1991, pp. 2793-2796, 39(11).
Gordeev et al., SSSR Ser. Khim, 1990, pp. 1392-1397, 6 (Russian language document ; English language abstract supplied).
Bakavoli, et al., J. Sci. Islamic Repub. Iran, 1995, pp. 158-162, 6(3) (Abstract).
Miyashita, et al., Chem. Pharm. Bull, 1998, pp. 390-399, 46(3).
Suzuki, et al., Chem. Pharm. Bull, 1998, pp. 199-206, 46(2).
Tanji, et al., Chem. Pharm. Bull, 1991, pp. 3037-3040, 39(11).
Miyashita, et al., Chem. Pharm. Bull, 1991, pp. 282-287, 39(2).
Higashino, et al., Chem. Pharm. Bull, 1987, pp. 4803-4812, 35(12).
Higashino, et al., Chem. Pharm. Bull, 1980, pp. 337-343, 28(1).
Miyashita, et al., Heterocycles, 1997, pp. 1-5, 45(1).
Miyashita, et al., Heterocycles, 1998, pp. 407-414, 47(1).
Miyashita, et al., Heterocycles, 1997, pp. 417-426, 44.
Miyashita, et al., Heterocycles, 1994, pp. 345-356, 39(1).
Higashino et al., Heterocycles, 1981, pp. 483-487, 15(1).
Higashino et al., Yakugaku Zasshi, 1979, pp. 1031-1036, 99(10) (Abstract).
Albert et al., J. Chem. Soc. (Perkin Trans 1), 1977, pp. 1819-1822, 16.
Albert et al., J. Chem. Soc. (Perkin Trans 1), 1972, pp. 457-461, 4.
Molina et al., J. Org. Chem., 1988, pp. 4654-4663, 53(20).
Molina et al., Tetrahedron Lett., 1987, pp. 4451-4454, 28(38).
Albert et al., J. Chem. Soc. (Perkin Trans 1), 1980, pp. 2918-2922, 12.
Albert et al., J. Chem. Soc. (Perkin Trans 1), 1975, pp. 345-349, 4.
Albert et al., J. Chem. Soc. (Perkin Trans 1), 1973, pp. 2037-2041, 19.
Baker et al., J. Pharm. Sci., 1967, pp. 1075-1081, 56(9).
LeWitt, Peter A., Pharmacotherapy, 20, pp. 26S-32S, 2000.
Tuite, Paul et a., Expert Opin. Investig. Drugs, 12, 1335-1352, 2003.
Bibbiani, F. et al., Experimental Neurology, 184, 285-294, 2003.
Spiros Konitsiotis, Expert. Opin. Investig. Drugs, 14, 377-392, 2005.
Anonymous, Drugs and Therapeutic Bulletin, 35, pp. 35-40, 1999.
Wolff, Manfred E., "Burger's Medicinal Chemistry, 5 ed., Part I", John Wiley & Sons, 1995, pp. 975-977.

Banker, G.S. et al., "Modern Pharmaceutics, 3ed.", Marcel Dekker, NY, 1996, pp. 451 and 596.

Kulisevsky, Jaime et al., Clinical Neuropharmacology, 25(1):25-31, Jan./Feb. 2002, abstract only.

Morelli, Micaela, Experimental Neurology, 184, 20-23, 2003.

Loscher W., Epilepsy Res. Jun. 2002; 50(1-2): 105-23.

Jennifer L., et al., J. Neurosci. 1999, 19(22): 10053-10064.

Wenning G. K., et al., J. Neural Transm. Suppl. 1999, 55:103-13, Medline abstract PMID: 10335497.

Rebecca J. Carter et a., The Journal of Neuroscience, Apr. 15, 1999, 19(8): 3248-3257.

Yanamoto H. Nataga et al., Evaluation of MCAO Stroke Models in Normotensive Rats: Standardized Neocortical Infarction by the 3VO Technique, Exp. Neurol. Aug. 2003; 182(2): 261-74.

Osborne, et al., Optic Nerve and Neuroprotection Strategies, Eye., Nov. 2004; 18 (11): 1075-84.

Jenner, Peter, Expert Opin. Investig. Drugs, 14(6), 2005, pp. 729-738.

TRIAZOLO [4,5-D] PYRIMIDINE DERIVATIVES AND THEIR USE AS PURINERGIC RECEPTOR ANTAGONISTS

CROSS-REFERENCE TO RELATED APPLICATIONS

This application is a Continuation of U.S. patent application Ser. No. 10/250,942, granted as U.S. Pat. No. 7,141,575, filed on Oct. 8, 2003, which is the National Phase of PCT/GB02/00091, filed Jan. 10, 2002, and published as WO 02/055083, which claims priority to Great Britain Application No. 0100624.6, filed Jan. 10, 2001, the contents of all are hereby incorporated by reference.

The present invention relates to triazolo[4,5-d]pyrimidine derivatives and their use in therapy. In particular, the present invention relates to the treatment of disorders in which the reduction of purinergic neurotransmission could be beneficial. The invention relates in particular to the blockade of adenosine receptors and particularly adenosine $A_{2A}$ receptors, and to the treatment of movement disorders such as Parkinson's disease.

Movement disorders constitute a serious health problem, especially amongst the elderly sector of the population. These movement disorders are often the result of brain lesions. Disorders involving the basal ganglia which result in movement disorders include Parkinson's disease, Huntington's chorea and Wilson's disease. Furthermore, dyskinesias often arise as sequelae of cerebral ischaemia and other neurological disorders.

There are four classic symptoms of Parkinson's disease: tremor, rigidity, akinesia and postural changes. The disease is also commonly associated with depression, dementia and overall cognitive decline. Parkinson's disease has a prevalence of 1 per 1,000 of the total population. The incidence increases to 1 per 100 for those aged over 60 years. Degeneration of dopaminergic neurones in the substantia nigra and the subsequent reductions in interstitial concentrations of dopamine in the striatum are critical to the development of Parkinson's disease. Some 80% of cells from the substantia nigra need to be destroyed before the clinical symptoms of Parkinson's disease are manifested.

Current strategies for the treatment of Parkinson's disease are based on transmitter replacement therapy (L-dihydroxyphenylacetic acid (L-DOPA)), inhibition of monoamine oxidase (e.g. Deprenyl®), dopamine receptor agonists (e.g. bromocriptine and apomorphine) and anticholinergics (e.g. benztrophine, orphenadrine). Transmitter replacement therapy in particular does not provide consistent clinical benefit, especially after prolonged treatment when "on-off" symptoms develop, and this treatment has also been associated with involuntary movements of athetosis and chorea, nausea and vomiting. Additionally current therapies do not treat the underlying neurodegenerative disorder resulting in a continuing cognitive decline in patients. Despite new drug approvals, there is still a medical need in terms of improved therapies for movement disorders, especially Parkinson's disease. In particular, effective treatments requiring less frequent dosing, effective treatments which are associated with less severe side-effects, and effective treatments which control or reverse the underlying neurodegenerative disorder, are required.

Blockade of $A_2$ adenosine receptors has recently been implicated in the treatment of movement disorders such as Parkinson's disease (Richardson, P. J. et al., *Trends Pharmacol. Sci.* 1997, 18, 338-344) and in the treatment of cerebral ischaemia (Gao, Y. and Phillis, J. W., *Life Sci.* 1994, 55, 61-65). The potential utility of adenosine $A_{2A}$ receptor antagonists in the treatment of movement disorders such as Parkinson's Disease has recently been reviewed (Mally, J. and Stone, T. W., *CNS Drugs*, 1998, 10, 311-320).

Adenosine is a naturally occurring purine nucleoside which has a wide variety of well-documented regulatory functions and physiological effects. The central nervous system (CNS) effects of this endogenous nucleoside have attracted particular attention in drug discovery, owing to the therapeutic potential of purinergic agents in CNS disorders (Jacobson, K. A. et al., *J. Med. Chem.* 1992, 35, 407-422). This therapeutic potential has resulted in considerable recent research endeavour within the field of adenosine receptor agonists and antagonists (Bhagwhat, S. S.; Williams, M. *Exp. Opin. Ther. Patents* 1995, 5,547-558).

Adenosine receptors represent a subclass ($P_1$) of the group of purine nucleotide and nucleoside receptors known as purinoreceptors. The main pharmacologically distinct adenosine receptor subtypes are known as $A_1$, $A_{2A}$, $A_{2B}$ (of high and low affinity) and $A_3$ (Fredholm, B. B., et al., *Pharmacol. Rev.* 1994, 46, 143-156). The adenosine receptors are present in the CNS (Fredholm, B. B., *News Physiol. Sci.*, 1995, 10, 122-128).

The design of $P_1$ receptor-mediated agents has been reviewed (Jacobson, K. A., Suzuki, F., *Drug Dev. Res.*, 1997, 39, 289-300; Baraldi, P. G. et al., *Curr. Med. Chem.* 1995, 2, 707-722), and such compounds are claimed to be, useful in the treatment of cerebral ischemia or neurodegenerative disorders, such as Parkinson's disease (Williams, M. and Burnstock, G. *Purinergic Approaches Exp. Ther.* (1997), 3-26. Editor: Jacobson, Kenneth A.; Jarvis, Michael F. Publisher: Wiley-Liss, New York, N.Y.)

It has been speculated that xanthine derivatives such as caffeine may offer a form of treatment for attention-deficit hyperactivity disorder (ADHD). A number of studies have demonstrated a beneficial effect of caffeine on controlling the symptoms of ADHD (Garfinkel, B. D. et al., *Psychiatry*, 1981, 26, 395-401). Antagonism of adenosine receptors is thought to account for the majority of the behavioural effects of caffeine in humans and thus blockade of adenosine $A_{2A}$ receptors may account for the observed effects of caffeine in ADHD patients. Therefore a selective $A_{2A}$ receptor antagonist may provide an effective treatment for ADHD but without the unwanted side-effects associated with current therapy.

Adenosine receptors have been recognised to play an important role in regulation of sleep patterns, and indeed adenosine antagonists such as caffeine exert potent stimulant effects and can be used to prolong wakefulness (Porkka-Heiskanen, T. et al., *Science*, 1997, 276, 1265-1268). Recent evidence suggests that a substantial part of the actions of adenosine in regulating sleep is mediated through the adenosine $A_{2A}$ receptor (Satoh, S., et al., *Proc. Natl. Acad. Sci., USA*, 1996). Thus, a selective $A_{2A}$ receptor antagonist may be of benefit in counteracting excessive sleepiness in sleep disorders such as hypersomnia or narcolepsy.

It has recently been observed that patients with major depression demonstrate a blunted response to adenosine agonist-induced stimulation in platelets, suggesting that a dysregulation of $A_{2A}$ receptor function may occur during depression (Berk, M. et al, 2001, *Eur. Neuropsychopharmacol.* 11, 183-186). Experimental evidence in animal models has shown that blockade of $A_{2A}$ receptor function confers antidepressant activity (El Yacoubi, M et al. *Br. J. Pharmacol.* 2001, 134, 68-77). Thus, $A_{2A}$ receptor antagonists may offer a novel therapy for the treatment of major depression and other affective disorders in patients.

The pharmacology of adenosine $A_{2A}$ receptors has been reviewed (Ongini, E.; Fredholm, B.B. *Trends Pharmacol. Sci.* 1996, 17(10), 364-372). One potential underlying mechanism in the aforementioned treatment of movement disorders by the blockade of $A_2$ adenosine receptors is the evidence of a functional link between adenosine $A_{2A}$ receptors to dopamine $D_2$ receptors in the CNS. Some of the early studies (e.g. Ferre, S. et al., Stimulation of high-affinity adenosine $A_2$ receptors decreases the affinity of dopamine $D_2$ receptors in rat striatal membranes. *Proc. Natl. Acad. Sci.* U.S.A. 1991, 88, 7238-41) have been summarised in two more recent articles (Fuxe, K. et al., *Adenosine Adenine Nucleotides Mol. Biol. Integr. Physiol.*, [Proc. Int. Symp.], 5th (1995), 499-507. Editors: Belardinelli, Luiz; Pelleg, Amir. Publisher: Kluwer, Boston, Mass.; Ferre, S. et al., *Trends Neurosci.* 1997, 20, 482-487).

As a result of these investigations into the functional role of adenosine $A_{2A}$ receptors in the CNS, especially in vivo studies linking $A_2$ receptors with catalepsy (Ferre et al., *Neurosci. Lett.* 1991, 130, 162-4; Mandhane, S. N. et al., *Eur. J. Pharmacol.* 1997, 328, 135-141) investigations have been made into agents which selectively bind to adenosine $A_{2A}$ receptors as potentially effective treatments for Parkinson's disease.

While many of the potential drugs for treatment of Parkinson's disease have shown benefit in the treatment of movement disorders, an advantage of adenosine $A_{2A}$ antagonist therapy is that the underlying neurodegenerative disorder may also be treated. The neuroprotective effect of adenosine $A_{2A}$ antagonists has been reviewed (Ongini, E.; Adami, M.; Ferri, C.; Bertorelli, R., *Ann. N.Y. Acad. Sci.* 1997, 825 (Neuroprotective Agents), 30-48). In particular, compelling recent evidence suggests that blockade of $A_{2A}$ receptor function confers neuroprotection against MPTP-induced neurotoxicity in mice (Chen, J-F., *J. Neurosci.* 2001, 21, RC143). In addition, several recent studies have shown that consumption of dietary caffeine, a known adenosine $A_{2A}$ receptor antagonist, is associated with a reduced risk of Parkinson's disease in man (Ascherio, A. et al, *Ann Neurol.*, 2001, 50, 56-63; Ross G W, et al., *JAMA*, 2000, 283, 2674-9). Thus, $A_{2A}$ receptor antagonists may offer a novel treatment for conferring neuroprotection in neurodegenerative diseases such as Parkinson's disease.

Xanthine derivatives have been disclosed as adenosine $A_2$ receptor antagonists as useful for treating various diseases caused by hyperfunctioning of adenosine $A_2$ receptors, such as Parkinson's disease (see, for example, EP-A-565377).

One prominent xanthine-derived adenosine $A_{2A}$ selective antagonist is CSC [8-(3-chlorostyryl)caffeine] (Jacobson et al., *FEBS Lett.*, 1993, 323, 141-144).

Theophylline (1,3-dimethylxanthine), a bronchodilator drug which is a mixed antagonist at adenosine $A_1$ and $A_{2A}$ receptors, has been studied clinically. To determine whether a formulation of this adenosine receptor antagonist would be of value in Parkinson's disease an open trial was conducted on 15 Parkinsonian patients, treated for up to 12 weeks with a slow release oral theophylline preparation (150 mg/day), yielding serum theophylline levels of 4.44 mg/L after one week. The patients exhibited significant improvements in mean objective disability scores and 11 reported moderate or marked subjective improvement (Mally, J., Stone, T. W. *J. Pharm. Pharmacol.* 1994, 46, 515-517).

KF 17837 [(E)-8-(3,4-dimethoxystyryl)-1,3-dipropyl-7-methylxanthine] is a selective adenosine $A_{2A}$ receptor antagonist which on oral administration significantly ameliorated the cataleptic responses induced by intracerebroventricular administration of an adenosine $A_{2A}$ receptor agonist, CGS 21680. KF 17837 also reduced the catalepsy induced by haloperidol and reserpine. Moreover, KF 17837 potentiated the anticataleptic effects of a subthreshold dose of L-DOPA plus benserazide, suggesting that KF 17837 is a centrally active adenosine $A_{2A}$ receptor antagonist and that the dopaminergic function of the nigrostriatal pathway is potentiated by adenosine $A_{2A}$ receptor antagonists (Kanda, T. et al., *Eur. J. Pharmacol.* 1994, 256, 263-268). The structure, activity relationship (SAR) of KF 17837 has been published (Shimada, J. et al., *Bioorg. Med. Chem. Lett.* 1997, 7,2349-2352). Recent data has also been provided on the $A_{2A}$ receptor antagonist KW-6002 (Kuwana, Y et al., *Soc. Neurosci. Abstr.* 1997, 23, 119.14; and Kanda, T. et al., *Ann. Neurol.* 1998, 43(4), 507-513).

New non-xanthine structures sharing these pharmacological properties include SCH 58261 and its derivatives (Baraldi, P. G. et al., Pyrazolo[4,3-e]-1,2,4-triazolo[1,5-c]pyrimidine Derivatives: Potent and Selective $A_{2A}$ Adenosine Antagonists. *J. Med. Chem.* 1996, 39, 1164-71). SCH 58261 (7-(2-phenylethyl)-5-amino-2-(2-furyl)-pyrazolo-[4,3-e]-1,2,4-triazolo[1,5-c]pyrimidine) is reported as effective in the treatment of movement disorders (Ongini, E. *Drug Dev. Res.* 1997, 42(2), 63-70) and has been followed up by a later series of compounds (Baraldi, P. G. et al., *J. Med. Chem.* 1998, 41(12), 2126-2133).

The foregoing discussion indicates that a potentially effective treatment for movement disorders in humans would comprise agents which act as antagonists at adenosine $A_{2A}$ receptors.

It has now been found that triazolo[4,5-d]pyrimidine derivatives, which are structurally unrelated to known adenosine receptor antagonists, exhibit unexpected antagonist binding affinity at adenosine ($P_1$) receptors, and in particular at the adenosine $A_{2A}$ receptor. Such compounds may therefore be useful for the treatment of disorders in which the blocking of purine receptors, particularly adenosine receptors and more particularly adenosine $A_{2A}$ receptors, may be beneficial. In particular such compounds may be suitable for the treatment of movement disorders, such as disorders of the basal ganglia which result in dyskinesias. Disorders of particular interest include Parkinson's disease, Alzheimer's disease, spasticity, Huntington's chorea and Wilson's disease.

Such compounds may also be particularly suitable for the treatment of depression, cognitive or memory impairment including Alzheimer's disease, acute or chronic pain, ADHD and narcolepsy, or for neuroprotection.

According to the present invention there is provided the use of a compound of formula (I):

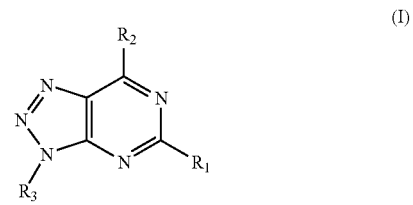

wherein $R_1$ is selected from H, alkyl, aryl, alkoxy, aryloxy, alkylthio, arylthio, halogen, CN, $NR_5R_6$, $NR_4COR_5$, $NR_4CONR_5R_6$, $NR_4CO_2R_7$ and $NR_4SO_2R_7$;

$R_2$ is selected from aryl attached via an unsaturated carbon;

$R_3$ is selected from H, alkyl, $COR_5$, $CO_2R_7$, $CONR_5R_6$, $CONR_4NR_5R_6$ and $SO_2R_7$;

$R_4$, $R_5$ and $R_6$ are independently selected from H alkyl and aryl or where $R_5$ and $R_6$ are in an $NR_5$& group, $R_5$ and $R_6$ may be linked to form a heterocyclic group, or where $R_4$, $R_5$ and & are in a (CONR$_4$NR$_5$R$_6$) group, $R_4$ and $R_5$ may be linked to form a heterocyclic group; and $R_7$ is selected from alkyl and aryl, or a pharmaceutically acceptable salt thereof or prodrug thereof, in the manufacture of a medicament for the treatment or prevention of a disorder in which the blocking of purine receptors, particularly adenosine receptors and more particularly $A_{2A}$ receptors, may be beneficial.

As used herein, the term "alkyl" means a branched or unbranched, cyclic or acyclic, saturated or unsaturated (e.g. alkenyl or alkynyl) hydrocarbyl radical which may be substituted or unsubstituted. Where cyclic, the alkyl group is preferably $C_3$ to $C_{12}$, more preferably $C_5$ to $C_{10}$, more preferably $C_5$, $C_6$ or $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and iso-pentyl), more preferably methyl. It will be appreciated therefore that the term "alkyl" as used herein includes alkyl (branched or unbranched), alkenyl (branched or unbranched), alkynyl (branched or unbranched), cycloalkyl, cycloalkenyl and cycloalkynyl.

As used herein, the term "lower alkyl" means methyl, ethyl, propyl (n-propyl or isopropyl) or butyl (n-butyl, isobutyl or tertiary-butyl).

As used herein, the term "aryl" means an aromatic group, such as phenyl or naphthyl, or a heteroaromatic group containing one or more heteroatom(s), such as pyridyl, pyrrolyl, quinolinyl, furanyl, thienyl, oxadiazolyl, thiadiazolyl, thiazolyl, oxazolyl, isoxazolyl, pyrazolyl, triazolyl, imidazolyl, pyrimidinyl, indolyl, pyrazinyl and indazolyl.

As used herein, the term "heteroaryl" means an aromatic group containing one or more heteroatom(s) preferably selected from N, O and S, such as pyridyl, pyrrolyl, quinolinyl, furanyl, thienyl, oxadiazolyl, thiadiazolyl, thiazolyl, oxazolyl, isoxazolyl, pyrazolyl, triazolyl, imidazolyl, pyrimidinyl, indolyl, pyrazinyl and indazolyl.

As used herein, the term "non-aromatic heterocyclyl" means a non-aromatic cyclic group containing one or more heteroatom(s) preferably selected from N, O and S, such as a cyclic amino group (including aziridinyl, azetidinyl, pyrrolidinyl, piperidyl, piperazinyl, morpholinyl) or a cyclic ether (including tetrahydrofuranyl).

As used herein, the term "alkoxy" means alkyl-O—. As used herein, the term "aryloxy" means aryl-O—.

As used herein, the term "halogen" means a fluorine, chlorine, bromine or iodine radical.

As used herein, the term "prodrug" means any pharmaceutically acceptable prodrug of a compound of the present invention.

Where any of $R_1$ to $R_{14}$ is selected from alkyl, alkoxy and alkylthio, particularly from alkyl and alkoxy, in accordance with formula (I) as defined above, then that alkyl group, or the alkyl group of the alkoxy or alkylthio group, may be substituted or unsubstituted. Where any of $R_1$ to $R_{14}$ is selected from aryl, aryloxy and arylthio, particularly from aryl and aryloxy, in accordance with formula (I) as defined above, then said aryl group, or the aryl group of the aryloxy group, may be substituted or unsubstituted. Where $R_5$ and $R_6$, or $R_4$ and $R_5$, are linked to form a heterocyclic group, the heterocyclic group may be substituted or unsubstituted. Where substituted, there will generally be 1 to 3 substituents present, preferably 1 substituent. Substituents may include:

carbon-containing groups such as
 alkyl,
 aryl, (e.g. substituted and unsubstituted phenyl (including alkylphenyl, alkoxyphenyl and halophenyl),
 arylalkyl; (e.g. substituted and unsubstituted benzyl);

halogen atoms and halogen containing groups such as
 haloalkyl (e.g. trifluoromethyl),
 haloaryl (e.g. chlorophenyl);

oxygen containing groups such as
 alcohols (e.g. hydroxy, hydroxyalkyl, hydroxyaryl, (aryl) (hydroxy)alkyl),
 ethers (e.g. alkoxy, aryloxy, alkoxyalkyl, aryloxyalkyl, alkoxyaryl, aryloxyaryl),
 aldehydes (e.g. carboxaldehyde),
 ketones (e.g. alkylcarbonyl, arylcarbonyl, alkylcarbonylalkyl, alkylcarbonylaryl, arylcarbonylalkyl, arylcarbonylaryl, arylalkylcarbonyl, arylalkylcarbonylalkyl, arylalkylcarbonylaryl)
 acids (e.g. carboxy, carboxyalkyl, carboxyaryl),
 acid derivatives such as esters
  (e.g. alkoxycarbonyl, aryloxycarbonyl, alkoxycarbonylalkyl, aryloxycarbonylalkyl, alkoxycarbonylaryl, aryloxycarbonylaryl, alkylcarbonyloxy, alkylcarbonyloxyalkyl), amides
  (e.g. aminocarbonyl, mono- or di-alkylaminocarbonyl, cyclicaminocarbonyl, aminocarbonylalkyl, mono- or di-alkylaminocarbonylalkyl, arylaminocarbonyl or arylalkylaminocarbonyl, alkylcarbonylamino, arylcarbonylamino or arylalkylcarbonylamino), carbamates
  (eg. alkoxycarbonylamino, aryloxycarbonylamino, arylalkyloxycarbonylamino, aminocarbonyloxy, mono- or di-alkylaminocarbonyloxy, arylaminocarbonyloxy or arylalkylaminocarbonyloxy) and ureas
  (eg. mono- or di-alkylaminocarbonylamino, arylaminocarbonylamino or arylalkylaminocarbonylamino);

nitrogen containing groups such as
 amines (e.g. amino, mono- or dialkylamino, cyclicamino, arylamino, aminoalkyl, mono- or dialkylaminoalkyl),
 azides,
 nitriles (e.g. cyano, cyanoalkyl),
 nitro,
 sulfonamides (e.g. aminosulfonyl, mono- or di-alkylamino sulfonyl, mono- or di-arylaminosulfonyl, alkyl- or arylsulfonyl amino, alkyl- or aryl-sulfonyl(alkyl)amino, alkyl- or aryl-sulfonyl(aryl)amino);

sulfur containing groups such as
 thiols, thioethers, sulfoxides, and sulfones
  (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl)

and heterocyclic groups containing one or more, preferably one, heteroatom,
 (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

Where any of $R_1$ to $R_{14}$ is selected from aryl or from an aryl-containing group such as aryloxy or arylthio, preferred substituent group(s) are selected from halogen, alkyl (substituted or unsubstituted; and where substituted particularly from alkoxyalkyl, hydroxyalkyl, aminoalkyl and haloalkyl), hydroxy, alkoxy, CN, $NO_2$, amines (including amino, mono- and di-alkylamino), alkoxycarbonyl, aminocarbonyl, carboxamido, sulfonamido, alkoxycarbonylamino and aryl, and particularly from unsubstituted alkyl, substituted, alkyl (including alkoxyalkyl and aminoalkyl), halogen and amines.

In one embodiment, where any of $R_1$ to $R_{14}$ is directly substituted by an alkyl substituent group, or by an alkyl-containing substituent group (such as alkoxy or alkylcarbonylamino for example), then the alkyl moiety of the substituent group directly attached to any of $R_1$ to $R_{14}$ may be further substituted by the substituent groups hereinbefore described and particularly by halogen, hydroxy, alkoxy, CN, amines (including amino, mono- and di-alkyl amino) and aryl.

In a further embodiment, where any of $R_1$ to $R_{14}$ is directly substituted by an aryl substituent group, or by an aryl-containing substituent group (such as aryloxy or arylaminocarbonylamino for example), then the aryl moiety of the substituent group directly attached to any of $R_1$ to $R_{14}$ may be further substituted by the substituent groups hereinbefore described and particularly by halogen, alkyl (substituted or unsubstituted, and where substituted particularly from alkoxyalkyl, hydroxyalkyl, aminoalkyl and haloalkyl), hydroxy, alkoxy, CN, $NO_2$, amines (including amino, mono- and di-alkylamino), alkoxycarbonyl, aminocarbonyl, carboxamido, sulfonamido, alkoxycarbonylamino and aryl. In a further embodiment, said aryl moiety is substituted by halogen, alkyl (including $CF_3$), hydroxy, alkoxy, CN, amines (including amino, mono- and di-alkyl amino) and $NO_2$. In a further embodiment, said aryl moiety is substituted by unsubstituted alkyl, substituted alkyl (particularly alkoxyalkyl and aminoalkyl), halogen and amines.

The terms "directly substituted" and "directly attached", as used herein, mean that the substituent group is bound directly to any of $R_1$ to $R_{14}$ without any intervening divalent atoms or groups.

In the compounds of formula (I); $R_1$ is selected from H, alkyl (including branched and unbranched alkyl, substituted and unsubstituted alkyl, and cyclic and acyclic alkyl), aryl (including heteroaryl), alkoxy, aryloxy, alkylthio, arylthio, halogen, CN, $NR_5R_6$ (including $NH_2$), $NRCOR_5$, $NRCONR_5R_6$, $NRCO_2R_7$ and $NR_4SO_2R_7$.

In one embodiment, the compounds of formula (I) are those wherein $R_1$ is selected from alkyl (including branched and unbranched alkyl, substituted and unsubstituted alkyl, and cyclic and acyclic alkyl), aryl (including heteroaryl), alkoxy, aryloxy, alkylthio, arylthio, halogen, CN, $NR_5R_6$ (including $NH_2$), $NR_4COR_5$, $NR_4CONR_5R_6$, $NR_4CO_2R_7$ and $NR_4SO_2R_7$.

Preferably, $R_1$ is selected from alkyl (including branched and unbranched alkyl, substituted and unsubstituted alkyl, and cyclic and acyclic alkyl), alkoxy, alkylthio, $NR_5R_6$ (including $NH_2$), $NR_4COR_5$, $NR_4CONR_5R_6$, $NR_4CO_2R_7$ and $NR_4SO_2R_7$, more preferably from $NR_5R_6$ (including $NH_2$), $NR_4COR_5$, $NR_4CONR_5R_6$, $NR_4CO_2R_7$ and $NR_4SO_2R_7$, more preferably from $NR_5R_6$ (including $NH_2$) and $NR_4COR_5$, more preferably from $NR_5R_6$ (including $NH_2$) and most preferably from $NH_2$.

Where $R_1$ is selected from $NR_5R_6$, in one embodiment $R_5$ and $R_6$ are independently selected from hydrogen, alkyl and aryl, preferably from hydrogen.

Where $R_1$ is selected from $NR_4COR_5$, in one embodiment $R_4$ is hydrogen.

Where $R_1$ is selected from alkyl, $R_1$ is preferably $C_{1-6}$ alkyl, more preferably $C_{1-6}$ saturated alkyl, and more preferably lower alkyl. In one embodiment, $R_1$ is selected from substituted alkyl, particularly haloalkyl (including $CF_3$) and arylalkyl (including heteroarylalkyl), and particularly haloalkyl (including $CF_3$).

Preferably, $R_2$ is a heteroaryl group, and preferably a heteroaryl group which is attached to the pyrimidine ring of formula (I) such that at least one heteroatom is adjacent to the unsaturated carbon atom attached to said pyrimidine ring. Preferably, $R_2$ is an N, O or S-containing heteroaryl group. $R_2$ may contain one or more heteroatom(s) selected from N, O and S.

In one embodiment, the aryl group of $R_2$ (including wherein $R_2$ is a heteroaryl group) is not ortho,ortho-disubstituted. Preferably, the aryl group of $R_2$ (including wherein $R_2$ is a heteroaryl group) is not substituted at either ortho position. As used herein, reference to ortho-substitution of the $R_2$ group means the ortho positions of the $R_2$ group relative to the point of attachment of $R_2$ to the pyrimidine moiety of formula (I).

In a preferred embodiment, $R_2$ is selected from furyl (including 2-furyl), thienyl (including 2-thienyl), pyridyl (including 2-pyridyl), thiazolyl (including 2- and 5-thiazolyl), pyrazolyl (including 3-pyrazolyl), triazolyl (including 4-triazolyl), pyrrolyl (including 2-pyrrolyl) and oxazolyl (including 5-oxazolyl). In a further embodiment, $R_2$ is selected from 2-furyl, 2-thienyl, 2-thiazolyl, 2-pyridyl, 3-pyrazolyl, 2-pyrrolyl, 4-triazolyl and 5-oxazolyl. In a further preferred embodiment, $R_2$ is selected from furyl, thienyl, pyridyl, thiazolyl and pyrazolyl, and particularly from 2-furyl, 2-thienyl, 2-thiazolyl 2-pyridyl and 3-pyrazolyl. In a further embodiment, $R_2$ is selected from furyl, thienyl and pyridyl, preferably 2-furyl, 2-thienyl and 2-pyridyl. In a particularly preferred embodiment, $R_2$ is selected from furyl, and preferably from 2-furyl, substituted or unsubstituted.

Where $R_2$ is other than a heteroaryl group, $R_2$ is preferably phenyl.

In the compounds of formula (I), $R_3$ is selected from H, alkyl (including branched and unbranched alkyl, substituted and unsubstituted alkyl, cyclic and acyclic alkyl), $COR_5$, $CO_2R_7$, $CONR_5R_6$, $CONR_4NR_5R_6$ and $SO_2R_7$.

Where $R_3$ is selected from alkyl, $R_3$ is preferably acyclic alkyl, preferably acyclic $C_{1-6}$ alkyl (including alkenyl and alkynyl), preferably acyclic $C_{1-6}$ saturated alkyl, preferably lower alkyl. In one embodiment, $R_3$ is selected from substituted or unsubstituted methyl, ethyl and propyl (n-propyl or isopropyl) groups.

Where $R_3$ is selected from alkyl, particularly from saturated acyclic $C_{1-6}$ alkyl, particularly from lower alkyl and particularly from methyl, ethyl and propyl, it is preferred that $R_3$ is substituted alkyl. Preferred substituents are aryl (including heteroaryl), cycloalkyl, non-aromatic heterocyclyl, CN, $COR_5$, $CO_2R_5$, $CONR_5R_6$, $CONR_4NR_5R_6$ and $C(=NR_4)NR_5R_6$, preferably aryl (including heteroaryl), $CONR_5R_6$, $CO_2R_5$ and $COR_5$ (preferably wherein $R_5$ is aryl), more preferably aryl (including heteroaryl), $CONR_5R_6$ and $CO_2R_5$, more preferably aryl (including heteroaryl) and $CONR_5R_6$, and most preferably aryl (including heteroaryl).

Where $R_3$ is selected from arylalkyl (including heteroarylalkyl), the aryl (including heteroaryl) group may be unsubstituted, or substituted as defined in detail below in respect of the group referred to as $R_{11}$. Preferably, the arylalkyl (including heteroarylalkyl group) is an arylmethyl (including heteroarylmethyl) group. The preferred aryl groups are set out below in detail in respect of the group referred to as Ar.

Where $R_3$ is selected from $CONR_5R_6$, $R_5$ and $R_6$ are selected from H, alkyl (including substituted alkyl such as arylalkyl (including heteroarylalkyl)) and aryl (including heteroaryl) or $R_5$ and $R_6$ may be linked to form a heterocyclic ring. In one embodiment, $R_5$ and $R_6$ are selected from unsubstituted alkyl and arylalkyl (including heteroarylalkyl). Said aryl groups may be substituted or unsubstituted. In a preferred embodiment one of $R_5$ and $R_6$ is hydrogen. In a further preferred embodiment, $R_5$ is H and $R_6$ is selected from arylalkyl (including heteroarylalkyl), preferably arylmethyl (including heteroarylmethyl).

In a preferred embodiment, $R_3$ is selected from H and substituted alkyl, preferably wherein said alkyl is substituted by aryl (including heteroaryl) or $CONR_5R_6$, and preferably by aryl (including heteroaryl), and more preferably by substituted aryl (including heteroaryl). In one embodiment, $R_3$ is selected from $(CR_9R_{10})_nR_8$ wherein n is 1 to 6 (preferably n is 1, 2 or 3, and preferably n is 1), $R_9$ and $R_{10}$ are independently selected from alkyl and aryl, and $R_8$ is selected from aryl (including heteroaryl), cycloalkyl, non-aromatic heterocyclic, CN, $COR_5$, $CO_2R_5$, $CONR_5R_6$, $CONR_4NR_5R_6$ and $C(=NR_4)NR_5R_6$, preferably aryl (including heteroaryl), $CONR_5R_6$, $CO_2R_5$ and $COR_5$ (preferably wherein $R_5$ is aryl), more preferably aryl (including heteroaryl), $CONR_5R_6$ and $CO_2R_5$, more preferably aryl (including heteroaryl) and $CONR_5R_6$, and most preferably aryl (including heteroaryl). Preferably, $R_9$ and $R_{10}$ are independently selected from H and alkyl (preferably acyclic saturated $C_{1-6}$ alkyl, preferably lower alkyl, preferably methyl, ethyl or propyl), more preferably H. Preferably, at least one of $R_9$ and $R_{10}$ is hydrogen, and preferably both $R_9$ and $R_{10}$ are hydrogen.

Where $R_8$ is aryl (including, heteroaryl), the aryl (including heteroaryl) group may be unsubstituted, or may be substituted as defined in detail below for $R_{11}$. The preferred aryl groups are set out below in detail in respect of the group referred to as Ar.

Where $R_8$ is selected from $CONR_5R_6$, $R_5$ and $R_6$ are selected from H, alkyl (including substituted alkyl such as arylalkyl (including heteroarylalkyl)) and aryl (including heteroaryl) or $R_5$ and $R_6$ may be linked to form a heterocyclic ring. In one embodiment, one or both of $R_5$ and $R_6$ are selected from unsubstituted alkyl and arylalkyl (including heteroarylalkyl). In a further embodiment, at least one of $R_5$ and $R^6$ is selected from aryl (including heteroaryl). Said aryl group may be substituted or unsubstituted. In a preferred embodiment, one of $R_5$ and $R_6$ is hydrogen.

Where $R_8$ is selected from $COR_5$, $R_5$ is preferably aryl (including heteroaryl).

Where $R_8$ is selected from $CO_2R_5$, $R_5$ is preferably alkyl or aryl.

In a further preferred embodiment, $R_3$ is selected from H and $(CR_9R_{10})_nR_8$, more preferably from $(CH_2)_nR_8$, preferably wherein $R_8$ is selected from aryl (including heteroaryl) and $CONR_5R_6$, more preferably wherein $R_8$ is selected from aryl (including heteroaryl), and more preferably wherein $R_8$ is selected from substituted aryl (including heteroaryl).

In a further embodiment, $R_3$ is selected from $(CR_9R_{10})_nR_{11}$ wherein $R_9$, $R_{10}$ and n are as defined above and $R_{11}$ is selected from the group consisting of substituted aryl (including heteroaryl) groups, preferably mono-, di- or tri-substituted aryl (including heteroaryl) groups represented by the formula $Ar(R_{12})_a(R_{13})_b(R_{14})_c$ wherein Ar is an aryl (including heteroaryl) group; wherein $R_{12}$, $R_{13}$ and $R_{14}$ are substituent group(s), the same or different; and wherein a, b and c are 0 or 1 such that $a+b+c \geq 1$.

In one embodiment, the group Ar is selected from phenyl. In an alternative embodiment, the group Ar is selected from heteroaryl groups such as those described hereinabove, preferably from mono or bicyclic heteroaryl groups, more preferably from pyridyl (including 2-pyridyl, 3-pyridyl and 4-pyridyl, preferably 2-pyridyl), indolyl (including 2-indolyl, 3-indolyl, 4-indolyl, 5-indolyl, 6-indolyl and 7-indolyl), furyl (including 2-furyl and 3-furyl, preferably 2-furyl), thienyl (including 2-thienyl and 3-thienyl, preferably 2-thienyl), isoindolyl, indolinyl, isoxazolyl, oxazolyl, thiazolyl, pyrazinyl, pyrimidinyl, quinolinyl, benzoxadiazolyl, benzothiadiazolyl, benzotriazolyl, indazolyl, benzodioxolyl and dihydrobenzofuranyl, more preferably from pyridyl (preferably 2-pyridyl), indolyl, furyl (preferably 2-furyl) and thienyl (preferably 2-thienyl), and most preferably from pyridyl (preferably 2-pyridyl), furyl (preferably 2-furyl) and thienyl (preferably 2-thienyl).

In one embodiment, the group Ar is selected from phenyl, pyridyl (preferably 2-pyridyl), furyl (preferably 2-furyl), thienyl (preferably 2-thienyl) and indolyl, and particularly from phenyl, pyridyl (preferably 2-pyridyl), furyl (preferably 2-furyl) and thienyl (preferably 2-thienyl).

The substituent groups $R_{12}$, $R_{13}$ and $R_{14}$ may be selected from any of the substituent groups described herein above.

In a preferred embodiment, $R_{12}$, $R_{13}$ and $R_{14}$ are selected from $NR_5R_6$ (including $NH_2$, and $NHR_5$) alkyl (substituted or unsubstituted; preferably $C_{1-6}$ acyclic alkyl), alkoxy (including fluoroalkoxy), halogen (including F, Cl, Br and I), $NO_2$, CN, hydroxy, NHOH, CHO, $CONR_5R_6$, $CO_2R_5$, $NR_4COR_5$ (preferably $NHCOR_5$), $NR_4CO_2R_7$ (preferably $NHCO_2R_7$), $NR_4SO_2R_7$ (preferably $NHSO_2R_7$), $OCO_2R_7$ and aryl (including heteroaryl).

In a more preferred embodiment, $R_{12}$, $R_{13}$ and $R_{14}$ are selected from $NR_5R_6$ (including $NH_2$ and $NHR_5$), alkyl (substituted or unsubstituted; and preferably $C_{1-6}$ acyclic saturated alkyl) and halogen (preferably F or Cl, particularly F).

In a particularly preferred embodiment, $R_{12}$, $R_{13}$ and $R_{14}$ are selected from $NR_5R_6$ (including $NH_2$ and $NHR_5$, preferably $NH_2$) and alkyl (substituted or unsubstituted; preferably $C_{1-6}$ acyclic saturated alkyl).

Where $R_{12}$, $R_{13}$ and $R_{14}$ are selected from substituted alkyl, said alkyl is preferably selected from alkoxyalkyl, hydroxyalkyl, aminoalkyl (including $NH_2$-alkyl, mono-alkylaminoalkyl and di-alkylaminoalkyl), haloalkyl (particularly fluoroalkyl (including $CF_3$)), cyanoalkyl, alkylthioalkyl, alkylcarboxyaminoalkyl, alkoxycarbonylaminoalkyl and alkylsulfonylamino, more preferably from alkoxyalkyl, hydroxyalkyl, aminoalkyl and haloalkyl (particularly fluoroalkyl (including $CF_3$)) and most preferably from alkoxyalkyl and aminoalkyl.

In one embodiment, the substituent groups $R_{12}$, $R_{13}$ and $R_{14}$ are selected from halogen, alkyl (including $CF_3$), hydroxy, alkoxy, alkylthio, CN, amines (including amino, mono- and di-alkyl amino) and $NO_2$.

Where the Ar group is phenyl, the phenyl ring may be mono-, di- or tri-substituted, preferably wherein the substituent group is selected from $NR_5R_6$, alkyl, alkoxy, halogen, $NO_2$, CN, hydroxy, $CONR_5R_6$, $CO_2R_5$, $NR_4COR_5$, $NR_4CO_2R_7$, $NR_4SO_2R_7$ and $OCO_2R_7$, as described above, and more preferably from $NR_5R_6$ (including $NH_2$ and $NHR_5$, and preferably $NH_2$), alkyl (substituted or unsubstituted; preferably $C_{1-6}$ acyclic saturated alkyl; and, where substituted, preferably from alkoxyalkyl, hydroxyalkyl, aminoalkyl and haloalkyl (particularly fluoroalkyl (including $CF_3$)), and more preferably from alkoxyalkyl and aminoalkyl) and halogen (preferably F or Cl, particularly F). Where (a+b+c) is 2 or 3, it is preferred that at least one of the substituent groups is $NR_5R_6$, particularly $NH_2$.

Where the Ar group is pyridyl, the pyridyl group (which is preferably a 2-pyridyl group) is preferably mono-substituted, preferably 6-substituted. The preferred substituent group(s) are selected from alkyl (including substituted and unsubstituted, saturated and unsaturated (such as alkenyl, including vinyl); and preferably $C_{1-6}$ acyclic alkyl), alkoxy, halogen, aryl, $NO_2$, NHOH and CHO, as described above, and more preferably from alkyl (substituted or unsubstituted; preferably $C_{1-6}$ acyclic saturated alkyl; and, where substituted, preferably from alkoxyalkyl, hydroxyalkyl, aminoalkyl and haloalkyl (particularly fluoroalkyl (including $CF_3$)), and more preferably from alkoxyalkyl and aminoalkyl).

In a preferred embodiment $R_3$ is selected from $CHR_9R_{11}$ wherein $R_9$ and $R_{11}$ are as defined above, and preferably wherein Ar is substituted pyridyl or substituted phenyl. Where Ar is substituted phenyl, preferably at least one of $R_{12}$ and $R_{13}$, or at least one of $R_{12}$, $R_{13}$ and $R_{14}$, is $NR_5R_6$, preferably $NH_2$.

In the compounds of formula (I), $R_4$, $R_5$ and $R_6$ are independently selected from H, alkyl (including branched and unbranched alkyl, substituted and unsubstituted alkyl, cyclic and acyclic alkyl) and aryl (including heteroaryl) or where $R_5$ and $R_6$ are in any $NR_5R_6$ group, $R_5$ and $R_6$ may be linked to form a heterocyclic ring, or where $R_4$, $R_5$ and $R_6$ are in a ($CONR_4NR_5R_6$) group, $R_4$ and $R_5$ may be linked to form a heterocyclic ring.

In the compounds of formula (I), $R_7$ is selected from alkyl (including branched and unbranched alkyl, substituted and unsubstituted alkyl, cyclic and acyclic alkyl) and aryl (including heteroaryl).

Where $R_4$ to $R_7$ are independently selected from alkyl, preferably $R_4$ to $R_7$ are selected from $C_{1-6}$ alkyl, preferably $C_{1-6}$ saturated alkyl and more preferably from lower alkyl.

Where $R_5$ and $R_6$, or $R_4$ and $R_5$, are linked to form a heterocyclic ring said heterocyclic ring may be saturated, partially unsaturated or aromatic, and is preferably saturated. Said heterocyclic ring is preferably a 5, 6 or 7-membered ring, preferably a 5 or 6-membered ring, and may contain one or more further heteroatom(s) preferably selected from N, O and S.

In a preferred embodiment, $R_1$ is $NH_2$, $R_2$ is 2-furyl and $R_3$ is arylmethyl (including heteroarylmethyl).

In one embodiment of the invention, the compounds of formula (I) are selected from those set out in claim 41.

In a further embodiment of the invention, the compounds of formula (I) are selected from those set out in claim 42.

Where chiral the compounds of formula (I) may be in the form of a racemic mixture of pairs of enantiomers or in enantiomerically pure form.

According to a further aspect of the present invention there is provided a method of treating or preventing a disorder in which the blocking of purine receptors, particularly adenosine receptors and more particularly adenosine $A_{2A}$ receptors, may be beneficial, the method comprising administration to a subject in need of such treatment an effective dose of a compound of formula (I) or a pharmaceutically acceptable salt or prodrug thereof.

The disorder may be caused by the hyperfunctioning of the purine receptors.

The disorders of particular interest are those in which the blocking of purine receptors, particularly adenosine receptors and more particularly adenosine $A_{2A}$ receptors, may be beneficial. These may include movement disorders such as Parkinson's disease, drug-induced Parkinsonism, post-encephalitic Parkinsonism, Parkinsonism induced by poisoning (for example MPTP, manganese, carbon monoxide) and post-traumatic Parkinson's disease (punch-drunk syndrome).

Other movement disorders in which the blocking of purine receptors, may be of benefit include progressive supernuclear palsy, Huntingtons disease, multiple system atrophy, corticobasal degeneration, Wilsons disease, Hallerrorden-Spatz disease, progressive pallidal atrophy, Dopa-responsive dystonia-Parkinsonism, spasticity or other disorders of the basal ganglia which result in abnormal movement or posture. The present invention may also be effective in treating Parkinson's with on-off phenomena; Parkinson's with freezing (end of dose deterioration); and Parkinson's with prominent dyskinesias.

The compounds of formula (I) may be used or administered in combination with one or more additional drugs useful in the treatment of movement disorders, such as L-DOPA or a dopamine agonist, the components being in the same formulation or in separate formulations for administration simultaneously or sequentially.

Other disorders in which the blocking of purine receptors, particularly adenosine receptors and more particularly adenosine $A_{2A}$ receptors may be beneficial include acute and chronic pain; for example neuropathic pain, cancer pain, trigeminal neuralgia, migraine and other conditions associated with cephalic pain, primary and secondary hyperalgesia, inflammatory pain, nociceptive pain, tabes dorsalis, phantom, limb pain, spinal cord injury pain, central pain, post-herpetic pain and HIV pain; affective disorders including mood disorders such as bipolar disorder, seasonal affective disorder, depression, manic depression, atypical depression and monodepressive disease; central and peripheral nervous system degenerative disorders including corticobasal degeneration, demyelinating disease (multiple sclerosis, disseminated sclerosis), Freidrich's ataxia, motoneurone disease (amyotrophic lateral sclerosis, progressive bulbar atrophy), multiple system atrophy, myelopathy, radiculopathy, peripheral neuropathy (diabetic neuropathy, tabes dorsalis, drug-induced neuropathy, vitamin deficiency), systemic lupus erythamatosis, granulomatous disease, olivo-ponto-cerebellar atrophy, progressive pallidal atrophy, progressive supranuclear palsy, spasticity; schizophrenia and related pyshoses; cognitive disorders including dementia, Alzheimers Disease, Frontotemporal dementia, multi-infarct dementia, AIDS dementia, dementia associated with Huntingtons Disease, Lewy body dementia, senile dementia, age-related memory impairment, cognitive impairment associated with dementia, Korsakoff syndrome, dementia pugilans; attention disorders such as attention-deficit hyperactivity disorder (ADHD), attention deficit disorder, minimal brain dysfunction, brain-injured child syndrome, hyperkinetic reaction childhood, and hyperactive child syndrome; central nervous system injury including traumatic brain injury, neurosurgery (surgical trauma), neuroprotection for head injury, raised intracranial pressure, cerebral oedema, hydrocephalus, spinal cord injury; cerebral ischaemia including transient ischaemic attack, stroke (thrombotic stroke, ischaemic stroke, embolic stroke, haemorrhagic stroke, lacunar stroke) subarachnoid haemorrhage, cerebral vasospasm, neuroprotection for stroke, peri-natal asphyxia, drowning, cardiac arrest, subdural haematoma; myocardial ischaemia; muscle ischaemia; sleep disorders such as hypersomnia and narcolepsy; eye disorders such as retinal ischaemia-reperfusion injury and diabetic neuropathy; cardiovascular disorders such as claudication and hypotension; and diabetes and its complications.

According to a further aspect of the present invention there is provided use of a compound of formula (I) or a pharmaceutically acceptable salt or prodrug thereof in the manufacture of a medicament for the treatment or prevention of movement disorders in a subject.

According to a further aspect of the invention there is provided a method of treating or preventing movement disorders comprising administration to a subject in need of such treatment an effective dose of a compound of formula (I) invention or a pharmaceutically acceptable salt or prodrug thereof.

compounds wherein $R_3$ is methyl, preferably other than compounds wherein $R_3$ is unsubstituted lower alkyl and more preferably other than compounds wherein $R_3$ is unsubstituted alkyl.

According to a further aspect of the invention there is provided a method of preparing the novel compounds of formula (1). Compounds of formula (1) may be prepared according to conventional synthetic methods. For example compounds of formula (1) where $R_1$ is $NH_2$ may be synthesised by standard methods such as those illustrated in Reaction Scheme 1.

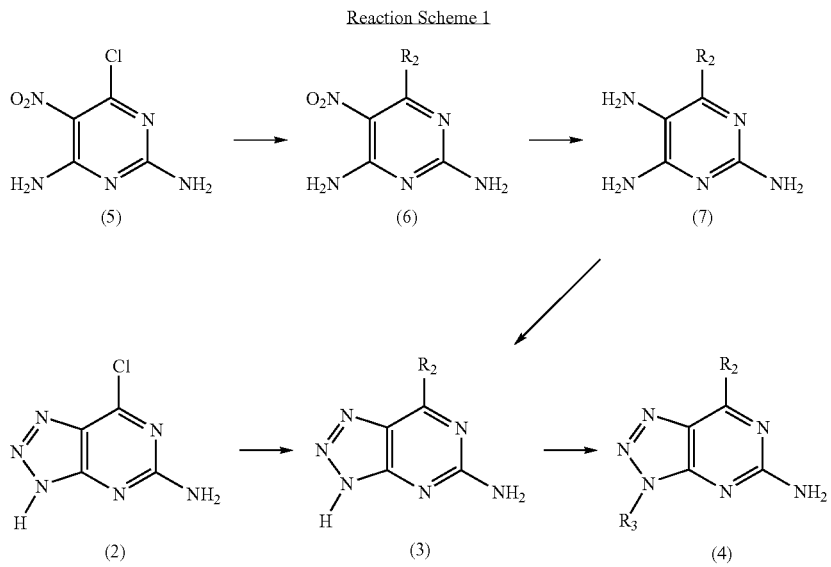

Reaction Scheme 1

According to a further aspect of the invention there is provided use of a compound of formula (I) or a pharmaceutically acceptable salt or prodrug thereof in the manufacture of a medicament for neuroprotection in a subject.

According to a further aspect of the invention there is provided a method of neuroprotection comprising administration to a subject in need of such treatment an effective dose of a compound of formula (I) or a pharmaceutically acceptable salt or prodrug thereof.

The medicament for or method of neuroprotection may be of use in the treatment of subjects who are suffering from or at risk from a neurodegenerative disorder, such as a movement disorder.

According to a further aspect of the invention, there is provided for use in therapy a compound of formula (I), or a pharmaceutically acceptable salt or prodrug thereof.

The present invention may be employed in respect of a human or animal subject, more preferably a mammal, more preferably a human subject.

According to a further aspect of the present invention, there is provided a compound of formula (I), per se, other than compounds wherein $R_1$ is H and $R_3$ is selected from methyl, more preferably other than compounds wherein $R_1$ is H and $R_3$ is selected from unsubstituted lower alkyl, more preferably other than compounds wherein $R_1$ is H and $R_3$ is selected from unsubstituted alkyl, and more preferably other than compounds wherein $R_1$ is H.

According to a further aspect of the present invention, there is provided a compound of formula (I), per se, other than Compounds of formula (4) where $R_3$ is alkyl (including arylalkyl, heteroarylalkyl and $(CR_9R_{10})_nCO_2R_5$) may be prepared from compounds of formula (3) by standard methods such as reaction with an appropriate alkyl halide, or substituted alkyl halide in the presence of a suitable base such as sodium hydride.

Compounds of formula (4) where $R_3$ is $(CR_9R_{10})_nCONR_5R_6$ or $(CR_9R_{10})_nCONR_4NR_5R_6$ may be prepared from compounds of formula (4) where $R_3$ is $(CR_9R_{10})_nCO_2R_5$ by standard methods such as direct reaction with an appropriate amine or hydrazine or by initial hydrolysis of the ester group $CO_2R_5$ to a carboxylic acid followed by reaction with an appropriate amine or hydrazine in the presence of a standard coupling reagent such as DCC.

Compounds of formula (4) where $R_3$ is $(CR_9R_{10})_nC(=NR_4)NR_5R_6$ may be prepared from compounds of formula (4) where $R_3$ is $(CR_9R_{10})_nCN$ by standard methods such as treatment with an appropriate amine in the presence of trimethyl aluminium.

Compounds of formula (4) where $R_3$ is $(CR_9R_{10})_nCN$ may be prepared from compounds of formula (3) by standard methods such as treatment with an appropriate substituted alkyl halide in the presence of a suitable base such as sodium hydride.

Compounds of formula (4) where $R_3$ is $CONR_5R_6$ or $CONR_4NR_5R_6$ may be prepared from compounds of formula (3) by standard methods such as treatment with an appropriate isocyanate ($R_5NCO$ or $R_6NCO$) or carbamoyl chloride ($R_5R_6NCOCl$ or $R_5R_6NR_4NCOCl$).

Compounds of formula (4) where $R_3$ is $COR_5$, $CO_2R_7$ or $SO_2R_7$ may be prepared from compounds of formula (3) by standard methods such as treatment with an appropriate acid chloride ($R_5COCl$), chloroformate ($ClCO_2R_7$) or sulphonyl chloride ($R_7SO_2Cl$) in the presence of a suitable base such as triethylamine.

Compounds of formula (3) may be prepared from the known chloro compound of formula (2) by standard methods such as aryl or heteroaryl coupling reactions. Suitable aryl or heteroaryl coupling reactions would include reaction with an appropriate aryl or heteroarylboronic acid derivative, an aryl or heteroaryl trialkylstannane derivative or an aryl or heteroarylzinc halide derivative in the presence of a suitable catalyst such as a palladium complex.

Compounds of formula (3) may also be prepared from compounds of formula (7) by standard methods such as treatment with isoamyl nitrite. Compounds of formula (7) are either known in the literature or may be prepared from compounds of formula (6) by standard methods such as reduction with hydrogen in the presence of a suitable catalyst such as Pd. Compounds of formula (6) are either known in the literature or may be prepared from the known compound of formula (5) by standard methods such as aryl or heteroaryl coupling reactions as described above.

Compounds of formula (1) where $R_1$ is $NR_5R_6$ may be prepared from compounds of formula (4) by standard methods such as reductive amination with an appropriate aldehyde or ketone, or by treatment with an appropriate alkyl halide in the presence of a suitable base.

Compounds of formula (1) where $R_1$ is $NR_4CONR_5R_6$, wherein $R_4$ is H, may be prepared from compounds of formula (4) by standard methods such as treatment with an appropriate isocyanate ($R_5NCO$ or $R_6NCO$) or carbamoyl chloride ($R_5R_6NCOCl$). Compounds of formula (1) where $R_1$ is $NR_4CONR_5R_6$, wherein $R_4$ is alkyl, may be prepared as described above having first performed an additional alkylation step as described above.

Compounds of formula (1) where $R_1$ is $NR_4COR_5$, $NR_4CO_2R_7$ or $NR_4SO_2R_7$, wherein $R_4$ is H, may be prepared from compounds of formula (4) by standard methods such as treatment with an appropriate acid chloride ($R_5COCl$), chloroformate ($ClCO_2R_7$) or sulphonyl chloride ($R_7SO_2Cl$) in the presence of a suitable base. Compounds of formula (1) where $R_1$ is $NR_4COR_5$, $NR_4CO_2R_7$ or $NR_4SO_2R_7$, wherein $R_4$ is alkyl, may be prepared as described above having first performed an additional alkylation step as described above.

Compounds of formula (1) where $R_1$ is $NH_2$ may also be synthesised by standard methods such as those illustrated in Reaction Scheme 2.

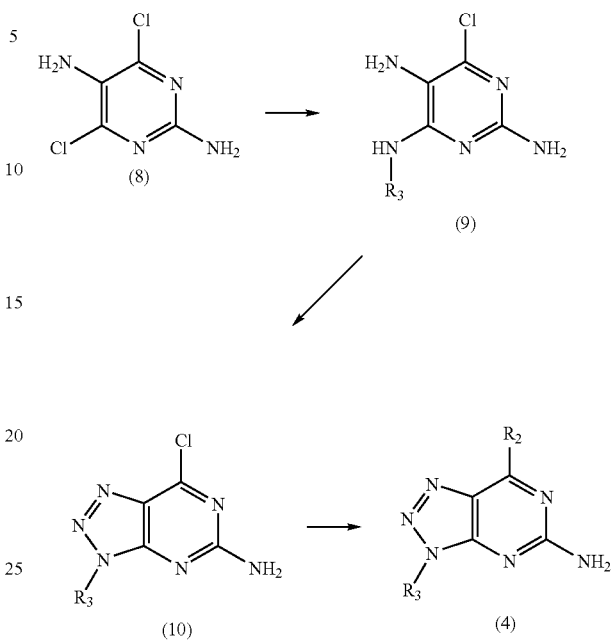

Reaction Scheme 2

Compounds of formula (4) where $R_3$ is alkyl (including arylalkyl, heteroarylalkyl and $(CR_9R_{10})_nCO_2R_5$) may be prepared from compounds of formula (10) by standard methods such as aryl or heteroaryl coupling reactions as described above. Compounds of formula (10) where $R_3$ is alkyl are either known in the literature or may be prepared by methods analogous to those described in the literature. For example compounds of formula (10) where $R_3$ is alkyl may be prepared from compounds of formula (9) where $R_3$ is alkyl by standard methods such as treatment with isoamyl nitrite. Compounds of formula (9) where $R_3$ is alkyl are either known in the literature or may be prepared by methods analogous to those described in the literature such as the treatment of the known compound of formula (8) with an appropriate amine in a suitable solvent preferably at elevated temperature.

Compounds of formula (1) where $R_1$ is $NH_2$ may also be synthesised by standard methods such as those illustrated in Reaction Scheme 3.

Reaction Scheme 3

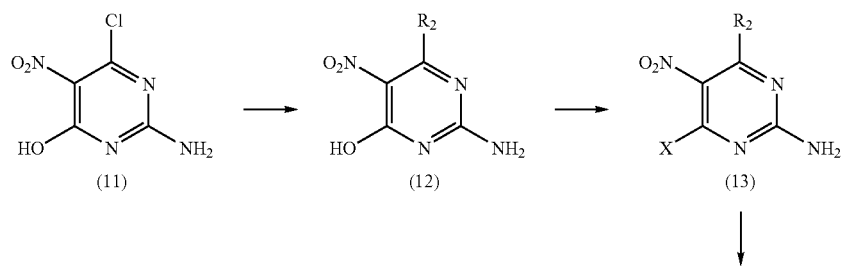

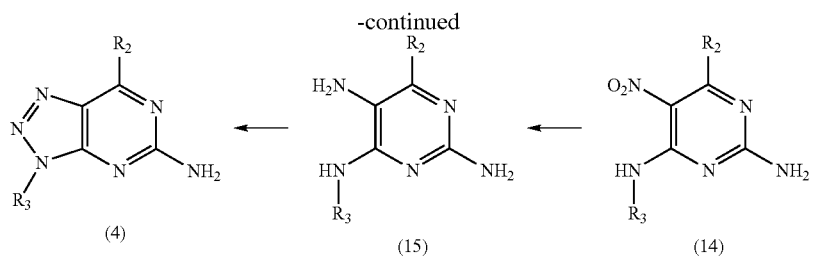

(4)     (15)     (14)

Compounds of formula (4) where $R_3$ is alkyl (including arylalkyl, heteroarylalkyl and $(CR_9R_{10})_nCO_2R_5$) may be prepared from compounds of formula (15) where $R_3$ is alkyl by standard methods such as treatment with isoamyl nitrite. Compounds of formula (15) where $R_3$ is alkyl may be prepared from compounds of formula (14) where $R_3$ is alkyl by standard methods such as reduction with hydrogen in the presence of a suitable catalyst such as Pd. Compounds of formula (14) where $R_3$ is alkyl are either known in the literature or may be prepared from compounds of formula (13), where X is a suitable leaving group such as a tosylate or triflate group, by standard methods such as treatment with a suitable amine in the presence of a suitable base such as triethylamine. Compounds of formula (13) where X is a suitable leaving group are either known in the literature or may be prepared from compounds of formula (12) by standard methods such as treatment with tosyl chloride or triflic anhydride in the prence of a suitable base such as triethylamine or 2,6-dimethylpyridine. Compounds of formula (12) are either known in the literature or may be prepared from the known compound of formula (11) by standard methods such, as aryl or heteroaryl coupling reactions as described above.

Other compounds of formula (1) may be prepared by standard methods such as those illustrated in Reaction Scheme 4.

Reaction Scheme 4

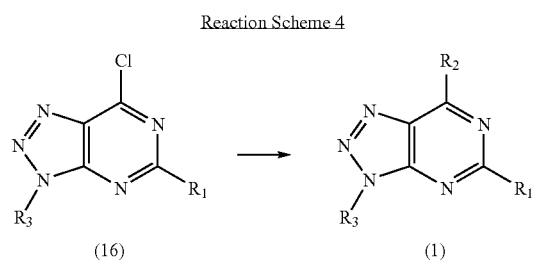

(16)     (1)

Compounds of formula (1) where $R_1$ is H, alkyl or aryl may be prepared from compounds of formula (16) where $R_1$ is H, alkyl or aryl by standard methods such as aryl or heteroaryl coupling reactions as described above. Compounds of formula (16) where $R_1$ is H, alkyl or aryl are either known in the literature or may be prepared by methods analogous to those described in the literature.

Compounds of formula (1) where $R_1$ is alkoxy, aryloxy, alkylthio, arylthio, CN or $NR_5R_6$ may be prepared from compounds of formula (1) where $R_1$ is halogen by standard methods such as nucleophilic displacement using an appropriate nucleophilic reagent such as an alcohol, thiol, cyanide or amine ($HNR_5R_6$) in the presence of a suitable base if required. Compounds of formula (1) where $R_1$ is halogen may be prepared from compounds of formula (16) where $R_1$ is halogen as described above. Compounds of formula (16) where $R_1$ is halogen are either known in the literature or may be prepared by methods analogous to those described in the literature.

Compounds of formula (1) where $R_1$ is $NR_4CONR_5R_6$, $NR_4COR_5$, $NR_4CO_2R_7$ or $NR_4SO_2R_7$, wherein $R_4$ is alkyl or aryl, may be prepared from compounds of formula (1) where $R_1$ is $NR_5R_6$, wherein $R_5$ is H and $R_6$ is alkyl or aryl, by the methods described above.

In certain cases it may be advantageous to prepare a compound of formula (1) where $R_3$ is selected to perform the function of a protecting group, for example a suitable protecting group would be a benzyl group or substituted benzyl group such as a 3,4-dimethoxybenzyl group. Compounds of this nature may prepared as described above and the protecting group $R_3$ may be removed by standard methods such as treatment with, for example, TFA to give a compound of formula (1) where $R_3$ is H. Compounds of formula (1) where $R_3$ is H may then be used to prepare other compounds of formula (1), where $R_3$ is as previously defined, by the methods described above.

In the compounds of formula (1) the groups $R_1$, $R_2$ and $R_3$ may be further substituted as defined above and it will be appreciated by those skilled in the art that suitable substituent groups may be introduced directly according to the methods described above or alternatively may be introduced by further functionalisation of substituent groups which themselves are introduced directly. For example where the group $R_1$, $R_2$ or $R_3$ contains a nitro substituent this may be reduced by standard methods to an amino group. The resulting amino group may then be further transformed by a variety of standard methods known to those skilled in the art to an alternative functional group such as an amide, urea, carbamate, sulphonamide or alkylamine.

According to a further aspect of the invention, there is provided a pharmaceutical composition comprising a compound of formula (I) in combination with a pharmaceutically acceptable carrier or excipient and a method of making such a composition comprising combining a compound of formula (I) with a pharmaceutically acceptable carrier or excipient.

The pharmaceutical compositions employed in the present invention comprise a compound of the present invention, or pharmaceutically acceptable salts or prodrugs thereof, and may also contain a pharmaceutically acceptable carrier and optionally other therapeutic ingredients known to those skilled in the art. The term, "pharmaceutically acceptable salts", refers to salts prepared from pharmaceutically acceptable non-toxic acids including inorganic acids and organic acids.

Where the compounds of formula (I) are basic, salts may be prepared from pharmaceutically acceptable non-toxic acids including inorganic and organic acids. Such acids include acetic, benzenesulfonic, benzoic, camphorsulfonic, citric, ethenesulfonic, fumaric, gluconic, glutamic, hippuric, hydrobromic, hydrochloric, isethionic, lactic, maleic, malic, mandelic, methanesulfonic, mucic, nitric, pamoic, pantothenic, phosphoric, succinic, sulfuric, tartaric, oxalic, p-toluenesulfonic and the like. Particularly preferred are hydrochloric, hydrobromic, phosphoric, and sulfuric acids, and most particularly preferred is the hydrochloride salt.

Any suitable route of administration may be employed for providing the patient with an effective dosage of a compound of the present invention. For example, oral, rectal, parenteral (intravenous, intramuscular), transdermal, subcutaneous, and the like may be employed.

Dosage forms include tablets, troches, dispersions, suspensions, solutions, capsules, patches, and the like. The most suitable route in any given case will depend on the severity of the condition being treated. The most preferred route of administration of the present invention is the oral route. The compositions may be conveniently presented in unit dosage form and prepared by any of the methods well known in the art of pharmacy.

In practical use, the compounds can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (e.g. intravenous). In preparing the compositions for oral dosage form, any of the usual pharmaceutical media may be employed as carriers, such as, for example, water, glycols, oils, alcohols, flavouring agents, preservatives, colouring agents, and the like in the case of oral liquid preparations (such as suspensions, solutions and elixirs) ori aerosols; or carriers such as starches, sugars, microcrystalline cellulose, diluents, granulating agents, lubricants, binders, disintegrating agents, and the like may be used in the case of oral solid preparations such as, for example, powders, capsules, and tablets, with the solid oral preparations being preferred over the liquid preparations. The most preferred solid oral preparation is tablets.

Because of their ease of administration, tablets and capsules represent the most advantageous oral dosage unit form in which case solid pharmaceutical carriers are employed. If desired, tablets may be coated by standard aqueous or non-aqueous techniques.

In addition to the common dosage forms set out above, the compounds may also be administered by controlled release means and/or delivery devices such as those described in U.S. Pat. Nos.: 3,845,770; 3,916,899; 3,536,809; 3,598,123; 3,630,200; 4,008,719; 4,687,660; and 4,769,027, the disclosures of which are hereby incorporated by reference.

Pharmaceutical compositions employed in the present invention suitable for oral administration may be presented as discrete units such as capsules, cachets, or tablets, or aerosol sprays each containing a predetermined amount of the active ingredient as a powder or granules, a solution or a suspension in an aqueous liquid, an oil-in-water emulsion, or a water-in-oil liquid emulsion. Such compositions may be prepared by any of the methods of pharmacy, but all methods include the step of bringing the active ingredient into association with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or moulding, optionally with one or more accessory ingredients. Compressed tablets may be prepared by compressing in a suitable machine the active ingredient in a free-flowing form such as powder or granules, optionally mixed with a binder, a lubricant, an inert diluent, and/or a surface active or dispersing agent. Moulded tablets may be made by moulding in a suitable machine a mixture of the powdered compound moistened with an inert liquid diluent.

The invention is further defined by reference to the following examples. It will be apparent to those skilled in the art that many modifications, both to materials and methods, may be practised without departing from the purpose and interest of this invention.

EXAMPLES

Synthetic Examples

The invention is illustrated with reference to the following Examples, as set out in Table 1.

TABLE 1

| Example | Structure | Compound Name |
|---------|-----------|---------------|
| 1 | 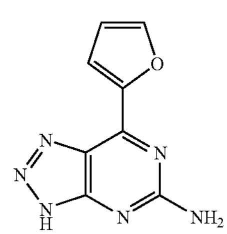 | 7-(2-furyl)-1H-[1,2,3]triazolo[4,5-d]pyrimidine-5-amine |

TABLE 1-continued
| Example | Structure | Compound Name |
|---|---|---|
| 2 | 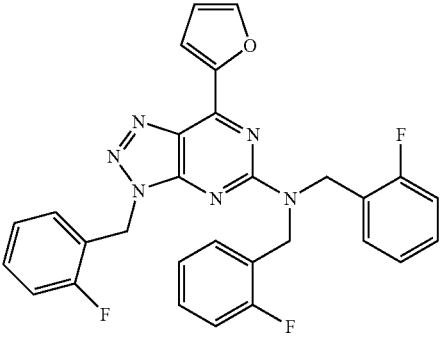 | N,N-bis(2-fluorobenzyl)-3-(2-fluorobenzyl)-7-(2-furyl)-3H-[1,2,3]triazolo[4,5-d]pyrimidine-5-amine |
| 3 | 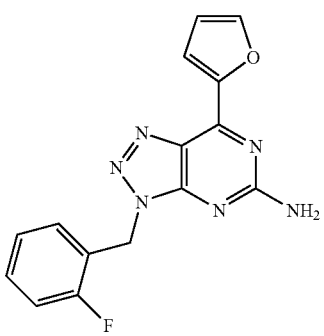 | 3-(2-fluorobenzyl)-7-(2-furyl)-3H-[1,2,3]triazolo[4,5-d]pyrimidine-5-amine |
| 4 | 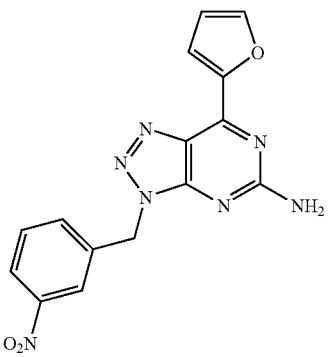 | 7-(2-furyl)-3-(3-nitrobenzyl)-3H-[1,2,3]triazolo[4,5-d]pyrimidine-5-amine |
| 5 | 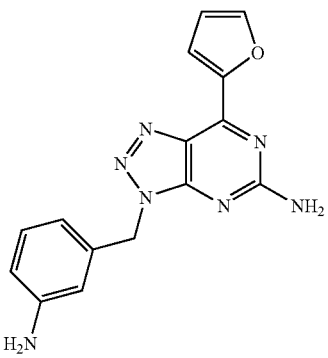 | 3-(3-aminobenzyl)-7-(2-furyl)-3H-[1,2,3]triazolo[4,5-d]pyrimidine-5-amine |

TABLE 1-continued

| Example | Structure | Compound Name |
| --- | --- | --- |
| 6 | 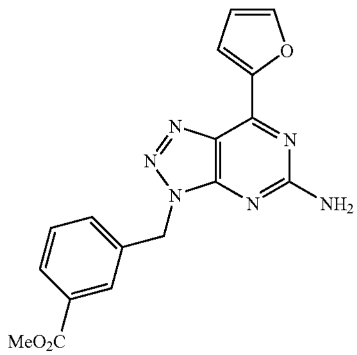 | methyl 3-(5-amino-7-(2-furyl)-3H-[1,2,3]triazolo[4,5-d]pyrimidin-3-yl)methylbenzoate |
| 7 | 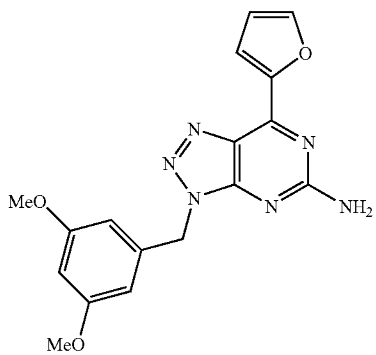 | 3-(3,5-dimethoxybenzyl)-7-(2-furyl)-3H-[1,2,3]triazolo[4,5-d]pyrimidine-5-amine |
| 8 | 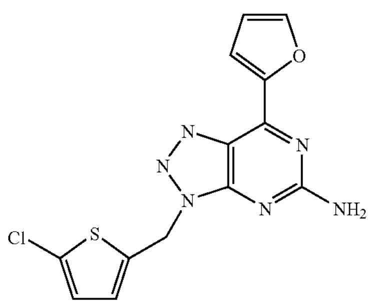 | 3-(5-chloro-2-thienyl)methyl-7-(2-furyl)-3H-[1,2,3]triazolo[4,5-d]pyrimidine-5-amine |
| 9 | 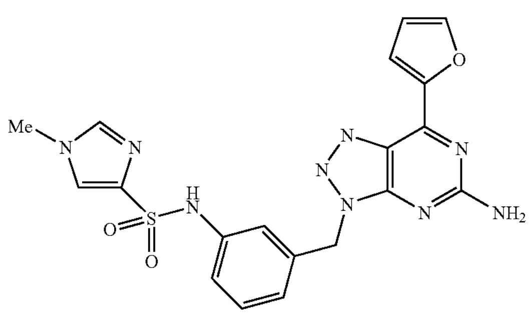 | N-(3-(5-amino-7-(2-furyl)-3H-[1,2,3]triazolo[4,5-d]pyrimidin-3-yl)methyl)phenyl-(1-methyl-1H-imidazol-4-yl)sulphonamide |

TABLE 1-continued

| Example | Structure | Compound Name |
|---|---|---|
| 10 | 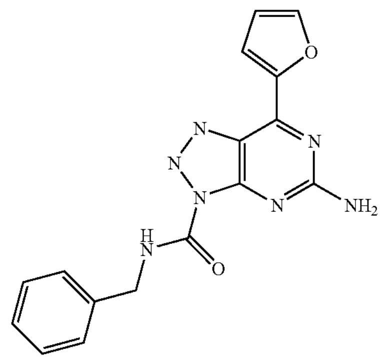 | 5-amino-N-benzyl-7-(2-furyl)-3H-[1,2,3]triazolo[4,5-d]pyrimidin-3-ylcarboxamide |
| 11 | 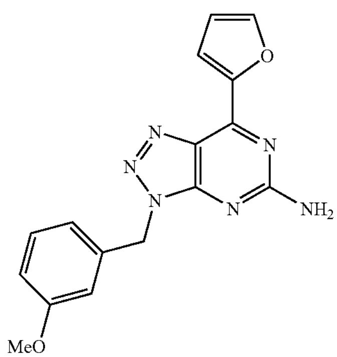 | 7-(2-furyl)-3-(3-methoxybenzyl)-3H-[1,2,3]triazolo[4,5-d]pyrimidine-5-amine |
| 12 | 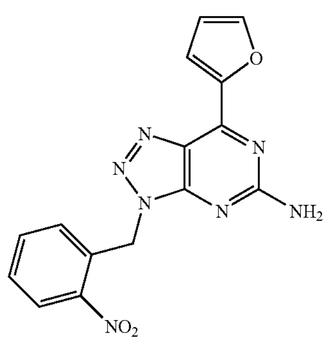 | 7-(2-furyl)-3-(2-nitrobenzyl)-3H-[1,2,3]triazolo[4,5-d]pyrimidine-5-amine |
| 13 | 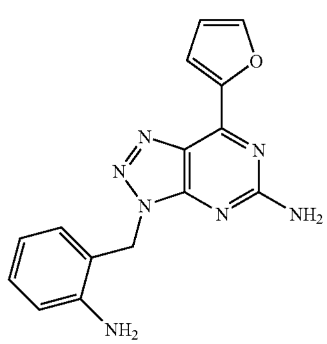 | 3-(2-aminobenzyl)-7-(2-furyl)-3H-[1,2,3]triazolo[4,5-d]pyrimidine-5-amine |

TABLE 1-continued

| Example | Structure | Compound Name |
| --- | --- | --- |
| 14 | 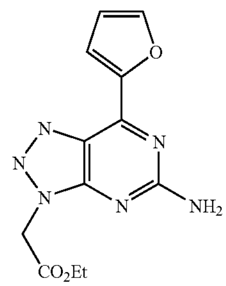 | ethyl 5-amino-7-(2-furyl)-3H-[1,2,3]triazolo[4,5-d]pyrimidin-3-ylacetate |
| 15 | 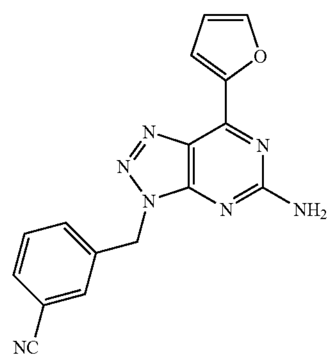 | 3-(3-cyanobenzyl)-7-(2-furyl)-3H-[1,2,3]triazolo[4,5-d]pyrimidine-5-amine |
| 16 | 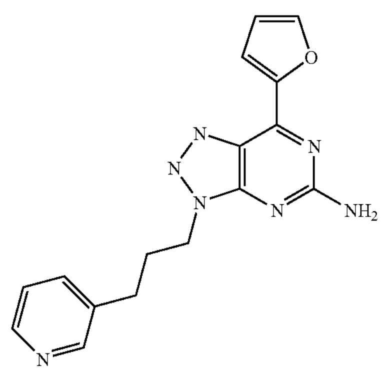 | 7-(2-furyl)-3-(3-(3-pyridyl)propyl)-3H-[1,2,3]triazolo[4,5-d]pyrimidine-5-amine |
| 17 | 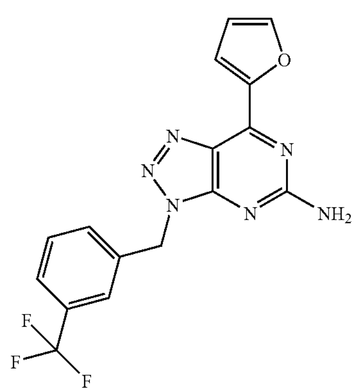 | 7-(2-furyl)-3-(3-trifluoromethylbenzyl)-3H-[1,2,3]triazolo[4,5-d]pyrimidine-5-amine |

TABLE 1-continued

| Example | Structure | Compound Name |
|---|---|---|
| 18 | 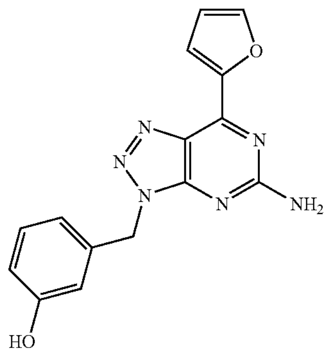 | 7-(2-furyl)-3-(3-hydroxybenzyl)-3H-[1,2,3]triazolo[4,5-d]pyrimidine-5-amine |
| 19 | 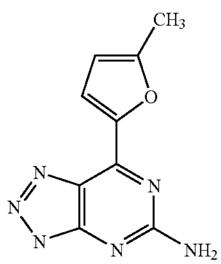 | 7-(5-methyl-2-furyl)-1H-[1,2,3]triazolo[4,5-d]pyrimidine-5-amine |
| 20 | 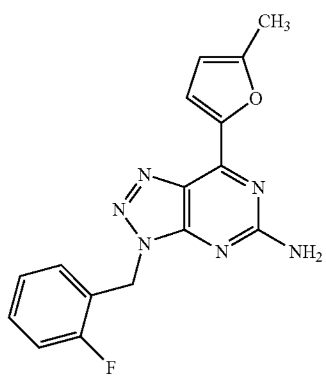 | 3-(2-fluorobenzyl)-7-(5-methyl-2-furyl)-3H-[1,2,3]triazolo[4,5-d]pyrimidine-5-amine |
| 21 | 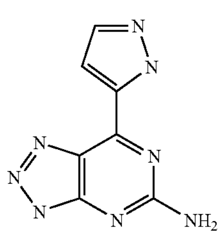 | 7-(1H-pyrazol-3-yl)-1H-[1,2,3]triazolo[4,5-d]pyrimidine-5-amine |
| 22 | 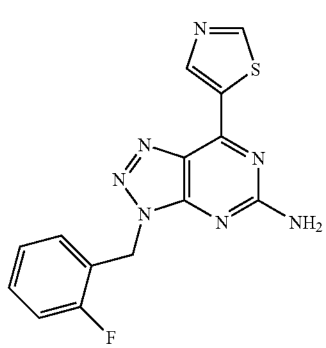 | 3-(2-fluorobenzyl)-7-(5-thiazolyl)-3H-[1,2,3]triazolo[4,5-d]pyrimidine-5-amine |

TABLE 1-continued

| Example | Structure | Compound Name |
|---|---|---|
| 23 | 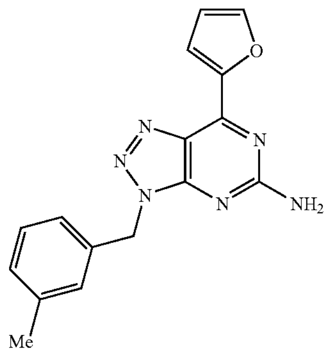 | 7-(2-furyl)-3-(3-methylbenzyl)-3H-[1,2,3]triazolo[4,5-d]pyrimidine-5-amine |
| 24 | 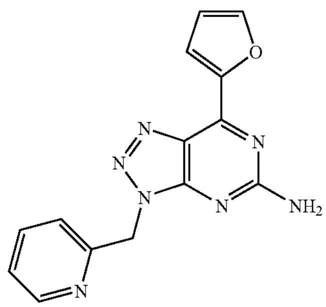 | 7-(2-furyl)-3-(2-pyridylmethyl)-3H-[1,2,3]triazolo[4,5-d]pyrimidine-5-amine |
| 25 | 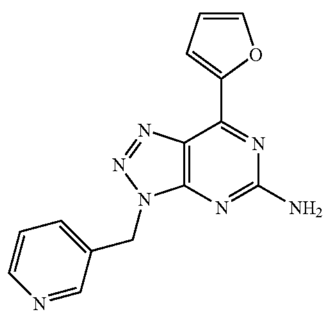 | 7-(2-furyl)-3-(3-pyridylmethyl)-3H-[1,2,3]triazolo[4,5-d]pyrimidine-5-amine |
| 26 | 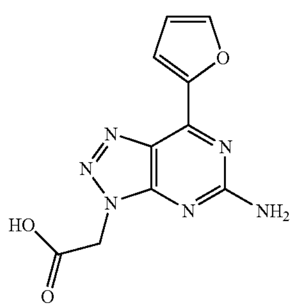 | (5-amino-7-(2-furyl)-3H-[1,2,3]triazolo[4,5-d]pyrimidin-3-yl)acetic acid |

TABLE 1-continued

| Example | Structure | Compound Name |
|---|---|---|
| 27 | 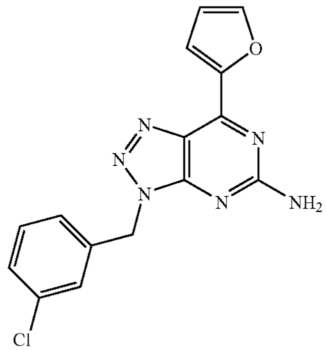 | 3-(3-chlorobenzyl)-7-(2-furyl)-3H-[1,2,3]triazolo[4,5-d]pyrimidine-5-amine |
| 28 | 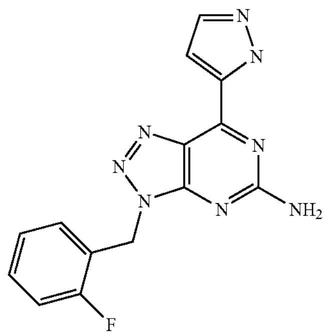 | 3-(2-fluorobenzyl)-7-(1H-pyrazol-3-yl)-3H-[1,2,3]triazolo[4,5-d]pyrimidine-5-amine |
| 29 | 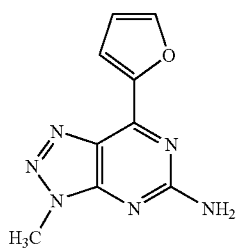 | 7-(2-furyl)-3-methyl-3H-[1,2,3]triazolo[4,5-d]pyrimidine-5-amine |
| 30 | 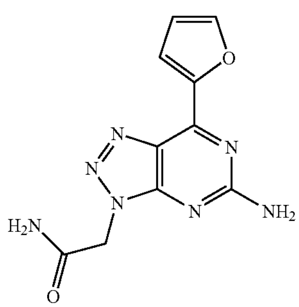 | (5-amino-7-(2-furyl)-3H-[1,2,3]triazolo[4,5-d]pyrimidin-3-yl)acetamide |
| 31 | 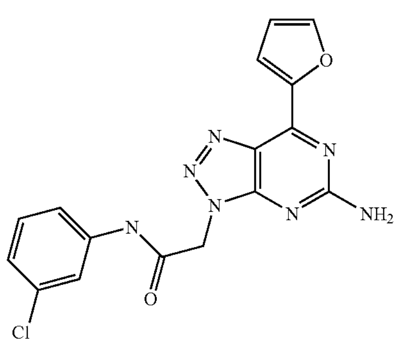 | (5-amino-7-(2-furyl)-3H-[1,2,3]triazolo[4,5-d]pyrimidin-3-yl)-N-(3-chlorophenyl)acetamide |

TABLE 1-continued

| Example | Structure | Compound Name |
| --- | --- | --- |
| 32 | 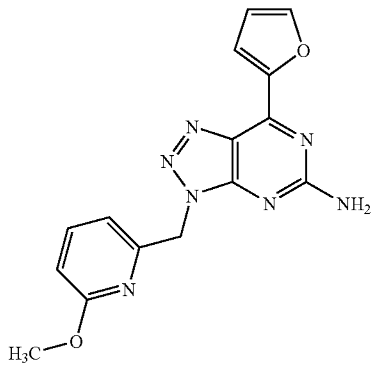 | 7-(2-furyl)-3-(6-methoxy-2-pyridylmethyl)-3H-[1,2,3]triazolo[4,5-d]pyrimidine-5-amine |
| 33 | 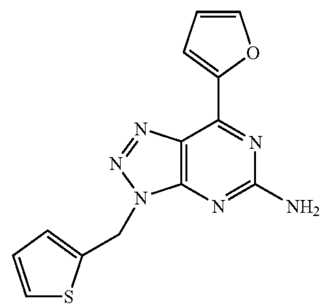 | 7-(2-furyl)-3-(2-thienylmethyl)-3H-[1,2,3]triazolo[4,5-d]pyrimidine-5-amine |
| 34 | 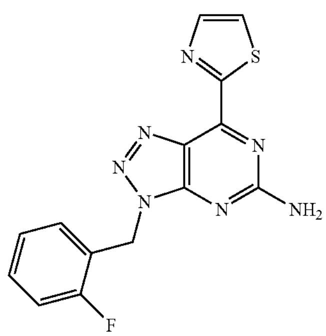 | 3-(2-fluorobenzyl)-7-(2-thiazolyl)-3H-[1,2,3]triazolo[4,5-d]pyrimidine-5-amine |
| 35 | 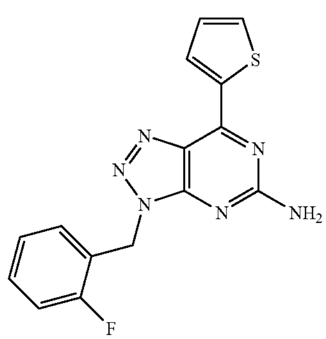 | 3-(2-fluorobenzyl)-7-(2-thienyl)-3H-[1,2,3]triazolo[4,5-d]pyrimidine-5-amine |

TABLE 1-continued

| Example | Structure | Compound Name |
| --- | --- | --- |
| 36 | 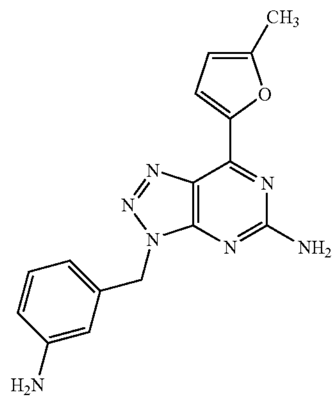 | 3-(3-aminobenzyl)-7-(5-methyl-2-furyl)-3H-[1,2,3]triazolo[4,5-d]pyrimidine-5-amine |
| 37 | 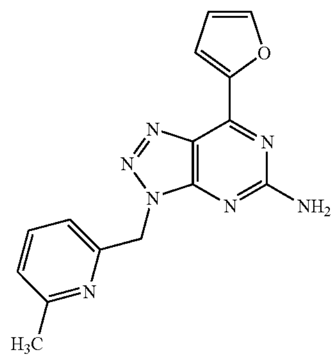 | 7-(2-furyl)-3-(6-methyl-2-pyridylmethyl)-3H-[1,2,3]triazolo[4,5-d]pyrimidine-5-amine |
| 38 | 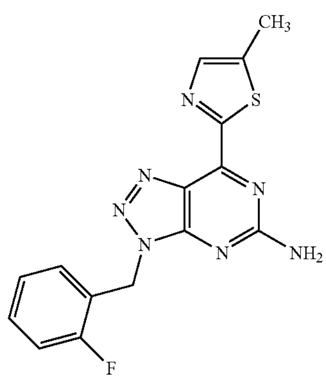 | 3-(2-fluorobenzyl)-7-(5-methyl-2-thiazolyl)-3H-[1,2,3]triazolo[4,5-d]pyrimidine-5-amine |
| 39 | 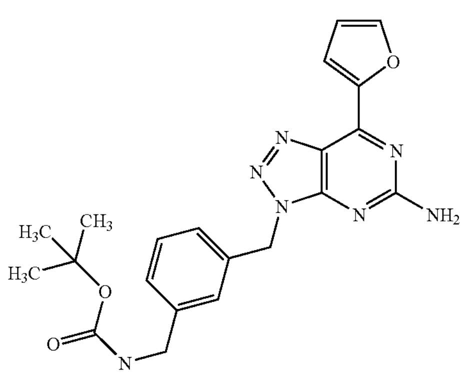 | tert-butyl N-(3-(5-amino-7-(2-furyl)-3H-[1,2,3]triazolo[4,5-d]pyrimidine-3-ylmethyl)benzyl)carbamate |

TABLE 1-continued

| Example | Structure | Compound Name |
|---|---|---|
| 40 | 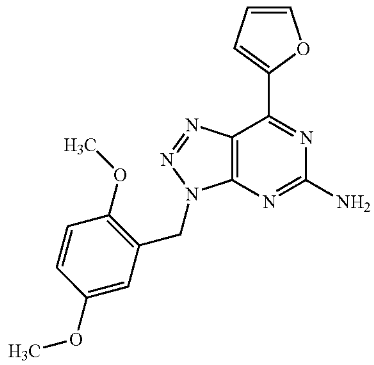 | 3-(2,5-dimethoxybenzyl)-7-(2-furyl)-3H-[1,2,3]triazolo[4,5-d]pyrimidine-5-amine |
| 41 | 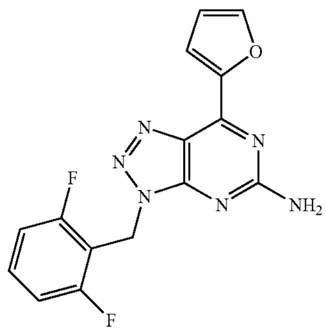 | 3-(2,6-difluorobenzyl)-7-(2-furyl)-3H-[1,2,3]triazolo[4,5-d]pyrimidine-5-amine |
| 42 | 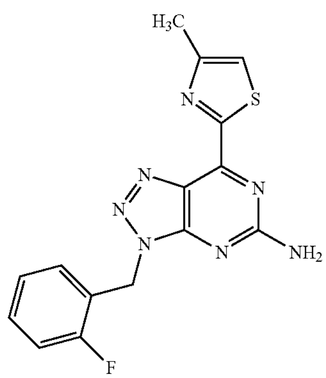 | 3-(2-fluorobenzyl)-7-(4-methyl-2-thiazolyl)-3H-[1,2,3]triazolo[4,5-d]pyrimidine-5-amine |
| 43 | 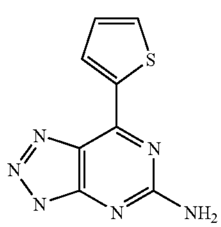 | 7-(2-thienyl)-1H-[1,2,3]triazolo[4,5-d]pyrimidine-5-amine |
| 44 | 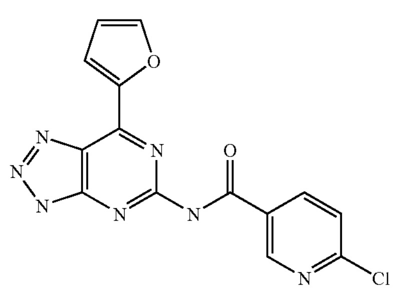 | 6-chloro-N-(7-(2-furyl)-1H-[1,2,3]triazolo[4,5-d]pyrimidin-5-yl)pyridine-3-carboxamide |

TABLE 1-continued

| Example | Structure | Compound Name |
|---|---|---|
| 45 | 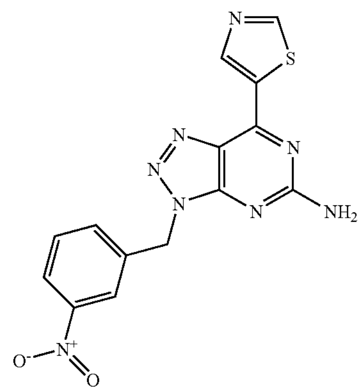 | 3-(3-nitrobenzyl)-7-(5-thiazolyl)-3H-[1,2,3]triazolo[4,5-d]pyrimidine-5-amine |
| 46 | 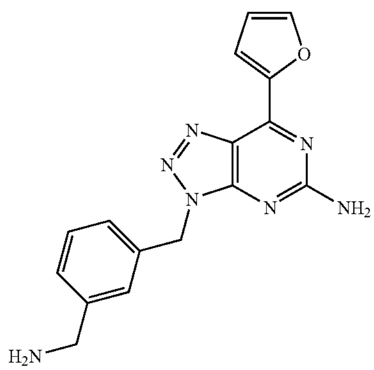 | 3-(3-aminomethylbenzyl)-7-(2-furyl)-3H-[1,2,3]triazolo[4,5-d]pyrimidine-5-amine |
| 47 | 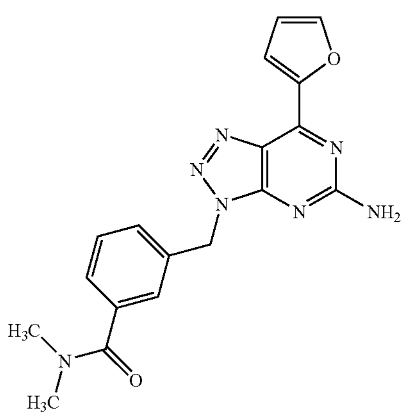 | 3-(5-amino-7-(2-furyl)-3H-[1,2,3]triazolo[4,5-d]pyrimidin-3-ylmethyl)-N,N-dimethylbenzamide |
| 48 | 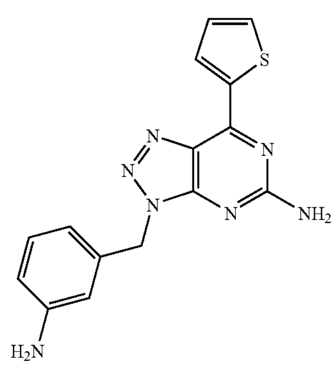 | 3-(3-aminobenzyl)-7-(2-thienyl)-3H-[1,2,3]triazolo[4,5-d]pyrimidine-5-amine |

TABLE 1-continued

| Example | Structure | Compound Name |
| --- | --- | --- |
| 49 | 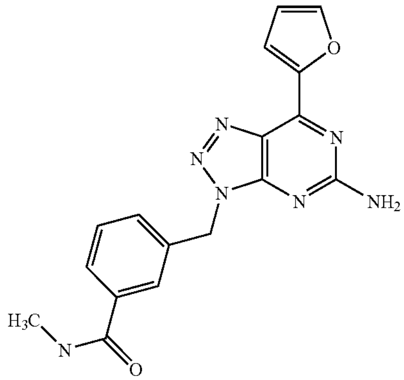 | 3-(5-amino-7-(2-furyl)-3H-[1,2,3]triazolo[4,5-d]pyrimidin-3-ylmethyl)-N-methylbenzamide |
| 50 | 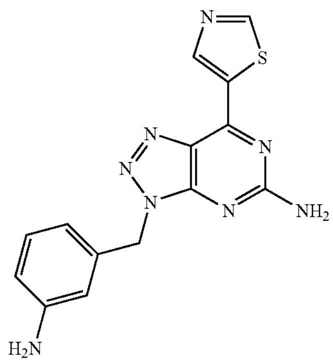 | 3-(3-aminobenzyl)-7-(5-thiazolyl)-3H-[1,2,3]triazolo[4,5-d]pyrimidine-5-amine |
| 51 | 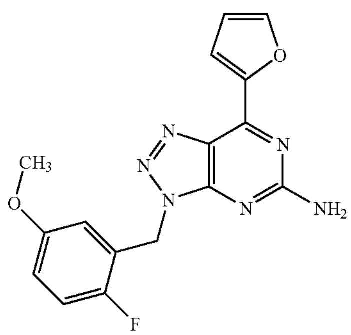 | 3-(2-fluoro-5-methoxybenzyl)-7-(2-furyl)-3H-[1,2,3]triazolo[4,5-d]pyrimidine-5-amine |
| 52 | 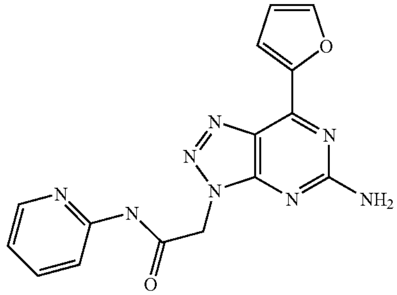 | (5-amino-7-(2-furyl)-3H-[1,2,3]triazolo[4,5-d]pyrimidin-3-yl)-N-(2-pyridyl)acetamide |

TABLE 1-continued

| Example | Structure | Compound Name |
| --- | --- | --- |
| 53 | 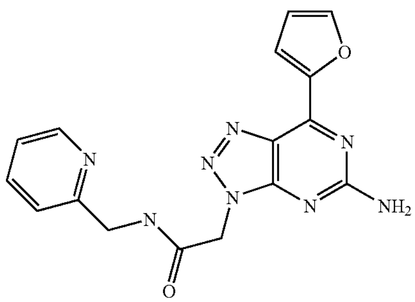 | (5-amino-7-(2-furyl)-3H-[1,2,3]triazolo[4,5-d]pyrimidin-3-yl)-N-(2-pyridylmethyl)acetamide |
| 54 | 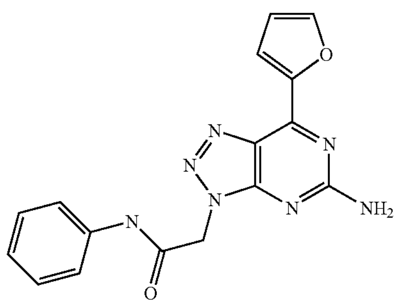 | (5-amino-7-(2-furyl)-3H-[1,2,3]triazolo[4,5-d]pyrimidin-3-yl)-N-phenylacetamide |
| 55 | 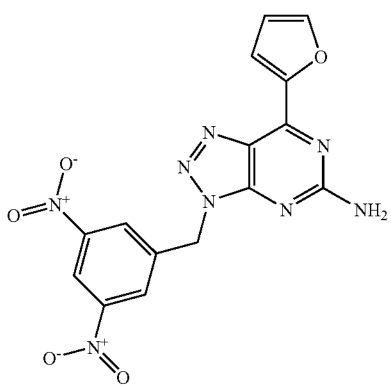 | 3-(3,5-dinitrobenzyl)-7-(2-furyl)-3H-[1,2,3]triazolo[4,5-d]pyrimidine-5-amine |
| 56 | 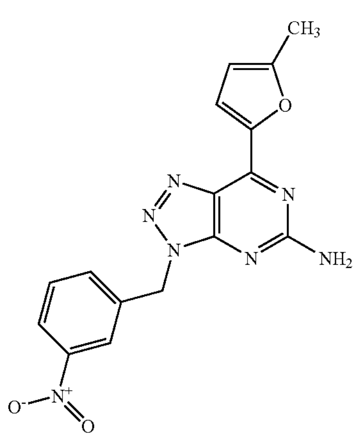 | 7-(5-methyl-2-furyl)-3-(3-nitrobenzyl)-3H-[1,2,3]triazolo[4,5-d]pyrimidine-5-amine |

TABLE 1-continued

| Example | Structure | Compound Name |
|---|---|---|
| 57 | 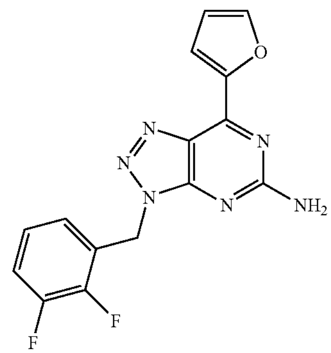 | 3-(2,3-difluorobenzyl)-7-(2-furyl)-3H-[1,2,3]triazolo[4,5-d]pyrimidine-5-amine |
| 58 | 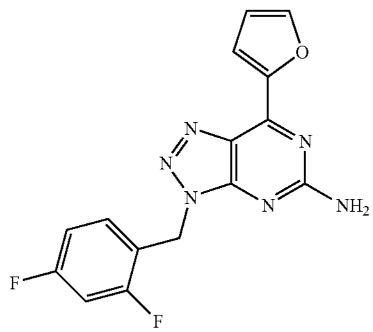 | 3-(2,4-difluorobenzyl)-7-(2-furyl)-3H-[1,2,3]triazolo[4,5-d]pyrimidine-5-amine |
| 59 | 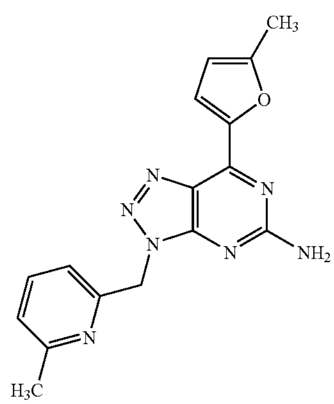 | 7-(5-methyl-2-furyl)-3-(6-methyl-2-pyridylmethyl)-3H-[1,2,3]triazolo[4,5-d-]pyrimidine-5-amine |
| 60 | 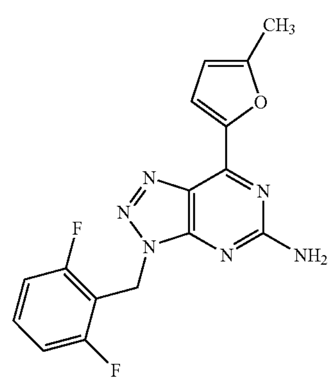 | 3-(2,6-difluorobenzyl)-7-(5-methyl-2-furyl)-3H-[1,2,3]triazolo[4,5-d]pyrimidine-5-amine |

TABLE 1-continued

| Example | Structure | Compound Name |
|---|---|---|
| 61 | 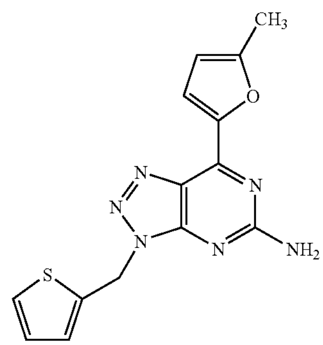 | 7-(5-methyl-2-furyl)-3-(2-thienylmethyl)-3H-[1,2,3]triazolo[4,5-d]pyrimidine-5-amine |
| 62 | 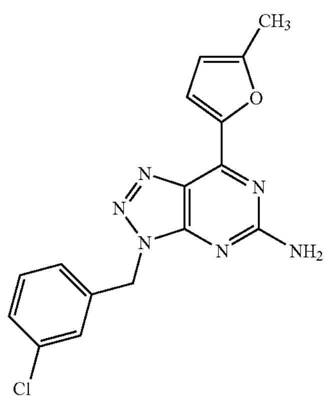 | 3-(3-chlorobenzyl)-7-(5-methyl-2-furyl)-3H-[1,2,3]triazolo[4,5-d]pyrimidine-5-amine |
| 63 | 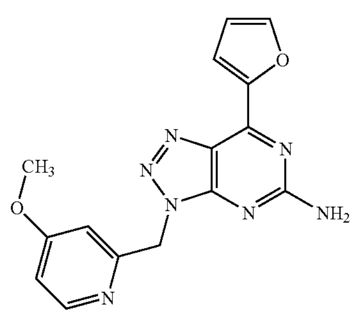 | 7-(2-furyl)-3-(4-methoxy-2-pyridylmethyl)-3H-[1,2,3]triazolo[4,5-d]pyrimidine-5-amine |
| 64 | 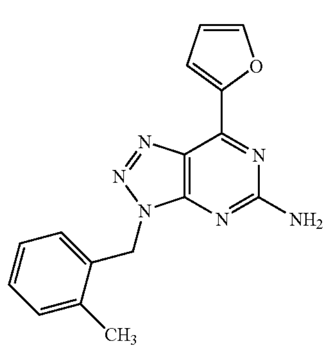 | 7-(2-furyl)-3-(2-methylbenzyl)-3H-[1,2,3]triazolo[4,5-d]pyrimidine-5-amine |

TABLE 1-continued

| Example | Structure | Compound Name |
| --- | --- | --- |
| 65 | 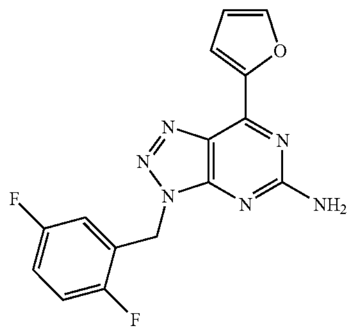 | 3-(2,5-difluorobenzyl)-7-(2-furyl)-3H-[1,2,3]triazolo[4,5-d]pyrimidine-5-amine |
| 66 | 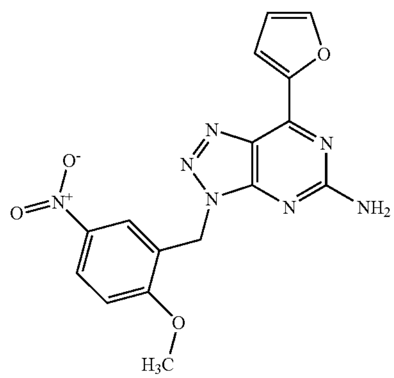 | 7-(2-furyl)-3-(2-methoxy-5-nitrobenzyl)-3H-[1,2,3]triazolo[4,5-d]pyrimidine-5-amine |
| 67 | 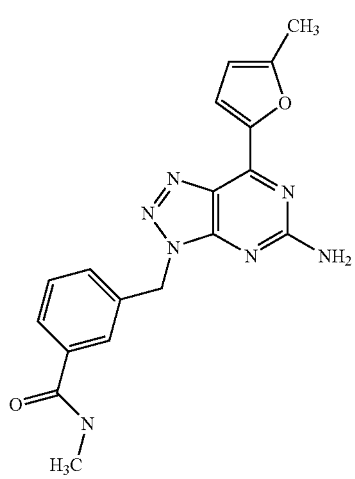 | 3-(5-amino-7-(5-methyl-2-furyl)-3H-[1,2,3]triazolo[4,5-d]pyrimidin-3-ylmethyl)-N-methylbenzamide |

TABLE 1-continued

| Example | Structure | Compound Name |
|---|---|---|
| 68 | 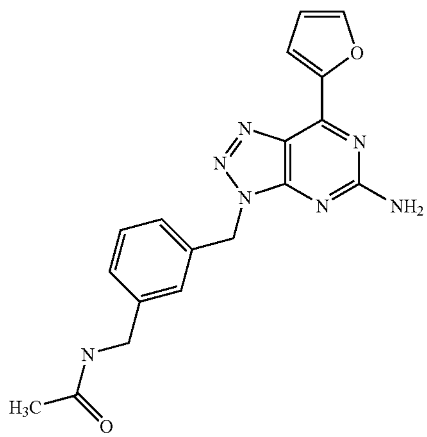 | N-(3-(5-amino-7-(2-furyl)-3H-[1,2,3]triazolo[4,5-d]pyrimidin-3-ylmethyl)benzyl)acetamide |
| 69 | 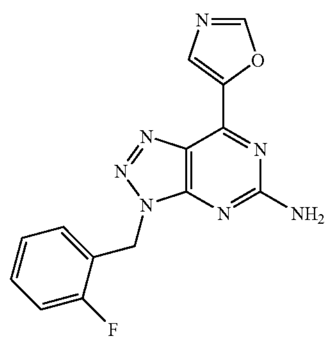 | 3-(2-fluorobenzyl)-7-(5-oxazolyl)-3H-[1,2,3]triazolo[4,5-d]pyrimidine-5-amine |
| 70 | 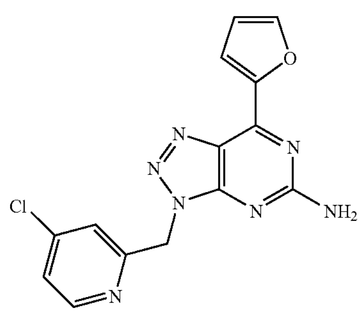 | 3-(4-chloro-2-pyridylmethyl)-7-(2-furyl)-3H-[1,2,3]triazolo[4,5-d]pyrimidine-5-amine |
| 71 | 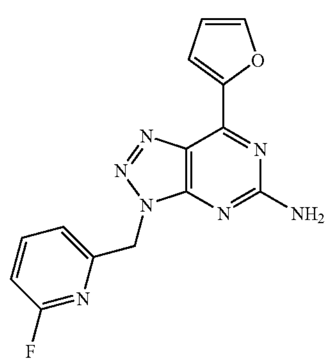 | 3-(6-fluoro-2-pyridylmethyl)-7-(2-furyl)-3H-[1,2,3]triazolo[4,5-d]pyrimidine-5-amine |

TABLE 1-continued

| Example | Structure | Compound Name |
|---|---|---|
| 72 | 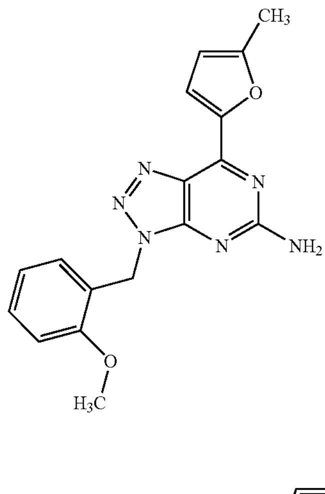 | 3-(2-methoxybenzyl)-7-(5-methyl-2-furyl)-3H-[1,2,3]triazolo[4,5-d]pyrimidine-5-amine |
| 73 | 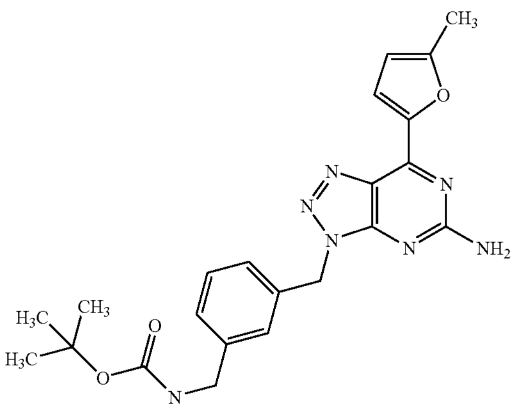 | tert-butyl N-(3-(5-amino-7-(5-methyl-2-furyl)-[1,2,3]triazolo[4,5-d]pyrimidine-3-ylmethyl)benzyl)carbamate |
| 74 | 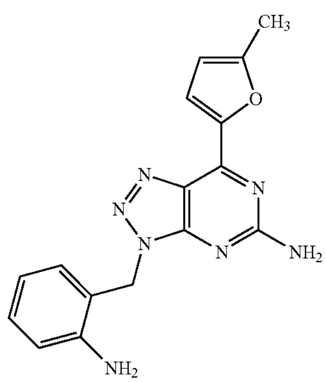 | 3-(2-aminobenzyl)-7-(5-methyl-2-furyl)-3H-[1,2,3]triazolo[4,5-d]pyrimidine-5-amine hydrochloride |
| 75 | 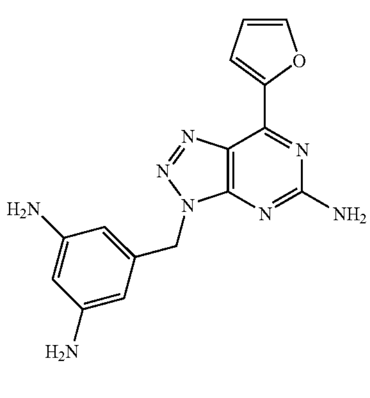 | 3-(3,5-diaminobenzyl)-7-(2-furyl)-3H-[1,2,3]triazolo[4,5-d]pyrimidine-5-amine |

TABLE 1-continued

| Example | Structure | Compound Name |
|---|---|---|
| 76 | 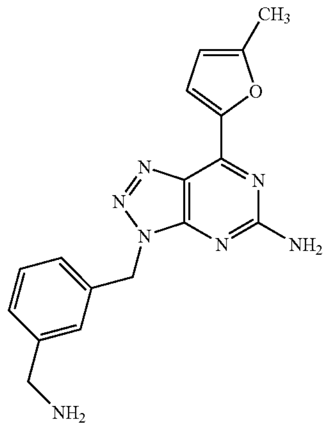 | 3-(3-aminomethylbenzyl)-7-(5-methyl-2-furyl)-3H-[1,2,3]triazolo[4,5-d]pyrimidine-5-amine hydrochloride |
| 77 | 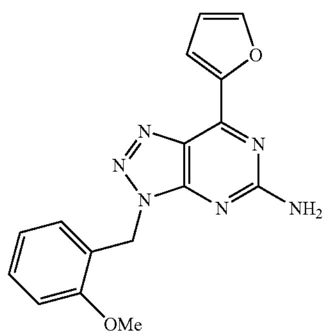 | 7-(2-furyl)-3-(2-methoxybenzyl)-3H-[1,2,3]triazolo[4,5-d]pyrimidine-5-amine |
| 78 | 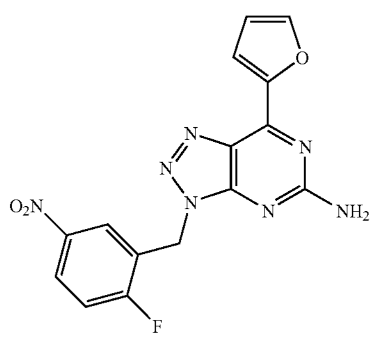 | 3-(2-fluoro-5-nitrobenzyl)-7-(2-furyl)-3H-[1,2,3]triazolo[4,5-d]pyrimidine-5-amine |
| 79 | 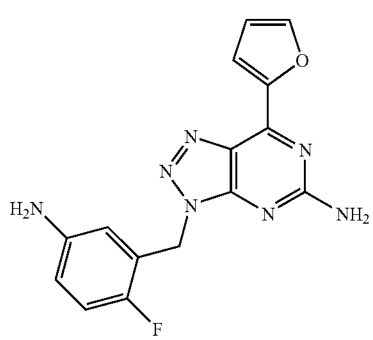 | 3-(5-amino-2-fluorobenzyl)-7-(2-furyl)-3H-[1,2,3]triazolo[4,5-d]pyrimidine-5-amine |

TABLE 1-continued
| Example | Structure | Compound Name |
|---|---|---|
| 80 | 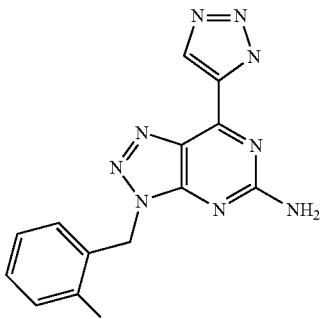 | 3-(2-fluorobenzyl)-7-(1H-triazol-4-yl)-3H-[1,2,3]triazolo[4,5-d]pyrimidine-5-amine |
| 81 | 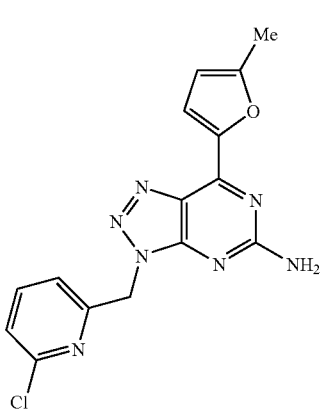 | 3-(6-chloro-2-pyridylmethyl)-7-(5-methyl-2-furyl)-3H-[1,2,3]triazolo[4,5-d]pyrimidine-5-amine |
| 82 | 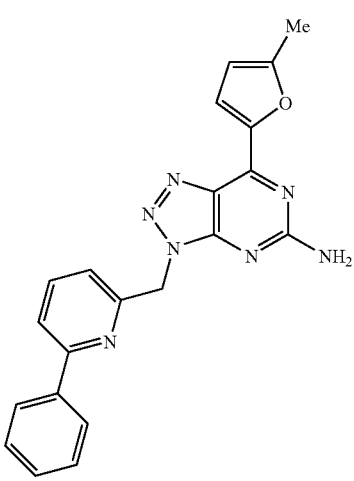 | 7-(5-methyl-2-furyl)-3-(6-phenyl-2-pyridylmethyl)-3H-[1,2,3]triazolo[4,5-d]pyrimidine-5-amine |
| 83 | 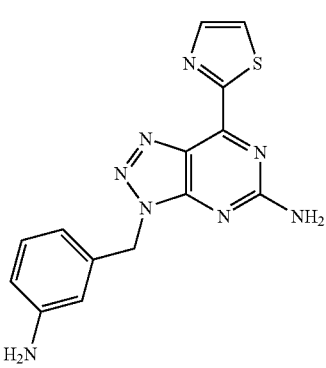 | 3-(3-aminobenzyl)-7-(2-thiazolyl)-3H-[1,2,3]triazolo[4,5-d]pyrimidine-5-amine |

TABLE 1-continued

| Example | Structure | Compound Name |
|---------|-----------|---------------|
| 84 | 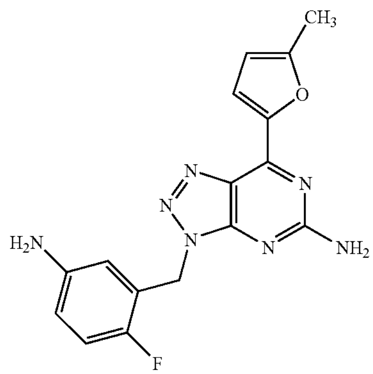 | 3-(5-amino-2-fluorobenzyl)-7-(5-methyl-2-furyl)-3H-[1,2,3]triazolo[4,5-d]pyrimidine-5-amine hydrochloride |
| 85 | 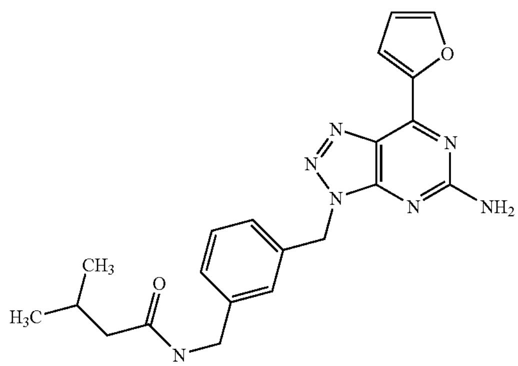 | N-(3-(5-amino-7-(2-furyl)-3H-[1,2,3]triazolo[4,5-d]pyrimidin-3-ylmethyl)benzyl)-3-methylbutanamide |
| 86 | 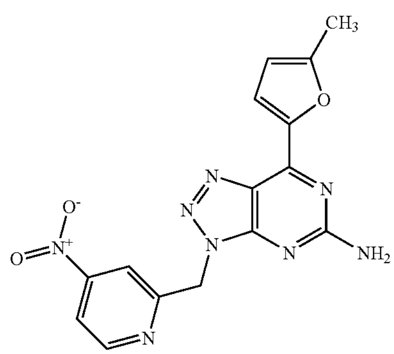 | 7-(5-methyl-2-furyl)-3-(4-nitro-2-pyridylmethyl)-3H-[1,2,3]triazolo[4,5-d]pyrimidine-5-amine |
| 87 | 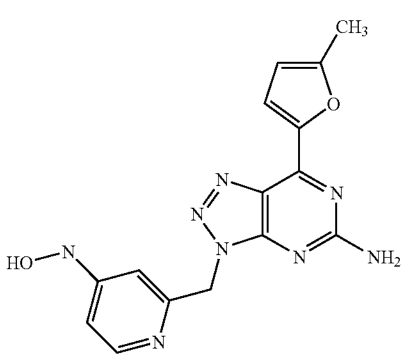 | 3-(4-hydroxylamino-2-pyridylmethyl)-7-(5-methyl-2-furyl)-3H-[1,2,3]triazolo[4,5-d]pyrimidine-5-amine |

TABLE 1-continued

| Example | Structure | Compound Name |
|---|---|---|
| 88 | 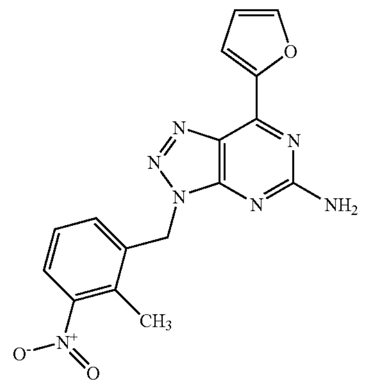 | 7-(2-furyl)-3-(2-methyl-3-nitrobenzyl)-3H-[1,2,3]triazolo[4,5-d]pyrimidine-5-amine |
| 89 | 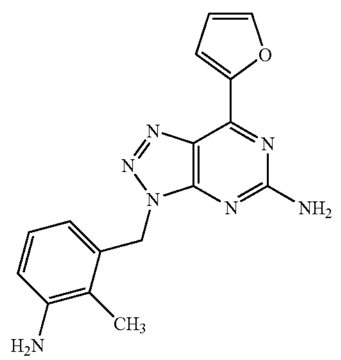 | 3-(3-amino-2-methylbenzyl)-7-(2-furyl)-3H-[1,2,3]triazolo[4,5-d]pyrimidine-5-amine |
| 90 | 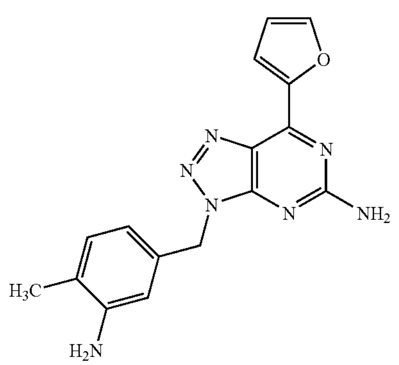 | 3-(3-amino-4-methylbenzyl)-7-(2-furyl)-3H-[1,2,3]triazolo[4,5-d]pyrimidine-5-amine |
| 91 | 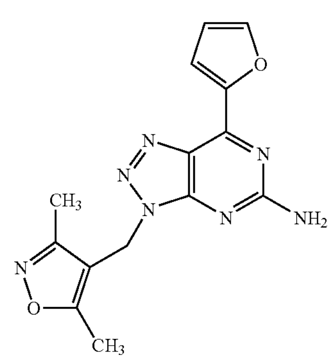 | 3-(3,5-dimethylisoxazol-4-ylmethyl)-7-(2-[1,2,3]triazolo[4,5-d]pyrimidine-5-amine |

TABLE 1-continued
| Example | Structure | Compound Name |
|---|---|---|
| 92 | 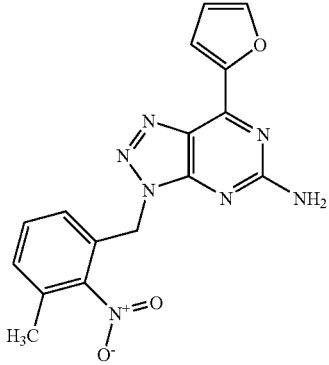 | 7-(2-furyl)-3-(3-methyl-2-nitrobenzyl)-3H-[1,2,3]triazolo[4,5-d]pyrimidine-5-amine |
| 93 | 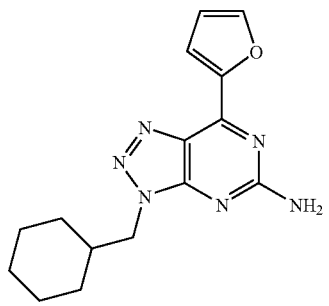 | 3-cyclohexylmethyl-7-(2-furyl)-3H-[1,2,3]triazolo[4,5-d]pyrimidine-5-amine |
| 94 | 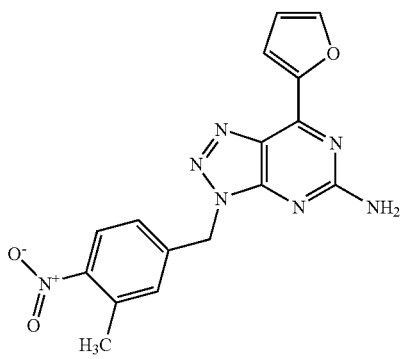 | 7-(2-furyl)-3-(3-methyl-4-nitrobenzyl)-3H-[1,2,3]triazolo[4,5-d]pyrimidine-5-amine |
| 95 | 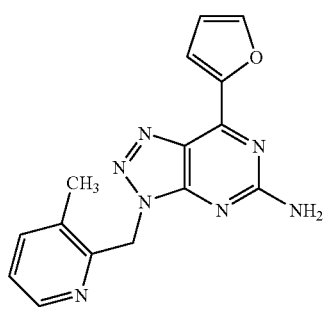 | 7-(2-furyl)-3-(3-methyl-2-pyridylmethyl)-3H-[1,2,3]triazolo[4,5-d]pyrimidine-5-amine |

TABLE 1-continued

| Example | Structure | Compound Name |
| --- | --- | --- |
| 96 | 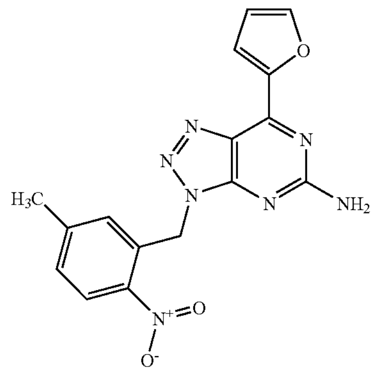 | 7-(2-furyl)-3-(5-methyl-2-nitrobenzyl)-3H-[1,2,3]triazolo[4,5-d]pyrimidine-5-amine |
| 97 | 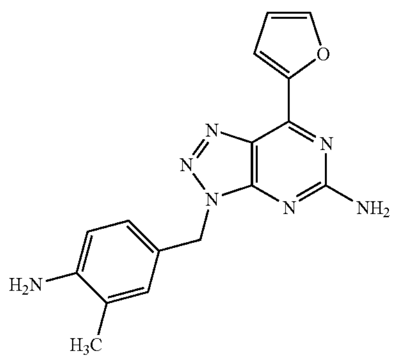 | 3-(4-amino-3-methylbenzyl)-7-(2-furyl)-3H-[1,2,3]triazolo[4,5-d]pyrimidine-5-amine |
| 98 | 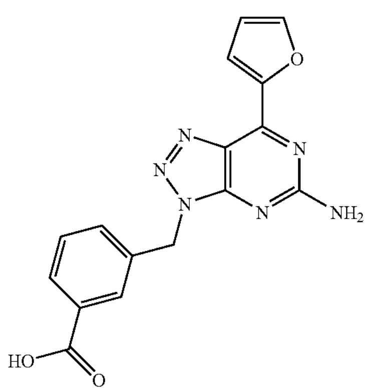 | 3-(5-amino-7-(2-furyl)-3H-[1,2,3]triazolo[4,5-d]pyrimidin-3-ylmethyl)benzoic acid |
| 99 | 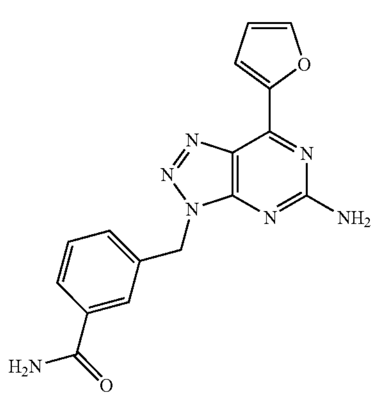 | 3-(5-amino-7-(2-furyl)-3H-[1,2,3]triazolo[4,5-d]pyrimidin-3-ylmethyl)benzamide |

TABLE 1-continued

| Example | Structure | Compound Name |
|---|---|---|
| 100 | 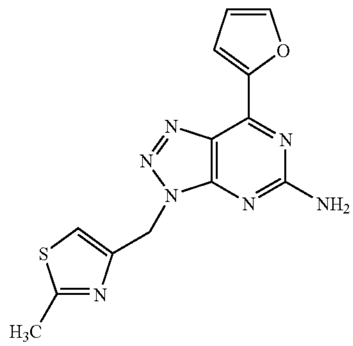 | 7-(2-furyl)-3-(2-methylthiazol-4-ylmethyl)-3H-[1,2,3]triazolo[4,5-d]pyrimidine-5-amine |
| 101 | 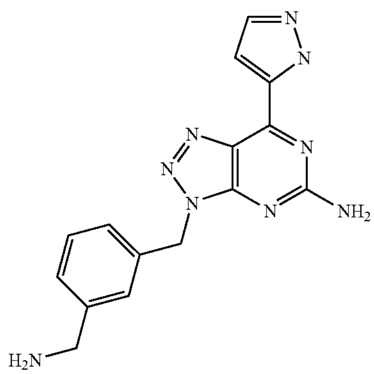 | 3-(3-aminomethylbenzyl)-7-(1H-pyrazol-3-yl)-3H-[1,2,3]triazolo[4,5-d]pyrimidine-5-amine |
| 102 | 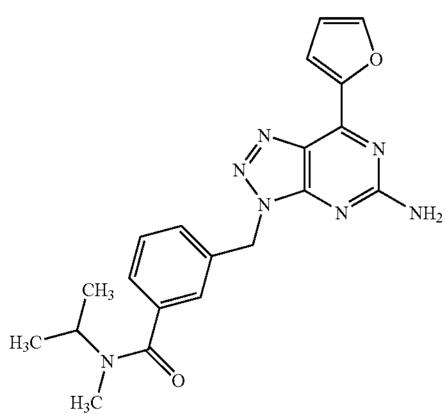 | 3-(5-amino-7-(2-furyl)-3H-[1,2,3]triazolo[4,5-d]pyrimidin-3-ylmethyl)-N-isopropyl-N-methylbenzamide |
| 103 | 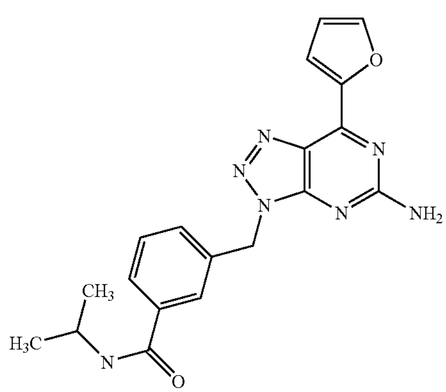 | 3-(5-amino-7-(2-furyl)-3H-[1,2,3]triazolo[4,5-d]pyrimidin-3-ylmethyl)-N-isopropylbenzamide |

TABLE 1-continued
| Example | Structure | Compound Name |
|---|---|---|
| 104 | 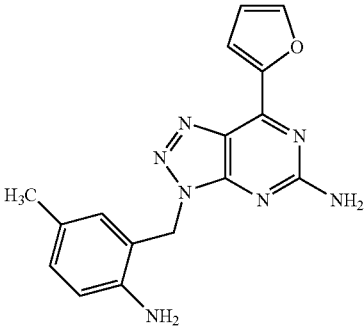 | 3-(2-amino-5-methylbenzyl)-7-(2-furyl)-3H-[1,2,3]triazolo[4,5-d]pyrimidine-5-amine |
| 105 | 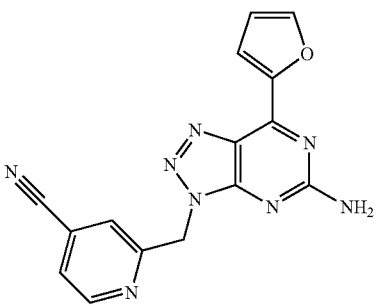 | 3-(4-cyano-2-pyridylmethyl)-7-(2-furyl)-3H-[1,2,3]triazolo[4,5-d]pyrimidine-5-amine |
| 106 | 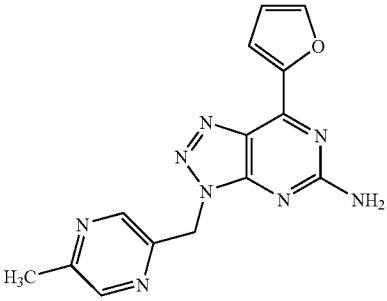 | 7-(2-furyl)-3-(5-methyl-2-pyrazinylmethyl)-3H-[1,2,3]triazolo[4,5-d]pyrimidine-5-amine |
| 107 | 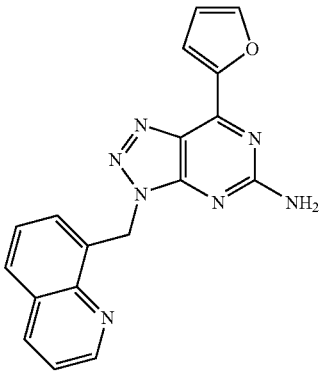 | 7-(2-furyl)-3-(8-quinolinylmethyl)-3H-[1,2,3]triazolo[4,5-d]pyrimidine-5-amine |

TABLE 1-continued

| Example | Structure | Compound Name |
|---------|-----------|---------------|
| 108 | 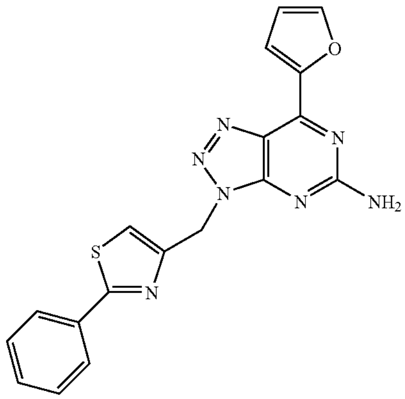 | 7-(2-furyl)-3-(2-phenylthiazol-4-ylmethyl)-3H-[1,2,3]triazolo[4,5-d]pyrimidine-5-amine |
| 109 | 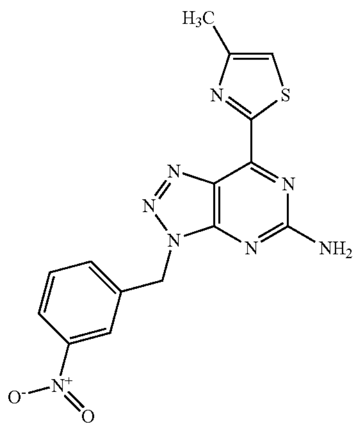 | 7-(4-methyl-2-thiazolyl)-3-(3-nitrobenzyl)-3H-[1,2,3]triazolo[4,5-d]pyrimidine-5-amine |
| 110 | 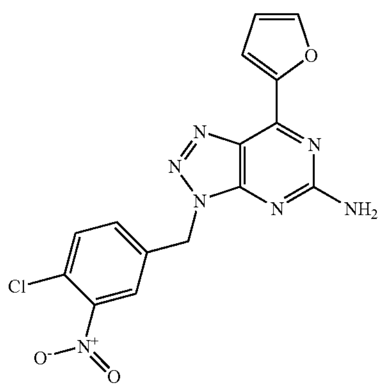 | 3-(4-chloro-3-nitrobenzyl)-7-(2-furyl)-3H-[1,2,3]triazolo[4,5-d]pyrimidine-5-amine |
| 111 | 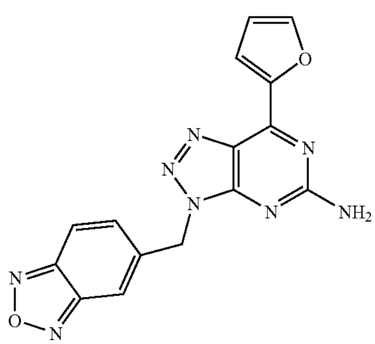 | 3-(1,2,5-benzoxadiazol-5-yl)-7-(2-furyl)-3H-[1,2,3]triazolo[4,5-d]pyrimidine-5-amine |

TABLE 1-continued

| Example | Structure | Compound Name |
|---|---|---|
| 112 | 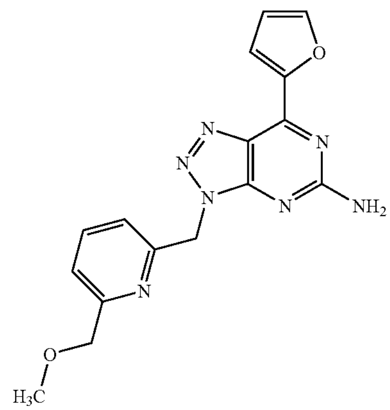 | 7-(2-furyl)-3-(6-methoxymethyl-2-pyridylmethyl)-3H-[1,2,3]triazolo[4,5-d]pyrimidine-5-amine |
| 113 | 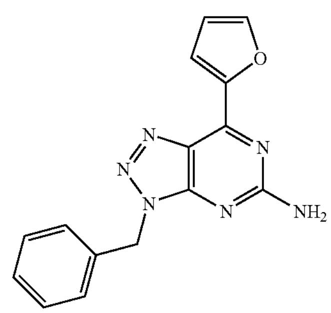 | 3-benzyl-7-(2-furyl)-3H-[1,2,3]triazolo[4,5-d]pyrimidine-5-amine |
| 114 | 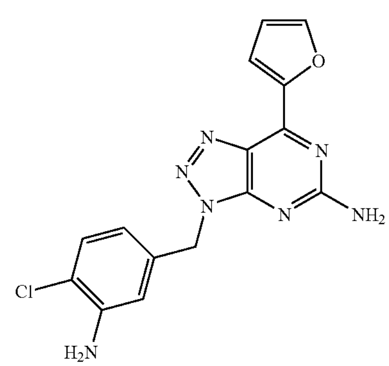 | 3-(3-amino-4-chlorobenzyl)-7-(2-furyl)-3H-[1,2,3]triazolo[4,5-d]pyrimidine-5-amine |
| 115 | 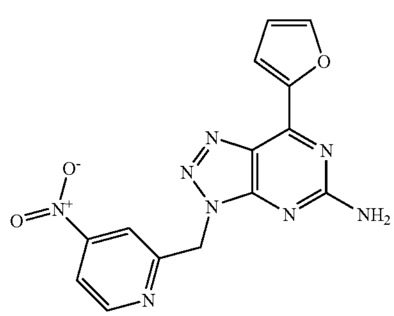 | 7-(2-furyl)-3-(4-nitro-2-pyridylmethyl)-3H-[1,2,3]triazolo[4,5-d]pyrimidine-5-amine |

TABLE 1-continued

| Example | Structure | Compound Name |
| --- | --- | --- |
| 116 | 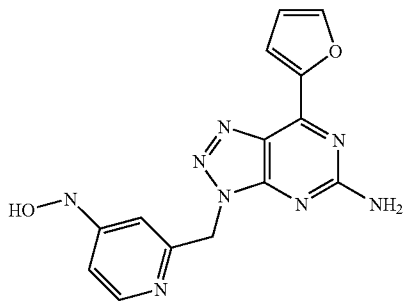 | 7-(2-furyl)-3-(4-hydroxylamino-2-pyridylmethyl)-3H-[1,2,3]triazolo[4,5-d]pyrimidine-5-amine |
| 117 | 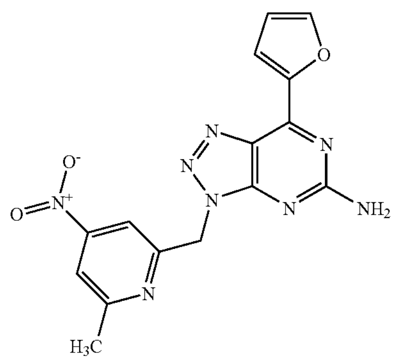 | 7-(2-furyl)-3-(6-methyl-4-nitro-2-pyridylmethyl)-3H-[1,2,3]triazolo[4,5-d]pyrimidine-5-amine |
| 118 | 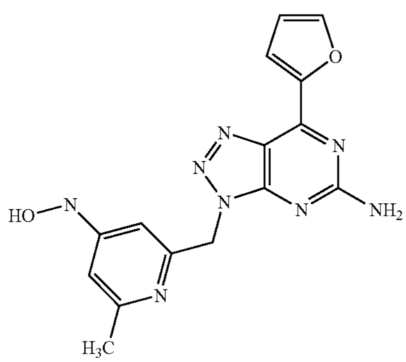 | 7-(2-furyl)-3-(4-hydroxylamino-6-methyl-2-pyridylmethyl)-3H-[1,2,3]triazolo[4,5-d]pyrimidine-5-amine |
| 119 | 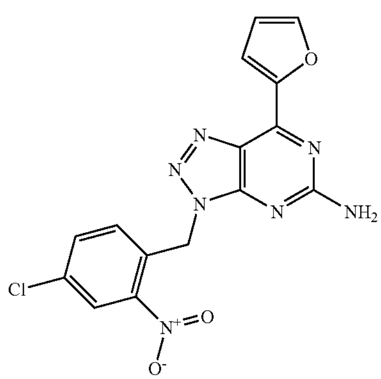 | 3-(4-chloro-2-nitrobenzyl)-7-(2-furyl)-3H-[1,2,3]triazolo[4,5-d]pyrimidine-5-amine |

TABLE 1-continued

| Example | Structure | Compound Name |
|---|---|---|
| 120 | 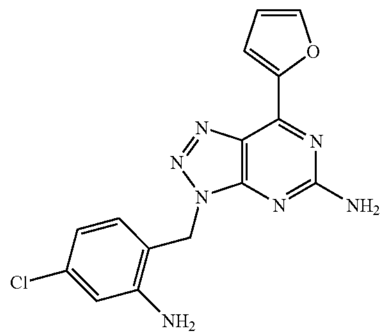 | 3-(2-amino-4-chlorobenzyl)-7-(2-furyl)-3H-[1,2,3]triazolo[4,5-d]pyrimidine-5-amine |
| 121 | 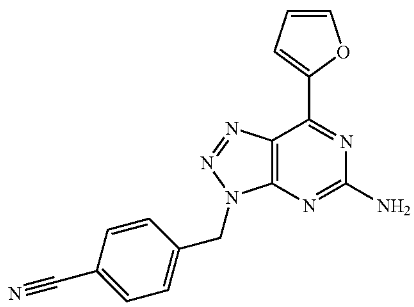 | 3-(4-cyanobenzyl)-7-(2-furyl)-3H-[1,2,3]triazolo[4,5-d]pyrimidine-5-amine |
| 122 | 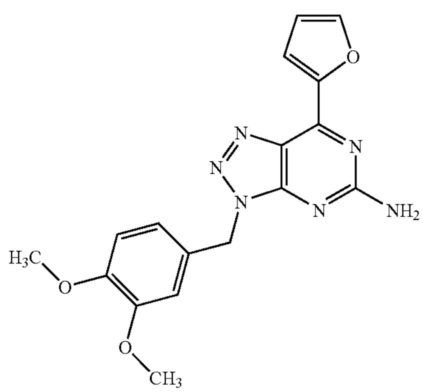 | 3-(3,4-dimethoxybenzyl)-7-(2-furyl)-3H-[1,2,3]triazolo[4,5-d]pyrimidine-5-amine trifluoroacetate salt |
| 123 | 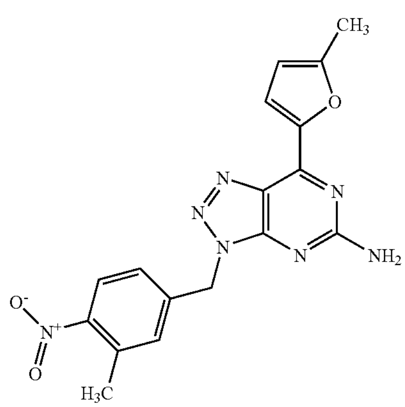 | 7-(5-methyl-2-furyl)-3-(3-methyl-4-nitrobenzyl)-3H-[1,2,3]triazolo[4,5-d]pyrimidine-5-amine |

TABLE 1-continued

| Example | Structure | Compound Name |
| --- | --- | --- |
| 124 | 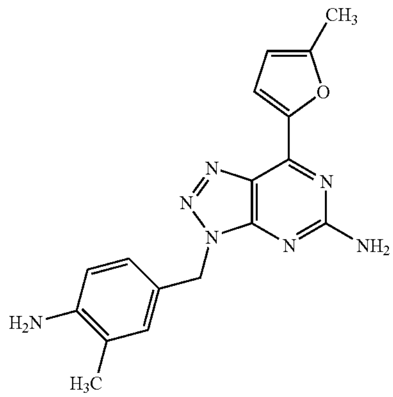 | 3-(4-amino-3-methylbenzyl)-7-(5-methyl-2-furyl)-3H-[1,2,3]triazolo[4,5-d]pyrimidine-5-amine |
| 125 | 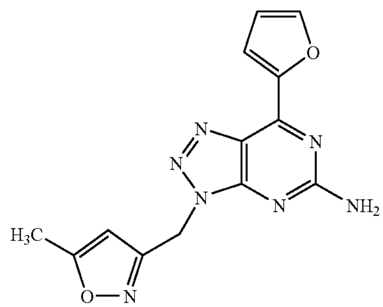 | 7-(2-furyl)-3-(5-methyl-3-oxazolyl)-3H-[1,2,3]triazolo[4,5-d]pyrimidine-5-amine |
| 126 | 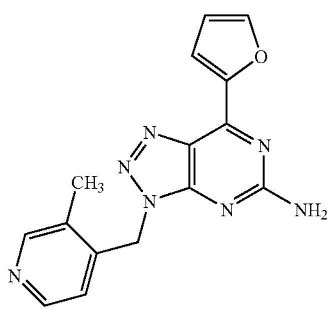 | 7-(2-furyl)-3-(3-methyl-4-pyridylmethyl)-3H-[1,2,3]triazolo[4,5-d]pyrimidine-5-amine |
| 127 | 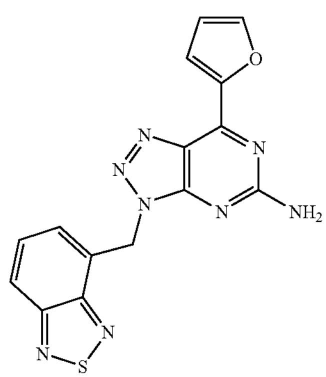 | 3-(1,2,5-benzothiadiazol-4-ylmethyl)-7-(2-furyl)-3H-[1,2,3]triazolo[4,5-d]pyrimidine-5-amine |

TABLE 1-continued

| Example | Structure | Compound Name |
|---|---|---|
| 128 | 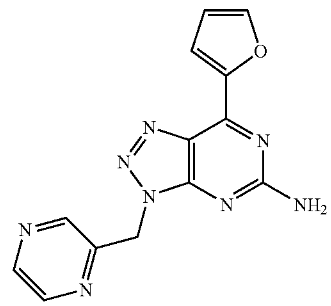 | 7-(2-furyl)-3-(2-pyrazinylmethyl)-3H-[1,2,3]triazolo[4,5-d]pyrimidine-5-amine |
| 129 | 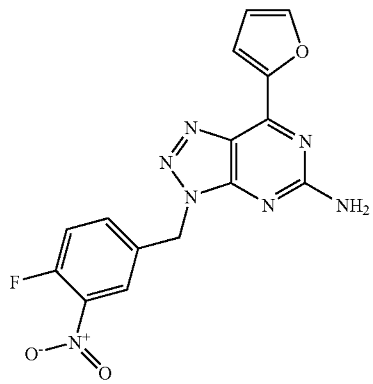 | 3-(4-fluoro-3-nitrobenzyl)-7-(2-furyl)-3H-[1,2,3]triazolo[4,5-d]pyrimidine-5-amine |
| 130 | 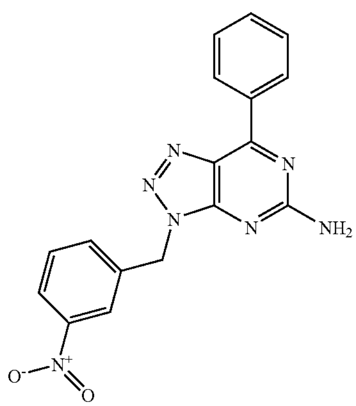 | 3-(3-nitrobenzyl)-7-phenyl-3H-[1,2,3]triazolo[4,5-d]pyrimidine-5-amine |
| 131 | 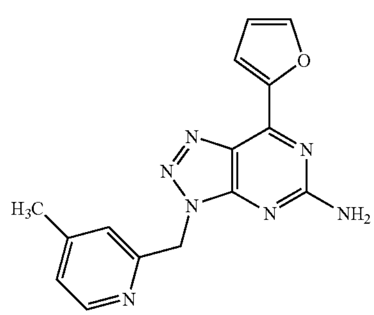 | 7-(2-furyl)-3-(4-methyl-2-pyridylmethyl)-3H-[1,2,3]triazolo[4,5-d]pyrimidine-5-amine |

TABLE 1-continued

| Example | Structure | Compound Name |
|---|---|---|
| 132 | 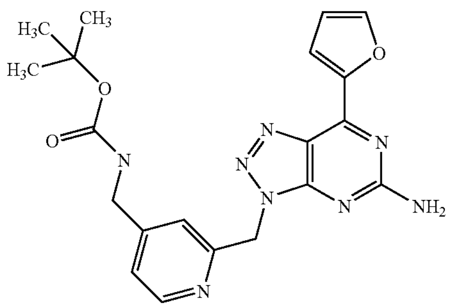 | tert-butyl N-(2-(5-amino-7-(2-furyl)-3H-[1,2,3]triazolo[4,5-d]pyrimidine-3-ylmethyl)-4-pyridylmethyl)carbamate |
| 133 | 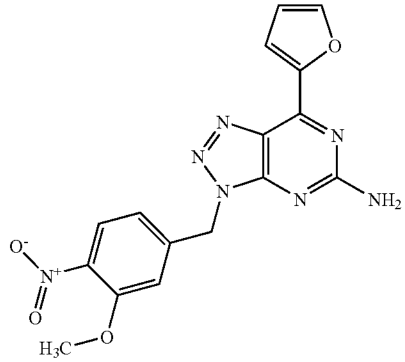 | 7-(2-furyl)-3-(3-methoxy-4-nitrobenzyl)-3H-[1,2,3]triazolo[4,5-d]pyrimidine-5-amine |
| 134 | 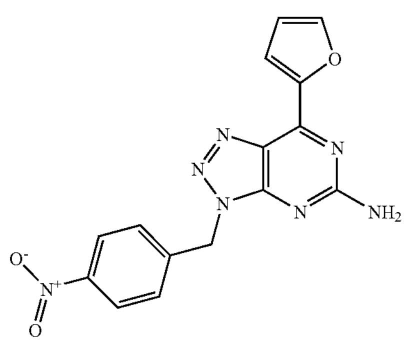 | 7-(2-furyl)-3-(4-nitrobenzyl)-3H-[1,2,3]triazolo[4,5-d]pyrimidine-5-amine |
| 135 | 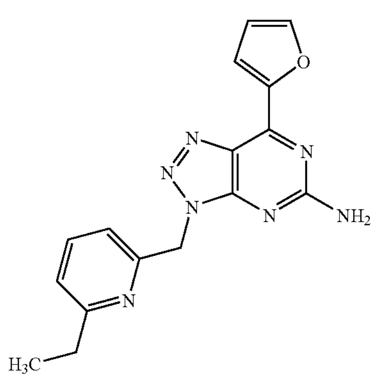 | 3-(6-ethyl-2-pyridylmethyl)-7-(2-furyl)-3H-[1,2,3]triazolo[4,5-d]pyrimidine-5-amine |

TABLE 1-continued

| Example | Structure | Compound Name |
|---|---|---|
| 136 | 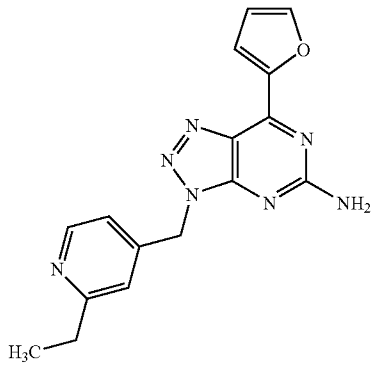 | 3-(2-ethyl-4-pyridylmethyl)-7-(2-furyl)-3H-[1,2,3]triazolo[4,5-d]pyrimidine-5-amine |
| 137 | 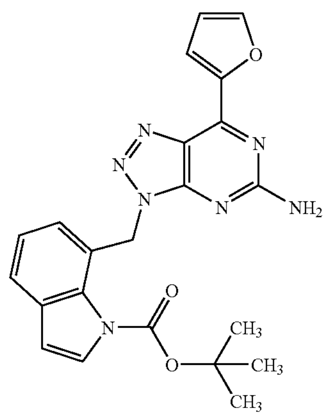 | tert-butyl 7-(5-amino-7-(2-furyl)-3H-[1,2,3]triazolo[4,5-d]pyrimidine-3-ylmethyl)indole-1-carboxylate |
| 138 | 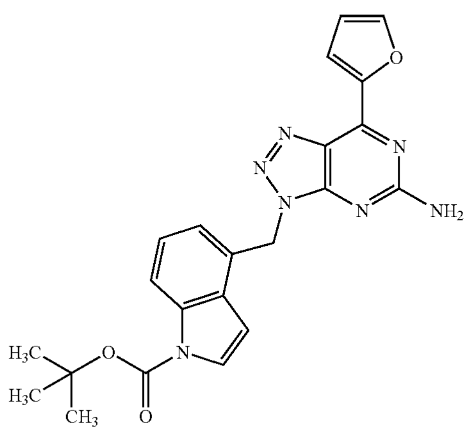 | tert-butyl 4-(5-amino-7-(2-furyl)-3H-[1,2,3]triazolo[4,5-d]pyrimidine-3-ylmethyl)indole-1-carboxylate |
| 139 | 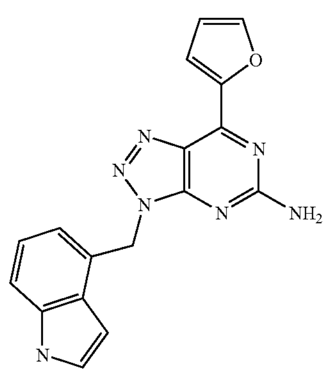 | 7-(2-furyl)-3-(4-indolylmethyl)-3H-[1,2,3]triazolo[4,5-d]pyrimidine-5-amine |

TABLE 1-continued

| Example | Structure | Compound Name |
|---|---|---|
| 140 | 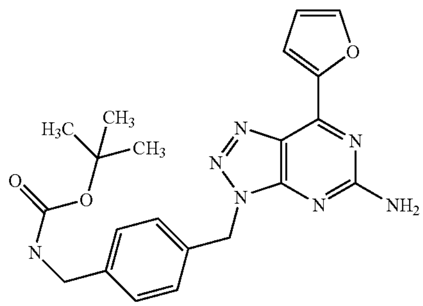 | tert-butyl N-(4-(5-amino-7-(2-furyl)-3H-[1,2,3]triazolo[4,5-d]pyrimidine-3-ylmethyl)benzyl)carbamate |
| 141 | 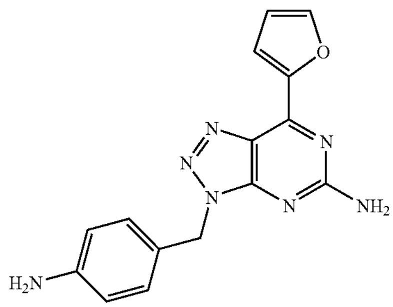 | 3-(4-aminobenzyl)-7-(2-furyl)-3H-[1,2,3]triazolo[4,5-d]pyrimidine-5-amine |
| 142 | 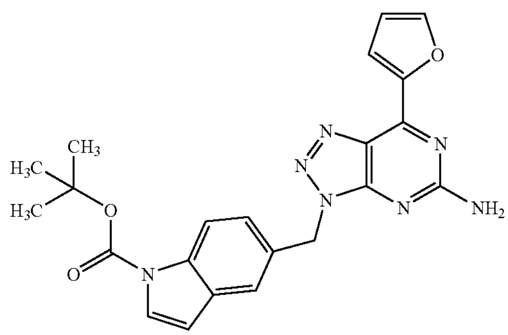 | tert-butyl 5-(5-amino-7-(2-furyl)-3H-[1,2,3]triazolo[4,5-d]pyrimidine-3-ylmethyl)indole-1-carboxylate |
| 143 | 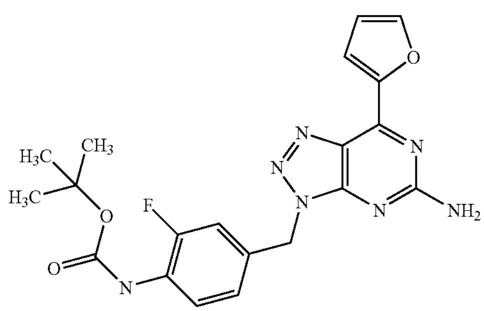 | tert-butyl N-(4-(5-amino-7-(2-furyl)-3H-[1,2,3]triazolo[4,5-d]pyrimidine-3-ylmethyl)-2-fluorophenyl)carbamate |
| 144 | 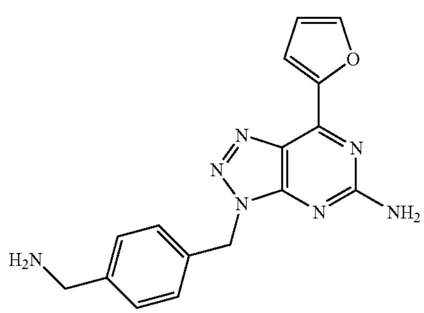 | 3-(4-aminomethylbenzyl)-7-(2-furyl)-3H-[1,2,3]triazolo[4,5-d]pyrimidine-5-amine |

TABLE 1-continued

| Example | Structure | Compound Name |
|---|---|---|
| 145 | 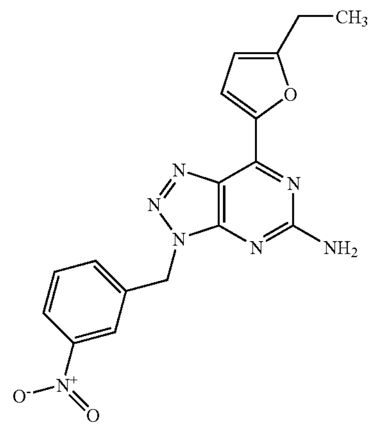 | 7-(5-ethyl-2-furyl)-3-(3-nitrobenzyl)-3H-[1,2,3]triazolo[4,5-d]pyrimidine-5-amine |
| 146 | 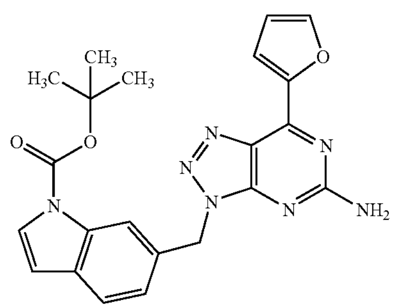 | tert-butyl 6-(5-amino-7-(2-furyl)-3H-[1,2,3]triazolo[4,5-d]pyrimidine-3-ylmethyl)indole-1-carboxylate |
| 147 | 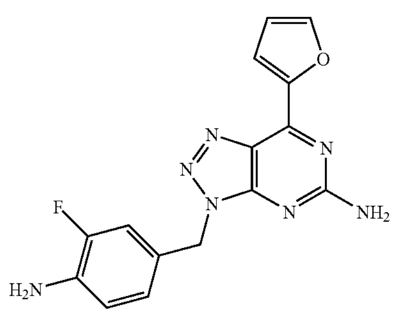 | 3-(4-amino-3-fluorobenzyl)-7-(2-furyl)-3H-[1,2,3]triazolo[4,5-d]pyrimidine-5-amine |
| 148 | 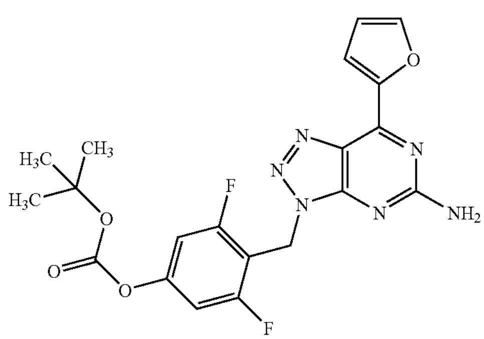 | tert-butyl (4-(5-amino-7-(2-furyl)-3H-[1,2,3]triazolo[4,5-d]pyrimidine-3-ylmethyl)-3,5-difluorophenyl)carbonate |

TABLE 1-continued

| Example | Structure | Compound Name |
|---|---|---|
| 149 | 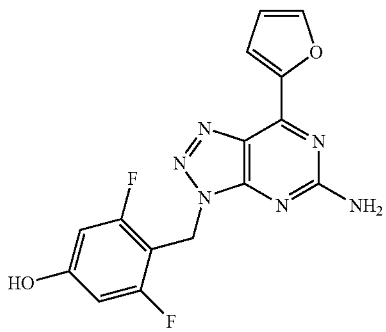 | 3-(2,6-difluoro-4-hydroxybenzyl)-7-(2-furyl)-3H-[1,2,3]triazolo[4,5-d]pyrimidine-5-amine |
| 150 | 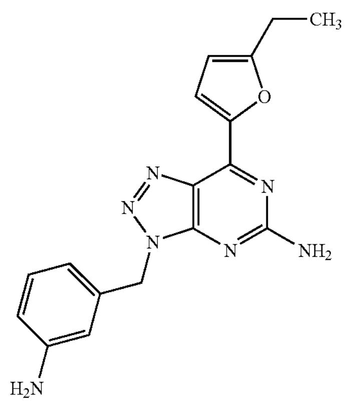 | 3-(3-aminobenzyl)-7-(5-ethyl-2-furyl)-3H-[1,2,3]triazolo[4,5-d]pyrimidine-5-amine |
| 151 | 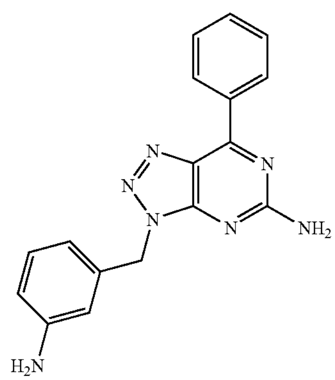 | 3-(3-aminobenzyl)-7-phenyl-3H-[1,2,3]triazolo[4,5-d]pyrimidine-5-amine |
| 152 | 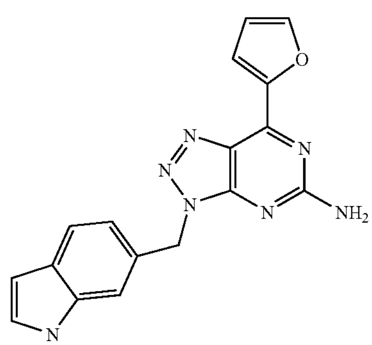 | 7-(2-furyl)-3-(6-indolylmethyl)-3H-[1,2,3]triazolo[4,5-d]pyrimidine-5-amine |

TABLE 1-continued

| Example | Structure | Compound Name |
|---------|-----------|---------------|
| 153 | 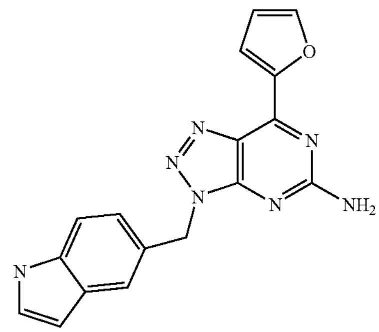 | 7-(2-furyl)-3-(5-indolylmethyl)-3H-[1,2,3]triazolo[4,5-d]pyrimidine-5-amine |
| 154 | 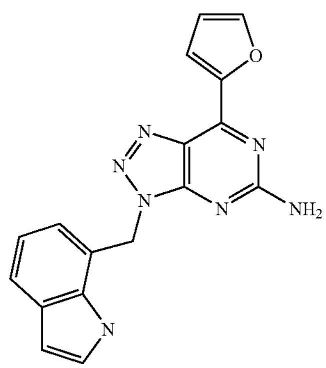 | 7-(2-furyl)-3-(7-indolylmethyl)-3H-[1,2,3]triazolo[4,5-d]pyrimidine-5-amine |
| 155 | 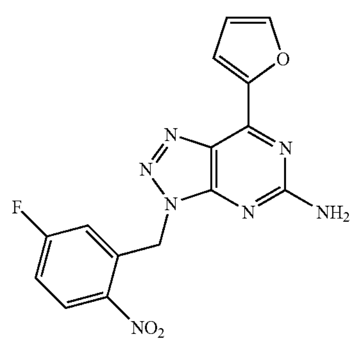 | 3-(5-fluoro-2-nitrobenzyl)-7-(2-furyl)-3H-[1,2,3]triazolo[4,5-d]pyrimidine-5-amine |
| 156 | 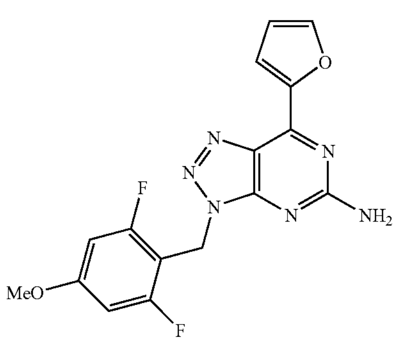 | 3-(2,6-difluoro-4-methoxybenzyl)-7-(2-furyl)-3H-[1,2,3]triazolo[4,5-d]pyrimidine-5-amine |

TABLE 1-continued

| Example | Structure | Compound Name |
|---|---|---|
| 157 | 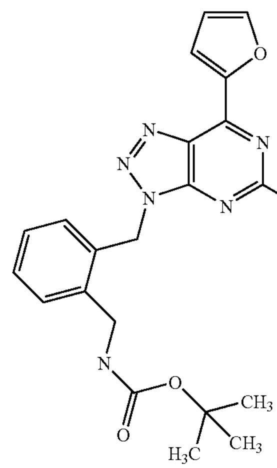 | tert-butyl N-(2-(5-amino-7-(2-furyl)-3H-[1,2,3]triazolo[4,5-d]pyrimidine-3-ylmethyl)benzyl)carbamate |
| 158 | 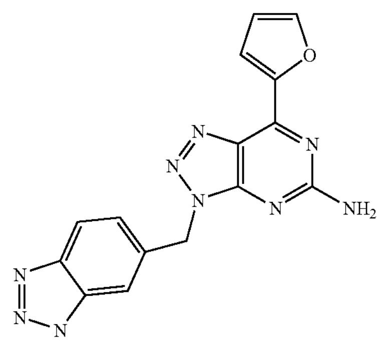 | 3-(1H-benzotriazol-5-ylmethyl)-7-(2-furyl)-3H-[1,2,3]triazolo[4,5-d]pyrimidine-5-amine |
| 159 | 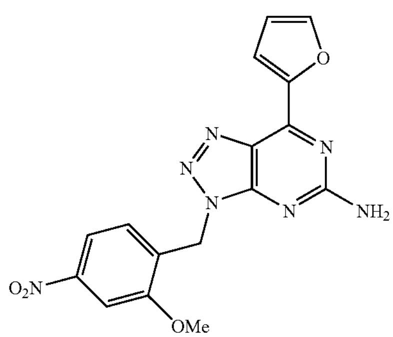 | 7-(2-furyl)-3-(2-methoxy-4-nitrobenzyl)-3H-[1,2,3]triazolo[4,5-d]pyrimidine-5-amine |
| 160 | 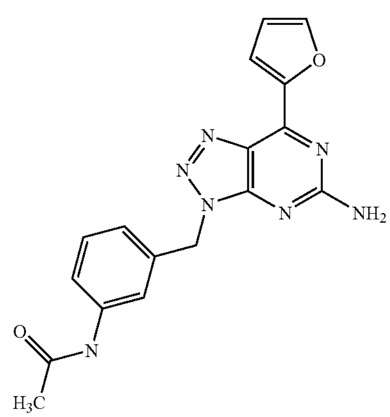 | N-(3-(5-amino-7-(2-furyl)-3H-[1,2,3]triazolo[4,5-d]pyrimidine-3-ylmethyl)phenylacetamide |

TABLE 1-continued

| Example | Structure | Compound Name |
|---|---|---|
| 161 | 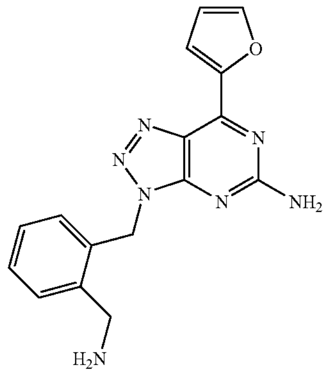 | 3-(2-aminomethylbenzyl)-7-(2-furyl)-3H-[1,2,3]triazolo[4,5-d]pyrimidine-5-amine |
| 162 | 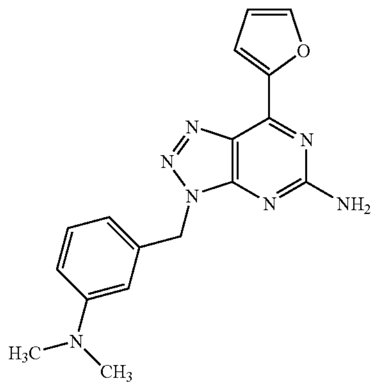 | 3-(3-(N,N-dimethylamino)benzyl)-7-(2-furyl)-3H-[1,2,3]triazolo[4,5-d]pyrimidine-5-amine |
| 163 | 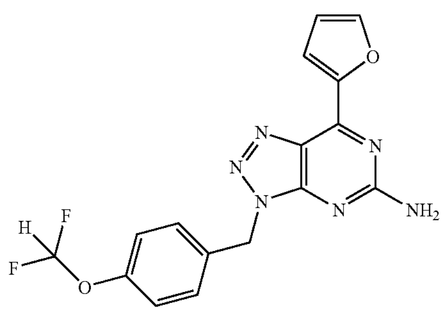 | 3-(4-difluoromethoxybenzyl)-7-(2-furyl)-3H-[1,2,3]triazolo[4,5-d]pyrimidine-5-amine |
| 164 | 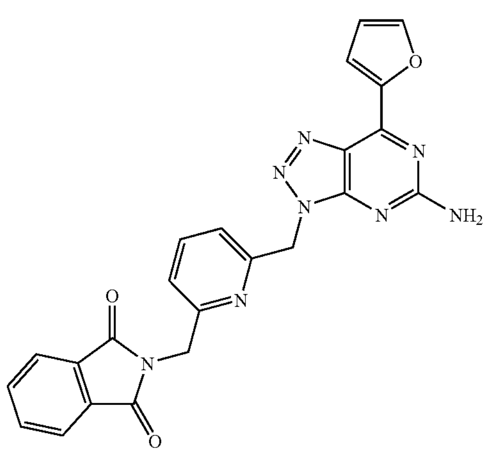 | 7-(2-furyl)-3-(6-phthalimidomethyl-2-pyridylmethyl)-3H-[1,2,3]triazolo[4,5-d]pyrimidine-5-amine |

TABLE 1-continued

| Example | Structure | Compound Name |
|---|---|---|
| 165 | 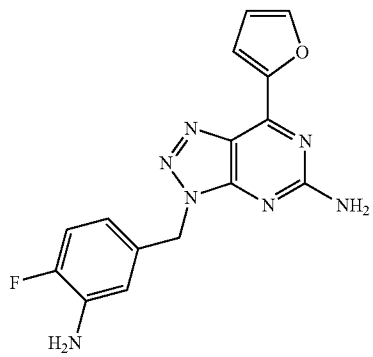 | 3-(3-amino-4-fluorobenzyl)-7-(2-furyl)-3H-[1,2,3]triazolo[4,5-d]pyrimidine-5-amine |
| 166 | 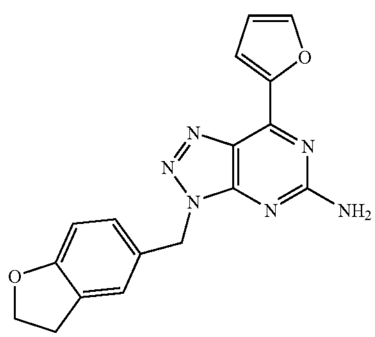 | 3-(2,3-dihydrobenzofuran-5-ylmethyl)-7-(2-furyl)-3H-[1,2,3]triazolo[4,5-d]pyrimidine-5-amine |
| 167 | 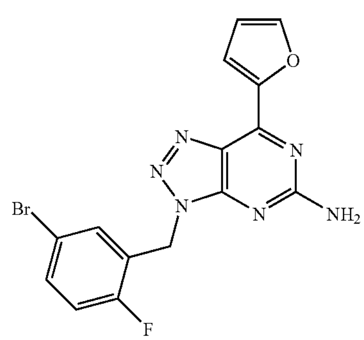 | 3-(5-bromo-2-fluorobenzyl)-7-(2-furyl)-3H-[1,2,3]triazolo[4,5-d]pyrimidine-5-amine |
| 168 | 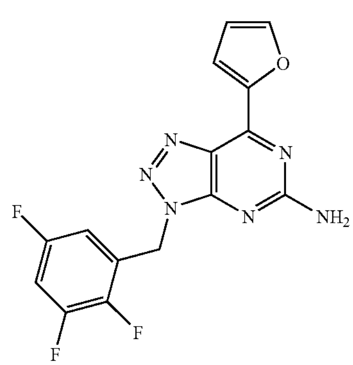 | 7-(2-furyl)-3-(2,3,5-trifluorobenzyl)-3H-[1,2,3]triazolo[4,5-d]pyrimidine-5-amine |

TABLE 1-continued

| Example | Structure | Compound Name |
| --- | --- | --- |
| 169 | 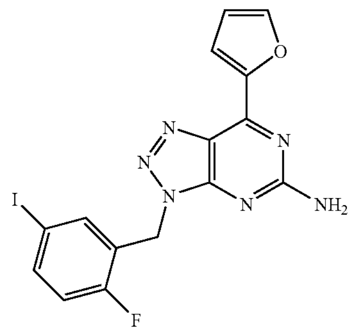 | 3-(2-fluoro-5-iodobenzyl)-7-(2-furyl)-3H-[1,2,3]triazolo[4,5-d]pyrimidine-5-amine |
| 170 | 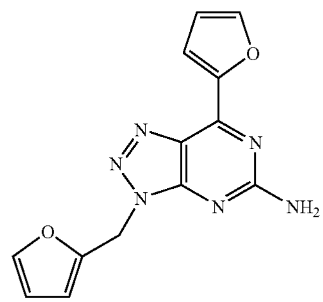 | 7-(2-furyl)-3-(2-furylmethyl)-3H-[1,2,3]triazolo[4,5-d]pyrimidine-5-amine |
| 171 | 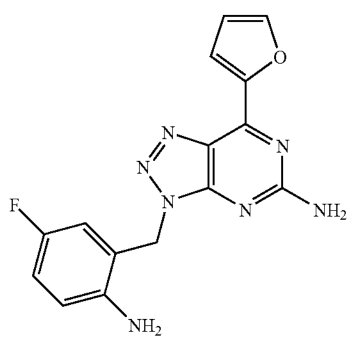 | 3-(2-amino-5-fluorobenzyl)-7-(2-furyl)-3H-[1,2,3]triazolo[4,5-d]pyrimidine-5-amine |
| 172 | 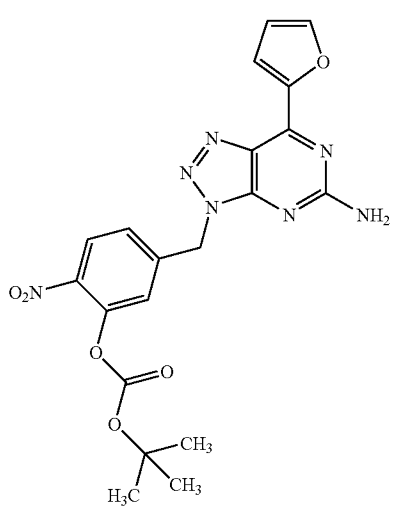 | tert-butyl (5-(5-amino-7-(2-furyl)-3H-[1,2,3]triazolo[4,5-d]pyrimidine-3-ylmethyl)-2-nitrophenyl)carbonate |

TABLE 1-continued

| Example | Structure | Compound Name |
| --- | --- | --- |
| 173 | 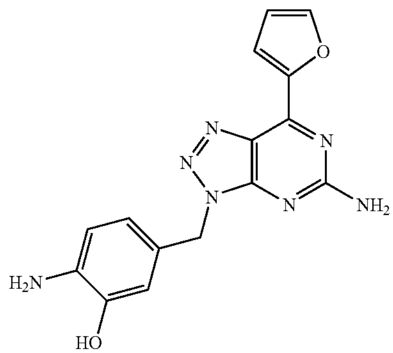 | 3-(4-amino-3-hydroxybenzyl)-7-(2-furyl)-3H-[1,2,3]triazolo[4,5-d]pyrimidine-5-amine |
| 174 | 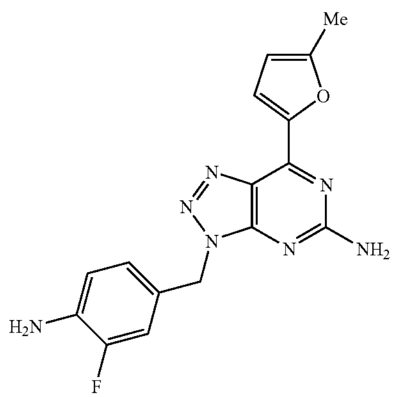 | 3-(4-amino-3-fluorobenzyl)-7-(5-methyl-2-furyl)-3H-[1,2,3]triazolo[4,5-d]pyrimidine-5-amine |
| 175 | 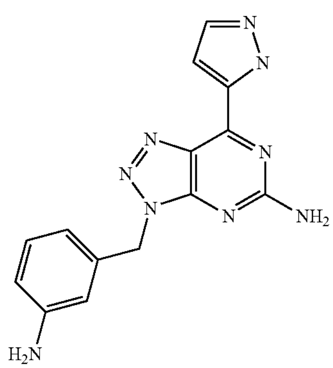 | 3-(3-aminobenzyl)-7-(1H-pyrazol-3-yl)-3H-[1,2,3]triazolo[4,5-d]pyrimidine-5-amine |
| 176 | 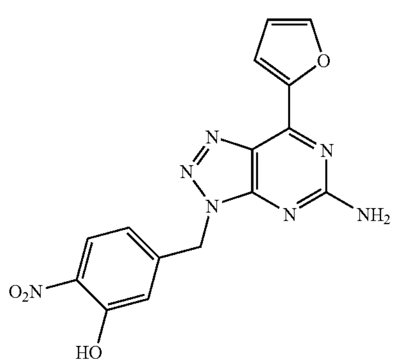 | 7-(2-furyl)-3-(3-hydroxy-4-nitrobenzyl)-3H-[1,2,3]triazolo[4,5-d]pyrimidine-5-amine |

TABLE 1-continued

| Example | Structure | Compound Name |
|---|---|---|
| 177 | 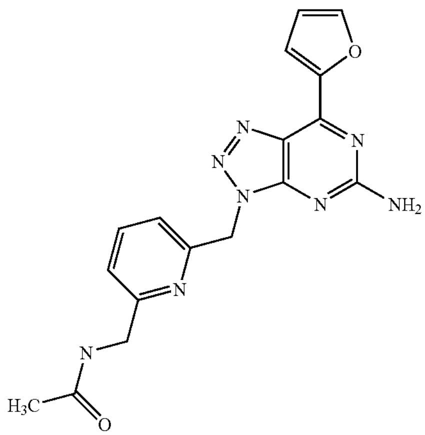 | N-(6-(5-amino-7-(2-furyl)-3H-[1,2,3]triazolo[4,5-d]pyrimidin-3-ylmethyl)-2-pyridylmethyl)acetamide |
| 178 | 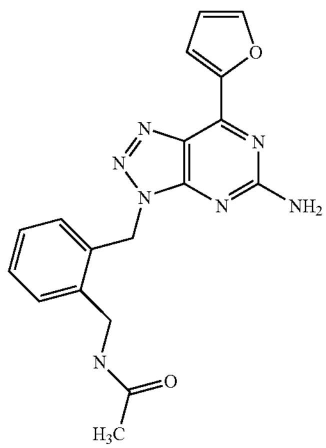 | N-(2-(5-amino-7-(2-furyl)-3H-[1,2,3]triazolo[4,5-d]pyrimidin-3-ylmethyl)benzyl)acetamide |
| 179 | 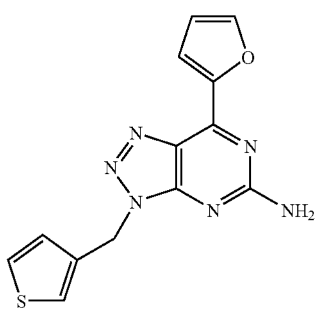 | 7-(2-furyl)-3-(3-thienylmethyl)-3H-[1,2,3]triazolo[4,5-d]pyrimidine-5-amine |
| 180 | 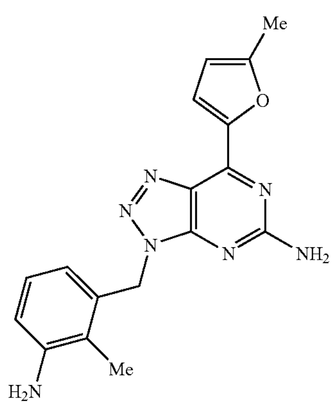 | 3-(3-amino-2-methylbenzyl)-7-(5-methyl-2-furyl)-3H-[1,2,3]triazolo[4,5-d]pyrimidine-5-amine |

TABLE 1-continued

| Example | Structure | Compound Name |
|---|---|---|
| 181 | 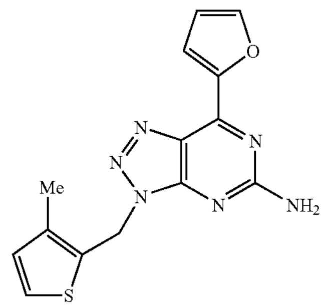 | 7-(2-furyl)-3-(3-methyl-2-thienyl)-3H-[1,2,3]triazolo[4,5-d]pyrimidine-5-amine |
| 182 | 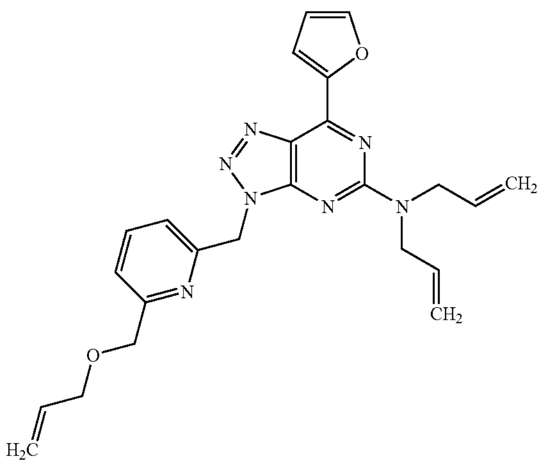 | 3-(6-allyloxymethyl-2-pyridylmethyl)-N,N-diallyl-7-(2-furyl)-3H-[1,2,3]triazolo[4,5-d]pyrimidine-5-amine |
| 183 | 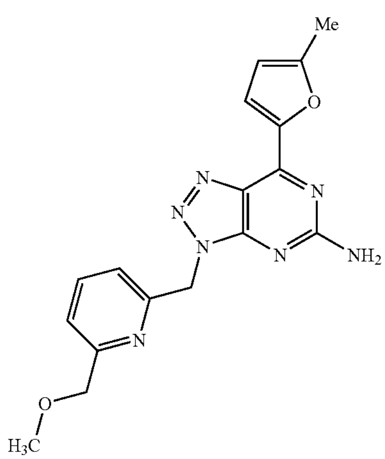 | 3-(6-methoxymethyl-2-pyridylmethyl)-7-(5-methyl-2-furyl)-3H-[1,2,3]triazolo[4,5-d]pyrimidine-5-amine |
| 184 | 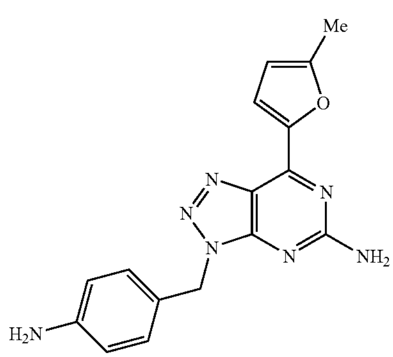 | 3-(4-aminobenzyl)-7-(5-methyl-2-furyl)-3H-[1,2,3]triazolo[4,5-d]pyrimidine-5-amine |

TABLE 1-continued
| Example | Structure | Compound Name |
|---------|-----------|---------------|
| 185 | 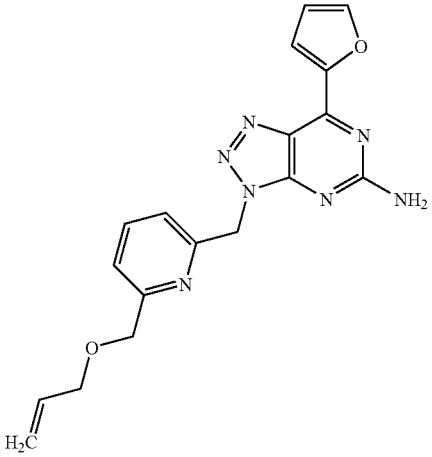 | 3-(6-allyloxymethyl-2-pyridylmethyl)-7-(2-furyl)-3H-[1,2,3]triazolo[4,5-d]pyrimidine-5-amine |
| 186 | 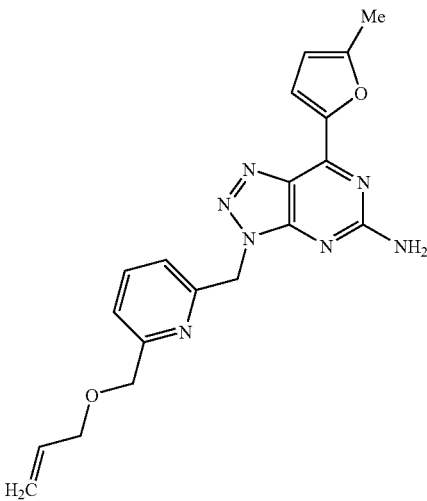 | 3-(6-allyloxymethyl-2-pyridylmethyl)-7-(5-methyl-2-furyl)-3H-[1,2,3]triazolo[4,5-d]pyrimidine-5-amine |
| 187 | 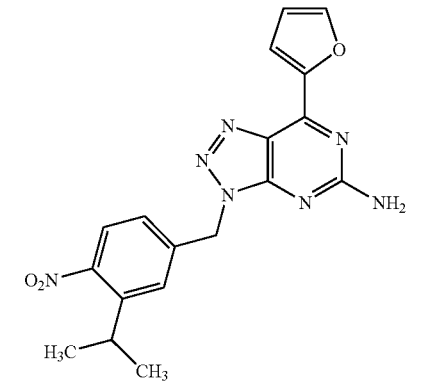 | 7-(2-furyl)-3-(3-isopropyl-4-nitrobenzyl)-3H-[1,2,3]triazolo[4,5-d]pyrimidine-5-amine |

TABLE 1-continued

| Example | Structure | Compound Name |
|---|---|---|
| 188 | 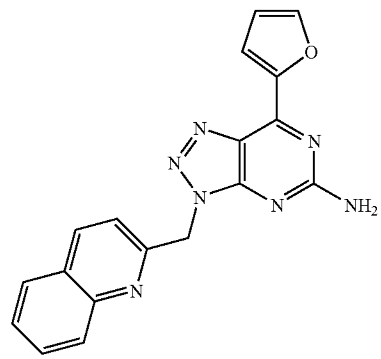 | 7-(2-furyl)-3-(quinolin-2-ylmethyl)-3H-[1,2,3]triazolo[4,5-d]pyrimidine-5-amine |
| 189 | 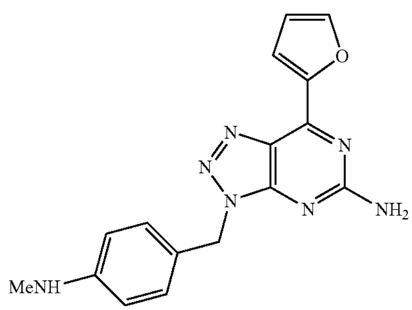 | 7-(2-furyl)-3-(4-(N-methylamino)benzyl)-3H-[1,2,3]triazolo[4,5-d]pyrimidine-5-amine |
| 190 | 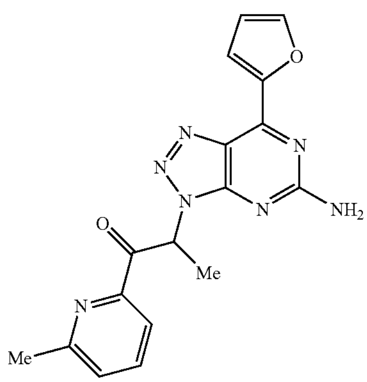 | 2-(5-amino-7-(2-furyl)-3H-[1,2,3]triazolo[4,5-d]pyrimidin-3-yl)-1-(6-methyl-2-pyridyl)propanone |
| 191 | 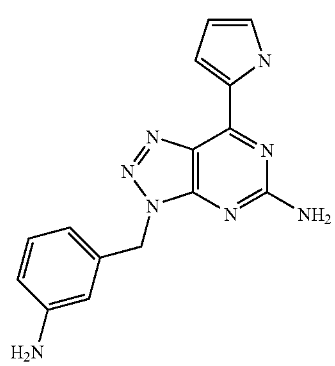 | 3-(3-aminobenzyl)-7-(1H-pyrrol-2-yl)-3H-[1,2,3]triazolo[4,5-d]pyrimidine-5-amine |

TABLE 1-continued

| Example | Structure | Compound Name |
|---|---|---|
| 192 | 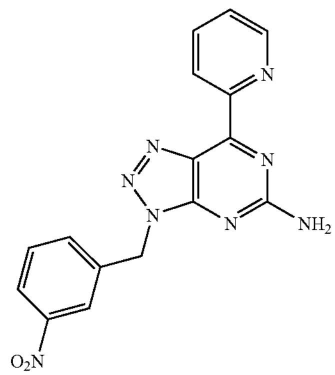 | 3-(3-nitrobenzyl)-7-(2-pyridyl)-3H-[1,2,3]triazolo[4,5-d]pyrimidine-5-amine |
| 193 | 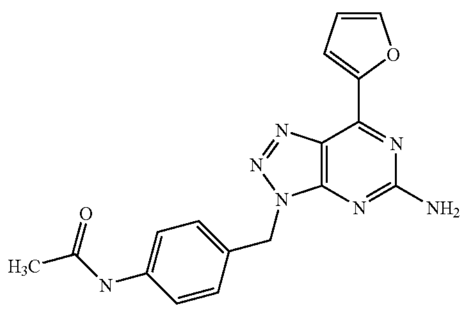 | N-(4-(5-amino-7-(2-furyl)-3H-[1,2,3]triazolo[4,5-d]pyrimidin-3-ylmethyl)phenyl)acetamide |
| 194 | 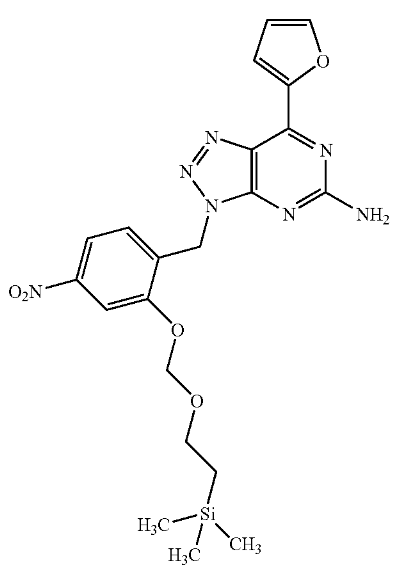 | 7-(2-furyl)-3-(4-nitro-2-(2-trimethylsilylethoxy)methoxybenzyl)-3H-[1,2,3]triazolo[4,5-d]pyrimidine-5-amine |

TABLE 1-continued

| Example | Structure | Compound Name |
| --- | --- | --- |
| 195 | 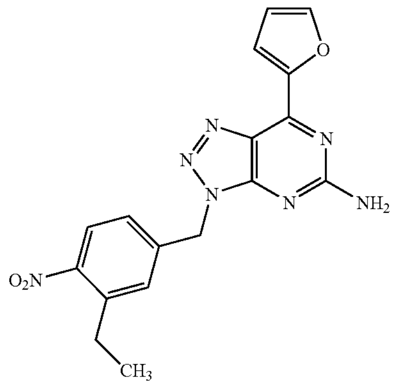 | 3-(3-ethyl-4-nitrobenzyl)-7-(2-furyl)-3H-[1,2,3]triazolo[4,5-d]pyrimidine-5-amine |
| 196 | 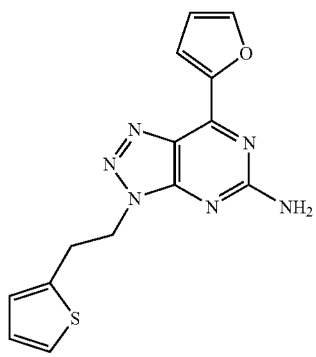 | 7-(2-furyl)-3-(2-(2-thienylethyl))-3H-[1,2,3]triazolo[4,5-d]pyrimidine-5-amine |
| 197 | 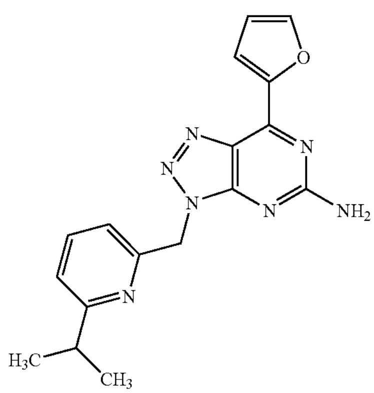 | 7-(2-furyl)-3-(6-isopropyl-2-pyridylmethyl)-3H-[1,2,3]triazolo[4,5-d]pyrimidine-5-amine |
| 198 | 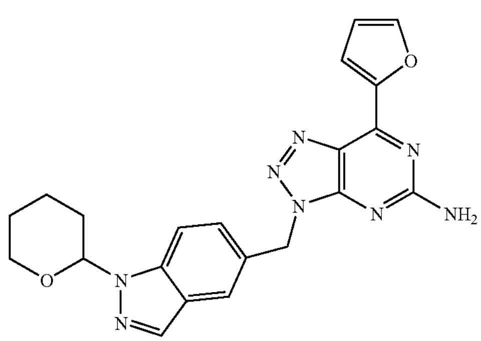 | 7-(2-furyl)-3-(1-(2H-tetrahyropyran-2-yl)indazol-5-ylmethyl)-3H-[1,2,3]triazolo[4,5-d]pyrimidine-5-amine |

TABLE 1-continued

| Example | Structure | Compound Name |
|---|---|---|
| 199 | 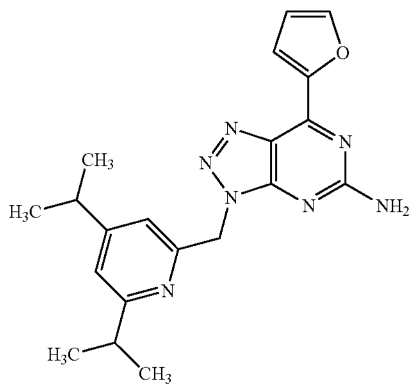 | 3-(4,6-diisopropyl-2-pyridylmethyl)-7-(2-furyl)-3H-[1,2,3]triazolo[4,5-d]pyrimidine-5-amine |
| 200 | 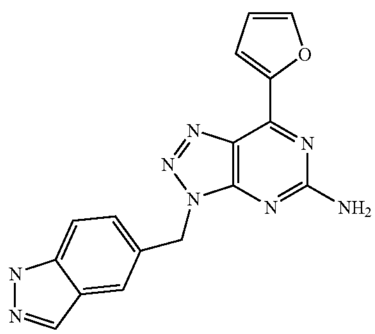 | 7-(2-furyl)-3-(5-indazolylmethyl)-3H-[1,2,3]triazolo[4,5-d]pyrimidine-5-amine |
| 201 | 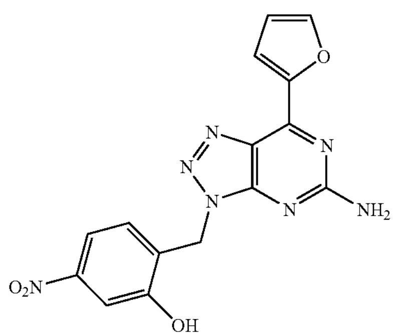 | 7-(2-furyl)-3-(2-hydroxy-4-nitrobenzyl)-3H-[1,2,3]triazolo[4,5-d]pyrimidine-5-amine |
| 202 | 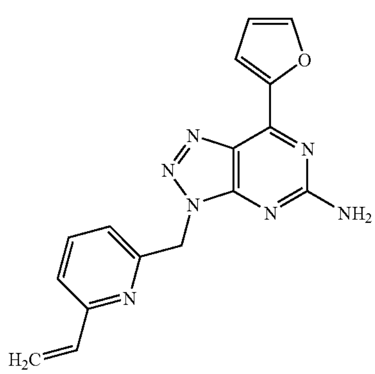 | 7-(2-furyl)-3-(6-vinyl-2-pyridylmethyl)-3H-[1,2,3]triazolo[4,5-d]pyrimidine-5-amine |

TABLE 1-continued

| Example | Structure | Compound Name |
|---|---|---|
| 203 | 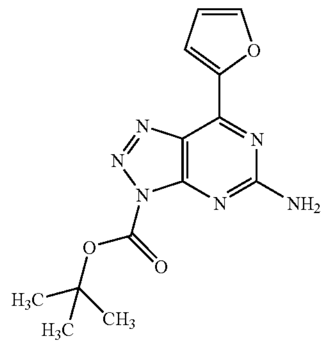 | tert-butyl 5-amino-7-(2-furyl)-3H-[1,2,3]triazolo[4,5-d]pyrimidine-3-carboxylate |
| 204 | 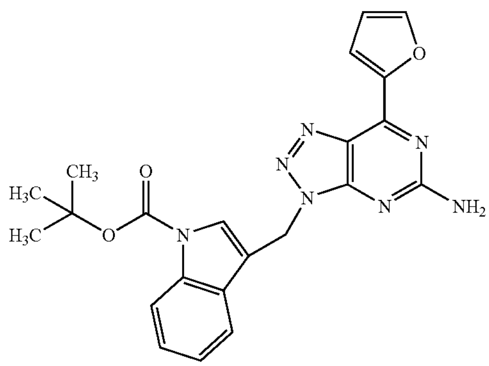 | tert-butyl 3-(5-amino-7-(2-furyl)-3H-[1,2,3]triazolo[4,5-d]pyrimidine-3-ylmethyl)indole-1-carboxylate |
| 205 | 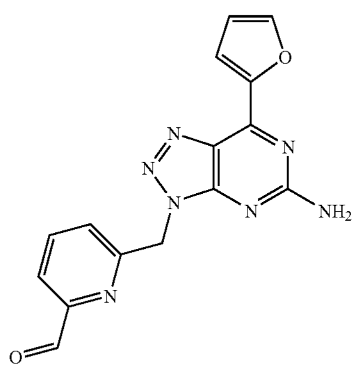 | 6-(5-amino-7-(2-furyl)-3H-[1,2,3]triazolo[4,5-d]pyrimidin-3-ylmethyl)pyridine-2-carboxaldehyde |
| 206 | 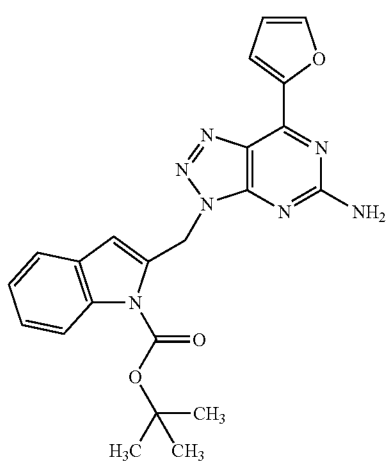 | tert-butyl 2-(5-amino-7-(2-furyl)-3H-[1,2,3]triazolo[4,5-d]pyrimidine-3-ylmethyl)indole-1-carboxylate |

TABLE 1-continued

| Example | Structure | Compound Name |
| --- | --- | --- |
| 207 | 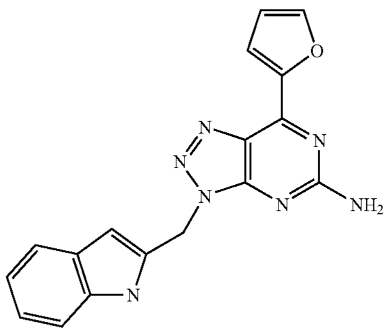 | 3-(2-indolylmethyl)-7-(2-furyl)-3H-[1,2,3]triazolo[4,5-d]pyrimidine-5-amine |
| 208 | 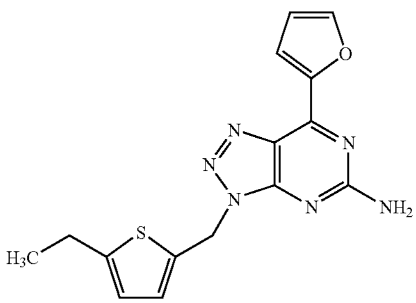 | 3-(5-ethyl-2-thienylmethyl)-7-(2-furyl)-3H-[1,2,3]triazolo[4,5-d]pyrimidine-5-amine |
| 209 | 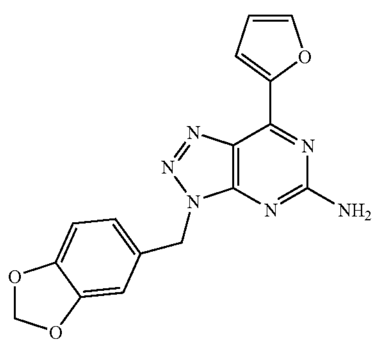 | 7-(2-furyl)-3-(3,4-methylenedioxybenzyl)-3H-[1,2,3]triazolo[4,5-d]pyrimidine-5-amine |
| 210 | 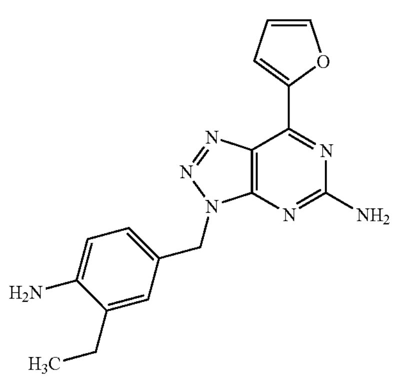 | 3-(4-amino-3-ethylbenzyl)-7-(2-furyl)-3H-[1,2,3]triazolo[4,5-d]pyrimidine-5-amine |

TABLE 1-continued

| Example | Structure | Compound Name |
|---|---|---|
| 211 | 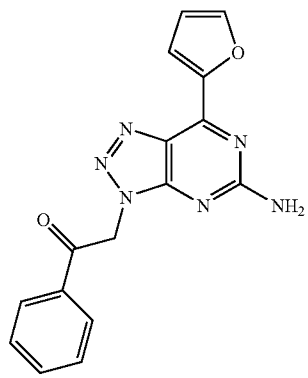 | 2-(5-amino-7-(2-furyl)-3H-[1,2,3]triazolo[4,5-d]pyrimidin-3-yl)-1-phenylethanone |
| 212 | 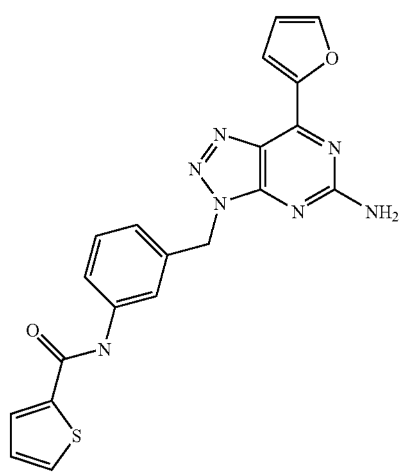 | N-(3-(5-amino-7-(2-furyl)-3H-[1,2,3]triazolo[4,5-d]pyrimidine-3-methyl)phenyl)thiophene-2-carboxamide |
| 213 | 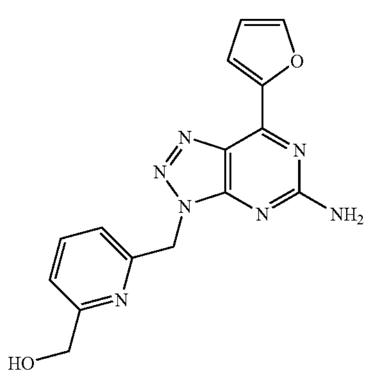 | 7-(2-furyl)-3-(6-hydroxymethyl-2-pyridylmethyl)-3H-[1,2,3]triazolo[4,5-d]pyrimidine-5-amine hydrochloride |

TABLE 1-continued
| Example | Structure | Compound Name |
|---|---|---|
| 214 | 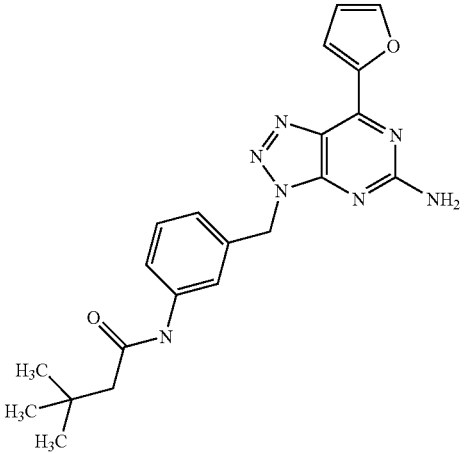 | N-(3-(5-amino-7-(2-furyl)-3H-[1,2,3]triazolo[4,5-d]pyrimidine-3-methyl)phenyl)-3,3-dimethylbutanamide |
| 215 | 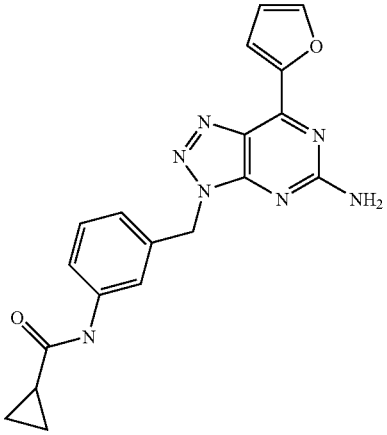 | N-(3-(5-amino-7-(2-furyl)-3H-[1,2,3]triazolo[4,5-d]pyrimidine-3-methyl)phenyl)cyclopropanecarboxamide |
| 216 | 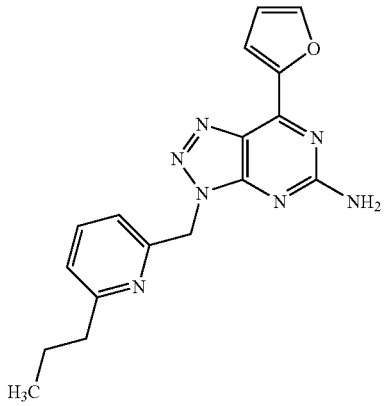 | 7-(2-furyl)-3-(6-n-propyl-2-pyridylmethyl)-3H-[1,2,3]triazolo[4,5-d]pyrimidine-5-amine |

TABLE 1-continued

| Example | Structure | Compound Name |
|---|---|---|
| 217 | 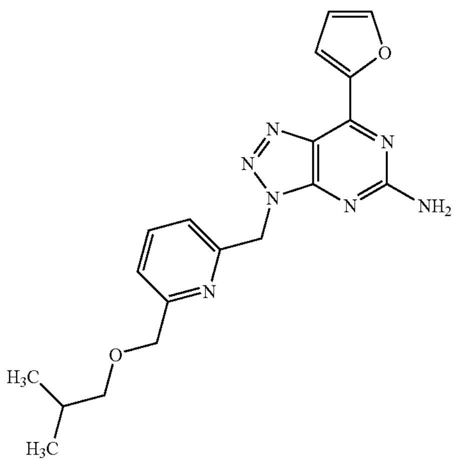 | 7-(2-furyl)-3-(6-isobutyloxymethyl-2-pyridylmethyl)-3H-[1,2,3]triazolo[4,5-d]pyrimidine-5-amine |
| 218 | 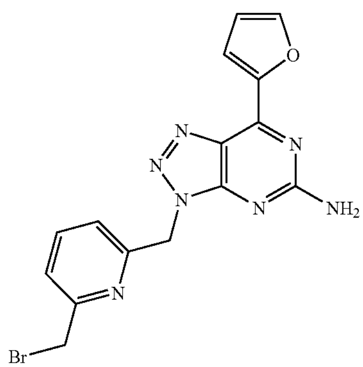 | 3-(6-bromomethyl-2-pyridylmethyl)-7-(2-furyl)-3H-[1,2,3]triazolo[4,5-d]pyrimidine-5-amine |
| 219 | 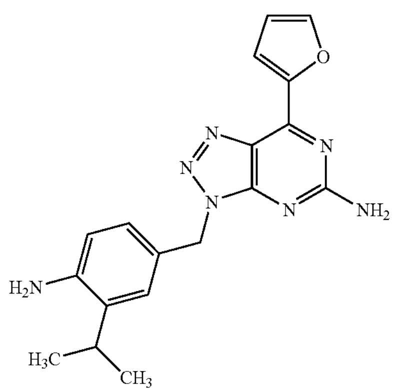 | 3-(4-amino-3-isopropylbenzyl)-7-(2-furyl)-3H-[1,2,3]triazolo[4,5-d]pyrimidine-5-amine |
| 220 | 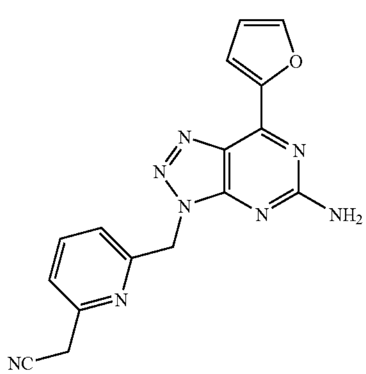 | 3-(6-cyanomethyl-2-pyridylmethyl)-7-(2-furyl)-3H-[1,2,3]triazolo[4,5-d]pyrimidine-5-amine |

TABLE 1-continued

| Example | Structure | Compound Name |
|---|---|---|
| 221 | 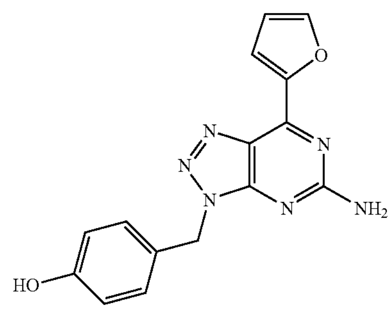 | 3-(4-hydroxybenzyl)-7-(2-furyl)-3H-[1,2,3]triazolo[4,5-d]pyrimidine-5-amine |
| 222 | 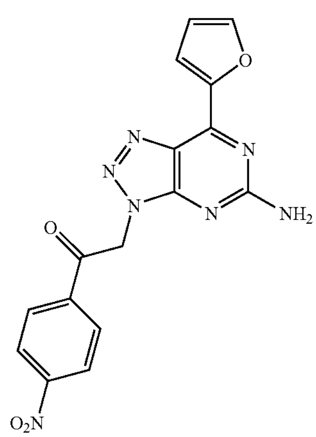 | 2-(5-amino-7-(2-furyl)-3H-[1,2,3]triazolo[4,5-d]pyrimidin-3-yl)-1-(4-nitrophenyl)ethanone |
| 223 | 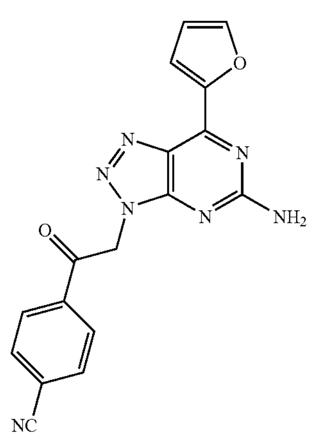 | 4-(5-amino-7-(2-furyl)-3H-[1,2,3]triazolo[4,5-d]pyrimidin-3-ylacetyl)-benzonitrile |

TABLE 1-continued

| Example | Structure | Compound Name |
| --- | --- | --- |
| 224 | 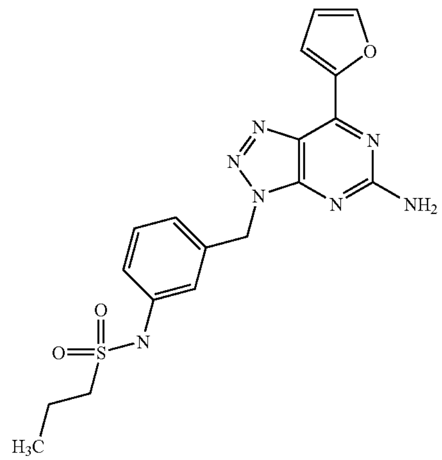 | N-(3-(5-amino-7-(2-furyl)-3H-[1,2,3]triazolo[4,5-d]pyrimidin-3-ylmethyl)phenyl)propanesulphonamide |
| 225 | 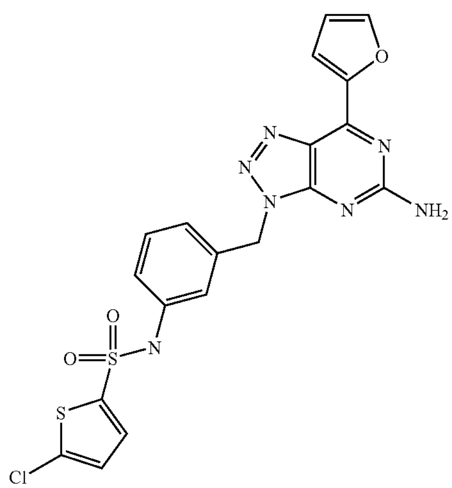 | N-(3-(5-amino-7-(2-furyl)-3H-[1,2,3]triazolo[4,5-d]pyrimidin-3-ylmethyl)phenyl)-5-chloro-2-thiophenesulphonamide |
| 226 | 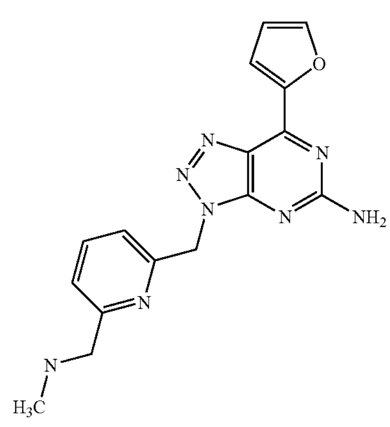 | 7-(2-furyl)-3-(6-(N-methylamino)methyl-2-pyridylmethyl)-3H-[1,2,3]triazolo[4,5-d]pyrimidine-5-amine hydrochloride |

TABLE 1-continued

| Example | Structure | Compound Name |
|---|---|---|
| 227 | 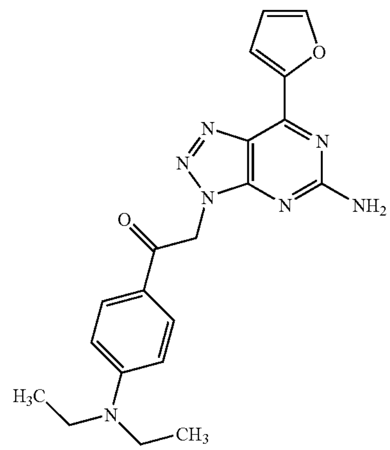 | 2-(5-amino-7-(2-furyl)-3H-[1,2,3]triazolo[4,5-d]pyrimidin-3-yl)-1-(4-(N,N-diethylamino)phenyl)ethanone |
| 228 | 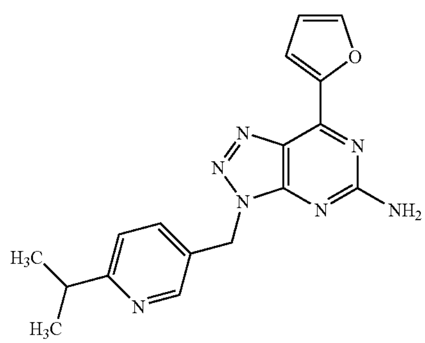 | 7-(2-furyl)-3-(6-isopropyl-3-pyridylmethyl)-3H-[1,2,3]triazolo[4,5-d]pyrimidine-5-amine |
| 229 | 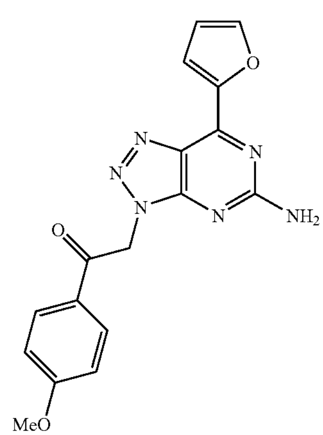 | 2-(5-amino-7-(2-furyl)-3H-[1,2,3]triazolo[4,5-d]pyrimidin-3-yl)-1-(4-methoxyphenyl)ethanone |

TABLE 1-continued

| Example | Structure | Compound Name |
| --- | --- | --- |
| 230 | 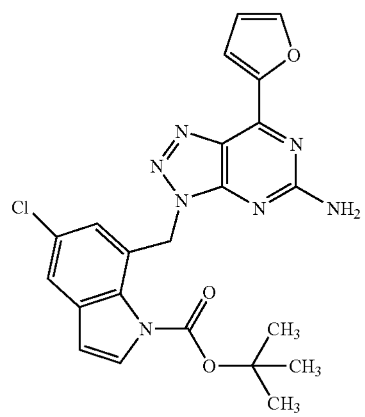 | tert-butyl 7-(5-amino-7-(2-furyl)-3H-[1,2,3]triazolo[4,5-d]pyrimidine-3-ylmethyl)-5-chloroindole-1-carboxylate |
| 231 | 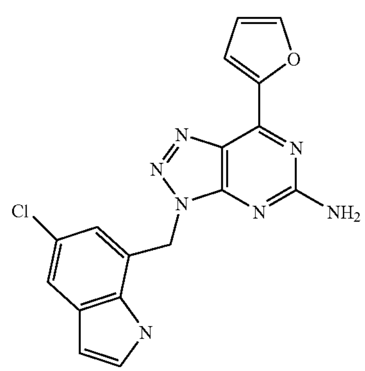 | 3-(5-chloro-7-indolyl)-7-(2-furyl)-3H-[1,2,3]triazolo[4,5-d]pyrimidine-5-amine |
| 232 | 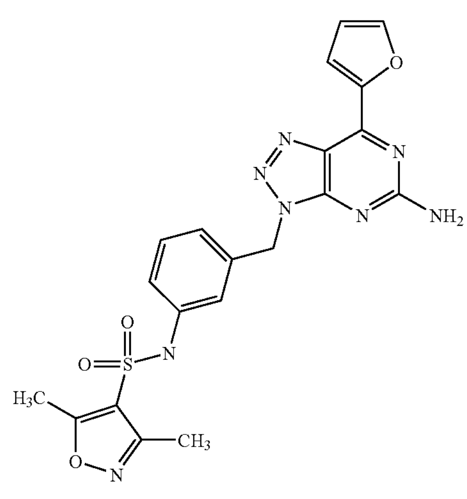 | N-(3-(5-amino-7-(2-furyl)-3H-[1,2,3]triazolo[4,5-d]pyrimidin-3-ylmethyl)phenyl)-3,5-dimethylisoxazol-4-ylsulphonamide |

TABLE 1-continued
| Example | Structure | Compound Name |
|---|---|---|
| 233 | 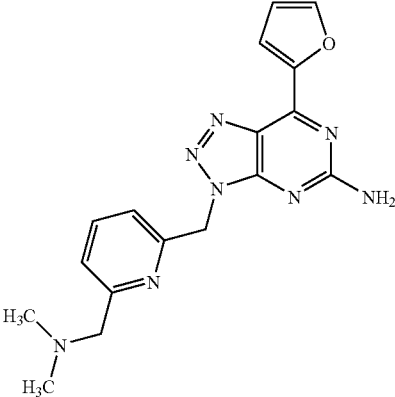 | 3-(6-(N,N-dimethylamino)methyl-2-pyridylmethyl)-7-(2-furyl)-3H-[1,2,3]triazolo[4,5-d]pyrimidine-5-amine |
| 234 | 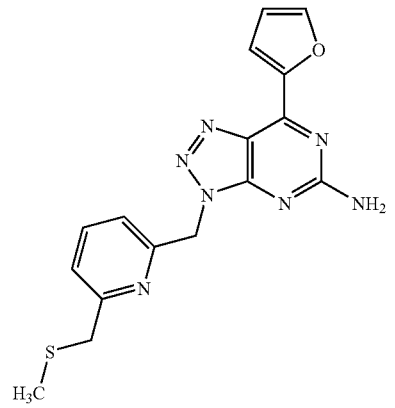 | 7-(2-furyl)-3-(6-methylthiomethyl-2-pyridylmethyl)-3H-[1,2,3]triazolo[4,5-d]pyrimidine-5-amine |
| 235 | 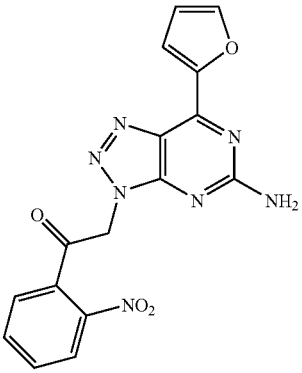 | 2-(5-amino-7-(2-furyl)-3H-[1,2,3]triazolo[4,5-d]pyrimidin-3-yl)-1-(2-nitrophenyl)ethanone |

TABLE 1-continued

| Example | Structure | Compound Name |
|---|---|---|
| 236 | 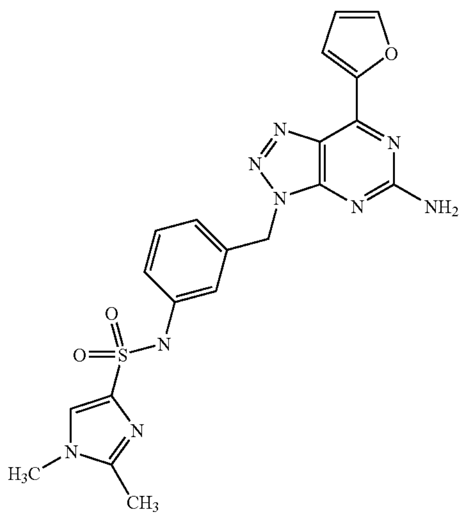 | N-(3-(5-amino-7-(2-furyl)-3H-[1,2,3]triazolo[4,5-d]pyrimidin-3-ylmethyl)phenyl)-1,2-dimethyl-1H-imidazol-4-ylsulphonamide |
| 237 | 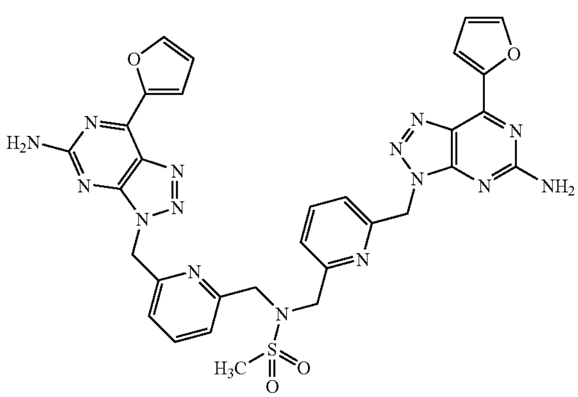 | N,N-bis(6-(5-amino-7-(2-furyl)-3H-[1,2,3]triazolo[4,5-d]pyrimidin-3-ylmethyl)-2-pyridylmethyl)methanesulphonamide |
| 238 | 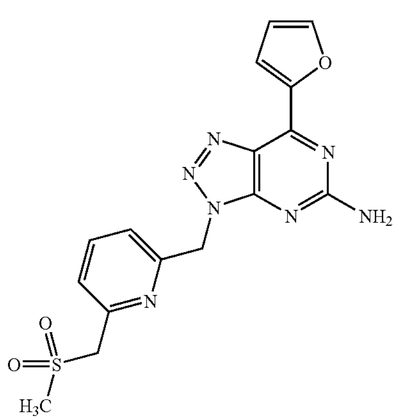 | 7-(2-furyl)-3-(6-methylsulphonylmethyl-2-pyridylmethyl)-3H-[1,2,3]triazolo[4,5-d]pyrimidine-5-amine |

TABLE 1-continued

| Example | Structure | Compound Name |
|---|---|---|
| 239 | 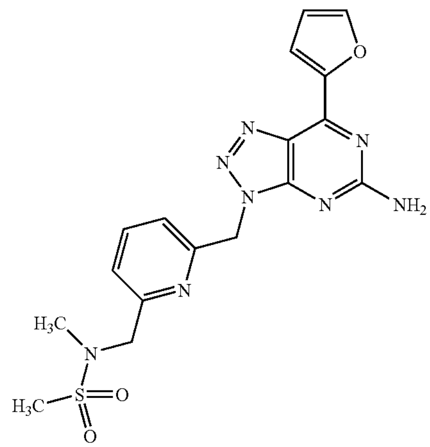 | N-(6-(5-amino-7-(2-furyl)-3H-[1,2,3]triazolo[4,5-d]pyrimidin-3-ylmethyl)-2-pyridylmethyl)-N-methyl methanesulphonamide |
| 240 | 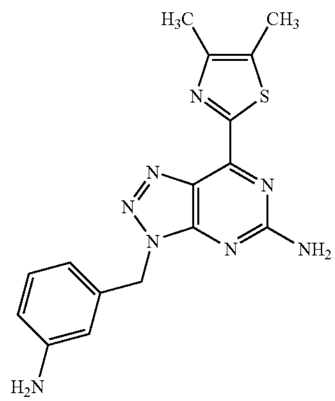 | 3-(3-aminobenzyl)-7-(4,5-dimethyl-2-thiazolyl)-3H-[1,2,3]triazolo[4,5-d]pyrimidine-5-amine |
| 241 | 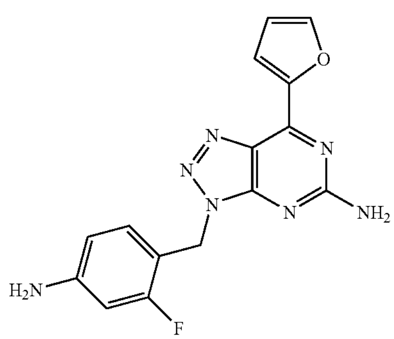 | 3-(4-amino-2-fluorobenzyl)-7-(2-furyl)-3H-[1,2,3]triazolo[4,5-d]pyrimidine-5-amine |
| 242 | 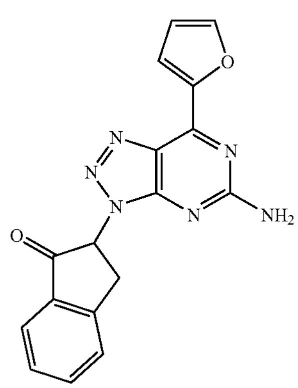 | 2-(5-amino-7-(2-furyl)-3H-[1,2,3]triazolo[4,5-d]pyrimidin-3-yl)-1-indanone |

TABLE 1-continued

| Example | Structure | Compound Name |
| --- | --- | --- |
| 243 | 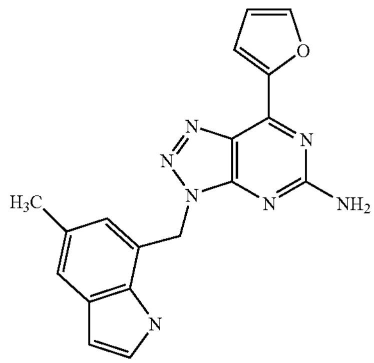 | 7-(2-furyl)-3-(5-methyl-7-indolylmethyl)-3H-[1,2,3]triazolo[4,5-d]pyrimidine-5-amine |
| 244 | 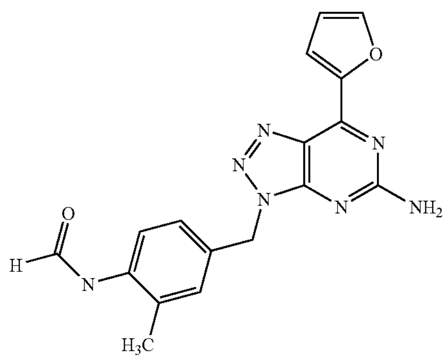 | N-(4-(5-amino-7-(2-furyl)-3H-[1,2,3]triazolo[4,5-d]pyrimidin-3-ylmethyl)-2-methylphenyl)formamide |
| 245 | 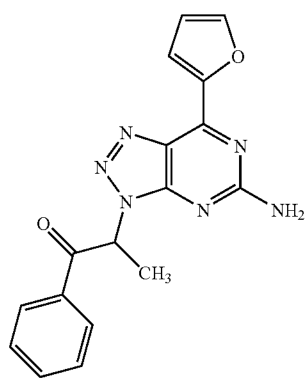 | 2-(5-amino-7-(2-furyl)-3H-[1,2,3]triazolo[4,5-d]pyrimidin-3-yl)-1-phenylpropanone |
| 246 | 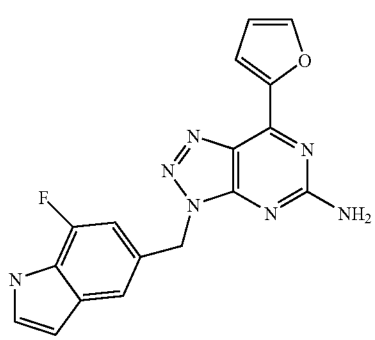 | 3-(7-fluoro-5-indolyl)-7-(2-furyl)-3H-[1,2,3]triazolo[4,5-d]pyrimidine-5-amine |

TABLE 1-continued

| Example | Structure | Compound Name |
|---|---|---|
| 247 | 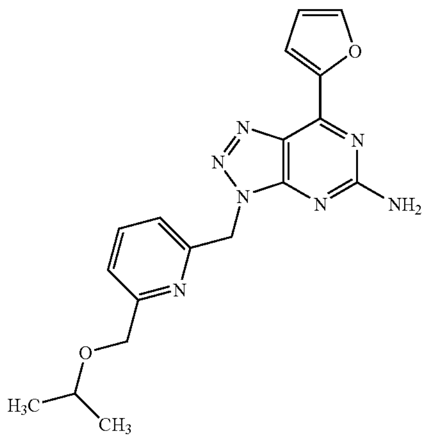 | 7-(2-furyl)-3-(6-isopropoxymethyl-2-pyridylmethyl)-3H-[1,2,3]triazolo[4,5-d]pyrimidine-5-amine |
| 248 | 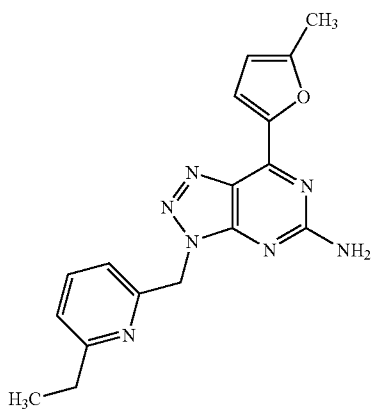 | 3-(6-ethyl-2-pyridylmethyl)-7-(5-methyl-2-furyl)-3H-[1,2,3]triazolo[4,5-d]pyrimidine-5-amine |
| 249 | 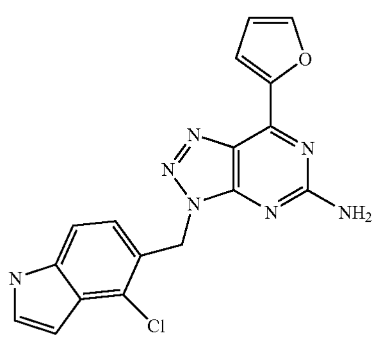 | 3-(4-chloro-5-indolyl)-7-(2-furyl)-3H-[1,2,3]triazolo[4,5-d]pyrimidine-5-amine |
| 250 | 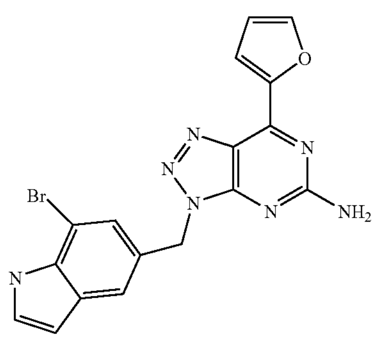 | 3-(7-bromo-5-indolyl)-7-(2-furyl)-3H-[1,2,3]triazolo[4,5-d]pyrimidine-5-amine |

TABLE 1-continued

| Example | Structure | Compound Name |
|---|---|---|
| 251 | 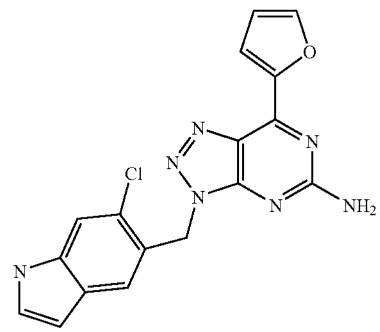 | 3-(6-chloro-5-indolyl)-7-(2-furyl)-3H-[1,2,3]triazolo[4,5-d]pyrimidine-5-amine |
| 252 | 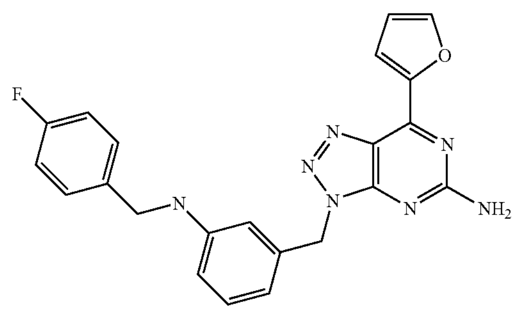 | 3-(3-(4-fluorobenzylamino)benzyl)-7-(2-furyl)-3H-[1,2,3]triazolo[4,5-d]pyrimidine-5-amine |
| 253 | 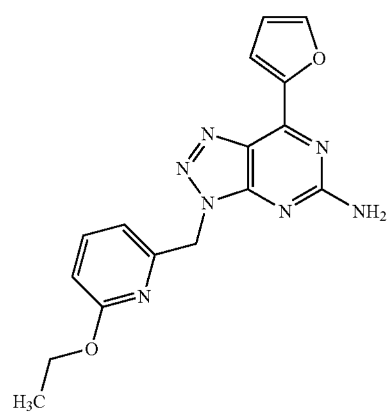 | 3-(6-ethoxy-2-pyridylmethyl)-7-(2-furyl)-3H-[1,2,3]triazolo[4,5-d]pyrimidine-5-amine |
| 254 | 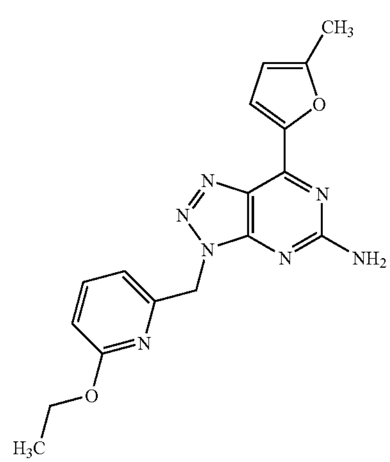 | 3-(6-ethoxy-2-pyridylmethyl)-7-(5-methyl-2-furyl)-3H-[1,2,3]triazolo[4,5-d]pyrimidine-5-amine |

TABLE 1-continued

| Example | Structure | Compound Name |
| --- | --- | --- |
| 255 | 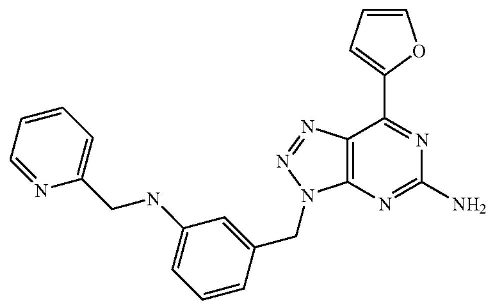 | 3-(3-(2-pyridylmethylamino)benzyl)-7-(2-furyl)-3H-[1,2,3]triazolo[4,5-d]pyrimidine-5-amine |
| 256 | 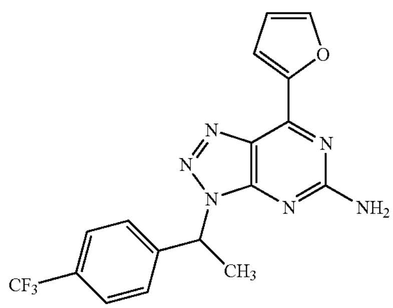 | 7-(2-furyl)-3-(1-(4-trifluoromethylphenyl)ethyl)-3H-[1,2,3]triazolo[4,5-d]pyrimidine-5-amine |
| 257 | 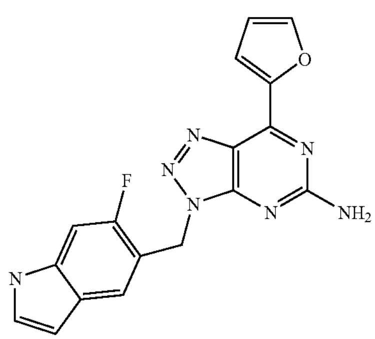 | 3-(6-fluoro-5-indolyl)-7-(2-furyl)-3H-[1,2,3]triazolo[4,5-d]pyrimidine-5-amine |
| 258 | 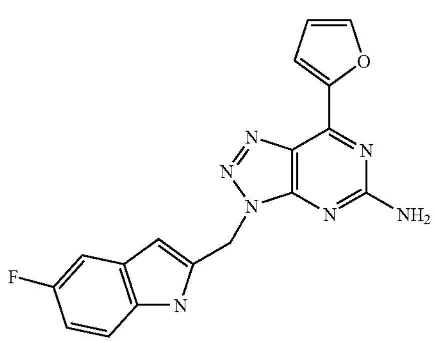 | 3-(5-fluoro-2-indolyl)-7-(2-furyl)-3H-[1,2,3]triazolo[4,5-d]pyrimidine-5-amine |

TABLE 1-continued

| Example | Structure | Compound Name |
| --- | --- | --- |
| 259 | 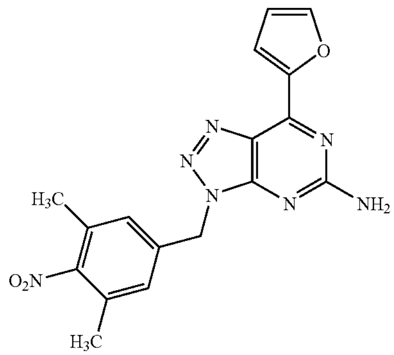 | 3-(3,5-dimethyl-4-nitrobenzyl)-7-(2-furyl)-3H-[1,2,3]triazolo[4,5-d]pyrimidine-5-amine |
| 260 | 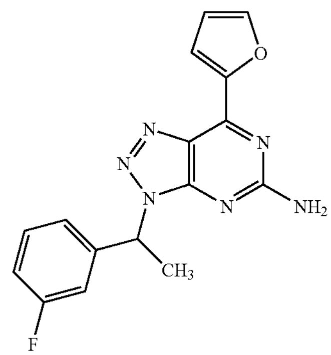 | 3-(1-(3-fluorophenyl)ethyl)-7-(2-furyl)-3H-[1,2,3]triazolo[4,5-d]pyrimidine-5-amine |
| 261 | 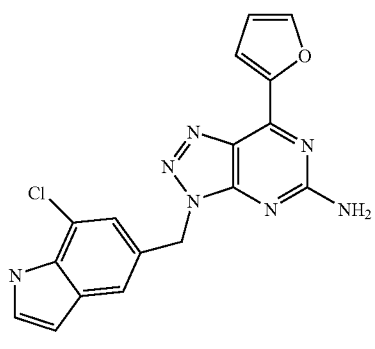 | 3-(7-chloro-5-indolyl)-7-(2-furyl)-3H-[1,2,3]triazolo[4,5-d]pyrimidine-5-amine |
| 262 | 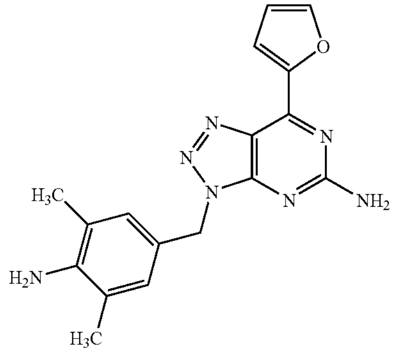 | 3-(4-amino-3,5-dimethylbenzyl)-7-(2-furyl)-3H-[1,2,3]triazolo[4,5-d]pyrimidine-5-amine |

TABLE 1-continued

| Example | Structure | Compound Name |
| --- | --- | --- |
| 263 | 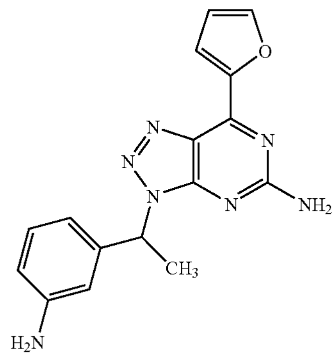 | 3-(1-(3-aminophenyl)ethyl)-7-(2-furyl)-3H-[1,2,3]triazolo[4,5-d]pyrimidine-5-amine |
| 264 | 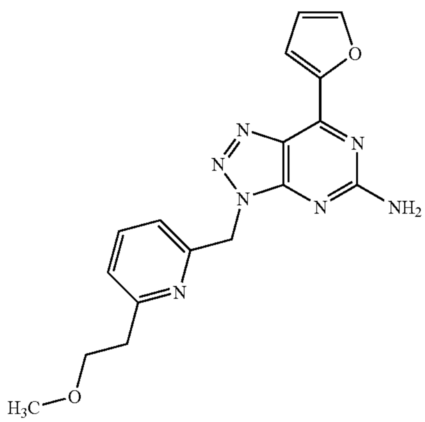 | 7-(2-furyl)-3-(6-(2-methoxyethyl)-2-pyridylmethyl)-3H-[1,2,3]triazolo[4,5-d]pyrimidine-5-amine |
| 265 | 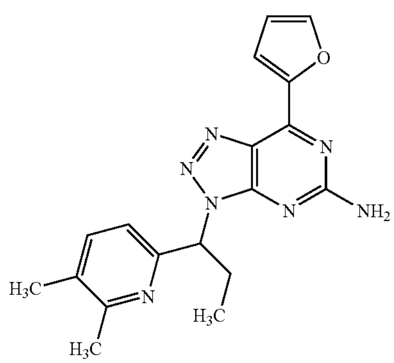 | 7-(2-furyl)-3-(1-(5,6-dimethyl-2-pyridyl)propyl)-3H-[1,2,3]triazolo[4,5-d]pyrimidine-5-amine |
| 266 | 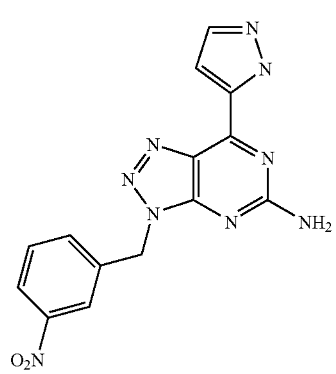 | 3-(3-nitrobenzyl)-7-(1H-pyrazol-3-yl)-3H-[1,2,3]triazolo[4,5-d]pyrimidine-5-amine hydrochloride |

TABLE 1-continued

| Example | Structure | Compound Name |
| --- | --- | --- |
| 267 | 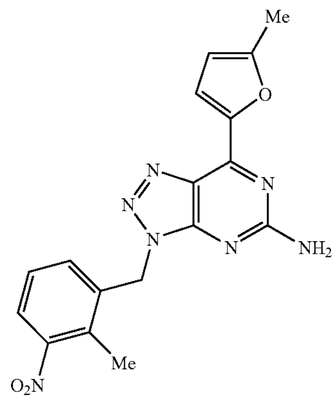 | 7-(5-methyl-2-furyl)-3-(2-methyl-3-nitrobenzyl)-3H-[1,2,3]triazolo[4,5-d]pyrimidine-5-amine |
| 268 | 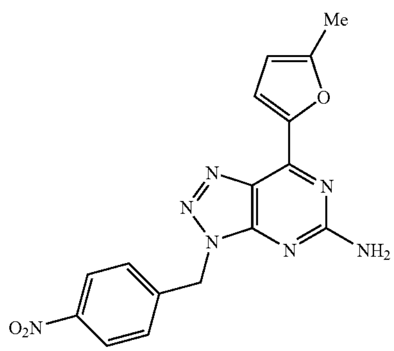 | 7-(5-methyl-2-furyl)-3-(4-nitrobenzyl)-3H-[1,2,3]triazolo[4,5-d]pyrimidine-5-amine |
| 269 | 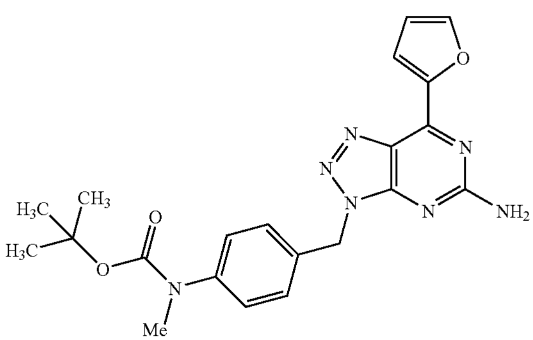 | tert-butyl N-(4-(5-amino-7-(2-furyl)-3H-[1,2,3]triazolo[4,5-d]pyrimidine-3-ylmethyl)phenyl)-N-methylcarbamate |
| 270 | 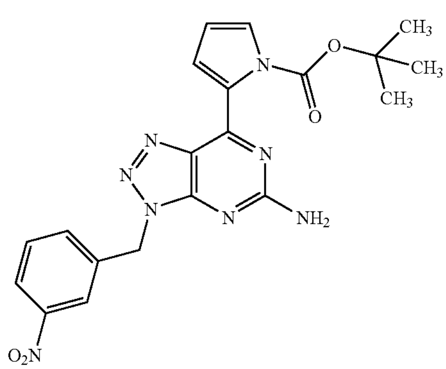 | tert-butyl 2-(5-amino-3-(3-nitrobenzyl)-3H-[1,2,3]triazolo[4,5-d]pyrimidin-7-yl)pyrrole-1-carboxylate |

TABLE 1-continued

| Example | Structure | Compound Name |
|---|---|---|
| 271 | 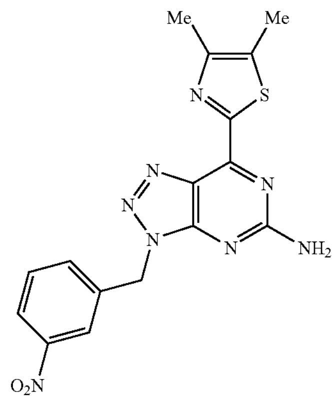 | 7-(4,5-dimethylthiazol-2-yl)-3-(3-nitrobenzyl)-3H-[1,2,3]triazolo[4,5-d]pyrimidine-5-amine |
| 272 | 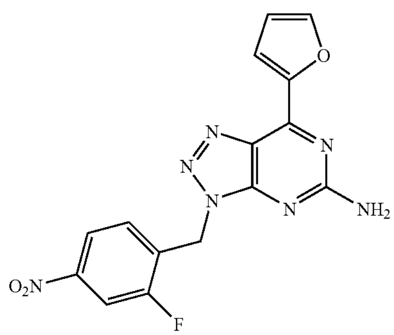 | 3-(2-fluoro-4-nitrobenzyl)-7-(2-furyl)-3H-[1,2,3]triazolo[4,5-d]pyrimidine-5-amine |
| 273 | 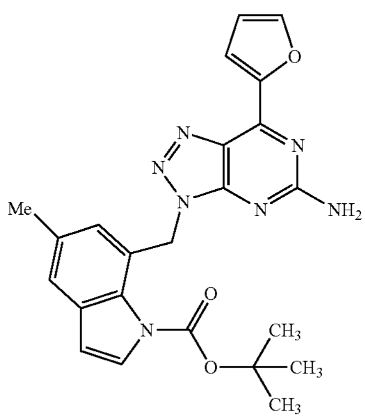 | tert-butyl 7-(5-amino-7-(2-furyl)-3H-[1,2,3]triazolo[4,5-d]pyrimidine-3-ylmethyl)-5-methylindole-1-carboxylate |
| 274 | 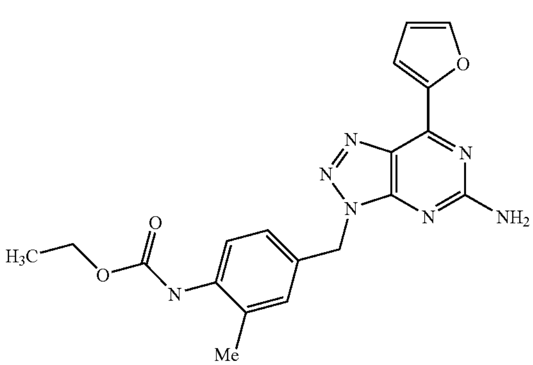 | ethyl N-(4-(5-amino-7-(2-furyl)-3H-[1,2,3]triazolo[4,5-d]pyrimidin-3-yl)methyl)-2-methylphenyl)carbamate |

The general synthetic methods used for the preparation of these Examples are set out below as Methods A to BH. Table 2 sets out the Method used for each Example, together with analytical data.

HPLC is carried out using the following conditions: Column. Waters Xterra RP 18 (50×4.6 mm); Particle size 5 μM; Mobile phase MeOH: 10 mM aq NH$_4$OAc (pH 7 buffer); Gradient 50:50 isocratic for 1 min. then linear gradient 50:50 to 80:20 over 5 min. then 80:20 isocratic for 3 min.; Flow rate 2.0 mL/min.; Detection wavelength λ=230 nM. Retention times are provided.

Method A 7-(2-Furyl)-1H-[1,2,3]triazolo[4,5-d]pyrimidine-5-amine (Example 1)

A solution of 7-chloro-1H-[1,2,3]triazolo[4,5-d]pyrimidine-5-amine (570 mg, 3.34 mmol) in N-methyl-2-pyrrolidinone (4 mL) was treated with PdCl$_2$(PPh$_3$)$_2$ (117 mg, 0.17 mmol) and 2-(tributylstannyl)furan (1.05 mL, 1 mmol), stirred at 80° C. for 5 h, diluted with EtOAc, filtered through a silica pad and concentrated in vacuo. The residue was triturated with diethyl ether and the title compound isolated as a yellow solid (438 mg, 65%).

Method B 3-(2-Fluorobenzyl)-7-(2-furyl)-3H-[1,2,3]triazolo[4,5-d]pyrimidine-5-amine (Example 3)

A solution of 7-(2-furyl)-1H-[1,2,3]triazolo[4,5-d]pyrimidine-5-amine (101 mg, 0.5 mmol) in DMF (2 mL), at 0° C., was treated with NaH (20 mg, 60%, 0.5 mmol), stirred for 20 mins then treated with 2-fluorobenzyl bromide (60 μL, 0.5 mmol). The reaction mixture was allowed to warm to room temperature, stirred for 1 h, quenched with water, extracted with EtOAc, dried (MgSO$_4$) and concentrated in vacuo. The crude product was purified by chromatography (EtOAc:Heptane, 1:4-EtOAc:Heptane, 2:1) to give N,N-bis(2-fluorobenzyl)-3-(2-fluorobenzyl)-7-(2-furyl)-3H-[1,2,3]triazolo[4,5-d]pyrimidine-5-amine (Example 2) (28 mg, 11%) as a yellow solid and the title compound (34 mg, 22%) as a yellow solid.

Method C 3-(3-Aminobenzyl)-7-(2-furyl)-3H-[1,2,3]triazolo[4,5-d]pyrimidine-5-amine (Example 5)

A solution of 7-(2-furyl)-3-(3-nitrobenzyl)-3H-[1,2,3]triazolo[4,5-d]pyrimidine-5-amine (152 mg, 0.45 mmol) in EtOH (2 mL) at 50° C. was treated with a solution of SnCl$_2$ (305 mg, 1.35 mmol) in conc. HCl (0.7 mL), stirred for 2 h, cooled, diluted with water, basified to pH 10 (5-M, NaOH) and filtered to give the title compound (127 mg, 92%) as a white solid.

Method D

N-(3-(5-Amino-7-(2-furyl)-3H-[1,2,3]triazolo[4,5-d]pyrimidin-3-yl)methyl)phenyl-(1-methyl-1H-imidazol-4-yl)sulphonamide (Example 9)

A solution of 3-(3-aminobenzyl)-7-(2 furyl)-3H-[1,2,3]triazolo[4,5-d]pyrimidine-5-amine (125 mg, 0.41 mmol) in DMF (2 mL) was treated with Et$_3$N (85 μL, 0.61 mmol) and 1-methylimidazole-4-sulphonyl chloride (74 mg, 0.41 mmol), stirred at room temperature overnight, poured into water, extracted with EtOAc, dried (MgSO$_4$) and concentrated in vacuo. The crude product was purified by chromatography [SiO$_2$; EtOAc:MeOH (1:10)] to give the title compound (26 mg, 14%) as a cream solid.

Method E

5-Amino-N-benzyl-7-(2-furyl)-3H-[1,2,3]triazolo[4,5-d]pyrimidin-3-ylcarboxamide (Example 10)

A solution of 7-(2-furyl)-1H-[1,2,3]triazolo[4,5-d]pyrimidine-5-amine (202 mg, 1.0 mmol) in DMF (3 mL) was treated with benzyl isocyanate (123 mL, 1.0 mmol) and a catalytic amount of DMAP, stirred at room temperature overnight, diluted with EtOAc and filtered to give the title compound (62 mg, 19%) as a peach coloured solid.

Method F

Ethyl 5-amino-7-(2-furyl)-3H-[1,2,3]triazolo[4,5-d]pyrimidin-3-ylacetate (Example 14)

A solution of 7-(2-furyl)-1H-[1,2,3]triazolo[4,5-d]pyrimidine-5-amine (101 mg, 0.5 mmol) in DMF (4 mL) was treated with 4-(N,N-dimethylamino)pyridine (5 mg, 0.04 mmol) and ethyl bromoacetate (55 mL, 0.5 mmol), stirred at room temperature for 16 h and purified directly by chromatography [SiO$_2$; EtOAc:Heptane (1:2)] to give the title compound (50 mg, 35%) as a white solid.

Method G 7-(2-Furyl)-3-(3-hydroxybenzyl)-3H-[1,2,3]triazolo[4,5-d]pyrimidine-5-amine (Example 18)

A solution of 7-(2-furyl)-3-(3-methoxybenzyl)-3H-[1,2,3]triazolo[4,5-d]pyrimidine-5-amine (119 mg, 0.37 mmol) in dichloromethane (20 mL) at 0° C. was treated with boron tribromide (1-M in dichloromethane, 8.8 mL, 8.8 mmol) portion-wise over 3 days, concentrated in vacuo and isolated by filtration to give the title compound (114 mg, 100%) as a yellow solid.

Method H 6-(5-Methyl-2-furyl)-5-nitropyrimidine-2,4-diamine

A solution of 6-chloro-5-nitropyrimidine-2,4-diamine (10 g, 60% pure, 32 mmol) in THF (300 mL) was treated with saturated aq NaHCO$_3$ (75 mL), 5-methylfuran-2-boronic acid (7.33 g, 0.058 mol) and Pd(PPh$_3$)$_4$ (1 g, 0.865 mmol) and refluxed with vigorous stirring under argon overnight. The mixture was cooled to room temperature, diluted with EtOAc (400 mL) and water (300 mL), filtered to remove insoluble material and the filtrate was extracted with EtOAc (2×100 mL). The combined organic phase was dried (MgSO$_4$), concentrated in vacuo and the resulting solid triturated with dichloromethane and filtered to give the title compound (6 g, 72%) as a yellow solid; mp 196.3-196.9° C.; IR ν$_{max}$ (Nujol)/cm$^{-1}$ 3442, 3169, 2930, 1629, 1463, 1377, 1027, and 790; NMR δ$_H$ (400 MHz, DMSO) 7.40 (2H, br s), 7.09 (2H, br s), 6.87 (1H, dd, J 0.5, 3.2 Hz), 6.26 (2H, dd, J 1.0, 3.3 Hz) and 2.28 (3H, s).

Method I

6-(5-Methyl-2-furyl)pyrimidine-2,4,5-triamine

A suspension of 6-(5-methyl-2-furyl)-5-nitropyrimidine-2,4-diamine (6.6 g, 29.6 mmol) and 10% Pd/C (0.66 g) in MeOH (100 mL) was heated at 40° C. under an atmosphere of $H_2$ for 3 h, cooled to room temperature, filtered through Celite, and concentrated in vacuo to give the title compound (5.8 g, 99%) as an off-whited solid; IR $v_{max}$ (DR)/cm$^{-1}$ 3333, 2237, 1634, 1458, 1237, 1025, 963 and 828; NMR $\delta_H$ (400 MHz, DMSO) 6.77 (1H, dd, J 0.5, 3.2 Hz), 6.21-6.17 (3H, m), 5.14 (2H, s), 4.21 (2H, s), and 2.35 (3H, s).

Method J

7-(5-Methyl-2-furyl)-1H-[1,2,3]triazolo[4,5-d]pyrimidine-5-amine (Example 19)

A solution of 6-(5-methyl-2-furyl)pyrimidine-2,4,5-triamine (5.8 g, 30.1 mmol) in dioxane (116 mL) was treated with isoamyl nitrite (4.1 mL, 30.5 mmol), heated at 80° C. for 3.5 h, cooled to room temperature and the resulting precipitate was filtered, washed with dioxane (10 mL) and heptane (2×15 mL) then triturated with heptane and filtered to give the title compound (4.7 g, 77%) as a sandy solid.

Method K

7-(1H-Pyrazol-3-yl)-1H-[1,2,3]triazolo[4,5-d]pyrimidine-5-amine (Example 21)

A solution of 7-(1-(2-(trimethylsilyl)ethoxymethyl)-1H-pyrazol-3-yl)-1H-[1,2,3]triazolo[4,5-d]pyrimidine-5-amine (120 mg, 0.361 mmol) in MeOH (2 mL) was treated with HCl (4-M in dioxan, 1 mL), stirred for 2 h, filtered and the resulting solid washed with $Et_2O$ to give the title compound (76 mg, 100%) as a yellow solid.

Method L

(2-Amino-6-(2-furyl)-5-nitropyrimidin-4-yl)4-methylbenzenesulphonate

A suspension of 2-amino-6-(2-furyl)-5-nitropyrimidine-4 (1H)-one (1.00 g, 4.50 mmol) in dichloromethane (50 mL) was treated with triethylamine (0.941 mL, 6.75 mmol) and p-toluenesulfonyl chloride (944 mg, 4.95 mmol), stirred for 1 h, diluted with dichloromethane (50 mL), washed with 2-M HCl (20 mL), dried (MgSO$_4$), concentrated in vacuo and purified by chromatography [SiO$_2$; isohexane:EtOAc (2:1)] to give the title compound (410 mg, 24%) as a yellow solid; NMR $\delta_H$ (400 MHz, CDCl$_3$) 7.95 (2H, d, J 8.5 Hz), 7.59-7.57 (1H, m), 7.39 (2H, d, J 8.5 Hz), 7.23-7.21 (1H, m), 6.59-6.51 (1H, m), 5.39 (2H, br s), 2.48 (3H, s); Retention time 5.68 min.

Method M

6-(2-Furyl)-5-nitro-N$^4$-(2-pyridylmethyl)pyrimidine-2,4-diamine

A solution of (2-amino-6-(2-furyl)-5-nitropyrimidin-4-yl) 4-methylbenzenesulphonate (478 mg, 1.27 mmol) in dimethoxyethane (15 mL) was treated with triethylamine (0.531 mL, 3.81 mmol) and 2-pyridinemethylamine (0.393 mL, 3.81 mmol), stirred for 16 h, poured into water (100 mL) and the resulting solid was filtered to give the title compound (275 mg, 69%) as a yellow solid; NMR $\delta_H$ (400 MHz, CDCl$_3$) 8.70-8.58 (2H, m), 7.70-7.66 (1H, m), 7.55-7.54 (1H, m), 7.28 (1H, d, J 8.0 Hz), 7.24-7.20 (1H, m), 7.07-7.06 (1H, m), 6.54-6.52 (1H, m), 5.26 (2H, br s) and 4.83 (2H, d, J 5.0 Hz); Retention time 1.44 min.

Method N

7-(2-Furyl)-3-(2-pyridylmethyl)-3H-[1,2,3]triazolo [4,5-d]pyrimidine-5-amine (Example 24)

A solution of 6-(2-furyl)-5-nitro-N$^4$-(2-pyridylmethyl)pyrimidine-2,4-diamine (270 mg, 0.864 mmol) and 10% Pd/C (92 mg, 0.086 mmol) in EtOH (30 mL) and EtOAc (10 mL) was stirred under an hydrogen atmosphere for 1 h, filtered through Celite and concentrated in vacuo. The resulting yellow oil was dissolved in dioxane (25 mL), treated with isoamyl nitrite (0.109 mL, 0.815 mmol), stirred at 100° C. for 6 h, cooled to room temperature, filtered through Celite, concentrated in vacuo and triturated with Et$_2$O to give the title compound (110 mg, 46%) as a yellow solid.

Method O

(5-Amino-7-(2-furyl)-3H-[1,2,3]triazolo[4,5-d]pyrimidin-3-yl)acetic acid (Example 26)

A solution of ethyl 5-amino-7-(2-furyl)-3H-[1,2,3]triazolo [4,5-d]pyrimidin-3-ylacetate (547 mg, 1.89 mmol) in MeOH (5 mL) was treated with aqueous NaOH (2 mL, 2-M, 4 mmol), refluxed for 10 min, cooled, acidified with aqueous HCl (1-M), filtered and dried to give the title compound (417 mg, 85%) as a white solid.

Method P

(5-Amino-7-(2-furyl)-3H-[1,2,3]triazolo[4,5-d]pyrimidin-3-yl)-N-(3-chlorophenyl)acetamide (Example 31)

A suspension of (5-amino-7-(2-furyl)-3H-[1,2,3]triazolo [4,5-d]pyrimidin-3-yl)acetic acid (140 mg, 0.5 mmol) in DMF (1 mL) was treated with carbonyl diimidazole (81 mg, 0.5 mmol), stirred at room temperature for 1 h, treated with 3-chloroaniline (53 μL, 0.5 mmol) and the mixture heated to 50° C. for 16 h. The reaction mixture was cooled, diluted with water (3 mL) and filtered to give the title compound (94 mg, 48%) as a cream solid.

Method Q

3-(2-Fluorobenzyl)-7-(2-thiazolyl)-3H-[1,2,3]triazolo[4,5-d]pyrimidine-5-amine (Example 34)

A stirred solution of thiazole (0.10 mL, 1.43 mmol) in dry THF (5 mL) at −78° C., under argon was treated with n-BuLi (0.9 mL, 1.6-M in hexanes, 1.43 mmol), stirred for 30 min, treated with a solution of ZnCl$_2$ (1.8 mL, 1-M in Et$_{20}$, 1.80 mmol) and allowed to warm gradually to room temperature. The mixture was treated with 7-chloro-3-(2-fluorobenzyl)-3H-[1,2,3]triazolo[4,5-d]pyrimidine-5-amine (200 mg, 0.714 mmol) and Pd(PPh$_3$)$_4$ (50 mg), refluxed for 2 h and partitioned between saturated NH$_4$Cl (20 mL) and EtOAc (20 mL). The organic phase was dried (MgSO$_4$), concentrated in vacuo and purified by chromatography [SiO$_2$; iso-hexane: EtOAc (1:1)] to give the title compound (70 mg, 30%) as a cream solid.

Method R

N-(2-Amino-6-(2-furyl)-5-nitropyrimidine-4-yl)-6-chloropyridine-3-carboxamide A solution of 6-(2-furyl)-5-nitropyrimidine-2,4-diamine (500 mg, 2.26 mmol) in pyridine (10 mL) was treated with 6-chloronicotinoyl chloride (438 mg, 2.49 mmol), stirred for 16 h at 80° C., cooled to room temperature, poured into water (100 mL) and extracted with EtOAc (2×25 mL) and the combined organic phase was dried ($MgSO_4$), concentrated in vacuo and purified by chromatography [$SiO_2$; isohexane:EtOAc (3:2)] to give the title compound (430 mg, 82%) as a yellow solid; NMR $\delta_H$ (400 MHz, DMSO) 11.14 (1H, s), 8.86 (1H, d, J 2.5 Hz), 8.27 (1H, dd, J 8.5, 2.5 Hz), 7.93 (1H, m), 7.77 (2H, br s), 7.65 (1H, d, J 7.5 Hz), 7.09 (1H, d, J 4.5 Hz), 6.72-6.70 (1H, m); Retention time 2.41 min.

Method T

6-Chloro-N-(7-(2-furyl)-1H-[1,2,3]triazolo[4,5-d]pyrimidin-5-yl)pyridine-3-carboxamide (Example 44)

A solution of N-(2-amino-6-(2-furyl)-5-nitropyrimidine-4-yl)-6-chloropyridine-3-carboxamide (153 mg, 0.423 mmol) and 10% Pd/C (82 mg, 42.3 µmol) in EtOH (20 mL) and EtOAc (5 mL) was stirred under an hydrogen atmosphere for 3 h, filtered through Celite and concentrated in vacuo to give N-(2,5-diamino-6-(2-furyl)pyrimidin-4-yl)-6-chloropyridine-3-carboxamide as a yellow oil. A solution of this product in EtOH (5 mL) and 2-M HCl (5 mL) at 0° C. was treated dropwise with an ice-cold solution of sodium nitrite (87 mg, 1.27 mmol) in water (2 mL). The mixture was stirred at 0° C. for 1 h, stirred at room temperature for 1 h, neutralised with 5-M NaOH, stirred for 16 h and the resulting solid was filtered to give title compound (40 mg, 28%) as a brown solid.

Method U

6-Chloro-$N^4$-(3-nitrobenzyl)pyrimidine-2,4,5-triamine

A mixture of 4,6-dichloropyrimidine-2,5-diamine (700 mg, 3.91 mmol), 3-nitrobenzylamine hydrochloride (885 mg, 4.69 mmol) and triethylamine (1.6 mL, 11.7 mmol) in n-BuOH (20 mL) was refluxed for 17 h, concentrated in vacuo and the residue partitioned between EtOAc (10 mL) and $H_2O$ (5 mL). The organic phase was dried ($MgSO_4$) and concentrated in vacuo to give the title compound as an orange solid (906 mg, 76%) which was used in the next reaction without further purification; NMR $\delta_H$ (400 MHz, $CDCl_3$) 8.16 (1H, s), 8.10 (1H, d, J 8.0 Hz), 7.80 (1H, d, J 7.5 Hz), 7.62 (1H, t, J 7.5 Hz), 7.25 (1H, t, J 6.0 Hz), 5.69 (2H, s), 4.67 (2H, d, J 6.0 Hz) and 3.93 (2H, br s);

Method V

3-Chloromethyl-N,N-dimethylbenzamide

A solution of 3-(chloromethyl)benzoyl chloride (426 µL, 3 mmol) and $Et_3N$ (626 µL, 4.5 mmol) in THF (5 mL) was treated with dimethylamine (1.5 mL, 2-M in THF, 3 mmol), stirred at room temperature for 1 h, poured into water, extracted with EtOAc, dried ($MgSO_4$) and concentrated in vacuo to give the title compound (580 mg, 98%) as a colourless oil; NMR $\delta_H$ (400 MHz, $CDCl_3$) 7.46-7.34 (4H, m), 4.59 (2H, s), 3.11 (3H, s) and 2.98 (3H, s); Anal. Calcd for $C_{12}H_{12}N_6O_2.0.2H_2O$: C, 49.38; H, 4.28, N, 28.79. Found: C, 49.25; H, 4.09; N, 28.47.

Method W

7-(2-Furyl)-3-(2-methoxy-5-nitrobenzyl)-3H-[1,2,3]triazolo[4,5-d]pyrimidine-5-amine (Example 66)

A solution of 7-(2-furyl)-1H-[1,2,3]triazolo[4,5-d]pyrimidine-5-amine (606 mg, 3 mmol) in DMF (5 mL) at 0° C., was treated with $CsCO_3$ (977 mg, 3 mmol), stirred for 1 h, treated with 2-methoxy-5-nitrobenzyl bromide (738 mg, 3 mmol) and stirred at room temperature for 1 h. The reaction mixture was diluted with water (10 mL), filtered and the resulting solid purified by chromatography [$SiO_2$; EtOAc:Heptane (2:1)] to give the title compound (279 mg, 25%) as a yellow solid.

Method X

3-(2-Fluorobenzyl)-7-(5-oxazolyl)-3H-[1,2,3]triazolo[4,5-d]pyrimidine-5-amine (Example 69)

A stirred solution of oxazole (138 mg, 2.0 mmol) in dry THF (10 mL) at −78° C., under argon was treated with n-BuLi (1.25 mL, 1.6-M in hexanes, 2.0 mmol), stirred for 30 min, treated with a solution of $ZnCl_2$ (2.0 mL, 1-M in $Et_2O$, 2.0 mmol)) and allowed to warm gradually to room temperature. The mixture was treated with 7-chloro-3-(2-fluorobenzyl)-3H-[1,2,3]triazolo[4,5-d]pyrimidine-5-amine (280 mg, 1.0 mmol) and $Pd(PPh_3)_4$ (100 mg), refluxed for 4 h and partitioned between saturated $NH_4Cl$ solution (10 mL) and EtOAc (10 mL). The organic phase was dried ($MgSO_4$), concentrated in vacuo and purified by chromatography [$SiO_2$; iso-hexane:EtOAc (1:1), then neat EtOAc] to give the title compound (6 mg, 2%) as a beige solid.

Method Y

3-(2-Fluorobenzyl)-7-(1H-triazol-4-yl)-3H-[1,2,3]triazolo[4,5-d]pyrimidine-5-amine (Example 80)

A mixture of 7-chloro-3-(2-fluorobenzyl)-3H-[1,2,3]triazolo[4,5-d]pyrimidine-5-amine (145 mg, 0.50 mmol), tributyl 1-(2-(trimethylsilyl)ethoxymethyl)-1H-triazol-5-ylstannane (336 mg, 0.75 mmol) and $Pd(PPh_3)_2Cl_2$ (35 mg, 0.05 mmol) in DMF (2 mL) was shaken at 80° C. for 17 h then purified directly by chromatography [$SiO_2$; iso-hexane:EtOAc (2:1)] to give 3-(2-fluorobenzyl)-7-(1-(2-trimethylsilyl)ethoxymethyl)-1H-triazol-5-yl)-3H-[1,2,3]triazolo[4,5-d]pyrimidine-5-amine as a colourless oil. This material was dissolved in MeOH (1 mL), treated with a solution of HCl (0.5 mL, 4-M in dioxane), stirred for 17 h, concentrated in vacuo and the residue triturated with $Et_2O$ to give the title compound (16 mg, 10%) as an off-white solid.

Method Z

3-(4-Hydroxylamino-2-pyridylmethyl)-7-(5-methyl-2-furyl)-3H-[1,2,3]triazolo[4,5-d]pyrimidine-5-amine (Example 87)

A solution of 7-(5-methyl-2-furyl)-3-(4-nitro-2-pyridylmethyl)-3H-[1,2,3]triazolo[4,5-d]pyrimidine-5-amine (60 mg, 0.17 mmol) in EtOH (40 mL), MeOH (20 mL) and water (15 mL) was treated with ammonium chloride (280 mg, 5.23 mmol) and zinc (138 mg, 2.05 mmol), stirred for 1 h, filtered through Celite, concentrated in vacuo to ~20 mL, diluted with brine (20 mL), extracted with EtOAc (3×20 mL) and the combined organic phase dried (MgSO$_4$) and concentrated in vacuo to give the title compound (40 mg, 73%) as a yellow solid.

Method AA

3-(3-Aminomethylbenzyl)-7-(1H-pyrazol-3-yl)-3H-[1,2,3]triazolo[4,5-d]pyrimidine-5-amine (example 101)

A stirred solution of the 7-(1-(2-(trimethylsilyl)ethoxymethyl)-1H-pyrazol-5-yl)-1H-[1,2,3]triazolo[4,5-d]pyrimidine-5-amine (330 mg, 1 mmol) in dry DMF (5 mL) was treated with NaH (40 mg, 60% in oil, 1 mmol), stirred for 15 min, treated with tert-butyl N-(3-(bromomethyl)benzyl)carbamate (300 mg, 1 mmol) and stirred for 1 h. The mixture was partitioned between EtOAc (20 mL) and H$_2$O (20 mL), the organic phase was dried (MgSO$_4$), concentrated in vacuo and purified by chromatography [SiO$_2$; iso-hexane:EtOAc (1:1)]. The resulting yellow syrup was dissolved in MeOH (3 mL), treated with HCl (2 mL, 4-M in dioxane), stirred for 17 h and the resulting solid filtered to give the title compound (258 mg, 80%) as a cream solid.

Method AB

2-Bromomethyl-6-(methoxymethyl)pyridine

A solution of 6-methoxymethyl-2-pyridinemethanol (860 mg, 5.64 mmol) and triphenylphosphine (1.78 g, 6.77 mmol) in dichloromethane (40 mL) at 0° C. was treated portionwise with CBr$_4$ (2.80 g, 8.43 mmol), stirred for 1 h, concentrated in vacuo and purified by chromatography [SiO$_2$; isohexane:EtOAc (3:1)] to give the title compound (1.20 g, 99%) as a colourless oil; NMR $\delta_H$ (400 MHz, CDCl$_3$) 7.71 (1H, t, J 8.0 Hz), 7.35 (2H, d, J 8.0 Hz), 4.58 (2H, s) and 4.54 (2H, s).

The following novel compounds were also synthesised by Method AB from the appropriate alcohol.

2-Bromomethyl-4-methylpyridine

NMR $\delta_H$ (400 MHz, CDCl$_3$) 8.43 (1H, d, J 5.0 Hz), 7.26-7.25 (1H, m), 7.03 (1H, d, J 5.0 Hz), 4.51 (2H, s) and 2.36 (3H, s).

2-Bromomethyl-6-ethylpyridine

NMR $\delta_H$ (400 MHz, CDCl$_3$) 7.60 (1H, t, J 7.5 Hz), 7.26 (1H, d, J 7.5 Hz), 7.08 (1H, d, J 7.5 Hz), 4.53 (2H, s), 2.82 (2H, q, J 7.5 Hz) and 1.30 (3H, t, J 7.5 Hz).

4-Bromomethyl-2-ethylpyridine

NMR $\delta_H$ (400 MHz, CDCl$_3$) 8.51 (1H, d, J 5.0 Hz), 7.17-7.16 (1H, m), 7.13-7.11 (1H, m), 4.37 (2H, s), 2.84 (2H, q, J 7.5 Hz) and 1.32 (3H, t, J 7.5 Hz).

tert-Butyl (4-bromomethyl-3,5-difluorophenyl)carbonate

NMR $\delta_H$ (400 MHz, CDCl$_3$) 6.80 (2H, m), 4.49 (2H, s) and 1.56 (9H, s).

2-Fluoro-5-iodobenzyl bromide

NMR $\delta_H$ (400 MHz, DMSO) 7.94-7.91 (1H, dd, J 2.5, 7.5 Hz), 7.76-7.71 (1H, m), 7.12-7.06 (1H, dd, J 8.5, 10.0 Hz) and 4.66-4.64 (2H, s).

2-Allyloxymethyl-6-bromomethylpyridine

NMR $\delta_H$ (400 MHz, CDCl$_3$) 7.71 (1H, t, J 7.5 Hz), 7.40 (1H, d, J 7.5 Hz), 7.34 (1H, d, J 7.5 Hz), 6.03-5.93 (1H, m), 5.37-5.32 (1H, m), 5.26-5.22 (1H, m), 4.64 (2H, s), 4.54 (2H, s) and 4.14-4.12 (2H, m).

4-Nitro-2-(2-trimethylsilylethoxy)methoxybenzyl bromide

NMR $\delta_H$ (400 MHz, CDCl$_3$) 7.99 (1H, d, J 2.0 Hz), 7.84 (1H, dd, J 8.4, 2.0 Hz), 7.49 (1H, d, J 8.4 Hz), 5.41 (2H, s), 4.55 (2H, s), 3.82 (2H, m), 0.96 (2H, m) and 0.01 (9H, s).

2-Bromomethyl-4,6-diisopropylpyridine

NMR $\delta_H$ (400 MHz, CDCl$_3$) 7.12 (1H, s), 6.93 (1H, s), 4.52 (2H, s), 3.03 (1H, sept, J 7.0 Hz), 2.87 (1H, sept, J 7.0 Hz), 1.29 (6H, d, J 7.0 Hz) and 1.25 (6H, d, J 7.0 Hz).

2-Bromomethyl-6-isopropylpyridine

NMR $\delta_H$ (400 MHz, CDCl$_3$) 7.63-7.59 (1H; m), 7.27-7.25 (1H, m), 7.10-7.08 (1H, m), 4.54 (2H, s), 3.06 (1H, sept, J 7.0 Hz) and 1.30 (6H, d, J 7.0 Hz).

2-Bromomethyl-6-vinylpyridine

NMR $\delta_H$ (400 MHz, CDCl$_3$) 7.66 (1H, t, J 7.5 Hz), 7.34-7.28 (2H, m), 6.81 (1H, dd, J 10.5, 17.5 Hz), 6.22 (1H, dd, J 1.0, 17.5 Hz), 5.51 (1H, dd, J 1.0, 10.5 Hz) and 4.55 (2H, s).

2-Bromomethyl-5-ethylthiophene

NMR $\delta_H$ (400 MHz, DMSO) 6.85-6.82 (1H, d, J 3.5 Hz), 6.71-6.68 (1H, d, J 3.5 Hz), 4.59-4.55 (2H, s), 2.81-2.75 (2H, m) and 1.25-1.20 (3H, m).

2-Bromomethyl-6-n-propylpyridine

NMR $\delta_H$ (400 MHz, CDCl$_3$) 7.59 (1H, t, J 7.5 Hz), 7.26 (1H, d, J 7.5 Hz), 7.06 (1H, d, J 7.5 Hz), 4.53 (2H, s), 2.76 (2H, t, J 7.5 Hz), 1.74 (2H, sext, J 7.5 Hz) and 0.97 (3H, t, J 7.5 Hz).

2-Bromomethyl-6-isobutyloxymethylpyridine

NMR $\delta_H$ (400 MHz, CDCl$_3$) 7.71 (1H, t, J 7.5 Hz), 7.41 (1H, d, J 7.5 Hz), 7.33 (1H, d, J 7.5 Hz), 4.62 (2H, s), 4.53 (2H, s), 3.33 (2H, d, J 6.5 Hz), 1.91-2.01 (1H, m) and 0.96 (6H, d, J 6.5 Hz).

5-Bromomethyl-2-isopropylpyridine

NMR $\delta_H$ (400 MHz, CDCl$_3$) 8.54 (1H, m), 7.65 (1H, dd, J 2.5, 8.0 Hz), 7.16 (1H, d, J 8.0 Hz), 4.47 (2H, s), 3.07 (1H, sept, J 7.0 Hz) and 1.30 (6H, d, J 7.0 Hz).

2-Bromomethyl-6-isopropyloxymethylpyridine

NMR $\delta_H$ (400 MHz, CDCl$_3$) 7.71-7.67 (1H, m), 7.42-7.40 (1H, m), 7.33-7.31 (1H, m), 4.63 (2H, s), 4.53 (2H, s), 3.75 (1H, sept, J 6.0 Hz) and 1.25 (6H, d, J 6.0 Hz).

Method AC

2-Bromomethyl-4-nitropyridine

A solution of 2-methyl-4-nitropyridine (1.79 g, 13.0 mmol) in CCl$_4$ (30 mL) was treated with N-bromosuccinimide (2.31 g, 13.0 mmol) and benzoyl peroxide (420 mg, 1.30 mmol), stirred at 80° C. for 16 h, cooled to room temperature, filtered through Celite, concentrated in vacuo and purified by chromatography [SiO$_2$; isohexane:EtOAc (15:1)] to give the title compound (700 mg, 25%) as a colourless oil; NMR $\delta_H$ (400 MHz, CDCl$_3$) 8.89 (1H, d, J 5.0 Hz), 8.19 (1H, d, J 2.0 Hz), 7.96 (1H, dd, J 5.0, 2.0 Hz) and 4.66 (2H, s).

The following novel compounds were also synthesised by bromination of the appropriate arylalkyl compounds using Method AC.

2-Bromomethyl-6-methyl-4-nitropyridine,

NMR $\delta_H$ (400 MHz, CDCl$_3$) 7.99-7.98 (1H, m), 7.79 (1H, d, J 2.0 Hz), 4.60 (2H, s) and 2.71 (3H, s).

tert-Butyl 7-bromomethylindole-1-carboxylate

NMR $\delta_H$ (400 MHz, CDCl$_3$) 7.57 (1H, d, J 4.0 Hz), 7.55 (1H, dd, J 8.0, 1.5 Hz), 7.27 (1H, d, J 7.5 Hz), 7.19 (1H, t, J 7.5 Hz), 6.58 (1H, d, J 3.5 Hz), 5.24 (2H, s) and 1.68 (9H, s).

tert-Butyl 5-bromomethylindole-1-carboxylate

NMR $\delta_H$ (400 MHz, CDCl$_3$) 8.11 (1H, br d, J 8.5 Hz), 6.72 (1H, d, J 3.5 Hz), 7.59 (1H, d, J 1.5 Hz), 7.35 (1H, dd, J 8.5, 1.5 Hz), 6.54 (1H, d, J 4.0 Hz), 4.64 (2H, s) and 1.67 (9H, s).

tert-Butyl 7-bromomethyl-5-chloroindole-1-carboxylate

NMR $\delta_H$ (400 MHz, CDCl$_3$) 7.58 (1H, d, J 3.5 Hz), 7.51 (1H, d, J 2.0 Hz), 7.27 (1H, m), 6.52 (1H, d, J 3.5 Hz), 5.15 (2H, s), and 1.67 (9H, s).

tert-Butyl 7-bromomethyl-5-methylindole-1-carboxylate

NMR $\delta_H$ (400 MHz, CDCl$_3$) 7.53 (1H, d, J 4.0 Hz), 7.32 (1H, s), 7.09 (1H, s), 6.49 (1H, d, J 3.5 Hz), 5.21 (2H, s), 2.41 (3H, s) and 1.66 (9H, s).

tert-Butyl 5-bromomethyl-7-fluoroindole-1-carboxylate

NMR $\delta_H$ (CDCl$_3$) 7.65 (1H, d, J 4.0 Hz), 7.35 (1H, d, J 1.5 Hz), 7.07 (1H, dd, J 13.0, 1.5 Hz), 6.56 (1H, dd, J 3.5, 1.5 Hz), 4.56 (2H, s) and 1.65 (9H, s).

tert-Butyl 5-bromomethyl-4-chloroindole-1-carboxylate

NMR $\delta_H$ (400 MHz, CDCl$_3$) 8.03 (1H, d, J 8.5 Hz), 7.63 (1H, d, J 4.0 Hz), 7.36 (1H, d, 8.5 Hz), 6.71 (1H, d, J 3.5 Hz), 4.75 (2H, s) and 1.67 (9H, s).

tert-Butyl 7-bromo-5-bromomethylindole-1-carboxylate

NMR $\delta_H$ (400 MHz, CDCl$_3$) 7.57 (1H, s), 7.56-7.52 (2H, m), 6.54 (1H, d, J 3.5 Hz), 4.56 (2H, s) and 1.66 (9H, s).

tert-Butyl 5-bromomethyl-6-chloroindole-1-carboxylate

NMR $\delta_H$ (400 MHz, CDCl$_3$) 8.23 (1H, br s), 7.60 (1H, s), 7.58 (1H, d, J 3.5 Hz), 6.51 (1H, d, J 4.5 Hz), 4.71 (2H, s) and 1.67 (9H, s).

tert-Butyl 5-bromomethyl-6-fluoroindole-1-carboxylate

NMR $\delta_H$ (400 MHz, CDCl$_3$) 7.88 (1H, br d, J, 11.0 Hz), 7.57 (1H, d, J 4.0 Hz), 7.54 (1H, d, J 7.0 Hz), 6.52 (1H, d, J 4.5 Hz), 4.64 (2H, s) and 1.67 (9H, s).

tert-Butyl 2-bromomethyl-5-fluoroindole-1-carboxylate

NMR $\delta_H$ (400 MHz, CDCl$_3$) 8.12 (1H, dd, J 9.0, 4.5 Hz), 7.15 (1H, dd, J 8.5, 2.5 Hz), 7.04 (1H, dt, J 9.0, 2.5 Hz), 6.66 (1H, s), 4.90 (2H, s) and 1.72 (9H, s).

tert-Butyl 5-bromomethyl-7-chloroindole-1-carboxylate

NMR $\delta_H$ (400 MHz, CDCl$_3$) 7.56 (1H, d, J 4. Hz), 7.49 (1H, d, J 2.0 Hz), 7.37 (1H, s), 6.54 (1H, d, J 3.5 Hz), 4.56 (2H, s) and 1.65 (9H, s).

2-(1-Bromopropyl)-5,6-dimethylpyridine

NMR $\delta_H$ (400 MHz, CDCl$_3$) 7.39 (1H, d, J 8.0 Hz), 7.18 (1H, d, J 8.0 Hz), 4.93 (1H, t, J 7.5 Hz), 2.49 (3H, s), 2.27 (3H, s), 2.29-2.24 (2-H, m) and 1.02 (3H, t, J 7.0 Hz); M/Z 228 (M+H)$^+$.

The following novel compound was synthesised by bromination of 2-(1-methoxypropyl)-6-methylpyridine using Method AC.

2-Bromo-1-(6-methylpyridin-2-yl)propanone

NMR $\delta_H$ (400 MHz, CDCl$_3$) 7.91 (1H, d, J 7.5 Hz), 7.74 (1H, t, J 7.5 Hz), 7.35 (1H, d, J 7.5 Hz), 6.13 (1H, q, J 7.0 Hz), 2.62 (3H, s) and 1.89 (3H, d, J 7.0 Hz).

Method AD tert-Butyl 7-methylindole-1-carboxylate

A stirred solution of 7-methylindole (1.18 g, 9 mmol) in dry THF (50 mL) was treated with NaH (360 mg, 60% in oil, 9 mmol), stirred for 10 min, treated with di-tert-butyl dicarbonate (2.3 mL, 9.3 mmol), stirred for 1 h, treated with 4-(N,N-dimethylamino)pyridine (catalytic amount) and stirred for 1 h. The mixture was partitioned between EtOAc (50 mL) and saturated NH$_4$Cl solution (30 mL) and the organic phase was dried (MgSO$_4$), concentrated in vacuo, and purified by chromatography [SiO$_2$; iso-hexane:EtOAc (5:1)] to give the title compound (2.35 g, 100%) as an orange oil; NMR $\delta_H$ (400 MHz, CDCl$_3$) 7.51 (1H, d, J 4.0 Hz), 7.37 (1H, d, J 7.5 Hz), 7.13 (1H, t, J 7.5 Hz), 7.08 (1H, d, 7.5 Hz), 6.51 (1H, d, J 4.0 Hz), 2.64 (3H, s) and 1.63 (9H, s).

The following novel compounds were synthesised from the appropriate indoles using Method AD.

tert-Butyl 5-chloro-7-methylindole-1-carboxylate

NMR δ$_H$ (400 MHz, CDCl$_3$) 7.52 (1H, d, J 4.0 Hz), 7.35 (1H, d, J 2.0 Hz), 7.07 (1H, d, J 1.5 Hz), 6.46 (1H, d, J 3.5 Hz), 2.61 (3H, s), and 1.63 (9H, s).

tert-Butyl 5,7-dimethylindole-1-carboxylate

NMR δ$_H$ (CDCl$_3$) 7.48 (1H, d, J 4.0 Hz) 7.16 (1H, s), 6.92 (1H, s), 6.44 (1H, d, J 4.0 Hz), 2.60 (3H, s) 2.38 (3H, s) and 1.62 (9H, s).

tert-Butyl 7-fluoro-5-methylindole-1-carboxylate

NMR δ$_H$ (CDCl$_3$) 7.59 (1H, d, J 4.0 Hz), 7.1-0 (1H, s), 6.84 (1H, d, J 13.5 Hz), 6.50-6.47 (1H, m), 2.40 (3H, s) and 1.64 (9H, s).

tert-Butyl 4-chloro-5-methylindole-1-carboxylate

NMR δ$_H$ (400 MHz, CDCl$_3$) 7.92 (1H, d, J 8.0 Hz), 7.57 (1H, d, J 3.5 Hz), 7.15 (1H, d, J 8.5 Hz), 6.66 (1H, d, J 3.5 Hz), 2.46 (3H, s) and 1.66 (9H, s).

tert-Butyl 7-bromo-5-methylindole-1-carboxylate

NMR δ$_H$ (400 MHz, CDCl$_3$) 7.47 (1H, d, J 3.5 Hz), 7.35 (1H, s), 7.26 (1H, s), 6.44 (1H, d, J 4.0 Hz), 2.38 (3H, s) and 1.64° (9H, s).

tert-Butyl 6-chloro-5-methylindole-1-carboxylate

NMR δ$_H$ (400 MHz, CDCl$_3$) 8.17 (1H, br s), 7.53 (1H, d, J 3.5 Hz), 7.38 (1H, s), 6.46 (1H, d, J 3.0 Hz), 2.44 (3H, s), 1.67 (9H, s).

tert-Butyl 6-fluoro-5-methylindole-1-carboxylate

NMR δ$_H$ (400 MHz, CDCl$_3$) 7.79 (1H, br d, J 10.5 Hz), 7.51 (1H, d, J 3.5 Hz), 7.30 (1H, d, J 7.5 Hz), 6.46 (1H, d, J 3.5 Hz), 2.34 (3H, s) and 1.66 (9H, s).

tert-Butyl 5-fluoro-2-methylindole-1-carboxylate

NMR δ$_H$ (400 MHz, CDCl$_3$) 8.04 (1H, dd, J 9.0, 4.5 Hz), 7.07 (1H, dd J 9.0, 2.5 Hz), 6.92 (1H, dt, J 9.5, 3.0 Hz), 6.27 (1H, s), 2.58 (3H, d, J 1.5 Hz) and 1.67 (9H, s).

tert-Butyl 7-chloro-5-methylindole-1-carboxylate

NMR δ$_H$ (400 MHz, CDCl$_3$) 7.50 (1H, d, J 3.5 Hz), 7.22 (1H, s), 7.14 (1H, s), 6.46 (1H, d, J 4.0 Hz), 2.38 (3H, s) and 1.64 (9H, s).

The following novel compound was synthesised from 2,6-difluoro-4-hydroxybenzyl alcohol using Method AD.

tert-Butyl (3,5-difluoro-4-hydroxymethylphenyl)carbonate

IR ν$_{max}$ (DR)/cm$^{-1}$ 3388, 2983, 1775, 1605, 1446, 1396, 1373, 1289, 1146, 1072, 967 and 882; NMR δ$_H$ (400 MHz, CDCl$_3$) 6.79 (2H, m), 4.75 (2H, d, J 6.5 Hz), 1.84 (1H, t, J 6.5 Hz) and 1.56 (9H, s).

Method AE

2,6-Difluoro-4-hydroxybenzyl alcohol

A mixture of 3,5-difluorophenol (25 g, 0.19 mol) and KOH (85%, 12.7 g, 0.19 mol) was treated dropwise with water (50 mL), stirred at 60° C. for 1 h, treated dropwise with formaldehyde solution (37%, 15.6 mL, 0.19 mol) and water (50 mL) and stirred overnight at 40° C. The mixture was cooled, acidified with 6-M HCl, filtered and the resulting solid washed with water and dried to give the title compound (15 g, 49%) as a white solid: NMR δ$_H$ (400 MHz, DMSO) 10.28 (1H, s), 6.43 (2H, m), 4.99 (1H, t, J 5.6 Hz) and 4.37 (2H, d, J 5.6 Hz).

Method AF

7-(2-Furyl)-3-(6-indolylmethyl)-3H-[1,2,3]triazolo[4,5-d]pyrimidine-5-amine (Example 152)

A mixture of tert-butyl 6-(5-amino-7-(2-furyl)-3H-[1,2,3]triazolo[4,5-d]pyrimidine-3-ylmethyl)indole-1-carboxylate (135 mg, 4.08 mmol), and NaOMe (22 mg, 4.08 mmol) in MeOH (10 mL) was refluxed for 1 h, treated with NaOMe (110 mg, 20.4 mmol), refluxed for a further 4 h then stirred at room temperature for 17 h. The mixture was concentrated in vacuo to half volume and the resulting precipitate was filtered and washed with H$_2$O to give the title compound (90 mg, 96%) as a cream solid.

Method AG

3-(2,6-Difluoro-4-methoxybenzyl)-7-(2-furyl)-3H-[1,2,3]triazolo[4,5-d]pyrimidine-5-amine (Example 156)

A solution of 3-(2,6-difluoro-4-hydroxybenzyl)-7-(2-furyl)-3H-[1,2,3]triazolo[4,5-d]pyrimidine-5-amine hydrochloride (130 mg, 0.34 mmol) in DMF (5 mL) at 0° C., was treated with CsCO$_3$ (223 mg, 0.68 mmol), stirred for 10 min, treated with methyl iodide (21 μL, 0.34 mmol) and stirred at room temperature for 30 min. The reaction mixture was diluted with water (10 mL) and filtered to give the title compound (122 mg, 100%) as a white solid.

Method AH

2-Fluoro-5-iodobenzyl alcohol

A solution of 2-fluoro-5-iodobenzaldehyde (1.173 g, 4.692 mmol) in isopropanol (25 mL) was treated with sodium borohydride (0.379 g, 10.02 mmol), stirred at room temperature for 18 h, poured into water (125 mL), and extracted with isopropyl ether (2×25 mL). The combined organic phase was dried (Na$_2$SO$_4$), and concentrated in vacuo to give the title compound (1.187 g, 99%) as a pale yellow solid; NMR δ$_H$ (400 MHz, CDCl$_3$) 7.77 (1H, m), 7.57 (1H, m), 6.82 (1H, t, J 8.8 Hz), 4.73 (2H, d, J 6.1 Hz), and 1.79 (1H, t, J 6.1 Hz).

Method AI

3-(tert-Butoxycarbonyloxy)-4-nitrobenzoic acid

A solution of 3-hydroxy-4-nitrobenzoic acid (1.83 g, 10 mmol) in THF (10 mL) was treated with Et$_3$N (3.4 mL, 24 mmol) and di-tert-butyl dicarbonate (2.40 mL, 11 mmol) and stirred at room temperature for 16 h. The reaction mixture was poured into 10% citric acid solution (20 mL), extracted with EtOAc (2×10 mL), dried (MgSO$_4$) and concentrated in vacuo to give the title compound (2.36 g, 83%) as a cream solid; IR $v_{max}$ (Nujol)/cm$^{-1}$ 2985, 1772, 1717 and 1592; NMR $\delta_H$ (400 MHz, DMSO) 13.85 (1H, s), 8.26 (1H, d, J 8.5 Hz), 8.04 (1H, dd, J 8.5, 2.0 Hz), 7.98 (1H, d, J 2.0 Hz) and 1.49 (9H, s).

Method AJ tert-Butyl (5-bromomethyl-2-nitrophenyl)carbonate

A solution of 3-(tert-butoxycarbonyloxy)-4-nitrobenzoic acid (2.26 g, 8 mmol) and N-methylmorpholine (1.85 mL, 16.8 mmol) in THF (20 mL) at 0° C., was treated with isobutylchloroformate (1.09 mL, 8.4 mmol) and stirred for 1 h. The reaction mixture was added to a cooled (−78° C.) solution of NaBH$_4$ (605 mg, 16 mmol) in MeOH (16 mL) and stirred at room temperature for 1 h. The reaction mixture was diluted with EtOAc (20 mL), washed with saturated NaHCO$_3$ (10 mL) and 10% citric acid solution (10 mL), dried (MgSO$_4$) and concentrated in vacuo to give tert-butyl (5-hydroxymethyl-2-nitrophenyl) carbonate (1.36 g, 86%) as a cream solid. This material was brominated directly using Method AB to give the title compound (961 mg, 58%) as a yellow oil: NMR $\delta_H$ (400 MHz, CDCl$_3$) 8.09 (1H, d, J 8.4 Hz), 7.41 (1H, dd, J 8.4, 2.0 Hz), 7.34 (1H, d, J 2.0 Hz), 4.47 (2H, s) and 1.58 (9H, s).

Method AK 3-(3-Nitrobenzyl)-7-(1H-pyrazol-3-yl)-3H-[1,2,3]triazolo[4,5-d]pyrimidine-5-amine hydrochloride (Example 266)

A solution of 7-chloro-3-(3-nitrobenzyl)-3H-[1,2,3]triazolo[4,5-d]pyrimidine-5-amine (306 mg, 1 mmol), 1-(2-(trimethylsilyl)ethoxymethyl)-1H-pyrazol-5-ylboronic acid (2 mmol), Pd(PPh$_3$)$_4$ (100 mg) and saturated NaHCO$_3$ (5 mL) in THF (20 mL) was refluxed for 2 h, diluted with water (20 mL), extracted with EtOAc(2×20 mL), dried (MgSO$_4$), concentrated in vacuo and purified by chromatography [SiO$_2$; CH$_2$Cl$_2$:EtOAc (6:1)] to give 3-(3-nitrobenzyl)-7-(1-(2-(trimethylsilyl)ethoxymethyl)-1H-pyrazol-5-yl)-3H-[1,2,3]triazolo[4,5-d]pyrimidine-5-amine (156 mg, 34%) as a pale yellow syrup.

A solution of 3-(3-nitrobenzyl)-7-(1-(2-(trimethylsilyl)ethoxymethyl)-1H-pyrazol-5-yl)-3H-[1,2,3]triazolo[4,5-d]pyrimidine-5-amine (156 mg, 0.34 mmol) in MeOH (2 mL) was treated with 4-M HCl in dioxane (4 mL) stirred at room temperature for 2 h, concentrated in vacuo, triturated with Et$_2$O and filtered to give the title compound (110 mg, 97%) as a yellow solid.

Method AL 3-(6-Acetamidomethyl-2-pyridylmethyl)-7-(2-furyl)-3H-[1,2,3]triazolo[4,5-d]pyrimidine-5-amine (Example 177)

A suspension of 7-(2-furyl)-3-(6-phthalimidomethyl-2-pyridylmethyl)-3H-[1,2,3]triazolo[4,5-d]pyrimidine-5-amine (210 mg, 0.465 mmol) in EtOH (50 mL) was treated with ethylenediamine (62 µl, 0.929 mmol), stirred for 3 h at 90° C. and the resulting clear solution, cooled to room temperature and concentrated in vacuo to give 3-(6-aminomethyl-2-pyridylmethyl)-7-(2-furyl)-3H-[1,2,3]triazolo[4,5-d]pyrimidine-5-amine. A solution of this material in pyridine (10 mL) at 0° C. was treated with acetyl chloride (109 ml, 1.53 mmol), stirred for 10 min, poured into water (70 mL), extracted with EtOAc (3×20 mL) and the combined organic phase was dried (MgSO$_4$), concentrated in vacuo and purified by chromatography [SiO$_2$; EtOAc] to give the title compound (110 mg, 65%) as a beige solid.

Method AM 3-(6-Allyloxymethyl-2-pyridylmethyl)-N,N-diallyl-7-(2-furyl)-3H-[1,2,3]triazolo[4,5-d]pyrimidine-5-amine (Example 182)

A solution of 7-(2-furyl)-3-(6-hydroxymethyl-2-pyridylmethyl)-3H-[1,2,3]triazolo[4,5-d]pyrimidine-5-amine (120 mg, 0.377 mmol) in DMF (5 mL) at 0° C. was treated with sodium hydride (30 mg, 0.743 mmol), stirred for 15 min, treated with allyl bromide (96 µl, 1.11 mmol), stirred at room temperature for 16 h, concentrated in vacuo to ~2 mL and purified by chromatography [SiO$_2$; isohexane:EtOAc (3:1)] to give the title compound (50 mg, 30%) as a yellow solid.

Method AN

6-Allyloxymethyl-2-pyridinemethanol

A solution of 2,6-pyridinedimethanol (5.0 g, 35.9 mmol) in DMF (30 mL) at 0° C. was treated with sodium hydride (1.44 g, 35.9 mmol), stirred for 30 min, treated with allyl bromide (3.42 ml, 39.5 mmol), stirred for 16 h at room temperature, poured into water (150 mL), extracted with EtOAc (3×30 mL) and the combined organic phase was dried (MgSO$_4$), concentrated in vacuo and purified by chromatography [SiO$_2$; isohexane:EtOAc (3:1 to 1:1)] to give the title compound (1.56 g, 24%) as a colourless oil: NMR $\delta_H$ (400 MHz, CDCl$_3$) 7.69 (1H, t, J 7.5 Hz), 7.37 (1H, d, J 7.5 Hz), 7.13 (1H, d, J 7.5 Hz), 6.04-5.93 (1H, m), 5.38-5.21 (2H, m), 4.74 (2H, d, J 5.0 Hz), 4.65 (2H, s), 4.15-4.09 (2H, m) and 3.76 (1H, t, J 5.0 Hz).

The following novel compounds were synthesised from the appropriate alcohols by Method AN 2-(1-Methoxypropyl)-6-methylpyridine NMR $\delta_H$ (400 MHz, CDCl$_3$) 7.58 (1H, t, J 8.0 Hz), 7.18 (1H, d, J 8.0 Hz), 7.04 (1H, d, J 8.0 Hz), 4.17 (1H, dd, J 5.5, 7.5 Hz), 3.30 (3H, s), 2.55 (3H, s), 1.84-1.69 (2H, m) and 0.93 (3H, t, J 7.5 Hz).

6-Isobutyloxymethylpyridine-2-methanol

NMR $\delta_H$ (400 MHz, CDCl$_3$) 7.69 (1H, t, J 7.5 Hz), 7.37 (1H, d, J 7.5 Hz), 7.13 (1H, d, J 7.5 Hz), 4.74 (2H, s), 4.63 (2H, s), 3.94 (1H, br s), 3.33 (2H, d, J 6.5 Hz), 1.91-2.01 (1H, m) and 0.96 (6H, d, J 6.5 Hz).

6-Isopropyloxymethylpyridine-2-methanol

NMR $\delta_H$ (400 MHz, CDCl$_3$) 7.70-7.66 (1H, m), 7.39 (1H, d, J 7.5 Hz), 7.11 (1H, d, J 8.0 Hz), 4.74 (2H, s), 4.64 (2H, s), 3.75 (1H, sept, J 6.0 Hz) and 1.25 (6H, d, J 6.0 Hz).

Method AO

3-Isopropyl-4-nitrobenzyl bromide

A solution of 4-nitrobenzyl bromide (432 mg, 2 mmol) in THF (5 mL) at −70° C., was treated dropwise with isopropylmagnesium chloride (1 mL, 2-M in Et$_2$O, 2 mmol), stirred for 1 h, treated with DDQ (499 mg, 2.2 mmol) and stirred at room temperature for 16 h. The reaction mixture was poured into water (10 mL), extracted with EtOAc (2×10 mL), dried (MgSO$_4$), concentrated in vacuo and filtered. The resulting solid was purified by chromatography [SiO$_2$; EtOAc:Heptane (1:4)] to give the title compound (183 mg, 35%) as a pale yellow solid which was used in the next reaction without further purification.

The following novel compound was also synthesised from 4-nitrobenzyl bromide using Method AO

3-Ethyl-4-nitrobenzyl bromide

NMR $\delta_H$ (400 MHz, CDCl$_3$) 7.87 (1H, d, J 8.3 Hz), 7.37 (1H, s), 7.35 (1H, d, J 8.3 Hz), 4.47 (2H, s), 2.92 (2H, q, J 7.5 Hz) and 1.30 (3H, t, J 7.5 Hz).

Method AP

2-(Trimethylsilyl)ethoxymethyl 4-nitro-2-((2-trimethylsilyl)ethoxymethoxy)benzoic acid A solution of 2-hydroxy-4-nitrobenzoic acid (1.83 g, 10 mmol) in THF (20 mL), was treated with N,N-diisopropylethylamine (3.92 mL, 22 mmol) and 2-(trimethylsilyl)ethoxymethyl chloride (3.46 mL, 20 mmol) and stirred for 16 h then purified directly by chromatography [SiO$_2$:EtOAc: heptane (1:4)] to give the title compound (5.82 mg, quantitative) as white solid which was used in the next reaction without further purification; NMR $\delta_H$ (400 MHz, CDCl$_3$) 8.09-8.07 (1H, m), 7.87-7.85 (2H, m), 5.50 (2H, s), 5.35 (2H, s), 3.78 (4H, t, J 8.5 Hz), 1.00-0.88 (4H, m), 0.00 (9H, s) and 0.03 (9H, s).

Method AQ

2-(2-Trimethylsilyl)ethoxymethoxy-4-nitrobenzyl alcohol

A solution of 2-(trimethylsilyl)ethoxymethyl 4-nitro-2-(2-(trimethylsilyl)ethoxymethoxy)benzoic acid (2.91 mg, 5 mmol) in Et$_2$O (10 mL) at 0° C., was treated with LiAlH$_4$ (190 mg, 22 mmol) and stirred for 30 min. The reaction mixture was poured into water (20 mL), extracted with EtOAc (2×10 mL), dried (MgSO$_4$) and concentrated in vacuo to give the title compound (1.35 g, 91%) as a slightly impure colourless oil; NMR $\delta_H$ (400 MHz, CDCl$_3$) 7.96-7.99 (1H, m), 7.90 (1H, dd, J 8.5, 2.0 Hz), 7.55 (1H, d, J 8.5 Hz), 5.35 (2H, s), 4.78 (2H, s), 3.80-3.74 (2H, m), 0.99-0.94 (2H, m) and 0.00 (9H, s).

Method AR

4,6-Diisopropyl-2-pyridinemethanol

A solution of 2-pyridinemethanol (5.00 g, 45.8 mmol), conc. sulfuric acid (2.44 ml, 45.8 mmol), iron(II) sulfate heptahydrate (1.53 g, 5.50 mmol) and isopropyl iodide (13.7 ml, 137 mmol) in DMSO (150 mL) was treated dropwise with hydrogen peroxide (27.5 wt % in H$_2$O, 17.0 mL, 137 mmol), with ice-bath cooling to maintain the internal temperature at 25-30° C. A further portion of iron(II) sulfate heptahydrate (1.53 g, 5.50 mmol) was added, the mixture was allowed to cool to room temperature over 1 h, poured into water (500 mL), basified to pH 9 with 5-M NaOH, extracted with dichloromethane (3×100 mL) and the combined organic phase was dried (MgSO$_4$), concentrated in vacuo and purified by chromatography [SiO$_2$; isohexane:EtOAc (3:2)] to give 4,6-diisopropyl-2-pyridinemethanol (500 mg, 6%) as a colourless oil; NMR $\delta_H$ (400 MHz, CDCl$_3$) 6.90 (1H, s), 6.85 (1H, s), 4.69 (2H, br s), 4.35 (1H, br s), 3.03 (1H, sept, J 7.0 Hz), 2.87 (1H, sept, J 7.0 Hz), 1.30 (6H, d, J 7.0 Hz) and 1.25 (6H, d, J 7.0 Hz), and 6-isopropyl-2-pyridinemethanol (900 mg, 13%) as a colourless oil.

The following novel compound was also synthesised from 2-pyridinemethanol by Method AR.

6-n-Propyl-2-pyridinemethanol

NMR $\delta_H$ (400 MHz, CDCl$_3$) 7.58 (1H, t, J 7.5 Hz), 7.03 (2H, t, J 7.5 Hz), 4.72 (2H, s), 4.15 (1H, br s), 2.77 (2H, t, J 7.5 Hz), 1.77 (2H, sept, J 7.5 Hz) and 0.97 (3H, t, J 7.5 Hz).

Method AS tert-Butyl 5-amino-7-(2-furyl)-3H-[1,2,3]triazolo[4,5-d]pyrimidine-3-carboxylate (Example 203)

A solution of 7-(2-furyl)-1H-[1,2,3]triazolo[4,5-d]pyrimidine-5-amine (300 mg, 1.49 mmol) in DMF (5 mL), at 0° C., was treated with 60% sodium hydride in mineral oil (60 mg, 1.49 mmol), stirred for 30 minutes, treated with tert butyl 4-(bromomethyl)phenylcarbonate (471 mg, 1.64 mmol), stirred at room temperature for 16 h, and purified by chromatography [SiO$_2$; EtOAc:heptane, (1:2)] to give the title compound (55 mg, 12%) as a beige solid.

Method AT

2-(5-Amino-7-(2-furyl)-3H-[1,2,3]triazolo[4,5-d]pyrimidin-3-yl)-1-phenylethanone (Example 211)

A solution of 7-(2-furyl)-1H-[1,2,3]triazolo[4,5-d]pyrimidine-5-amine (101 mg, 0.5 mmol) in DMF (2 mL) was treated with 2-bromoacetophenone (100 mg, 0.5 mmol) and triethylamine (105 μL, 0.75 mmol), stirred at room temperature for 3 days, diluted with water (100 mL) and filtered. The resulting solid was purified by chromatography [SiO$_2$; Hexane:EtOAc, (3:1 to 1:1)] to give the title compound (20 mg, 13%) as a yellow solid.

Method AU

7-(2-Furyl)-3-(6-hydroxymethyl-2-pyridylmethyl)-3H-[1,2,3]triazolo[4,5-d]pyrimidine-5-amine hydrochloride (Example 213)

A solution of 6-(5-amino-7-(2-furyl)-3H-[1,2,3]triazolo[4,5-d]pyrimidin-3-ylmethyl)pyridine-2-carboxaldehyde (62 mg, 0.193 mmol) in MeOH (20 mL) was treated with acetic acid (5 mL), dimethylamine (2-M in MeOH, 1.93 mL, 3.86 mmol) and sodium cyanoborohydride (242 mg, 3.86 mmol), stirred for 16 h and concentrated in vacuo. The residue was treated with saturated NaHCO$_3$ solution (20 mL), extracted with EtOAc (3×10 mL) and the combined organic phase dried (MgS$_4$), concentrated in vacuo and purified by chromatography [SiO$_2$; EtOAc] to give the free base as a yellow solid. The solid was suspended in MeOH (1 mL), treated with HCl (4-M in dioxane, 0.25 mL), stirred for 10 min, concentrated in vacuo and triturated with Et$_2$O to give the title compound (22 mg, 29%) as a yellow solid.

Method AV 3-(6-Cyanomethyl-2-pyridylmethyl)-7-(2-furyl)-3H-
[1,2,3]triazolo[4,5-d]pyrimidine-5-amine (Example
220)

A solution of 3-(6-bromomethyl-2-pyrinylmethyl)-7-(2-furyl)-3H-[1,2,3]triazolo[4,5-d]pyrimidine-5-amine (200 mg, 0.517 mmol) and sodium cyanide (51 mg, 1.03 mmol) in DMF (5 mL) was stirred at 60° C. for 16 h, poured into water (40 mL), extracted with EtOAc (3×8 mL), the combined organic phase dried (MgSO$_4$), concentrated in vacuo and purified by chromatography [SiO$_2$; isohexand:EtOAc (1:1)] to give title compound (50 mg, 26%) as a yellow solid.

Method AW 3-(4-Hydroxybenzyl)-7-(2-furyl)-3H-[1,2,3]triazolo
[4,5-d]pyrimidine-5-amine (Example 221)

A solution of 7-(2-furyl)-1H-[1,2,3]triazolo[4,5-d]pyrimidine-5-amine (400 mg, 1.98 mmol) in DMF (3 mL), at 0° C., was treated with 60% sodium hydride in mineral oil (80 mg, 1.98 mmol), stirred for 30 min, treated with 4-(2-(trimethylsilyl)ethoxymethoxy)benzyl bromide (1.23 g, 3.96 mmol), stirred at room temperature for 48 h and purified by chromatography [SiO$_2$; EtOAc:heptane, (1:2)]. The resulting yellow solid was dissolved in MeOH:DMF (1:2), passed through an ion exchange cartridge (Isolute SPE SCX-2), concentrated in vacuo, and washed with water and ether to give the title compound (41 mg, 7%) as a pale yellow solid.

Method AX

N-(3-(5-Amino-7-(2-furyl)-3H-[1,2,3]triazolo[4,5-d]
pyrimidin-3-ylmethyl)phenyl)propanesulphonamide
(Example 224)

A solution of 7-(2-furyl)-1H-[1,2,3]triazolo[4,5-d]pyrimidine-5-amine (153 mg, 0.5 mmol) in pyridine (2 mL) at 0° C. was treated with propanesulfonyl chloride (62 µL, 0.55 mmol) and shaken at room temperature for 16 h. The mixture was poured into water (50 mL), extracted with EtOAc (2×10 mL), washed with 10% citric acid (10 mL) and the combined organic phase dried (MgSO$_4$) and concentrated in vacuo to give the title compound (111 mg, 54%) as a cream solid.

Method AY 7-(2-Furyl)-3-(6-(N-methylamino)methyl-2-pyridyl-
methyl)-3H-[1,2,3]triazolo[4,5-d]pyrimidine-5-
amine (Example 226)

A solution of N-methyl-2,2,2-trifluoroacetamide (197 mg, 1.55 mmol) in DMF (5 mL) at 0° C. was treated with sodium hydride (60% dispersion in mineral oil; 62 mg, 1.55 mmol), stirred for 15 min, treated with 3-(6-bromomethyl-2-pyridylmethyl)-7-(2-furyl)-3H-[1,2,3]triazolo[4,5-d]pyrimidine-5-amine (120 mg, 0.310 mmol), stirred at 50° C. for 1 h, cooled to room temperature, poured into water (20 mL), extracted with EtOAc (3×10 mL) and the combined organic phase dried (MgSO$_4$) and concentrated in vacuo to give N-(6-(5-amino-7-(2-furyl)-3H-[1,2,3]triazolo[4,5-d]pyrimidin-3-ylmethyl)-2-pyridylmethyl)-N-methyltrifluoroacetamide. A solution of this product in MeOH (20 mL) was treated with a solution of sodium (71 mg, 3.10 mmol) in MeOH (10 mL), stirred for 16 h, concentrated in vacuo, treated with EtOAc (20 mL), filtered through Celite and concentrated in vacuo. The resulting solid was suspended in MeOH (2 mL), treated with HCl (4-M in dioxane, 1.0 mL), stirred for 10 min, concentrated in vacuo and triturated with Et$_2$O to give the title compound (80 mg, 58%) as a yellow solid.

Method AZ 3-(1H-Benzotriazol-5-ylmethyl)-7-(2-furyl)-3H-[1,2,
3]triazolo[4,5-d]pyrimidine-5-amine (Example 158)

A mixture of 5-methyl-1H-benzotriazole (666 mg, 5 mmol) in THF (20 mL) was treated with NaH (60% dispersion, 200 mg, 5 mmol), stirred at room temperature for 10 min, treated with di-tert-butyl dicarbonate (115 mg, 5 mmol) and stirred overnight. The mixture was treated with saturated NaHCO$_3$ solution (10 mL), extracted with EtOAc (2×10 mL), dried (MgSO$_4$), filtered through a plug of SiO$_2$ and concentrated in vacuo to give tert-butyl 5-methylbenzotriazole-1-carboxylate (as a mixture with the 6-methyl regioisomer) (1.08 g, 92%) as a colourless oil.

A solution of tert-butyl 5-methyl-1H-benzotriazole-1-carboxylate (as a mixture with the 6-methyl regioisomer) (1.08 g, 4.63 mmol), benzoyl peroxide (112 mg, 0.46 mmol) and N-bromosuccinnimide (0.76 g, 4.63 mmol) in CCl$_4$ (25 mL) was refluxed overnight, cooled, filtered, concentrated in vacuo and purified by, chromatography [SiO$_2$; isohexane:EtOAc (10:1)] to give tert-butyl 5-(bromomethyl)-1H-benzotriazole-1-carboxylate (666 mg, 46%) (as a mixture with the 6-bromomethyl regioisomer) as a colourless oil.

A solution of 7-(2-furyl)-1H-[1,2,3]triazolo[4,5-d]pyrimidine-5-amine (404 mg, 2 mmol) in DMF (4 mL) was treated with NaH (60% dispersion, 80 mg, 2 mmol), stirred at room temperature for 10 min, treated with a solution of tert-butyl 5-(bromomethyl)-1H-benzotriazole-1-carboxylate (as a mixture with the 6-bromomethyl regioisomer) (624 mg, 2 mmol) in DMF (2 mL) and stirred overnight. The mixture was concentrated in vacuo and purified by chromatography [SiO$_2$, isohexane:EtOAc (2:1)] to give tert-butyl 5-(5-amino-7-(2-furyl)-3H-triazolo[4,5-d]pyrimidin-3-yl)methyl-1H-benzotriazol-1-carboxylate (135 mg, 24%) (as a mixture with the 6-substituted regioisomer) as a white solid.

A solution of tert-butyl 5-(5-amino-7-(2-furyl)-3H-triazolo[4,5-d]pyrimidin-3-yl)methyl-1H-benzotriazol-1-carboxylate (as a mixture with the 6-substituted regioisomer) (135 mg, 0.31 mmol) in MeOH (5 mL) and THF (5 mL was treated with 40% aqueous dimethylamine (0.176 mL, 1.56 mmol), refluxed for 25 min, concentrated in vacuo and the resulting solid triturated with ether, filtered, triturated with MeOH, filtered and dried to give the title compound (31 mg, 30%) as a yellow solid.

Method BA

Ethyl 4-((5-amino-7-(2-furyl)-3H-[1,2,3]triazolo[4,
5-d]pyrimidine-3-yl)methyl)-2-methylphenylcar-
bamate (Example 274)

A suspension of 3-(4-amino-3-methylbenzyl)-7-(2-furyl)-3H-[1,2,3]triazolo[4,5-d]pyrimidine-5-amine (260 mg, 0.812 mmol) in pyridine (5 mL) at room temperature was treated dropwise with ethyl chloroformate (0.155 mL, 1.62 mmol), stirred for 30 min, poured into water (30 mL), extracted with EtOAc (2×10 mL) and the combined organic phase was dried (MgSO$_4$) and concentrated in vacuo to give the title compound (318 mg, 100%) as a beige solid.

Method BB

N-(4-(5-Amino-7-(2-furyl)-3H-[1,2,3]triazolo[4,5-d]pyrimidin-3-ylmethyl)-2-methylphenyl)formamide (Example 244)

A mixture of ethyl 4-((5-amino-7-(2-furyl)-3H-[1,2,3]triazolo[4,5-d]pyrimidine-3-yl)methyl)-2-methylphenylcarbamate (318 mg, 0.81 mmol) and LiAlH$_4$ (62 mg, 1.62 mmol) in dry THF (30 mL) was refluxed overnight, cooled to room temperature, treated with 13% aqueous NaOH solution (0.1 mL) then water (0.3 mL), stirred for 30 min, filtered through Celite and concentrated in vacuo. The resulting solid was triturated with THF and filtered to give the title compound (20 mg, 7%) as a yellow solid.

Method BC

7-Fluoro-5-methylindole

A solution of chloral hydrate (7.3 g, 44 mmol), sodium sulphate decahydrate (52 g, 160 mmol) and H$_2$O (100 mL) was added slowly to a stirred solution of 2-fluoro-4-methylaniline (5.0 g, 40 mmol), hydroxylamine hydrochloride (11.1 g, 160 mmol) and conc. HCl (3 mL) in H$_2$O (50 mL). The reaction mixture was refluxed for 1 h, stirred at room temperature for 5 h, filtered and the resulting solid crystallised from MeOH/H$_2$O to yield brown crystals (1.53 g). This material was added in small portions with stirring to conc. sulphuric acid (20 mL) at 70° C., stirred for 1 h, then added slowly with rapid stirring to ice/H$_2$O (200 mL), extracted twice with EtOAc (2×25 mL) and the combined organic phase dried (MgSO$_4$) and concentrated in vacuo to give 7-fluoro-5-methylisatin (1.68 g, 24%) as a dark red gum.

A solution of 7-fluoro-5-methylisatin (1.68 g, 9.43 mmol) in dry THF (50 mL) was added slowly to an ice cold, stirred suspension of LiAlH$_4$ (1.18 g, 31 mmol) in dry THF (50 mL), refluxed for 2 h, cooled to room temperature then treated sequentially with H$_2$O (1.2 mL), 15% NaOH (1.2 mL) and H$_2$O (3 mL). The solution was filtered through a pad of Celite, washing the filter cake thoroughly with THF, the deep blue filtrate was concentrated in vacuo and purified by chromatography [SiO$_2$; iso-Hexane:EtOAc (9:1)] to give the title compound (480 mg, 41%) as a pale blue oil; NMR δ$_H$ (CDCl$_3$) 8.19 (1H, br s), 7.21-7.16 (2H, m), 6.74 (1H, d, J 12.0 Hz), 6.51-6.46 (1H, m) and 2.42 (3H, s).

Method BE

3-(7-Fluoro-5-indolyl)-7-(2-furyl)-3H-[1,2,3]triazolo[4,5-d]pyrimidine-5-amine (Example 246)

A stirred suspension of 7-(2-furyl)-1H-[1,2,3]triazolo[4,5-d]pyrimidine-5-amine (303 mg, 1.5 mmol) in DMF (2 mL) was treated with NaH (60% dispersion in oil, 60 mg, 1.5 mmol), stirred for 10 min, treated slowly with a solution of tert-butyl 5-bromomethyl-7-fluoroindole-1-carboxylate (460 mg, 1.5 mmol) in DMF (1 mL), stirred for 2 h then the mixture was purified directly by chromatography [SiO$_2$; iso-hexane:EtOAc (2:1)] to give the BOC protected product (180 mg, 0.417 mmol) as a pale green solid. This material was dissolved in MeOH (5 mL), treated with sodium methoxide (113 mg, 2 mmol), refluxed for 4 h, cooled to room temperature, diluted with H$_2$O and filtered to give the title compound (118 mg, 81%) as a cream solid.

Method BF

3-(3-(4-Fluorobenzylamino)benzyl)-7-(2-furyl)-3H-[1,2,3]triazolo[4,5-d]pyrimidine-5-amine (Example 252)

A suspension of 3-(3-aminobenzyl)-7-(2-furyl)-3H-[1,2,3]triazolo[4,5-d]pyrimidine-5-amine (200 mg, 0.65 mmol) and 4A molecular sieves in THF (10 mL) was treated with 4-fluorobenzaldehyde (0.04 mL, 0.37 mmol), heated to 40° C. for 3 h, cooled to room temperature, treated sodium triacetoxyborohydride (400 mg, 1.89 mmol) and acetic acid (0.1 mL) and stirred for 15 minutes. The reaction was quenched by addition of sat. NaHCO$_3$ (5 mL), extracted with EtOAc (2×5 mL) and the combined organic phase dried (MgSO$_4$), concentrated in vacuo and purified by chromatography [(SiO$_2$; EtOAc:Heptane (1:2)] to give the title compound (60 mg, 44%) as a white solid.

Method BG

2-(2-Methoxyethyl)-6-(triphenylmethoxy)methylpyridine

A stirred solution of (methoxymethyl)triphenylphosphonium chloride (2.79 g, 8.13 mmol) in THF (50 mL) at 0° C. was treated dropwise with n-BuLi (1.6-M in hexanes, 5.08 mL, 8.13 mmol), stirred for 1 h, treated with a solution of 6-(triphenylmethoxy)methylpyridine-2-carboxaldehyde (1.54 g, 4.06 mmol) in THF (15 mL) and allowed to warm to room temperature overnight. The reaction was treated with saturated NH$_4$Cl solution (5 mL), diluted with water (50 mL), extracted with EtOAc (2×50 mL) and the combined organic phase diluted with iso-hexane (50 mL), dried (MgSO$_4$), filtered through silica and concentrated in vacuo to give 2-(2-methoxyethenyl)-6-(triphenylmethoxy)methylpyridine (1.58 g) as a yellow oil. A solution of this crude alkene and 10% Pd/C (216 mg, 0.203 mmol) in EtOAc (50 mL) was stirred under a hydrogen atmosphere for 16 h, filtered through Celite and concentrated in vacuo to give the title compound (1.08 g, 65%) as a yellow oil; NMR 5H (400 MHz, CDCl$_3$) 7.67-7.64 (1H, m), 7.52-7.49 (6H, m), 7.32-7.21 (10H, m), 7.09-7.07 (1H, m), 4.34 (2H, s), 3.69 (2H, t, J 6.5 Hz), 3.32 (3H, s) and 2.98 (2H, t, J 6.5 Hz); M/Z 410 (M+H)$^+$.

Method BH

2-Bromomethyl-6-(2-methoxyethyl)pyridine

A solution of 2-(2-methoxyethyl)-6-(triphenylmethoxy)methylpyridine (1.08 g, 2.64 mmol) in 4-M HCl in dioxan (10 mL, 40.0 mmol) was stirred for 4 h and concentrated in vacuo. The residue was partitioned between dichloromethane (15 mL) and saturated NaHCO$_3$ solution (15 mL), the aqueous phase was extracted with dichloromethane (10 mL) and the combined organic phase was dried (MgSO$_4$) and concentrated in vacuo to give 6-(2-methoxyethyl)pyridine-2-methanol. A solution of this product in dichloromethane (40 mL) at 0° C. was treated with triphenylphosphine (830 mg, 3.16 mmol) followed portionwise by carbon tetrabromide (1.31 g, 3.96 mmol), stirred for 1 h, concentrated in vacuo and purified by chromatography [SiO$_2$; isohexane:EtOAc (4:1)] to give the title compound (303 mg, 50%) as a yellow oil; NMR δ$_H$ (400 MHz, CDCl$_3$) 7.60 (1H, t, J 7.5 Hz), 7.28 (1H, d, J 7.5 Hz), 7.13 (1H, d, J 7.5 Hz), 4.53 (2H, s), 3.76 (2H, t, J 6.5 Hz), 3.35 (3H, s) and 3.05 (2H, t, J 6.5 Hz).

Experimental data for Examples 1-274 are provided in Table 2.

HPLC is carried out using the following conditions: Column. Waters Xterra RP 18 (50×4.6 mm); Particle size 5 μM; Mobile phase MeOH: 10 mM aq NH$_4$OAc (pH 7 buffer); Gradient 50:50 isocratic for 1 min. then linear gradient 50:50 to 80:20 over 5 min. then 80:20 isocratic for 3 min.; Flow rate 2.0 mL/min.; Detection wavelength λ=230 nM. Retention times are provided in Table 2.

TABLE 2

| Example | Method | Yield(%) | Physical Data |
|---|---|---|---|
| 1 | A | 65 | IR ν$_{max}$(Nujol)/cm$^{-1}$ 3403, 3329, 3134, 2925, 1656, 1634, 1582, 1565, 1463 and 1377; NMR δ$_H$(400MHz, DMSO) 6.83-6.87(1H, m), 7.12(2H, s), 7.89(1H, d, J3.1Hz), 8.09-8.10(1H, m), 15.52(1H, s); M/Z 203(M+H)$^+$. |
| 2 | B | 11 | IR ν$_{max}$(Nujol)/cm$^{-1}$ 2924, 2854, 1612, 1587, 1526, 1489, 1456, 1372, 1221 and 753; NMR δ$_H$(400MHz, DMSO) 4.98(2H, s), 5.14(2H, s), 5.71(2H, s), 6.85-6.87(1H, m), 7.00-7.14(3H, m), 7.14-7.46(9H, m), 7.89(1H, d, J3.5Hz), 8.16(1H, d<J1.0Hz); Anal. Calcd for C$_{29}$H$_{21}$F$_3$N$_6$O•0.25 H$_2$O: C, 65.59; H, 4.08; N, 15.83. Found: C, 65.46; H, 4.03; N, 15.76. |
| 3 | B | 22 | IR ν$_{max}$(Nujol)/cm$^{-1}$ 3480, 3312, 3195, 3118, 2925, 2854, 1652, 1609, 1581, 1487, 1456, 1436, 1027 and 759; NMR δ$_H$(400MHz, DMSO) 5.60(2H, s), 6.84-6.86(1H, m), 7.15-7.29(3H, m), 7.32-7.43(3H, m), 7.89(1H, d, J2.9Hz), 8.12(1H, s). |
| 4 | B | 9 | mp 221.0-221.1° C.; IR ν$_{max}$(Nujol)/cm$^{-1}$ 3470, 3310, 3191, 3144, 2924, 2854, 1642, 1610, 1521, 1463 and 1354; NMR δ$_H$(400MHz, DMSO) 5.85(2H, s), 6.87(1H, s), 7.37(2H, s), 7.63-7.73(2H, m), 7.91(1H, d, J2.8Hz), 8.13(1H, s), 8.18(1H, s), 8.20(1H, s). Anal. Calcd for C$_{15}$H$_{11}$N$_7$O$_3$: C, 50.57; H, 3.11; N, 27.52. Found: C, 50.99; H, 3.23; N, 27.21. |
| 5 | C | 92 | mp 259.8-259.9° C.; IR ν$_{max}$(Nujol)/cm$^{-1}$ 3452, 3367, 3318, 3185, 3142, 2922, 1651, 1602, 1514, 1463 and 1377; NMR δ$_H$(400MHz, DMSO) 5.09(2H, s), 5.49(2H, s), 6.35(1H, s), 6.41(1H, d, J7.5Hz), 6.45(1H, d, J8.0Hz), 6.85-6.86(1H, m), 6.96(1H, t, J8.0Hz), 7.30(2H, s), 7.90(1H, d, J3.5Hz), 8.11(1H, s). Anal. Calcd for C$_{15}$H$_{13}$N$_7$O: C, 56.63; H, 4.50; N, 30.82. Found: C, 56.82; H, 4.25; N, 30.57. |
| 6 | B | 21 | IR ν$_{max}$(Nujol)/cm$^{-1}$ 3405, 3328, 3211, 3155, 2925, 2854, 1719, 1603, 1577, 1463, 1023 and 731; NMR δ$_H$(400MHz, DMSO) 3.84(3H, s), 5.76(2H, s), 6.85-6.87(1H, m), 7.33-7.38(2H, s), 7.50-7.59(2H, m), 7.89-7.92(3H, s), 8.12-8.13(1H, m); Anal. Calcd for C$_{17}$H$_{14}$N$_6$O$_3$•0.25 H$_2$O: C, 57.54; H, 4.12; N, 23.68. Found: C, 57.42; H, 3.75; N, 23.37. |
| 7 | B | 27 | IR ν$_{max}$(Nujol)/cm$^{-1}$ 3506, 3309, 3189, 3131, 2925, 2854, 1635, 1606, 1580, 1502, 1417, 1204, 1025 and 762; NMR δ$_H$(400MHz, DMSO) 3.70(6H, s), 5.58(2H, s), 6.44(3H, s), 6.84-6.87(1H, m), 7.34(2H, s), 7.90(1H, d, J3.5Hz), 8.11-8.12(1H, m); Anal. Calcd for C$_{17}$H$_2$$_{16}$N$_6$O$_3$•0.5 H$_2$O: C, 56.50; H, 4.74; N, 23.26. Found: C, 56.44; H, 4.56; N, 22.98. |
| 8 | B | 21 | IR ν$_{max}$(Nujol)/cm$^{-1}$ 3488, 3314, 3146, 2922, 2853, 1667, 1608, 1583, 1463 and 1378; NMR δ$_H$(400MHz, DMSO) 5.79(2H, s), 6.84-6.87(1H, m), 7.01(1H, d, J4.0Hz), 7.05(1H, d, J4.0Hz), 7.38(2H, s), 7.89(1H, d, J3.5Hz), 8.11-8.13(1H, m). |
| 9 | D | 14 | IR ν$_{max}$(Nujol)/cm$^{-1}$ 3458, 3299, 3174, 3111, 2923, 1625, 1605, 1463 and 1377; NMR δ$_H$(400MHz, DMSO) 3.61(3H, s), 5.58(2H, s), 6.84-6.94(3H, m), 7.06-7.11(1H, d, J8.5Hz), 7.19(1H, t, J8.0Hz), 7.34(2H, s), 7.64-7.67(2H, m), 7.91(1H, d, J3.0Hz), 8.12(1H, s), 10.21(1H, s); Anal. Calcd for C$_{29}$H$_{21}$F$_3$N$_6$O•0.25 H$_2$O: C, 65.59; H, 4.08; N, 15.83. Found: C, 65.46; H, 4.03; N, 15.76. |
| 10 | E | 18 | IR ν$_{max}$(Nujol)/cm$^{-1}$ 3404, 3313, 3202, 3122, 2923, 2854, 1724, 1639, 1609, 1557, 1456, 1407 and 1379; NMR δ$_H$(400MHz, DMSO) 4.60(2H, d, J6.0Hz), 6.86-6.89(1H, m), 7.25-7.32(1H, m), 7.33-7.44(4H, m), 7.67(2H, s), 7.91(1H, d, J3.5Hz), 8.14-8.16(1H, m), 9.25(1H, t, J6.0Hz). |
| 11 | B | 40 | IR ν$_{max}$(Nujol)/cm$^{-1}$ 3327, 3207, 2924, 2854, 1650, 1602, 1583, 1566, 1513 and 1487; NMR δ$_H$(400MHz, DMSO) 3.72(3H, s), 5.63(2H, s), 6.80(1H, d, J7.5Hz), 6.85-6.89(3H, m), 7.26(1H, t, J7.5Hz), 7.33(2H, s), 7.90(1H, d, J3.5Hz), 8.11(1H, s); Anal. Calcd for C$_{16}$H$_{14}$N$_6$O$_2$•0.25 H$_2$O: C, 58.80; H, 4.47; N, 25.71. Found: C, 58.90; H, 4.40; N, 25.75. |
| 12 | B | 21 | IR ν$_{max}$(Nujol)/cm$^{-1}$ 3374, 3311, 3202, 1636, 1606, 1586, 1530, 1511, 1465, 1439, 1377 and 1343; NMR δ$_H$(400MHz, DMSO) 6.03(2H, s), 6.86-6.89(1H, m), 6.98(1H, d, J7.5Hz), 7.36(2H, s), 7.60-7.73(2H, m), 7.92(1H, d, J3.5Hz), 8.14(1H, s), 8.2(1H, d, J8.0Hz): Anal. Calcd for C$_{15}$H$_{11}$N$_7$O$_3$•0.35 H$_2$O: C, 52.43; H, 3.43; N, 28.54. Found: C, 52.51; H, 3.33; N, 28.21. |
| 13 | C | 67 | IR ν$_{max}$(Nujol)/cm$^{-1}$ 3489, 3313, 3191, 1638, 1603, 1505, 1460 and 1378; NMR δ$_H$(400MHz, DMSO) 5.27(2H, s), 5.47(2H, s), 6.50(1H, t, J7.5Hz), 6.67-6.78(2H, m), 6.86(1H, s), 7.01(1H, t, J7.0Hz), 7.36(2H, s), 7.90(1H, d, J3.0Hz), 8.12(1H, s). |
| 14 | F | 35 | IR ν$_{max}$(Nujol)/cm$^{-1}$ 3447, 3327, 3205, 2922, 2853, 1725, 1652, 1611 and 1458; NMR δ$_H$(400MHz, DMSO) 8.13(1H, d, J1.0Hz), 7.90(1H, d, J3.5Hz), 7.38(2H, s), 6.87-6.85(1H, m), 5.40(2H, s), 4.18(2H, q, J7.0Hz) and 1.21(3H, t, J7.0Hz); Anal. Calcd for C$_{12}$H$_{12}$N$_6$O$_2$+0.2 H$_2$O: C, 49.38; H, 4.28, N, 28.79. Found: C, 49.25; H, 4.09; N, 28.47. |
| 15 | B | 15 | IR ν$_{max}$(Nujol)/cm$^{-1}$ 3490, 3307, 3189, 2230, 1959, 1728, 1642, 1611, 1583, 1565, 1463, 1377, 1283, 1234, 1030 and 761; NMR δ$_H$(400MHz, DMSO) 5.75(2H, s), 6.82-6.89(1H, m), 7.35(2H, s), 7.57-7.59(2H, m), 7.79-7.81(2H, m), 7.91(1H, d, J3.5Hz), 8.12(1H, s). |

TABLE 2-continued

| Example | Method | Yield(%) | Physical Data |
|---|---|---|---|
| 16 | B | 6 | IR ν$_{max}$(Nujol)/cm$^{-1}$ 3309, 3184, 2726, 1639, 1608, 1585, 1456, 1377, 1026, 1002, 953 and 750; NMR δ$_H$(400MHz, DMSO) 2.22(2H, quin, J7.0Hz), 2.67(2H, t, J7.0Hz), 4.45(2H, t, J7.0Hz), 6.83-6.88(1H, m), 7.23-7.35(3H, m), 7.66(1H, dt, J8.0, 2.0Hz), 7.89(1H, dd, J3.5, 1.0Hz), 8.10-8.13(1H, m); Anal. calcd for C$_{16}$H$_{15}$N$_7$O•0.6 H$_2$O: C, 57.86; H, 4.92; N, 29.52. Found: C, 57.58; H, 4.53; N, 29.66. |
| 17 | B | 7 | IR ν$_{max}$(Nujol)/cm$^{-1}$ 3379, 3336, 3208, 1655, 1604, 1513, 1456, 1325, 11687, 1124, 1025 and 755; NMR δ$_H$(400MHz, DMSO) 5.79(2H, s), 6.83-6.88(1H, m), 7.36(2H, s), 7.53(1H, d, J7.5Hz), 7.60(1H, t, J7.5Hz), 7.67-7.76(2H, m), 7.91(1H, d, J3.5Hz), 8.13(1H, s); Anal. Calcd. for C$_{16}$H$_{11}$F$_3$N$_6$O: C, 53.34; H, 3.08; N, 23.31. Found: C, 53.38; H, 3.18; N, 23.15. |
| 18 | G | 100 | IR ν$_{max}$(Nujol)/cm$^{-1}$ 3451, 3206, 2361, 2261, 1655, 1604, 1459, 1378, 1195, 1028 and 774; NMR δ$_H$(400MHz, DMSO) 5.57(2H, s), 6.57-6.63(1H, m), 6.65-6.74(2H, m), 6.83-6.88(1H, m), 7.14(1H, t, J7.5Hz), 7.91(1H, d, J 3.0Hz), 8.12(1H, d, J1.0Hz). |
| 19 | J | 77 | mp 291.8-292.0° C.; IR ν$_{max}$(DR)/cm$^{-1}$ 3436, 3178, 1651, 1615, 1398, 1226, 1029 and 977; NMR δ$_H$(400MHz, DMSO) 15.5-15.3(1H, br s), 7.84(1H, d, J 3.5Hz), 7.07(2H, br s), 6.48(1H, dd, J3.5, J1.0Hz), 2.44(3H, s). |
| 20 | B | 47 | mp 213.5.-213.7° C.; IR ν$_{max}$(DR)/cm$^{-1}$ 3300, 3218, 3098, 2957, 2927, 2744, 2368, 1645, 1602, 1570, 1537, 1508, 1490, 1438, 1328 and 1233; NMR δ$_H$(400MHz, DMSO) 7.86(1H, d, J3.0Hz), 7.43-736(1H, m), 7.31(2H, br s), 7.28-7.15(3H, m), 6.50(1H, dd, J1.0, J3.5Hz), 5.68(2H, s) and 2.45(3H, s). |
| 21 | K | 99 | IR ν$_{max}$(DR)/cm$^{-1}$ 3151, 2360, 1654, 1182, 998, 824, 681, and 572; NMR δ$_H$(400MHz, DMSO) 10.28(1H, d, J2.0Hz) and 9.73(1H, d, J2.5Hz) |
| 22 | A | 8 | IR ν$_{max}$(DR)/cm$^{-1}$ 3479, 3289, 3169, 1597, 1502, 1226, 1119, 999, 880 and 757; NMR δ$_H$(400MHz, DMSO) 9.43(1H, s), 9.25(1H, s), 7.48-7.34(3H, m) 7.30-7.22(2H, m), 7.21-7.15(1H, m) and 5.72(2H, s). |
| 23 | B | 20 | mp 187.3-187.7° C.; IR ν$_{max}$(DR)/cm$^{-1}$ 3993, 3489, 3319, 3197, 2951, 2725, 2353, 1954, 1719, 1633, 1604, 1503, 1420, 1232, 1032 and 740; NMR δ$_H$(400MHz, DMSO) 2.27(3H, s) 5.62(2H, s), 6.82-6.88(1H, m), 7.02-7.16(3H, m), 7.24(1H, t, J7.5Hz), 7.33(2H, s), 7.90(1H, d, J3.5Hz) 8.12(1H, s). |
| 24 | N | 46 | mp 196.9-197.1° C.; IR ν$_{max}$(DR)/cm$^{-1}$ 3448, 3321, 3200, 1649, 1616, 1509, 1488; NMR δ$_H$(400MHz, DMSO) 8.49-8.47(1H, m), 8.12-8.11(1H, m), 7.91(1H, d, J3.5Hz), 7.81-7.77(1H, m), 7.34-7.30(1H, m), 7.27(2H, br s), 7.24(1H, d, J8.0Hz), 6.86-6.85(1H, m), 5.77(2H, s). |
| 25 | N | 50 | IR ν$_{max}$(DR)/cm$^{-1}$ 3326, 3211, 2956, 2856, 1641, 1612, 1507, 1491; NMR δ$_H$(400MHz, CDCl$_3$) 8.77-8.76(1H, m), 8.58-8.56(1H, m), 8.08(1H, d, J3.5Hz), 7.78(1H, m), 7.75-7.72(1H, m), 7.29-7.25(1H, m), 6.71-6.69(1H, m), 5.68(2H, s), 5.37(2H, br s); Anal. Calcd for C$_{14}$H$_{11}$N$_7$O•0.2 H$_2$O•0.4 C$_4$H$_8$O$_2$: C, 56.41; H, 4.43, N, 29.52. Found: C, 56.10; H, 4.33; N, 29.52. |
| 26 | O | 85 | mp 291.0-291.1° C.; IR ν$_{max}$(Nujol)/cm$^{-1}$ 3401, 3317, 3205, 2995, 1714, 1646, 1615, 1587, 1483 and 1247; NMR δ$_H$(400MHz, DMSO) 13.58-13.31(1H, s), 8.12(1H, s), 7.91(1H, d, J3.5Hz), 7.36(2H, s), 6.87-6.86(1H, m) and 5.29(2H, s); Anal. Calcd for C$_{10}$H$_8$N$_6$O$_3$•0.6 H$_2$O: C, 44.32; H, 3.42, N, 31.01. Found: C, 44.26; H, 3.07; N, 30.74. |
| 27 | B | 19 | mp 209.9-210.1° C.; IR ν$_{max}$(DR)/cm$^{-1}$ 3504, 3312, 3201, 2948, 1611, 1503, 1435, 1279, 1220, 1025 and 755; NMR δ$_H$(400MHz, DMSO) 5.69(2H, s), 6.82-6.87(1H, m), 7.19-7.25(1H, m), 7.33(2H, s), 7.37-7.40(3H, m), 7.90(1H, d, J3.5Hz), 8.10-8.13(1H, m). Anal. Calcd for C$_{15}$H$_{11}$N$_6$OCl•0.2 H$_2$O: C, 54.54; H, 3.48; N, 25.44. Found: C, 54.69; H, 3.33; N, 25.09. |
| 28 | K | 40 | IR ν$_{max}$(DR)/cm$^{-1}$ 3282, 2852, 1630, 1368, 1120, 871and 618; NMR δ$_H$(400MHz, DMSO) 7.94(1H, d, J2.5Hz), 7.45-7.36(2H, m), 7.29-7.22(2H, m), 7.21-7.16(1H, m) and 5.71(2H, s). |
| 29 | B | 8 | IR ν$_{max}$(DR)/cm$^{-1}$ 3999, 3483, 3438, 3310, 3207, 2950, 2732, 2452, 1846, 1657, 1486, 1312, 1030 and 754; NMR δ$_H$(400MHz, DMSO) 4.02(3H, s), 6.81-6.88(1H, m), 7.25(2H, s), 7.88(1H, d, J3.5Hz), 8.09-8.11(1H, m). |
| 30 | P | 39 | IR ν$_{max}$(Nujol)/cm$^{-1}$ 3500-3200, 2946, 2835, 1700 and 1523; NMR δ$_H$(400MHz, DMSO) 8.11(1H, s), 7.89(1H, d, J3.5Hz), 7.69(1H, s), 7.34(1H, s), 7.26(2H, s), 6.87-6.84(1H, m) and 5.08(2H, s). |
| 31 | P | 48 | IR ν$_{max}$(Nujol)/cm$^{-1}$ 3457, 3313, 1666, 1617, 1523 and 1442; NMR δ$_H$(400MHz, DMSO) 10.68(1H, s), 8.12(1H, s), 7.91(1H, d, J3.5Hz), 7.75(1H, s), 7.45(1H, d, J8.0Hz), 7.37(1H, t, J8.0Hz), 7.30(2H, s), 7.15(1H, d, J8.0Hz), 6.88-6.84(1H, m and 5.39(2H, s); Anal. Calcd for C$_{16}$H$_{12}$N$_7$O$_2$Cl•0.8 H$_2$O: C, 50.02; H, 3.57, N, 25.27. Found: C, 50.15; H, 3.48; N, 25.12. |
| 32 | N | 76 | mp 191.4-192.0° C.; IR ν$_{max}$(DR)/cm$^{-1}$ 3511, 3306, 3194, 2955, 1638, 1476; NMR δ$_H$(400MHz, DMSO) 8.12-8.11(1H, m), 7.91(1H, dd, J3.5, 1.0Hz), 7.66(1H, dd, J8.0, 7.0Hz), 7.27(2H, br s), 6.87-6.85(1H, m), 6.73-6.70(2H, m), 5.69(2H, s), 3.68(3H, s); Anal. Calcd for C$_{15}$H$_{13}$N$_7$O$_2$•0.2 C$_4$H$_8$O$_2$: C, 55.66; H, 4.32, N, 28.76. Found: C, 55.88; H, 4.17; N, 28.59. |
| 33 | B | 11 | mp 204.1-204.2° C.; IR ν$_{max}$(DR)/cm$^{-1}$ 3490, 3321, 3200, 2923, 2711, 2490, 1749, 1605, 1502, 1376, 1272, 1034 and 761; NMR δ$_H$(400MHz, DMSO) 5.83(2H, s), 6.83-6.86(1H, m), 7.01(1H, dd, J5.0, 3.5Hz), 7.16(1H, dd, J3.5, 1.0Hz), 7.34(2H, s), 7.48(1H, dd, J5.0, 1.5Hz), 7.89(1H, d, J3.5Hz), 8.09-8.12(1H, m). |
| 34 | Q | 30 | mp 225-230° C.; IR ν$_{max}$(DR)/cm$^{-1}$ 3520, 3344, 1734, 1611, 1438, 1240, 996, 833 and 761; NMR δ$_H$(400MHz, DMSO) 8.26(1H, d, J3.0Hz), 8.15(1H, d, J |

TABLE 2-continued

| Example | Method | Yield(%) | Physical Data |
|---|---|---|---|
| | | | 3.0Hz), 7.50-7.44(2H, br s), 7.42-7.36(1H, m), 7.29-7.21(1H, m), 7.21-7.15(1H, m) and 5.73(2H, s). |
| 35 | H | 51 | mp 174.0-174.2° C.; IR $\nu_{max}$(DR)/cm$^{-1}$ 3473, 3317, 3188, 2740, 1736, 1648, 1243, 1004 and 752; NMR $\delta_H$(400MHz, DMSO) 8.68(1H, dd, J4.0, 1.5Hz), 7.99(1H, dd, J5.0, 1.0Hz), 7.43-7.35(2H, m), 7.31-7.16(5H, m) and 5.71(2H, s). |
| 36 | C | 50 | mp 231.7-234.0° C.; IR $\nu_{max}$(DR)/cm$^{-1}$ 3498, 3404, 3309, 2931, 1607, 1539, 1498, 1317, 1101 and 1027; NMR $\delta_H$(400MHz, DMSO) 7.86(1H, dd, J0.5, 3.5Hz), 7.24(2H, br s,), 6.96(1H, t, J7.8Hz), 6.50(1H, dd, J1.0, 3.5Hz), 6.48-6.43(1H, m), 6.43-6.38(1H, m), 6.36(1H, t, J1.7Hz), 5.46(2H, s), 5.07(2H, br s) and 2.43(3H, s). |
| 37 | N | 60 | mp 200.8-218.9° C.; NMR $\delta_H$(400MHz, DMSO) 8.12-8.11(1H, m), 7.91(1H, d, J3.5Hz), 7.64(1H, t, J7.5Hz), 7.29(2H, br s), 7.18(1H, d, J7.5Hz), 6.90(1H, d, J7.5Hz), 6.86-6.85(1H, m), 5.70(2H, s) and 2.42(3H, s). |
| 38 | Q | 35 | mp 242.0-242.1° C.; IR $\nu_{max}$(DR)/cm$^{-1}$ 3513, 3294, 1570, 1234, 999 and 755; NMR $\delta_H$(400MHz, DMSO) 7.96(1H, s), 7.46-7.34(3H, m), 7.30-7.13(3H, m), 5.72(2H, s) and 2.60(3H, s). |
| 39 | B | 26 | IR $\nu_{max}$(Nujol)/cm$^{-1}$ 3464, 3340, 3189, 2966, 2748, 1692, 1643 and 1605; NMR $\delta_H$(400MHz, DMSO) 8.11-8.09(1H, m), 7.90(1H, d, J3.5Hz), 7.33-7.24(4H, m), 7.19-7.12(2H, m), 7.09(1H, s), 6.86-6.84(1H, m), 5.64(2H, s), 4.07(2H, d, J6.0Hz) and 1.33(9H, s). |
| 40 | B | 12 | IR $\nu_{max}$(Nujol)/cm$^{-1}$ 3474, 3323, 3184, 3006, 2971, 2941, 2837, 1648, 1606 and 1496; NMR $\delta_H$(400MHz, DMSO) 8.13-8.10(1H, m), 7.90(1H, d, J3.5Hz), 7.32(2H, s), 6.98(1H, d, J9.0Hz), 6.89-6.84(2H, m), 6.48(1H, d, J3.0Hz), 5.57(2H, s), 3.76(3H, s) and 362(3H, s). |
| 41 | B | 32 | mp 213.8-213.9° C.; IR $\nu_{max}$(DR)/cm$^{-1}$ 3996, 3654, 3507, 3320, 2930, 2562, 2621, 1944, 1837, 1676, 1428, 1230, 1095, 1026 and 797; NMR $\delta_H$(400MHz, DMSO) 5.65(2H, s), 6.81-6.86(1H, m), 7.16(2H, t, J8.5Hz), 7.31(2H, s), 7.44-7.56(1H, m), 7.86(1H, dd, J3.5, 1.0Hz), 8.07-8.13(1H, m). Anal. Calcd for $C_{15}H_{10}N_6OF_2$: C, 54.88; H, 3.07; N, 25.59. Found: C, 54.57; H, 3.05; N, 25.23. |
| 42 | Q | 29 | mp 265.7-26.2° C.; IR $\nu_{max}$(DR)/cm$^{-1}$ 3491, 3370, 3120, 1614, 1232, 972, 753 and 514; NMR $\delta_H$(400MHz, DMSO) 7.72(1H, s), 7.51-7.43(2H, s), 7.42-7.35(1H, m), 7.30-7.14(3H, m), 5.73(2H, s) and 2.55(3H, s). |
| 43 | H | 65 | mp 281.1-280.2° C.; IR $\nu_{max}$(DR)/cm$^{-1}$ 3466, 3326, 1641, 1503, 1379, 1240, 1056, and 825; NMR $\delta_H$(400MHz, DMSO) 15.5(1H, br s), 8.6(1H, dd, J1.0, 4.0Hz), 7.96(1H, dd, J1.0, 5.0Hz), 7.36(1H, dd, J4.0, 5.0Hz) and 7.0(2H, br s). |
| 44 | S/T | 28 | IR $\nu_{max}$(DR)/cm$^{-1}$ 3255, 1686, 1590, 1458; NMR $\delta_H$(400MHz, DMSO) 11.24(1H, s), 8.95-8.94(1H, m), 8.37-8.35(1H, m), 8.08-8.07(1H, m), 7.96-7.95(1H, m), 7.68(1H, d, J8.0Hz), 6.85-6.84(1H, m). |
| 45 | A | 59 | mp 190.4-190.8° C.; IR $\nu_{max}$(DR)/cm$^{-1}$ 3322, 3162, 1665, 1576, 1351, 1119, 1000, 809 and 604; NMR $\delta_H$(400MHz, DMSO) 9.44(1H, s), 9.26(1H, s), 8.24-8.16(2H, m), 7.95(1H, s), 7.74-7.63(2H, m), 7.45(2H, br s) and 5.87(2H, s). |
| 46 | K | 99 | IR $\nu_{max}$(Nujol)/cm$^{-1}$ 2967, 1651 and 1463; NMR $\delta_H$(400MHz, DMSO) 8.35-8.24(3H, s), 8.14-8.11(1H, m), 7.91(1H, d, J3.5Hz), 7.47-7.39(2H, m), 7.36-7.31(2H, s), 6.88-6.84(1H, m), 5.67(2H, s) and 3.98(2H, q, J5.5Hz); Anal. Calcd for $C_{16}H_{15}N_7O\cdot 2HCl\cdot 0.9\ H_2O$: C, 46.82; H, 4.62; N, 23.89. Found: C, 47.10; H, 4.40; N, 23.84. |
| 47 | B | 26 | IR $\nu_{max}$(Nujol)/cm$^{-1}$ 3375, 3194, 2929, 2753, 1732, 1657, 1515, 1400 and 1334; NMR $\delta_H$(400MHz, DMSO) 8.14-8.11(1H, m), 7.90(1H, d, J3.0Hz), 7.45-7.29(6H, m), 6.88-6.84(1H, m), 5.71(2H, s), 2.95(3H, s) and 2.85(3H, s); Anal. Calcd for $C_{18}H_{17}N_7O_2\cdot 0.5\ H_2O$: C, 58.06; H, 4.87, N, 26.33. Found: C, 58.16; H, 4.65; N, 26.06. |
| 48 | C | 49 | mp 265.9-266.0° C.; IR $\nu_{max}$(DR)/cm$^{-1}$ 3448, 3363, 3316, 3189, 1645, 1597, 1511, 1440 and 1103; NMR $\delta_H$(400MHz, DMSO) 8.69(1H, dd, J1.2, 3.7Hz), 7.95(1H, dd, J1.2, 5.0Hz), 7.38(1H, dd, J3.9, 5.0Hz), 7.26(2H, br s), 6.97(1H, t, J7.7Hz), 6.48-6.45(1H, m), 6.44-6.40(1H, m), 6.36(1H, t, J1.7Hz), 5.5(2H, s) and 5.11(2H, br s). |
| 49 | B | 8 | IR $\nu_{max}$(Nujol)/cm$^{-1}$ 3488, 3319, 2952, 1641, 1503 and 1420; NMR $\delta_H$(400MHz, DMSO) 8.49-8.42(1H, m), 8.14(1H, d, J1.0Hz), 7.91(1H, d, J3.5Hz), 7.78-7.71(2H, m), 7.48-7.32(4H, m), 6.88-6.85(1H, m), 5.72(2H, s) and 2.75(3H, d, J4.5Hz). |
| 50 | C | 60 | mp 228.2-228.3° C.; IR $\nu_{max}$(DR)/cm$^{-1}$ 3441, 3318, 3197, 1738, 1648, 1515, 1122, 1006, 888 and 747; NMR $\delta_H$(400MHz, DMSO) 9.45(1H, s), 9.27(1H, s), 7.44(2H, br s), 6.97(1H, t, J8.0Hz), 6.49-6.39(2H, m), 6.35(1H, s), 5.52(2H, s), and 5.13(2H, s). |
| 51 | N | 70 | mp 182.9-183.1° C.; IR $\nu_{max}$(DR)/cm$^{-1}$ 3488, 3311, 3199, 2943, 1611, 1504; NMR $\delta_H$(400MHz, DMSO) 8.10(1H, d, J3.5Hz), 7.78(1H, m), 7.01(1H, t, J 9.0Hz), 6.79(1H, dt, J9.0, 3.5Hz), 6.75-6.73(1H, m), 6.71-6.70(1H, m), 5.70(2H, s), 5.38(2H, br s), 3.71(3H, s); Anal. Calcd for $C_{16}H_{13}N_6O_2F\cdot 0.1\ H_2O$: C, 56.17; H, 3.89, N, 24.56. Found: C, 56.27; H, 3.85; N, 24.22. |
| 52 | P | 70 | mp 263.8-264.0° C.; IR $\nu_{max}$(Nujol)/cm$^{-1}$ 3305, 3192, 1705, 1635 and 1442; NMR $\delta_H$(400MHz, DMSO) 11.04(1H, s), 8.37(1H, d, J4.0Hz), 8.15-8.11(1H, m), 7.96(1H, d, J7.0Hz), 7.91(1H, d, J3.0Hz), 7.79(1H, dt, J7.5, 2.0Hz), 7.32(2H, s), 7.18-7.11(1H, m), 6.88-6.85(1H, m) and 5.46(2H, s). |

TABLE 2-continued

| Example | Method | Yield(%) | Physical Data |
| --- | --- | --- | --- |
| 53 | P | 77 | mp 256.1-256.4° C.; IR $\nu_{max}$(Nujol)/cm$^{-1}$ 3454, 3311, 2993, 1664, 1488 and 1439; NMR $\delta_H$(400MHz, DMSO) 8.86(1H, t, J6.0Hz), 8.50(1H, d, J4.5Hz), 8.12(1H, s), 7.90(1H, d, J3.5Hz), 7.79(1H, dt, J7.5, 1.5Hz), 7.41-7.25(4H, m), 6.88-6.84(1H, m) and 5.23(2H, s), 4.41(2H, d, J6.0Hz); Anal. Calcd for $C_{16}H_{14}N_8O_2\cdot0.25\ H_2O$: C, 54.16; H, 4.12, N, 31.58. Found: C, 54.01; H, 4.03; N, 31.44. |
| 54 | P | 61 | mp 292.2-292.3° C.; IR $\nu_{max}$(Nujol)/cm$^{-1}$ 3433, 3323, 2975, 2941, 1673 and 1446; NMR $\delta_H$(400MHz, DMSO) 10.50(1H, s), 8.13(1H, s), 7.92(1H, d, J3.0Hz), 7.57(2H, d, J7.5Hz), 7.37-7.27(4H, m), 7.08(1H, t, J7.5Hz), 6.89-6.84(1H, m) and 5.38(2H, s). |
| 55 | B | 18 | mp 264.5-264.8° C.; IR $\nu_{max}$(DR)/cm$^{-1}$ 4007, 3489, 3308, 3190, 1649, 1552, 1433, 1349, 1227, 1082, 1030 and 729; NMR $\delta_H$(400MHz, DMSO) 5.99(2H, s), 6.84-6.89(1H, m), 7.39(2H, s), 7.91(1H, d, J3.5Hz), 8.11-8.15(1H, m), 8.59(2H, d, J2.0Hz), 8.78(1H, t, J2.0Hz). |
| 56 | B | 30 | IR $\nu_{max}$(DR)/cm$^{-1}$ 3508, 3300, 3181, 1611, 1572, 1504, 1420, 1352, 1225 and 1030; NMR $\delta_H$(400MHz, DMSO) 8.22-8.16(2H, m), 7.86(1H, d, J3.2Hz), 7.63-7.72(2H, m), 7.35(2H, br s), 6.50(1H, dd, J1.0, 3.5Hz), 5.82(2H, s) and 2.45(3H, s). |
| 57 | B |  | mp 188.8-188.9° C.; IR $\nu_{max}$(Nujol)/cm$^{-1}$ 3492, 3302, 3189, 2951, 1635 and 1505; NMR $\delta_H$(400MHz, DMSO) 8.14-8.10(1H, m), 7.90(1H, d, J3.0Hz), 7.47-7.32(3H, m), 7.20(1H, q, J7.0Hz), 7.05(1H, t, J7.0Hz), 6.88-6.83(1H, m) and 5.75(2H, s). |
| 58 | B | 15 | mp 207.0-207.4° C.; IR $\nu_{max}$(Nujol)/cm$^{-1}$ 3496, 3229, 3201, 3057, 2965, 2743, 1785 and 1615; NMR $\delta_H$(400MHz, DMSO) 8.13-8.10(1H, m), 7.89(1H, d, J 3.5Hz), 7.40-7.27(4H, m), 7.08(1H, dt, J8.5, 3.0Hz), 6.87-6.84(1H, m) and 5.66(2H, s). |
| 59 | B | 30 | mp 187.9-188.7° C. IR $\nu_{max}$(DR)/cm$^{-1}$ 3338, 3202, 1659, 1607, 1567, 1523, 1457, 1424, 1321, 1204 and 1025; NMR $\delta_H$(400MHz, DMSO) 7.88(1H, d, J 3.5Hz), 7.65(1H, t, J7.5Hz), 7.29(2H, br s), 7.18(1H, d, J7.5Hz), 6.89(1H, d, J8.0Hz), 6.51(1H, d, J3.0Hz), 5.69(2H, s), 2.46(3H, s) and 2.42(3H, s); Anal. Calcd for $C_{16}H_{15}N_7O\cdot0.2\ H_2O$: C, 59.14; H, 4.78, N, 30.17. Found: C, 59.37; H, 4.66; N, 29.86. |
| 60 | B | 33 | mp 209.7-209.8° C.; IR $\nu_{max}$(DR)/cm$^{-1}$ 3404, 3330, 3226, 3109, 2961, 2926, 2742, 1637, 1601, 1508, and 1474; NMR $\delta_H$(400MHz, DMSO) 7.83(1H, dd, J 0.5, 3.2Hz), 7.54-7.46(1H, m), 7.3(2H, br s), 7.16(2H, t, J8.2Hz), 6.49(1H, dd, J1.0, 3.5Hz), 5.63(2H, s) and 2.44(3H, s). |
| 61 | B | 20 | mp 193.8-194.1° C.; IR $\nu_{max}$(DR)/cm$^{-1}$ 3336, 3218, 2980, 2753, 2432, 1734, 1654, 1611, 1438, 1381, 1331 and 1224; NMR $\delta_H$(400MHz, DMSO) 7.86(1H, d, J3.0Hz), 7.49(1H, dd, J1.5, 5.0Hz), 7.3(2H, br s), 7.16(1H, dd, J1.0, 3.5Hz), 7.0(1H, dd, J3.5, 5.0Hz), 6.50(1H, dd, J1.0, 3.5Hz), 5.82(2H, s) and 2.45(3H, s). |
| 62 | B | 40 | mp 210.4-210.5° C.; IR $\nu_{max}$(DR)/cm$^{-1}$ 3511, 3300, 3179, 2940, 2740, 2688, 1986, 1832, 1734, 1634, 1500 and 1436; NMR $\delta_H$(400MHz, DMSO) 7.87(1H, d, J3.5Hz), 7.40-7.37(3H, m), 7.30(2H, br s), 7.23-7.18(1H, m), 6.51(1H, dd, J1.0, 5.1Hz), 5.68(2H, s) and 2.45(3H, s). |
| 63 | N | 41 | mp 201.1-201.2° C.; IR $\nu_{max}$(DR)/cm$^{-1}$ 3453, 3317, 3195, 1638, 1599, 1510, 1434; NMR $\delta_H$(400MHz, DMSO) 8.28(1H, d, J6.0Hz), 8.12-8.11(1H, m), 7.91(1H, d, J3.5Hz), 7.29(2H, br s), 6.91(1H, dd, J6.0, 2.5Hz), 6.87-6.85(2H, m), 5.71(2H, s), 3.81(3H, s). |
| 64 | B | 9 | mp 218.0-218.1° C.; IR $\nu_{max}$(DR)/cm$^{-1}$ 3999, 3376, 3209, 2916, 2747, 2326, 1957, 1782, 1610, 1515, 1278, 1023 and 763; NMR $\delta_H$(400MHz, DMSO) 2.42(3H, s), 5.64(2H, s), 6.86(2H, s), 6.91(1H, d, J7.5Hz), 7.13(1H, t, J7.0Hz), 7.17-7.26(2H, m), 7.32(2H, s), 7.90(1H, d, J3.5Hz), 8.12(1H, s). |
| 65 | B | 25 | mp 208.1-208.2° C.; IR $\nu_{max}$(Nujol)/cm$^{-1}$ 3347, 3199, 2981, 2932, 2764, 2719, 1660 and 1612; NMR $\delta_H$(400MHz, DMSO) 8.14-8.11(1H, m), 7.90(1H, d, J 3.5Hz), 7.41-7.22(4H, m), 7.15-7.09(1H, m), 6.87-6.83(1H, m) and 5.69(2H, s); Anal. Calcd for $C_{15}H_{10}F_2N_6O\cdot0.5\ H_2O$: C, 53.42; H, 3.29, N, 24.92. Found: C, 53.72; H, 3.06; N, 24.77. |
| 66 | W | 25 | mp 243.4-243.9° C.; IR $\nu_{max}$(Nujol)/cm$^{-1}$ 4008, 3483, 3316, 3196, 1734, 1599 and 1505; NMR $\delta_H$(400MHz, DMSO) 8.32(1H, dd, J9.0, 3.0Hz), 8.21(1H, d, J3.0Hz), 8.12-8.10(1H, m), 7.68(1H, d, J3.5Hz), 7.31(1H, d, J9.0Hz), 7.00(2H, s), 6.85-6.82(1H, m), 5.94(2H, s) and 3.93(3H, s); Anal. Calcd for $C_{16}H_{13}N_7O_4$: C, 52.32; H, 3.57, N, 26.68. Found: C, 52.16; H, 3.56; N, 26.67. |
| 67 | B | 32 | mp 252.9-253.0° C.; IR $\nu_{max}$(DR)/cm$^{-1}$ 3511, 33260, 2945, 1732, 1626, 1573, 1499, 1422, 1327 and 1222; NMR $\delta_H$(400MHz, DMSO) 8.4(1H, d, J4.5Hz), 7.87(1H, d, J3.0Hz), 7.77-7.71(2H, m), 7.47-7.38(2H, m), 7.3(2H, br s), 6.50(1H, dd, J1.0, 3.5Hz), 5.70(2H, s), 2.75(3H, d, J4.5Hz) and 2.45(3H, s). |
| 68 | R | 58 | mp 228.1-229.3° C.; IR $\nu_{max}$(Nujol)/cm$^{-1}$ 3508, 3263, 2990, 2946, 2837, 1646 and 1419; NMR $\delta_H$(400MHz, DMSO) 8.29(1H, t, J6.0Hz), 8.14-8.09(1H, m), 7.90(1H, d, J3.5Hz), 7.33(2H, s), 7.29(1H, t, J7.5Hz), 7.21-7.09(3H, m), 6.88-6.83(1H, m), 5.64(2H, s), 4.20(1H, d, J6.0Hz) and 1.83(3H, s); Anal. Calcd for $C_{18}H_{17}N_7O_2\cdot0.25\ H_2O$: C, 58.77; H, 4.79, N, 26.65. Found: C, 58.86; H, 4.54; N, 26.24. |
| 69 | X | 2 | NMR $\delta_H$(400MHz, DMSO) 8.53(1H, s), 7.69(1H, s), 7.58(2H, br s), 7.45-7.36(1H, m), 7.29-7.22(2H, m), 7.21-7.15(1H, m) and 5.73(2H, s); Retention time 1.14 min. |

TABLE 2-continued

| Example | Method | Yield(%) | Physical Data |
|---|---|---|---|
| 70 | N | 39 | NMR δ$_H$(400MHz, DMSO) 8.45(1H, d, J5.0, 1.0Hz), 8.13-8.12(1H, m), 7.91(1H, dd, J3.5, 1.0Hz), 7.51-7.48(2H, m), 7.31(2H, br s), 6.87-6.85(1H, m), 5.80(2H, s); Retention time 1.75 min. |
| 71 | N | 65 | mp 228.7-228.9° C.; IR ν$_{max}$(DR)/cm$^{-1}$ 3408, 3326, 3210, 1648, 1614, 1511; NMR δ$_H$(400MHz, DMSO) 8.13-8.12(1H, m), 8.02-7.96(1H, m), 7.92(1H, d, J3.5Hz), 7.33(2H, br s), 7.20(1H, dd, J7.5, 2.0Hz), 7.12(1H, dd, J8.0, 2.0Hz), 6.87(1H, dd, J3.5, 1.0Hz), 5.75(2H, s); Anal. Calcd for C$_{14}$H$_{11}$N$_7$OF•0.2 H$_2$O•0.1C$_4$H$_{10}$O$_2$: C, 53.66; H, 3.57, N, 30.42. Found: C, 53.68; H, 3.44; N, 30.24. |
| 72 | B | 28 | mp 195.4-196.5° C.; IR ν$_{max}$(DR)/cm$^{-1}$ 3328, 3210, 2956, 2836, 2740, 1736, 1648, 1608, 1438, 1322 and 1250; NMR δ$_H$(400MHz, DMSO) 7.87(1H, d, J 3.5Hz), 7.33-7.25(3H, m), 7.05(1H, d, J7.5Hz), 6.88(1H, td, J1.0, 7.5Hz), 6.87(1H, dd, J2.0, 7.5Hz), 6.50(1H, dd, J1.0, 3.5Hz), 5.58(2H, s), 3.83(3H, s) and 2.45(3H, s). |
| 73 | B | 28 | mp 178.7-179.3° C.; IR ν$_{max}$(DR)/cm$^{-1}$ 3468, 3346, 3172, 2988, 2747, 2130, 1943, 1696, 1610, 1418, 1330, and 1177; NMR δ$_H$(400MHz, DMSO) 7.86(1H, d, J3.01Hz), 7.34-7.26(4H, m), 7.20-7.10(2H, m) 7.09(1H, s), 6.50(1H, dd, J1.0, 3.5Hz), 5.63(2H, s), 4.2(2H, d, J6.0Hz), 2.45(3H, s) and 1.34(9H, s). |
| 74 | C | 40 | mp 214.6-215.2° C.; IR ν$_{max}$(DR)/cm$^{-1}$2877, 1653, 1596, 1523, 1470, 1355, 1284, 1241, 1210 and 1109; NMR δ$_H$(400MHz, DMSO) 7.87(1H, d, J3.0Hz), 7.16(1H, t, J7.0Hz), 7.0-6.75(3H, m), 6.51(1H, d, J3.0Hz), 5.58(2H, s) and 2.45(3H, s). |
| 75 | C | 3 | NMR δ$_H$(400MHz, DMSO) 4.74(4H, s), 5.33(2H, s), 5.62(2H, d, J2.0Hz), 5.71(1H, t, J2.0Hz), 6.83-6.88(1H, m), 7.29(2H, s), 7.91(1H, dd, J3.5, 1.0Hz), 8.10-8.12(1H, m); Retention time 2.95 min. |
| 76 | K | 100 | IR ν$_{max}$(DR)/cm$^{-1}$ 3011, 1650, 1525, 1468, 1351, 1284 and 1210; NMR δ$_H$(400MHz, CD$_3$OD) 8.36(1H, d, J3.5Hz), 7.53-7.42(4H, m), 6.72(1H, dd, J1.0Hz, 3.5Hz), 5.76(2H, s), 4.11(2H, s) and 2.61(3H, s). |
| 77 | W | 25 | mp 212.1-214.3° C.; IR ν$_{max}$(DR)/cm$^{-1}$ 4007, 3474, 3323, 3199, 2934, 2747, 2105, 1647, 1603, 1492, 1245, 1028 and 754; NMR δ$_H$(400MHz, DMSO) 3.82(3H, s), 5.60(2H, s), 6.78-6.93(3H, m), 7.05(1H, d, J8.5Hz), 7.24-7.38(3H, m), 7.90(1H, d, J3.0Hz), 8.12(1H, s). |
| 78 | B | 21 | IR ν$_{max}$(DR)/cm$^{-1}$ 4002, 3482, 3313, 3201, 2938, 2739, 2339, 2107, 1936, 1731, 1650, 1436, 1253, 1082 and 751; NMR δ$_H$(400MHz, DMSO) 5.82(2H, s), 6.84-6.88(1H, m), 7.38(2H, s), 7.58(1H, t, J9.0Hz), 7.90(1H, d, J3.0Hz), 8.12(1H, d, J1.0Hz), 8.23-8.28(1H, m), 8.29-8.35(1H, m). |
| 79 | C | 64 | mp 308.2-308.3° C.; IR ν$_{max}$(DR)/cm$^{-1}$ 4013, 3456, 3322, 3193, 2958, 2745, 2103, 1861, 1653, 1516, 1237, 1026 and 777; NMR δ$_H$(400MHz, DMSO) 4.95(2H, s), 5.56(2H, s), 6.15-6.20(1H, m), 6.44-6.51(1H, m), 6.84-6.93(2H, m), 7.34(2H, s), 7.91(1H, d, J3.0Hz) 8.12(1H, d, J1.0Hz). |
| 80 | Y | 10 | NMR δ$_H$(400MHz, DMSO) 8.84(1H, br s), 7.46-7.35(2H, m), 7.32-7.14(4H, m) and 5.72(2H, s); Retention time 0.84 min. |
| 81 | B | 47 | mp 229.3-229.4° C.; IR ν$_{max}$(DR)/cm$^{-1}$ 3514, 3292, 3166, 1614, 1503; NMR δ$_H$(400MHz, DMSO) 7.88-7.84(2H, m), 7.47(1H, d, J8.0Hz), 7.31(2H, br s), 7.22(1H, d, J7.0Hz), 6.52-6.51(1H, m), 5.75(2H, s), 2.46(3H, s); Anal. Calcd for C$_{15}$H$_{12}$N$_7$OCl•0.1 H$_2$O: C, 52.44; H, 3.58, N, 28.54. Found: C, 52.62; H, 3.59; N, 28.20. |
| 82 | H | 36 | mp 205.0-205.3° C.; NMR δ$_H$(400MHz, DMSO) 7.97-7.85(5H, m), 7.46-7.41(3H, m), 7.32(2H, br s), 7.13(1H, d, J8.5Hz), 6.53-6.52(1H, m), 5.85(2H, s), 2.46(3H, s). |
| 83 | C | 19 | mp 252.8-253.3° C.; NMR δ$_H$(400MHz, MeOD) 8.21(1H, d, J3.0Hz), 7.98(1H, d, J3.5Hz), 7.62-7.52(2H, m), 7.37-7.31(2H, m) and 5.81(2H, s); Retention time 0.83 min. |
| 84 | C | 53 | mp 235.8-236.5° C.; IR δ$_H$ν$_{max}$(DR)/cm$^{-1}$ 3309, 2836, 2033, 1823, 1651, 1505, 1468, 1354, 1250 and 1209; NMR δ$_H$(400MHz, CD$_3$OD) 8.18(1H, d, J4.0Hz), 7.47-7.37(3H, m), 6.61(1H, dd, J1.0, 3.5Hz), 5.82(2H, s) and 2.57(3H, s). |
| 85 | R | 72 | mp 215.9-217.5° C.; IR ν$_{max}$(Nujol)/cm$^{-1}$ 3308, 2955, 2869, 1634, 1505 and 1435; NMR δ$_H$(400MHz, DMSO) 8.27(1H, t, J5.5Hz), 8.13(1H, d, J1.0Hz), 7.91(1H, d, J3.5Hz), 7.36(2H, s), 7.31(1H, t, J7.5Hz), 7.17(2H, t, J7.5Hz), 7.09(1H, s), 6.89-6.84(1H, m), 5.64(2H, s), 4.21(2H, d, J6.0Hz), 1.93(2H, s) and 0.79(6H, d, J6.5Hz). |
| 86 | B | 51 | NMR δ$_H$(400MHz, DMSO) 8.84(1H, d, J5.5Hz), 8.14(1H, d, J2.0Hz), 8.08(1H, dd, J5.5, 1.0Hz), 7.89(1H, d, J5.5Hz), 7.34(2H, br s), 6.53-6.52(1H, m), 5.98(2H, s), 2.46(3H, s); Retention time 1.85 min. |
| 87 | Z | 73 | NMR δ$_H$(400MHz, DMSO) 9.10(1H, s), 8.69(1H, s), 8.05(1H, d, J5.5Hz), 7.89(1H, d, J3.0Hz), 7.32(2H, br s), 6.59-6.57(1H, m), 6.53-6.51(1H, m), 6.37-6.36(1H, m), 5.60(2H, s), 2.46(3H, s); M/Z 339(M+H)$^+$; Retention time 0.79 min. |
| 88 | B | 11 | mp 258.8-259.0° C.; IR ν$_{max}$(DR)/cm$^{-1}$ 4014, 3316, 3204, 2746, 2561, 2106, 1962, 1606, 1526, 1436, 1351, 1029 and 758; NMR δ$_H$(400MHz, DMSO) 2.46(3H, s), 5.79(2H, s), 6.86-6.88(1H, m), 7.23(1H, d, J7.5Hz), 7.30-7.50(3H, m), 7.81(1H, d, J8.0Hz), 7.91(1H, d, J3.5Hz), 8.13-8.15(1H, m). Anal. Calcd for C$_{16}$H$_{13}$N$_7$O$_3$: C, 54.70; H, 3.73; N, 27.89. Found: C, 54.70; H, 3.77; N, 27.48. |
| 89 | C | 57 | mp 247.1-247.2° C.; IR ν$_{max}$(DR)/cm$^{-1}$ 3322, 1740, 1600, 1240, 1167, 959 and 770: NMR δ$_H$(400MHz, DMSO) 2.10(3H, s), 4.93(2H, s), 5.56(2H, s), 6.11(1H, d, J6.5Hz), 6.58(1H, d, J8.0Hz), 6.80(1H, t, J7.5Hz), 6.85-6.87(1H, m), 7.35(2H, s), 7.90(1H, d, J3.5Hz), 8.12-8.14(1H, m). |

TABLE 2-continued

| Example | Method | Yield(%) | Physical Data |
|---|---|---|---|
| 90 | C | 38 | mp 268.5-269.1° C.; IR $\nu_{max}$(DR)/cm$^{-1}$ 4010, 3451, 3317, 3182, 2957, 2749, 2104, 1844, 1652, 1608, 1487, 1335, 1025 and 764; NMR $\delta_H$(400MHz, DMSO) 1.99(3H, s), 4.89(2H, s), 5.47(2H, s), 6.36-6.43(2H, m), 6.84-6.89(2H, m), 7.35(2H, s), 7.91(1H, d, J3.5Hz) 8.12-8.14(1H, m). |
| 91 | B | 15 | mp 284.3-284.5° C.; IR $\nu_{max}$(DR)/cm$^{-1}$ 3321, 3216, 1612, 1031, 765 and 552; NMR $\delta_H$(400MHz, DMSO) 8.12(1H, d, J1.0Hz), 7.88(1H, d, J3.5Hz), 7.35(2H, br s), 6.85(1H, dd, J3.5, 1.5Hz), 5.44(2H, s), 2.52(3H, s) and 2.25(3H, s) |
| 92 | B | 8 | mp 267.9-268.5° C.; NMR $\delta_H$(400MHz, DMSO) 2.32(3H, s), 5.69(2H, s), 6.85-6.89(1H, s), 7.04-7.10(1H, m), 7.33-7.54(4H, m), 7.90(1H, d, J3.5Hz), 8.13-8.15(1H, m). |
| 93 | B | 4 | IR $\nu_{max}$(Nujol)/cm$^{-1}$ 3316, 3193, 2926, 2851, 1637, 1508 and 1437; NMR $\delta_H$(400MHz, DMSO) 8.11-8.09(1H, m), 7.89(1H, dd, J3.5, 1.0Hz), 7.27(2H, s), 6.86-6.83(1H, m), 4.26(2H, d, J7.5Hz), 2.04-1.90(1H, m), 1.72-1.50(5H, m) and 1.25-0.95(5H, m). |
| 94 | B | 15 | mp 237.8-238.0° C.; NMR $\delta_H$(400MHz, DMSO) 2.49(3H, s), 5.76(2H, s), 6.84-6.88(1H, m), 7.28(1H, dd, J8.5, 1.5Hz), 7.30-7.42(3H, m), 7.91(1H, d, J3.5Hz), 7.97(1H, d, J8.5Hz), 8.11-8.14(1H, m). Anal. Calcd for $C_{16}H_{13}N_7O_3 \cdot 0.1 H_2O$: C, 54.42; H, 3.77; N, 27.77. Found: C, 54.73; H, 3.78; N, 27.40. |
| 95 | N | 32 | mp 249.8-250.0° C.; IR $\nu_{max}$(DR)/cm$^{-1}$ 3437, 3317, 3210, 2964, 2865, 1610, 1508; NMR $\delta_H$(400MHz, DMSO) 8.19-8.17(1H, m), 8.12(1H, m), 7.92-7.91(1H, m), 7.66-7.63(1H, m), 7.24-7.20(3H, m), 6.86(1H, dd, J3.5, 1.5Hz), 5.80(2H, s), 2.44(3H, s). |
| 96 | B | 4 | mp 226.6-226.9° C.; NMR $\delta_H$(400MHz, DMSO) 2.32(3H, s), 5.98(2H, s), 6.84(1H, s), 6.85-6.90(1H, m), 7.35(2H, s), 7.43(1H, d, J7.5Hz), 7.91(1H, d, J7.5Hz), 8.07-8.15(2H, m). |
| 97 | C | 63 | mp 245.3-246.1° C.; IR $\nu_{max}$(DR)/cm$^{-1}$ 4010, 3406, 3320, 3198, 2929, 2746, 1608, 1507, 1414, 1285, 1022 and 753; NMR $\delta_H$(400MHz, DMSO) 2.00(3H, s), 4.86(2H, s), 5.42(2H, s), 6.54(1H, d, J8.0Hz), 6.82-6.85(1H, m), 6.90(1H, dd, J8.0, 2.0Hz), 6.92-6.95(1H, m), 7.29(2H, s), 7.88(1H, d, J3.5Hz), 8.09-8.12(1H, m). Anal. Calcd for $C_{16}H_{15}N_7O \cdot 0.2 H_2O$: C, 59.14; H, 4.78; N, 30.17. Found: C, 59.44; H, 4.74; N, 29.82. |
| 98 | O | 98 | IR $\nu_{max}$(Nujol)/cm$^{-1}$ 3324, 3206, 1698, 1650 and 1611; NMR $\delta_H$(400MHz, DMSO) 13.56-12.46(1H, s), 8.13-8.11(1H, s), 7.92-7.84(3H, m), 7.56-7.31(3H, m), 6.87-6.85(1H, m) and 7.74(2H, s). |
| 99 | P | 66 | IR $\nu_{max}$(Nujol)/cm$^{-1}$ 3324, 1644, 1491 and 1417; NMR $\delta_H$(400MHz, DMSO) 8.12(1H, s), 7.98-7.93(1H, s), 7.91(1H, d, J3.0Hz), 7.81(1H, d, J6.5Hz), 7.77(1H, s), 7.47-7.29(5H, m), 6.86(1H, s) and 5.77-5.68(2H, m). |
| 100 | B | 13 | mp 285.7-285.9° C.; IR $\nu_{max}$(DR)/cm$^{-1}$ 3345, 3197, 1664, 1613, 1116, 766 and 600; NMR $\delta_H$(400MHz, DMSO) 8.13-8.02(1H, m) 7.90(1H, d, J3.5Hz), 7.37-7.27(3H, m), 6.86(1H, dd, J3.5, 2.0Hz), 5.67(2H, s) and 2.52(3H, s). |
| 101 | AA | 32 | mp 279.9-280.3° C.; NMR $\delta_H$(400MHz, DMSO) 8.33(3H, br s), 7.93(1H, d, J 2.0Hz), 7.51-7.39(2H, m), 7.39-7.31(3H, m), 5.69(2H, s) and 3.98(2H, q, J 5.5Hz). |
| 102 | P | 23 | IR $\nu_{max}$(Nujol)/cm$^{-1}$ 3480, 3322, 3202, 283, 1608 and 1506; NMR $\delta_H$(400MHz, DMSO) 8.12(1H, s), 7.90(1H, d, J3.5Hz), 7.47-7.25(5H, m), 6.87-6.84(1H, m), 5.72(2H, s), 3.77-3.61(1H, s), 2.76(3H, s), 1.10(3H, s) and 0.99(3H, s). |
| 103 | P | 58 | IR $\nu_{max}$(Nujol)/cm$^{-1}$ 3298, 2972, 1635 and 1418; NMR $\delta_H$(400MHz, DMSO) 8.21(1H, d, J7.5Hz), 8.12(1H, s), 7.91(1H, d, J3.0Hz), 7.82-7.74(2H, m), 7.48-7.29(4H, m), 6.86(1H, s), 5.71(2H, s), 4.13-4.01(1H, m) and 1.13(6H, d, J6.5Hz). |
| 104 | C | 10 | mp 249.9-250.5° C.; NMR $\delta_H$(400MHz, DMSO) 2.07(3H, s), 5.06(2H, s), 5.43(2H, s), 6.60-6.65(2H, m), 6.81-6.89(2H, m), 7.37(2H, s), 7.90(1H, dd, J3.5, 1.0Hz), 8.12(1H, d, J1.0Hz). Anal. Calcd for $C_{16}H_{15}N_7O \cdot 0.2 H_2O$: C, 59.14; H, 4.78; N, 30.17. Found: C, 59.53; H, 4.75; N, 29.87. |
| 105 | B | 16 | mp 263.2-263.5° C.; IR $\nu_{max}$(DR)/cm$^{-1}$ 3499, 3307, 3192, 2958, 2238, 1610, 1490; NMR $\delta_H$(400MHz, DMSO) 8.73(1H, d, J5.0Hz), 8.13-8.12(1H, m), 7.92-7.90(1H, m), 7.85-7.81(2H, m), 7.30(2H, br s), 6.87-6.86(1H, m), 5.87(2H, s). |
| 106 | B | 16 | mp 288.1-288.2° C.; IR $\nu_{max}$(DR)/cm$^{-1}$ 3324, 3196, 1609, 1489, 1166, 1004, 798 and 550; NMR $\delta_H$(400MHz, DMSO) 8.59(1H, s), 8.44(1H, s), 8.12(1H, s), 7.90(1H, d, J3.5Hz), 7.31(2H, br s), 6.86(1H, dd, J3.5, 1.5Hz), 5.81(2H, s) and 2.48(3H, s). |
| 107 | B | 22 | mp 276.4-277.4° C.; IR $\nu_{max}$(DR)/cm$^{-1}$ 3443, 3324, 3202, 1610, 1324, 1229, 1030 and 788; NMR $\delta_H$(400MHz, DMSO) 9.01(1H, dd, J4.0, 2.0Hz), 8.45(1H, dd, J8.5, 2.0Hz), 8.14-8.12(1H, m), 7.97(1H, d, J8.0Hz), 7.93(1H, d, J3.5Hz), 7.64(1H, 1H, dd, J8.5, 4.0Hz), 7.52(1H, t, J7.0Hz), 7.31(2H, br s), 7.15(1H, d, J7.5Hz), 6.87(1H, dd, J3.5, 2.0Hz) and 6.31(2H, s). |
| 108 | B | 30 | mp 215.0-215.3° C.; IR $\nu_{max}$(DR)/cm$^{-1}$ 3325, 3198, 1612, 1246, 1026, 727 and 567; NMR $\delta_H$(400MHz, DMSO) 8.14-8.12(1H, m), 7.91(1H, dd, J3.5, 1.0Hz), 7.90-7.85(2H, m), 7.52(1H, s), 7.51-7.46(3H, m), 7.36(2H, br s), 6.86(1H, dd, J3.5, 1.5Hz), and 5.81(2H, s). |
| 109 | Q | 23 | mp 289.8-289.9° C.; IR $\nu_{max}$(DR)/cm$^{-1}$ 3350, 2924, 2863, 1981, 1723, 1618, 1351, 1100, 974, 766 and 524; NMR $\delta_H$(400MHz, DMSO) 8.23-8.16(2H, m), 7.77-7.62(3H, m), 7.49(2H, br s), 5.88(2H, s) and 2.56(3H, s). |

TABLE 2-continued

| Example | Method | Yield(%) | Physical Data |
|---|---|---|---|
| 110 | B | 31 | mp 247.4-247.5° C.; IR $\nu_{max}$(DR)/cm$^{-1}$ 3999, 3470, 3316, 3198, 2929, 2744, 2345, 2103, 1924, 1837, 1773, 1649, 1435, 1355, 1237, 1029 and 768; NMR $\delta_H$(400MHz, DMSO) 5.79(2H, s), 6.85-6.87(1H, m), 7.36(2H, s), 7.56(1H, dd, J8.5, 2.0Hz), 7.76(1H, d, J8.0Hz), 7.91(1H, dd, J3.5, 1.0Hz), 8.04(1H, d, J 2.0Hz), 8.12-8.13(1H, m). Anal. Calcd for $C_{15}H_{10}N_7O_3Cl$: C, 48.47; H, 2.71; N, 26.36. Found: C, 48.63; H, 2.80; N, 26.22. |
| 111 | B | 14 | mp 244.1-244.6° C.; NMR $\delta_H$(400MHz, DMSO) 5.84(2H, s), 6.85-6.89(1H, m), 7.37(2H, s), 7.54(1H, dd, J9.5, 1.5Hz), 7.84(1H, t, J1.0Hz), 7.92(1H, d, J3.5Hz), 8.08(1H, dd, J9.0, 1.0Hz), 8.12-8.15(1H, m). Anal. Calcd for $C_{15}H_{10}N_8O_2$•0.75 $C_3H_7NO$: C, 53.25; H, 3.95; N, 31.50. Found: C, 53.08; H, 3.79; N, 31.38. |
| 112 | B | 28 | mp 190.4-191.4° C.; IR $\nu_{max}$(DR)/cm$^{-1}$ 3482, 3308, 3194, 2940, 2880, 1610, 1508; NMR $\delta_H$(400MHz, DMSO) 8.13-8.12(1H, m), 7.92(1H, d, J3.5Hz), 7.78(1H, t, J8.0Hz), 7.35-7.32(3H, m), 7.04(1H, d, J7.5Hz), 6.86(1H, dd, J 3.5, 2.0Hz), 5.75(2H, s), 4.43(2H, s), 3.33(3H, s). |
| 113 | B | 39 | IR $\nu_{max}$(Nujol)/cm$^{-1}$ 3499, 3316, 3193, 2946, 1651 and 1509; NMR $\delta_H$(400MHz, DMSO) 8.13-8.10(1H, m), 7.90(1H, d, J3.5Hz), 7.39-7.26(7H, m), 6.87-6.84(1H, m) and 5.67(2H, s); Anal. Calcd for $C_{15}H_{12}N_6O$•0.75 $H_2O$: C, 58.91; H, 4.45, N, 27.48. Found: C, 58.84; H, 4.10; N, 27.32. |
| 114 | C | 67 | mp 256.7-257.1° C.; IR $V_{max}$(DR)/cm$^{-1}$ 4003, 3452, 3324, 3203, 2950, 2746, 2102, 1733, 1654, 1516, 1420, 1305, 1221, 1106, 1024 and 761; NMR $\delta_H$(400MHz, DMSO) 5.38(2H, s), 5.51(2H, s), 6.46(1H, dd, J8.5, 2.5Hz), 6.58(1H, d, J2.0Hz), 6.84-6.87(1H, m), 7.15(1H, d, J8.0Hz), 7.32(2H, s), 7.91(1H, dd, J3.5, 1.0Hz), 8.11-8.13(1H, m). Anal. Calcd for $C_{15}H_{12}N_7OCl$•0.3 $H_2O$: C, 51.90; H, 3.66; N, 28.24. Found: C, 52.12; H, 3.48; N, 27.86. |
| 115 | B | 12 | NMR $\delta_H$(400MHz, DMSO) 8.84(1H, d, J5.5Hz), 8.15-8.12(2H, m), 8.08-8.06(1H, m), 7.92-7.91(1H, m), 7.32(2H, br s), 6.87(1H, dd, J3.5, 1.5Hz), 5.99(2H, s); Retention time 1.28 min |
| 116 | Z | 87 | NMR $\delta_H$(400MHz, DMSO) 9.08(1H, br s), 8.66(1H, br s), 8.13-8.12(1H, m), 8.06-8.04(1H, m), 7.93-7.91(1H, m), 7.32(2H, br s), 6.87-6.86(1H, m), 6.60-6.58(1H, m), 6.38-6.37(1H, m), 5.61(2H, s); M/Z 325(M+H)$^+$. |
| 117 | B | 9 | IR $\nu_{max}$(DR)/cm$^{-1}$ 3491, 3310, 3198, 2976, 1612; NMR $\delta_H$(400MHz, DMSO) 8.14-8.13(1H, m), 7.99-7.98(1H, m), 7.93-7.91(1H, m), 7.80-7.79(1H, m), 7.34(2H, br s), 6.88-6.86(1H, m), 5.90(2H, s), 2.57(3H, s). |
| 118 | Z | 91 | NMR $\delta_H$(400MHz, DMSO) 13.45(1H, br s), 9.50(1H, br s), 8.15-8.14(1H, m), 7.92(1H, d, J3.5Hz), 7.39(2H, br s), 6.87-6.86(1H, m), 6.56(1H, br s), 6.15(1H, br s), 5.67(2H, s), 2.39(3H, s); M/Z 339(M+H)$^+$. |
| 119 | B | 15 | mp >230° C.; IR $\nu_{max}$(DR)/cm$^{-1}$ 3993, 3509, 3314, 3195, 2997, 2950, 2682, 2561, 2101, 1943, 1780, 1613, 1501, 1433, 1345, 1100, 1027, 889 and 780; NMR $\delta_H$(400MHz, DMSO) 6.00(2H, s), 6.85-6.90(1H, m), 7.05(1H, d, J8.5Hz), 7.37(2H, s), 7.78(1H, dd, J8.5, 2.0Hz), 7.91(1H, d, J3.5Hz), 8.14(1H, d, J1.0Hz), 8.27(1H, d, J2.5Hz). Anal. Calcd for $C_{15}H_{10}N_7O_3Cl$•0.3 $H_2O$: C, 47.77; H, 2.83; N, 26.00. Found: C, 47.65; H, 2.71; N, 25.85. |
| 120 | C | 19 | mp 211.4-211.6° C.; IR $\nu_{max}$(DR)/cm$^{-1}$ 4015, 3325, 3218, 2969, 2878, 2101, 1653, 1508, 1423, 1275, 1023, 834 and 761; NMR $\delta_H$(400MHz, DMSO) 5.45(2H, s), 5.60(2H, s), 6.51(1H, dd, J8.0, 2.0Hz), 6.70-6.79(2H, m), 6.83-6.89(1H, m), 7.38(2H, s), 7.90(1H, d, J3.5Hz), 8.12(1H, s). |
| 121 | B | 13 | mp 292.3-292.4° C.; IR $\nu_{max}$(DR)/cm$^{-1}$ 3324, 3207, 2098, 1602, 1527, 1352, 1024 and 813; NMR $\delta_H$(400MHz, CDCl3) 8.10(1H, d, J3.0Hz), 7.79(1H, d, J1.5Hz), 7.64(2H, d, J8.5Hz), 7.49(2H, d, J8.5Hz), 6.71(1H, dd, J3.5, 1.5Hz), 5.71(2H, s) and 5.38(2H, br s). |
| 122 | A | 50 | mp 227.5-228.5° C.; IR $\nu_{max}$(DR)/cm$^{-1}$, 3265, 1701, 1521, 1480, 1413, 1355, 1309, 1204 and 1147; NMR $\delta_H$(400MHz, DMSO) 8.11(1H, d, J1.0Hz), 7.9(1H, d, J3.5Hz), 7.3(2H, br s), 7.04(1H, d, J2.0Hz), 6.90(1H, d, J8.0Hz), 6.85(1H, dd, J1.5, 3.5Hz), 6.79(1H, dd, J2.0, 8.0Hz), 5.57(2H, s), 3.71(3H, s,) and 3.72(3H, s). |
| 123 | B | 35 | mp 214.6-216.2° C.; IR $\nu_{max}$(DR)/cm$^{-1}$ 3512, 3295, 3173, 2988, 2736, 2415, 1636, 1437, 1340 and 1228; NMR $\delta_H$(400MHz, DMSO) 7.97(1H, d, J8.5Hz), 7.87(1H, d, J3.0Hz), 7.40(1H, d, J1.0Hz), 7.31(2H, br s), 7.27(1H, dd, J1.5, 8.0Hz), 6.51(1H, dd, J1.0, 3.5Hz), 5.74(2H, s), 2.48(3H, s) and 2.46(3H, s). |
| 124 | C | 65 | mp 215.7-216.7° C.; IR $\nu_{max}$(DR)/cm$^{-1}$3328, 2928, 2424, 2345, 1609 and 1263; NMR $\delta_H$(400MHz, DMSO) 7.85(1H, d, J3.5Hz), 7.26(2H, br s), 6.93(1H, d, J1.5Hz), 6.89(1H, dd, J2.0, 8.0Hz), 6.54(1H, d, J8.0Hz), 6.49(1H, J1.0, 3.5Hz), 5.40(2H, s), 4.89(2H, br s), 2.45(3H, s) and 2.27(3H, s). |
| 125 | B | 29 | mp 221.5-221.6° C.; IR $\nu_{max}$(DR)/cm$^{-1}$ 3506, 3294, 3178, 2683, 1613, 1315, 1027 and 697; NMR $\delta_H$(400MHz, DMSO) 8.13-8.11(1H, m), 7.90(1H, d, J 4.5Hz), 7.38(2H, br s), 6.86(1H, dd, J3.5, 1.5Hz), 6.18-6.16(1H, m), 5.70(2H, s) and 2.36(3H, s). |
| 126 | N | 26 | mp 229.6-230.3° C.; IR $\nu_{max}$(DR)/cm$^{-1}$ 3317, 3198, 1602, 1499; NMR $\delta_H$(400MHz, DMSO) 8.44-8.43(1H, m), 8.31(1H, d, J5.0Hz), 8.14-8.13(1H, m), 7.92(1H, d, J3.0Hz), 7.35(2H, br s), 6.88-6.86(1H, m), 6.70(1H, d, J5.0Hz), 5.71(2H, s), 2.39(3H, s). |
| 127 | B | 13 | mp 275.0-273.3° C.; IR $\nu_{max}$(DR)/cm$^{-1}$ 3449, 3310, 3202, 1605, 1487, 1420, 1023, 836, 760 and 551; NMR $\delta_H$(400MHz, DMSO) 8.15-8.11(1H, m), 8.07(1H, d, J9.0Hz), 7.91(1H, d, J3.5Hz), 7.68(1H, dd, J9.0, 6.5Hz), 7.38-7.29(3H, m), 6.86(1H, dd, J3.5, 1.5Hz) and 6.15(2H, s). |

TABLE 2-continued

| Example | Method | Yield(%) | Physical Data |
|---|---|---|---|
| 128 | B | 16 | mp 129.1-131.0° C.; IR $\nu_{max}$(DR)/cm$^{-1}$ 3993, 3470, 3310, 3197, 1610, 1508, 1420, 1239, 1002 and 796; NMR $\delta_H$(400MHz, DMSO) 8.74(1H, d, J1.5Hz), 8.61(1H, d, J2.5Hz), 8.57-8.54(1H, m), 8.13-8.11(1H, m), 7.91(1H, d, J 3.5Hz), 7.31(2H, br s), 6.86(1H, dd, J3.5, 2.0Hz) and 5.88(2H, s). |
| 129 | B | 20 | mp 266.5-266.7° C.; IR $\nu_{max}$(DR)/cm$^{-1}$ 4018, 3487, 3310, 3193, 2744, 1636, 1585, 1539, 1507, 1437, 1347, 1266, 1238 and 1196; NMR $\delta_H$(400MHz, DMSO) 8.15(1H, dd, J2.5, 7.5Hz), 8.12(1H, d, J1.0Hz), 7.90(1H, d, J3.5Hz), 7.73-7.68(1H, m), 7.58(1H, dd, J11.3, 8.8Hz), 7.36(2H, br s), 6.88(1H, dd, J1.5, 3.5Hz) and 5.78(2H, s). |
| 130 | H | 32 | mp 149.0-149.6° C.; IR $\nu_{max}$(DR)/cm$^{-1}$ 4072, 3332, 3198, 1654, 1604, 1348, 1237, 1111, 1012, 775, 691 and 570; NMR $\delta_H$(400MHz, DMSO) 8.79-8.70(2H, m), 8.25-8.14(2H, m), 7.77-7.58(5H, m), 7.38(2H, br s) and 5.87(2H, s). |
| 131 | B | 22 | mp 225.7-225.8° C.; NMR $\delta_H$(400MHz, DMSO) 8.33(1H, d, J4.5Hz), 8.13-8.12(1H, m), 7.92-7.91(1H, m), 7.30(2H, br s), 7.15(1H, d, J5.0Hz), 7.07-7.06(1H, m), 6.86(1H, dd, J1.5, 3.5Hz), 5.72(2H, s), 2.28(3H, s); Anal. Calcd for $C_{15}H_{13}N_7O \cdot 0.7 H_2O$: C, 56.31; H, 4.54, N, 30.65. Found: C, 56.57; H, 4.24; N, 30.33. |
| 132 | N | 10 | IR $\nu_{max}$(DR)/cm$^{-1}$ 3332, 2977, 1694, 1608; NMR $\delta_H$(400MHz, DMSO) 8.41(1H, d, J4.5Hz), 8.14-8.13(1H, m), 7.92(1H, d, J3.5Hz), 7.43(1H, t, J6.0Hz), 7.33(2H, br s), 7.16(1H, d, J4.5Hz), 6.97-6.96(1H, m), 6.87(1H, dd, J 2.0, 3.5Hz), 5.76(2H, s), 4.10(2H, d, J6.0Hz), 1.31(9H, s). |
| 133 | B | 14 | mp 209.7-209.9° C.; IR $\nu_{max}$(Nujol)/cm$^{-1}$ 3506, 3311, 3196, 2996, 2951, 1637, 1518 and 1283; NMR $\delta_H$(400MHz, DMSO) 8.15-8.12(1H, m), 7.91(1H, dd, J3.5, 1.0Hz), 7.84(1H, d, J8.0Hz), 7.43(1H, d, J1.5Hz), 7.42-7.35(2H, s), 6.88-6.82(2H, m), 5.77(2H, s) and 3.91(3H, s). |
| 134 | B | 14 | mp 240.9-241.1° C. IR $\nu_{max}$(DR)/cm$^{-1}$ 4010, 3629, 3499, 3313, 3196, 2946, 2733, 2447, 1943, 1638, 1528, 1420, 1351, 1222, 1025 and 960. NMR $\delta_H$(400MHz, DMSO) 5.85(2H, s), 6.84-6.89(1H, m), 7.36(2H, s), 7.50(2H, dt, J8.5, 2.0Hz), 7.92(1H, dd, J3.5, 1.0Hz), 8.12-8.14(1H, m), 8.22(2H, dt, J9.0, 2.0Hz). Anal. Calcd for $C_{15}H_{11}N_7O_3 \cdot 0.6 H_2O$: C, 51.75; H, 3.53; N, 28.17. Found: C, 52.08; H, 3.22; N, 27.96. |
| 135 | B | 18 | mp 208.6-208.8° C.; IR $\nu_{max}$(DR)/cm$^{-1}$ 3432, 3304, 3191, 2961, 1616, 1500, 1434; NMR $\delta_H$(400MHz, DMSO) 8.14-8.13(1H, m), 7.93-7.91(1H, m), 7.67(1H, t, J7.5Hz), 7.35(2H, br s), 7.19(1H, d, J7.5Hz), 6.90-6.86(2H, m), 5.73(2H, s), 2.68(2H, q, J7.5Hz), 1.14(3H, t, J7.5Hz). |
| 136 | B | 18 | mp 172.7-173.2° C.; NMR $\delta_H$(400MHz, DMSO) 8.42(1H, d, J5.5Hz), 8.14(1H, m), 7.92(1H, d J3.5Hz), 7.39(2H, br s), 7.11-7.10(1H, m), 6.97(1H, d, J5.5Hz), 6.87(1H, dd, J2.0, 3.5Hz), 5.70(2H, s), 2.71(2H, q, J7.5Hz), 1.18(3H, t, J7.5Hz). |
| 137 | B | 13 | mp 176.3-176.5° C.; IR $\nu_{max}$(DR)/cm$^{-1}$ 3452, 3326, 3209, 2973, 1734, 1611, 1328, 1026 and 774; NMR $\delta_H$(400MHz, DMSO) 8.13(1H, d, J2.5Hz), 7.90(1H, d, J3.5Hz), 7.72(1H, d, J3.5Hz), 7.61(1H, d, J8.5Hz), 7.34(2H, br s), 7.19(1H, t, J8.0Hz), 6.86(1H, dd, J3.5, 2.0Hz), 6.77(1H, d, J4.0Hz), 6.75(1H, d, J7.5Hz), 6.07(2H, s) and 1.54(9H, s). |
| 138 | B | 26 | mp 58.5-62.6° C.; IR $\nu_{max}$(DR)/cm$^{-1}$ 3430, 3315, 3210, 3973, 1718, 1165, 834 and 772; NMR $\delta_H$(400MHz, DMSO) 8.13-8.11(1H, m), 8.03(1H, d, J8.0Hz), 7.89(1H, d, J3.5Hz), 7.73(1H, d, J4.0Hz), 7.39(2H, br s), 7.30(1H, t, J 8.5Hz), 7.08(1H, d, J7.0Hz), 6.91(1H, d, J4.5Hz), 6.86(1H, dd, J3.5, 1.5Hz), 5.90(2H, s) and 1.62(9H, s). |
| 139 | K | 85 | mp 192.3-193.5° C.; NMR $\delta_H$(400MHz, DMSO) 11.27(1H, br s), 8.12(1H, d, J2.5Hz), 7.90(1H, d, J3.5Hz), 7.39-7.33(2H, m), 7.04(1H, t, J8.0Hz), 6.87-6.83(2H, m), 6.56-6.52(1H, m) and 5.86(2H, s). |
| 140 | B | 20 | mp 184.0-185.2° C.; IR $\nu_{max}$(DR)/cm$^{-1}$ 3638, 3462, 3331, 3184, 2976, 1686, 1174, 1026 and 756; NMR $\delta_H$(400MHz, DMSO) 8.13(1H, d, J1.0Hz), 7.90(1H, d, J3.5Hz), 7.45-7.31(3H, m), 7.27-7.17(4H, m), 6.86(1H, dd, J3.5, 2.0Hz), 5.64(2H, s), 4.08(2H, d, J6.0Hz) and 1.37(9H, s). |
| 141 | C | 45 | mp 240.3-240.4° C. IR $\nu_{max}$(DR)/cm$^{-1}$ 3320, 3198, 2929, 1610, 1505, 1438, 1280, 1233, 1028, 956 and 759; NMR $\delta_H$(400MHz, DMSO) 5.85(2H, s), 6.84-6.89(1H, m), 7.36(2H, s), 7.50(2H, dt, J8.5, 2.0Hz), 7.92(1H, dd, J3.5, 1.0Hz), 8.12-8.14(1H, m), 8.22(2H, dt, J9.0Hz). |
| 142 | B | 14 | mp 189.0-189.1° C.; IR $\nu_{max}$(DR)/cm$^{-1}$ 3506, 3304, 3180, 1735, 1609, 1167, 1029 and 766; NMR $\delta_H$(400MHz, DMSO) 8.15-8.11(1H, m), 8.02(1H, d, J 8.5Hz), 7.91(1H, d, J3.5Hz), 7.68(1H, d, J3.5Hz), 7.53(1H, s), 7.37(2H, br s), 7.29(1H, dd, J8.5, 1.5Hz), 6.86(1H, dd, J3.5, 2.0Hz), 6.70(1H, d, J3.5Hz), 5.75(2H, s) and 1.61(9H, s). |
| 143 | B | 18 | mp 167.0-167.3° C.; IR $\nu_{max}$(DR)/cm$^{-1}$ 3650, 3485, 3320, 3194, 2978, 1726, 1168, 953 and 756; NMR $\delta_H$(400MHz, DMSO) 9.00(1H, br s), 8.13(1H, s), 7.91(1H, d, J3.5Hz), 7.57(1H, t, J8.0Hz), 7.39(2H, br s), 7.16(1H, d, J11.5Hz), 7.04(1H, d, J8.5Hz), 6.86(1H, dd, J3.5, 2.0Hz), 5.64(2H, br s) and 1.44(9H, s). |
| 144 | K | 56 | mp >300° C. dec; IR $\nu_{max}$(DR)/cm$^{-1}$ 2903, 2030, 1606, 1464, 1033, 779 and 589; NMR $\delta_H$(400MHz, DMSO) 8.30(2H, br s), 8.14(1H, s), 7.92(1H, d, J3.5Hz), 7.46(2H, d, J8.0Hz), 7.32(2H, d, J8.0Hz), 6.92-6.84(1H, m), 5.69(2H, s) and 4.04-3.96(2H, m). |
| 145 | H | 30 | IR $\nu_{max}$(DR)/cm$^{-1}$ 3511, 3292, 3164, 2971, 1609, 1525, 1437, 1354 and 1239; NMR $\delta_H$(400MHz, DMSO) 8.19(2H, m), 7.90(1H, d, J3.5Hz), |

TABLE 2-continued

| Example | Method | Yield(%) | Physical Data |
|---|---|---|---|
| | | | 7.72-7.64(2H, m), 7.36(2H, br s), 6.53(1H, d, J3.5Hz), 5.83(2H, s), 2.80(2H, q, J7.5Hz) and 1.27(3H, t, J7.5Hz). |
| 146 | B | 35 | mp 180.0-180.5° C.; IR $\nu_{max}$(DR)/cm$^{-1}$ 3325, 3206, 2976, 1734, 1604, 1341, 1024 and 768; NMR $\delta_H$(400MHz, DMSO) 7.92(1H, d, J3.0Hz), 7.84(1H, s), 7.67(1H, d, J4.0Hz), 7.62(1H, d, J8.0Hz), 7.37(2H, br s), 7.26(1H, d, J8.0Hz), 6.87(1H, dd, J3.5, 1.5Hz), 6.70(1H, d, J3.5Hz), 5.80(2H, s) and 1.51(9H, s). |
| 147 | K | 57 | mp >200° C. dec; IR $\nu_{max}$(DR)/cm$^{-1}$ 2816, 2004, 1660, 1507, 1427, 1277, 1030, 746 and 524; NMR $\delta_H$(400MHz, DMSO) 8.15-8.12(1H, m), 7.91(1H, d, J3.5Hz), 7.14(1H, d, J12.0Hz), 7.06-6.94(2H, m), 6.86(1H, dd, J3.5, 2.0Hz) and 5.57(2H, s). |
| 148 | B | 43 | Mp 259.8-259.9° C. IR $\nu_{max}$(DR)/cm$^{-1}$ 3382, 3214, 2986, 2731, 2090, 1767, 1730, 1606, 1487, 1372, 1275, 1137, 1029, 873 and 771; NMR $\delta_H$(400MHz, DMSO) 1.49(9H, s), 5.63(2H, s), 6.85-6.86(1H, m), 7.20-7.27(2H, m), 7.40(2H, s), 7.87(1H, d, J3.0Hz), 8.11-8.14(1H, m). |
| 149 | K | 96 | IR $\nu_{max}$(Nujol)/cm$^{-1}$ 3375, 3061, 1653, 1509 and 1474; NMR $\delta_H$(400MHz, DMSO) 11.15-10.13(1H, s), 8.43-7.36(3H, s), 8.14-8.12(1H, m), 7.89(1H, dd, J3.5, 1.0Hz), 6.87-6.84(1H, m), 6.59-6.51(2H, m) and 5.51(2H, s). |
| 150 | C | 37 | IR $\nu_{max}$(DR)/cm$^{-1}$ 4043, 3461, 3312, 3198, 2970, 2748, 2438, 1923, 1650, 1514, 1497 and 1324; NMR $\delta_H$(400MHz, DMSO) 7.9(1H, d, J3.5Hz), 7.31(2H, br s), 6.97(1H, t, J8.0Hz), 6.53(1H, d, J3.5Hz), 6.45(1H, dd, J1.5, 8.0Hz), 6.40(1H, d, J7.5Hz), 6.34(1H, t, J1.7Hz), 5.48(2H, s), 5.12(2H, s), 2.80(2H, q, J7.5Hz) and 1.27(3H, t, J7.5Hz). |
| 151 | C | 48 | mp 251.2-251.5° C.; IR $\nu_{max}$(DR)/cm$^{-1}$ 3449, 3365, 3314, 3196, 2954, 2742, 1731, 1642, 1598, 1556, 1463 and 1407; NMR $\delta_H$(400MHz, DMSO) 8.76-8.72(2H, m), 7.67-7.62(3H, m), 7.36(2H, br s), 6.97(1H, t, J8.0Hz), 6.46(1H, dd, J1.5, 8.0Hz), 6.43(1H, d, J7.5Hz), 6.36(1H, t, J1.7Hz), 5.52(2H, s) and 5.13(2H, s). |
| 152 | AF | 86 | mp 298.9-299.0° C.; IR $\nu_{max}$(DR)/cm$^{-1}$ 3422, 3321, 3105, 3942, 1601, 1351, 1219, 1019 and 762; NMR $\delta_H$(400MHz, DMSO) 11.09(1H, br s), 8.13(1H, s), 7.91(1H, d, J3.0Hz), 7.51(1H, d, J8.5Hz), 7.43-7.31(3H, m), 7.28(1H, s), 7.00(1H, d, J8.0Hz), 6.89-6.83(1H, m), 6.39(1H, s) and 5.73(2H, br s). |
| 153 | AF | 75 | mp 226.8-227.4° C.; IR $\nu_{max}$(DR)/cm$^{-1}$ 3475, 3320, 2739, 1645, 1506, 1223, 1008 and 778; NMR $\delta_H$(400MHz, DMSO) 11.14(1H, br s), 8.14-8.10(1H, m), 7.90(1H, d, J3.5Hz), 7.50(1H, s), 7.40-7.31(4H, m), 7.09(1H, d, J8.0, 1.5Hz), 6.85(1H, dd, J3.5, 1.5Hz), 6.43-6.38(1H, m) and 5.70(2H, s). |
| 154 | AF | 77 | mp 295.3-295.5° C.; IR $\nu_{max}$(DR)/cm$^{-1}$ 3215, 1610, 1005, 758, 650 and 565; NMR $\delta_H$(400MHz, DMSO) 11.36(1H, br s), 8.15-8.11(1H, m), 7.91(1H, d, J 3.5Hz), 7.51(1H, d, J8.0Hz), 7.46(1H, t, J2.5Hz), 7.43(2H, br s), 6.92(1H, t, J7.5Hz), 6.86(1H, dd, J3.5, 2.0Hz), 6.71(1H, d, J7.0Hz), 6.53-6.49(1H, m) and 5.93(2H, s). |
| 155 | B | 35 | mp 258.6-258.7° C.; IR $\nu_{max}$(Nujol)/cm$^{-1}$ 3386, 3206, 1646, 1607 and 1481; NMR $\delta_H$(400MHz, DMSO) 8.33(1H, dd, J9.0, 4.5Hz), 8.15(1H, s), 7.92(1H, d, J3.5Hz), 7.55-7.47(1H, m), 7.47-7.35(2H, s), 6.93-6.85(2H, m) and 6.03(2H, s). |
| 156 | AG | 99 | mp 274.2-274.3° C.; IR $\nu_{max}$(Nujol)/cm$^{-1}$ 3482, 3305, 3197, 2963, 1606, 1499 and 1420; NMR $\delta_H$(400MHz, DMSO) 8.12(1H, s), 7.87(1H, d, J3.0Hz), 7.37(2H, s), 6.86-6.77(3H, m), 5.55(2H, s) and 3.79(3H, s); Anal. Calcd for $C_{16}H_{12}N_6O_2F_2$•0.5 $H_2O$: C, 52.32; H, 3.57, N, 22.88. Found: C, 52.62; H, 3.31; N, 22.72. |
| 157 | B | 24 | mp 204.2-204.4° C.; NMR $\delta_H$(400MHz, DMSO) 1.41(9H, s), 4.37, (2H, d, J 6.0Hz), 5.72(2H, s), 6.83(1H, d, J6.0Hz), 6.85-6.88(1H, m, J7.5Hz), 7.14-7.22(1H, m), 7.30(2H, d, J4.0Hz), 7.36(2H, s), 7.48(1H, t, J6.0Hz), 7.91(1H, d, J3.5Hz), 8.12-8.14(1H, m). Anal. Calcd for $C_{21}H_{23}N_7O_3$: C, 59.85; H, 5.50; N, 23.25. Found: C, 59.69; H, 5.54; N, 22.74. |
| 158 | AZ | | mp >300° C. dec; IR $\nu_{max}$(DR)/cm$^{-1}$ 3212, 1607, 1438, 1212, 1029 and 770; NMR $\delta_H$(400MHz, DMSO) 15.74(1H, br s), 8.13(1H, s), 7.91(1H, d, J3.5Hz), 7.80(2H, br s), 7.54-7.30(3H, s), 6.86(1H, dd, J4.0, 2.0Hz) and 5.85(2H, s). |
| 159 | B | 16 | Mp 235.9-237.8° C.; NMR $\delta_H$(400MHz, DMSO) 8.15-8.13(1H, m), 7.93-7.91(1H, d, J3.5Hz), 7.84-7.82(1H, d, J2.5Hz), 7.80-7.76(1H, dd, J2.5, 8.5Hz), 7.43-7.37(2H, s) 7.04-7.00(1H, d, J8.5Hz), 6.89-6.86(1H, dd, J 2.0, 3.5Hz), 5.71-5.69(2H s), and 3.99-3.97(3H s). |
| 160 | B | 28 | mp 277.4-277.9° C.; NMR $\delta_H$(400MHz, DMSO) 9.93(1H, s), 8.15-8.12(1H, m), 7.92(1H, d, J3.5Hz), 7.55(1H, d, J8.0Hz), 7.38(2H, s), 7.34(1H, s), 7.27(1H, t, J8.0Hz), 6.96(1H, d, J7.5Hz), 6.88-6.85(1H, m), 5.63(2H, s) and 1.99(3H, s). |
| 161 | K | 100 | mp >250° C. dec; IR $\nu_{max}$(DR)/cm$^{-1}$ 3035, 1968, 1654, 1464, 1354, 1247, 1032 and 746; NMR $\delta_H$(400MHz, DMSO) 4.39(2H, q, J5.5Hz), 5.81(2H, s), 6.84-6.89(1H, m), 7.13(1H, d, J7.5Hz), 7.31-7.46(3H, m), 7.55(1H, d, J7.5Hz), 7.90(1H, d, J3.5Hz), 8.12-8.16(1H, m) and 8.44(3H, s). Anal. Calcd for $C_{16}H_{15}N_7O$•2HCl•1.5 $H_2O$: C, 45.62; H, 4.79; N, 23.27. Found: C, 45.63; H, 4.71; N, 23.14. |
| 162 | B | 14 | mp 195.1-195.2° C.; IR $\nu_{max}$(DR)/cm$^{-1}$ 3490, 3375, 3310, 3199, 2895, 1734, 1609, 1507, 1421, 1228, 1026, 1001 and 760; NMR $\delta_H$(400MHz, DMSO) 2.86(6H, s), 5.58(2H, s), 6.48(1H, d, J7.5Hz), 6.64(1H, dd, J8.0, 2.0Hz), |

TABLE 2-continued

| Example | Method | Yield(%) | Physical Data |
|---|---|---|---|
| | | | 6.72-6.75(1H, m), 6.84-6.87(1H, m), 7.12(1H, t, J7.5Hz), 7.35(2H, s), 7.90(1H, d, J3.5Hz) and 8.10-8.14(1H, m). |
| 163 | B | 20 | IR $\nu_{max}$(DR)/cm$^{-1}$ 3489, 3324, 3199, 2560, 1605, 1235, 1121, 1048 and 762; NMR $\delta_H$(400MHz, DMSO) 8.12(1H, d, J2.5Hz), 7.90(1H, d, J3.5Hz), 7.44-7.32(4H, m), 7.16(2H, d, J9.0Hz), 6.86(1H, dd, J3.5, 1.5Hz) and 5.67(2H, s). |
| 164 | B | 16 | mp 120.1-121.0° C.; IR $\nu_{max}$(DR)/cm$^{-1}$ 3318, 1772, 1709, 1607, 1462, 1395; NMR $\delta_H$(400MHz, DMSO) 8.15-8.14(1H, m), 7.81(1H, d, J3.5Hz), 7.77(1H, t, J8.0Hz), 7.71-7.65(4H, m), 7.33(1H, d, J8.0Hz), 7.21(2H, br s), 7.12(1H, d, J8.0Hz), 6.88(1H, dd, J1.5, 3.5Hz), 5.68(2H, s) and 5.08(2H, s). |
| 165 | C | 60 | mp 259.7-259.8° C.; IR $\nu_{max}$(DR)/cm$^{-1}$ 3457, 3315, 3183, 2959, 2747, 1734, 1653, 1608, 1518, 1441, 1420 and 1386; NMR $\delta_H$(400MHz, DMSO) 8.12(1H, d, J1.0Hz), 7.90(1H, d, J3.5Hz), 7.35(2H, br s), 6.93(1H, dd, J8.0, 11.5Hz), 6.86(1H, dd, 1.5, J3.5Hz), 6.58(1H, dd, J2.0, J8.5Hz) 6.47-6.39(1H, m), 5.49(2H, s) and 5.19(2H, s). |
| 166 | B | 10 | mp 210.3-211.2° C.; NMR $\delta_H$(400MHz, DMSO) 8.15-8.10(1H, m), 7.89(1H, d, J4.5Hz), 7.35(2H, br s), 7.18(1H, s), 7.08(1H, d, J8.0Hz), 6.85(1H, dd, J 3.5, 1.5Hz), 6.72(1H, d, J8.0Hz), 5.55(1H, s), 4.49(2H, t, J8.5Hz) and 3.13(2H, t, J8.5Hz). |
| 167 | B | 11 | IR $\nu_{max}$(Nujol)/cm$^{-1}$ 3486, 3319, and 1606; NMR $\delta_H$(400MHz, DMSO) 8.15-8.10(1H, m), 7.92-7.87(1H, d, J3.5Hz), 7.64-7.56(1H, m), 7.54-7.47(1H, m), 7.46-7.35(2H, s), 7.32-7.22(1H, t, J9.5Hz), 6.88-6.84(1H, dd, J2.0, 3.5Hz), and 5.71-5.65(2H s); Anal. Calcd for C$_{15}$H$_{10}$N$_6$OFBr•0.5 H$_2$O: C, 45.25; H, 2.78; N, 21.11. Found: C, 45.10; H, 2.48; N, 20.69. |
| 168 | B | 12 | Mp 204.0-204.2° C.; IR $\nu_{max}$(Nujol)/cm$^{-1}$ 3343 and 3208; NMR $\delta_H$(400MHz, DMSO) 8.14-8.12(1H, m), 7.91-7.89(1H, dd, J1.0, 3.5Hz), 7.62-7.53(1H, m), 7.45-7.37(2H, s), 7.05-6.97(1H, m), 6.88-6.85(1H, dd, J2.0, 3.5Hz), and 5.76-5.74(2H, s). |
| 169 | B | 11 | IR $\nu_{max}$(Nujol)/cm$^{-1}$ 3490 and 3321; NMR $\delta_H$(400MHz, DMSO) 8.15-8.13(1H, m), 7.91-7.89(1H, d, J3.5Hz), 7.78-7.72(1H, m), 7.67-7.63(1H, dd, J 2.0, 7.0Hz), 7.46-7.38(2H, s), 7.15-7.08(1H, dd, J9.0, 10.0Hz) 6.88-6.85(1H, dd, J2.0, 3.5Hz), and 5.67-5.64(2H, s). |
| 170 | B | 18 | IR $\nu_{max}$(Nujol)/cm$^{-1}$ 3495 and 3304; NMR $\delta_H$(400MHz, DMSO) 8.14-8.12(1H, m), 7.90-7.88(1H, dd, J1.0, 3.5Hz), 7.64-7.62(1H, dd, J1.0, 2.0Hz), 7.43-7.37(2H, s), 6.87-6.84(1H, dd, J1.5, 3.5Hz), 6.51-6.48(1H, dd, J1.0, 3.5Hz), 6.46-6.44(1H, dd, J2.0, 3.5Hz) and 5.67-5.65(2H, s). |
| 171 | C | 59 | mp 219.3° C.; IR $\nu_{max}$(Nujol)/cm$^{-1}$ 3508, 3421, 3307, 3190, 2949, 1609 and 1506; NMR $\delta_H$(400MHz, DMSO) 8.14(1H, s), 7.91(1H, d, J3.5Hz), 7.43(2H, s), 6.92-6.85(2H, m), 6.72(1H, dd, J8.5, 5.0Hz), 6.52(1H, dd, J9.5, 3.0Hz), 5.47(2H, s) and 5.19(2H, s). |
| 172 | B | 18 | IR $\nu_{max}$(Nujol)/cm$^{-1}$ 3490, 3304, 3182, 2986, 1779, 1762, 1603, 1345 and 1231; NMR $\delta_H$(400MHz, DMSO) 8.16(1H, d, J8.5Hz), 8.15-8.13(1H, m), 7.92(1H, d, J3.5Hz), 7.46(1H, d, J2.0Hz), 7.45-7.36(2H, s), 7.32(1H, dd, J8.5, 1.5Hz), 6.88-6.86(1H, m), 5.84(2H, s) and 1.47(9H, s). |
| 173 | C | 78 | mp 239.6-239.8° C.; IR $\nu_{max}$(Nujol)/cm$^{-1}$ 3323, 2936, 2733, 1772, 1734, 1609, 1508 and 1282; NMR $\delta_H$(400MHz, DMSO) 9.07(1H, s), 8.13-8.11(1H, m), 7.89(1H, d, J3.5Hz), 7.34(2H, s), 6.87-6.84(1H, m), 6.59-6.50(3H, m), 5.41(2H, s) and 4.57(2H, s). |
| 174 | K | 81 | mp >200° C. dec; IR $\nu_{max}$(DR)/cm$^{-1}$ 3144, 2570, 2004, 1654, 1458, 1369, 1280, 1037 and 760; NMR $\delta_H$(400MHz, DMSO) 7.87(1H, d, J3.5Hz), 7.13(1H, d, J 11.5Hz), 7.05-6.91(2H, m), 6.51(1H, dd, J3.5, 1.0Hz), 5.55(2H, s) and 2.45(3H, s). |
| 175 | C | 17 | mp 279.3-281.3° C.; IR $\nu_{max}$(DR)/cm$^{-1}$ 3462, 3202, 2952, 1653, 1510, 1462, 1416, 1342, 1293 and 1261; NMR $\delta_H$(400MHz, DMSO)13.52(1H, br s), 7.97(1H, br s), 7.31(1H, s), 7.25(2H, br s), 6.96(1H, t, J7.5Hz), 6.46(1H, dd, J 1.0, 8.0Hz), 6.42(1H, d, J7.0), 6.34(1H, s), 5.50(2H, s) and 5.13(2H, s). |
| 176 | K | 51 | IR $\nu_{max}$(Nujol)/cm$^{-1}$ 3651, 3488, 3317, 1637, 1507 and 1331; NMR $\delta_H$(400MHz, DMSO) 11.04(1H, s), 8.15-8.13(1H, m), 7.92(1H, dd, J3.5, 1.0Hz), 7.87(1H, d, J8.5Hz), 7.41(2H, s), 6.88-6.86(1H, m), 6.85-6.81(2H, m) and 5.72(2H, s); Anal. Calcd for C$_{15}$H$_{11}$N$_7$O$_4$•1.0 H$_2$O: C, 48.52; H, 3.53, N, 26.24. Found: C, 48.68; H, 3.20; N, 26.24. |
| 177 | AL | 65 | mp 245.9-247.0° C.; IR $\nu_{max}$(DR)/cm$^{-1}$ 3284, 3194, 1654, 1609, 1523; NMR $\delta_H$(400MHz, DMSO) 8.41(1H, t, J6.0Hz), 8.14-8.13(1H, m), 7.92(1H, dd, J 1.0, 3.5Hz), 7.73(1H, t, J7.5Hz), 7.37(2H, br s), 7.21(1H, d, J7.5Hz), 6.93(1H, d, J7.5Hz), 6.88-6.86(1H, m), 5.74(2H, s), 4.28(2H, d, J6.0Hz), 1.88(3H, s); Anal. Calcd for C$_{17}$H$_{16}$N$_8$O$_2$•0.5 H$_2$O•0.1C$_3$H$_7$NO: C, 54.58; H, 4.69, N, 29.80. Found: C, 54.90; H, 4.43; N, 29.46. |
| 178 | R | 20 | mp 216.7-218.4° C.; IR $\nu_{max}$(DR)/cm$^{-1}$ 3854, 3143, 2569, 2004, 1654, 1518, 1437, 1279, 1207, 1037 and 868; NMR $\delta_H$(400MHz, DMSO) 1.90(3H, s), 4.48(2H, d, J6.0Hz), 5.73(2H, s), 6.82-6.89(2H, m), 7.15-7.23(1H, m), 7.25-7.46(4H, m), 7.91(1H, d, J3.5Hz), 8.12-8.15(1H, m), 8.39(1H, t, J5.5Hz). |
| 179 | B | 11 | Mp 215.8-216.9° C.; IR $\nu_{max}$(Nujol)/cm$^{-1}$ 3482 and 3305; NMR $\delta_H$(400MHz, DMSO)8.13-8.11(1H, m), 7.91-7.89(1H, d, J3.5Hz), 7.55-7.52(1H, dd, J 3.0, 5.0Hz), 7.42-7.40(1H, m), 7.39-7.34(2H, s), 7.11-7.08(1H, dd, J1.5, 5.0Hz), 6.87-6.85(1H, dd J1.5, 3.5Hz) and 5.66-5.64(2H, s); Anal. Calcd for C$_{13}$H$_{10}$N$_6$OS: C, 52.34; H, 3.38, N, 28.16. Found: C, 52.53; H, 3.57; N, 28.22. |

TABLE 2-continued

| Example | Method | Yield(%) | Physical Data |
|---|---|---|---|
| 180 | C | 25 | mp 278.4-279.9° C.; IR ν$_{max}$(DR)/cm$^{-1}$ 3468, 3184, 2967, 1735, 1604, 1436, 1322, 1234 and 1204; NMR δ$_H$(400MHz, DMSO) 7.87(1H, d, J3.0Hz), 7.30(2H, br s), 6.80(1H, t, J8.0Hz), 6.58(1H, dd, J1.0, 8.0Hz), 6.51(1H, dd, J3.0, 1.0Hz), 6.11(1H, d, J7.0Hz), 5.54(2H, s), 4.93(2H, br s), 2.45(3H, s) and 2.1(3H, s). |
| 181 | B | 12 | IR ν$_{max}$(Nujol)/cm$^{-1}$ 3501 and 3316; NMR δ$_H$(400MHz, DMSO) 8.13-8.11(1H, m), 7.90-7.87(1H, dd, J1.0, 3.5Hz), 7.43-7.32(2H, s), 7.40-7.37(1H, d, J5.0Hz), 6.90-6.87(1H, d, J5.0Hz), 6.86-6.84(1H, dd, J2.0, 3.5Hz), 5.73-5.72(2H, s), and 2.37-2.35(3H, s). |
| 182 | AM | 30 | mp 92.3-92.7° C.; IR ν$_{max}$(DR)/cm$^{-1}$ 3124, 3073, 2926, 1609, 1520, 1411; NMR δ$_H$(400MHz, DMSO) 8.18-8.17(1H, m), 7.93(1H, d, J3.0Hz), 7.80(1H, t, J 7.5Hz), 7.37(1H, d, J7.5Hz), 7.19(1H, d, J7.5Hz), 6.87(1H, dd, J1.5, 3.5Hz), 5.94-5.75(3H, m), 5.78(2H, s), 5.28-5.07(6H, m), 4.48(2H, s), 4.43-4.12(4H, m), 4.02-3.99(2H, m); Anal. Calcd for C$_{24}$H$_{25}$N$_7$O$_2$: C, 65.00; H, 5.68, N, 22.10. Found: C, 65.23; H, 5.80; N, 21.60. |
| 183 | B | 27 | mp 152.0-153.5° C.; IR ν$_{max}$(DR)/cm$^{-1}$ 3515, 3300, 3183, 2934, 2822, 1631, 1450, 1434; NMR δ$_H$(400MHz, DMSO) 7.89(1H, d, J3.0Hz), 7.79(1H, t, J 7.5Hz), 7.33(2H, br s), 7.34(1H, d, J7.5Hz), 7.02(1H, d, J7.5Hz), 6.53-6.51(1H, m), 5.74(2H, s), 4.43(2H, s), 2.46(3H, s), 3.33(3H, s); Anal. Calcd for C$_{17}$H$_{17}$N$_7$O$_2$: C, 58.11; H, 4.88, N, 27.89. Found: C, 57.75; H, 4.85; N, 27.59. |
| 184 | C | 76 | mp 219.7-220.4° C. IR ν$_{max}$(DR)/cm$^{-1}$ 3450, 3312, 2920, 2728, 1737, 1638, 1438, 1354, 1326, 1291 and 1234; NMR δ$_H$(400MHz, DMSO) 7.85(1H, d, J3.0Hz), 7.30(2H, br s), 7.01(2H, d, J8.5Hz), 6.52-6.47(3H, m), 5.41(2H, s), 5.12(2H, s) and 2.44(3H, s). |
| 185 | B | 15 | mp 155.6-157.1° C.; IR ν$_{max}$(DR)/cm$^{-1}$ 3332, 3197, 2857, 1655, 1605, 1525, 1420; NMR δ$_H$(400MHz, DMSO) 8.14-8.13(1H, m), 7.92(1H, d, J3.5Hz), 7.79(1H, t, J7.5Hz), 7.37(1H, d, J7.5Hz), 7.36(2H, br s), 7.05(1H, d, J7.5Hz), 6.88-6.86(1H, m), 5.98-5.86(1H, m), 5.76(2H, s), 5.29-5.24(1H, m), 5.17-5.13(1H, m), 4.48(2H, s), 4.06-4.00(2H, m); Anal. Calcd for C$_{18}$H$_{17}$N$_7$O$_2$: C, 59.50; H, 4.72, N, 26.97. Found: C, 59.39; H, 4.70; N, 26.99. |
| 186 | B | 23 | mp 149.0-149.3° C.; IR ν$_{max}$(DR)/cm$^{-1}$ 3514, 3295, 3168, 2861, 1634, 1502, 1435; NMR δ$_H$(400MHz, DMSO) 7.88(1H, d, J3.5Hz), 7.79(1H, t, J7.5Hz), 7.37(1H, d, J7.5Hz), 7.33(2H, br s), 7.04(1H, d, J7.5Hz), 6.52-6.51(1H, m), 5.96-5.86(1H, m), 5.74(2H, s), 5.30-5.24(1H, m), 5.17-5.13(1H, m), 4.49(2H, s), 4.06-4.00(2H, m), 2.46(3H, s); Anal. Calcd for C$_{19}$H$_{19}$N$_7$O$_2$•0.2 H$_2$O: C, 59.90; H, 5.13, N, 25.73. Found: C, 59.71; H, 5.02; N, 25.64. |
| 187 | B | 20 | mp 191.7-191.9° C.; IR ν$_{max}$(Nujol)/cm$^{-1}$ 3501, 3307, 3189, 2974, 1611, 1527 and 1338; NMR δ$_H$(400MHz, DMSO) 8.12-8.15(1H, m), 7.91(1H, d, J3.5Hz), 7.76(1H, d, J8.5Hz), 7.67(1H, d, J2.0Hz), 7.44-7.36(2H, s), 7.16(1H, dd, J8.5, 2.0Hz), 6.87-6.85(1H, m), 5.78(2H, s), 3.22(1H, quin, J6.5Hz) and 1.22(6H, d, J6.5Hz). |
| 188 | B | 32 | mp 228.9-229.9° C.; IR ν$_{max}$(DR)/cm$^{-1}$ 3461, 3317, 3195, 1606, 1504, 1320, 1026 and 818; NMR δ$_H$(400MHz, DMSO) 8.16-8.14(1H, m), 7.98(1H, d, J8.0Hz), 7.94(1H, d, J3.5, 1.0Hz), 7.91(1H, d, J8.0Hz), 7.78-7.73(1H, m), 7.64-7.58(1H, m), 7.36(1H, d, J8.5Hz), 7.36(2H, br s), 6.88(1H, dd, J3.5, 1.5Hz) and 5.98(2H, s). |
| 189 | K | 23 | NMR δ$_H$(400MHz, DMSO) 8.14-8.12(1H, m), 7.92-7.89(1H, dd, J1.0, 3.5Hz), 7.35-7.31(2H, d, J8.5Hz), 7.28-7.16(2H, s), 6.88-6.85(1H, dd, J1.5, 3.5Hz), 5.66-5.64(2H, s), and 2.82-2.80(3H, s); M/Z 322(M+H)$^+$. |
| 190 | B | 37 | mp 290.2-290.3° C.; IR ν$_{max}$(DR)/cm$^{-1}$ 3491, 3338, 3205, 3128, 2936, 1710, 1616, 1490, 1458; NMR δ$_H$(400MHz, DMSO) 8.13-8.12(1H, m), 7.93(1H, t, J7.5Hz), 7.90(1H, dd, J1.0, 3.5Hz), 7.84(1H, d, J7.5Hz), 7.56(1H, d, J7.5Hz), 7.34(2H, br s), 6.86(1H, dd, J2.0, 3.5Hz), 6.69(1H, q, J7.5Hz), 2.48(3H, s), 1.98(3H, d, J7.5Hz); Anal. Calcd for C$_{17}$H$_{15}$N$_7$O$_2$: C, 58.45; H, 4.33, N, 28.05. Found: C, 58.26; H, 4.42; N, 27.67. |
| 191 | C | 16 | mp 186.1-189.1° C.; IR ν$_{max}$(DR)/cm$^{-1}$ 3458, 1598, 1509, 1460, 1329, 1267 and 1220; NMR δ$_H$(400MHz, DMSO) 11.73(1H, s), 7.59(1H, s), 7.17(1H, s), 6.97(1H, t, J7.8Hz), 6.95-6.83(2H, br s), 6.45(1H, dd, J1.5, 8.0Hz), 6.40(1H, d, J8.0Hz), 6.38-6.31(1H, m), 5.47(2H, s) and 5.13(2H, s). |
| 192 | Q | 2 | NMR δ$_H$(400MHz, CD$_3$OD) 8.84(1H, d, J4.5Hz), 8.77(1H, d, J8.0Hz), 8.33(1H, t, J1.7Hz), 8.2(1H, dd, J2.0, 8.0Hz), 8.06(1H, td, J7.8, 2.0Hz), 7.81(1H, d, J7.5Hz), 7.65-7.58(2H, m) and 5.88(2H, s); M/Z 349(M+H)$^+$; Retention time 1.77 min. |
| 193 | B | 6 | mp 253.6-254.0° C.; IR ν$_{max}$(DR)/cm$^{-1}$ 3320, 1611, 1414, 1315, 1255, 1026 and 767; NMR δ$_H$(400MHz, DMSO) 2.01(3H, s), 5.59(2H, s), 6.84-6.88(1H, m), 7.22(2H, d, J8.5Hz), 7.36(2H, s), 7.54(2H, d, J8.5Hz) 7.90(1H, d, J3.5Hz), 8.11-8.14(1H, m), 9.97(1H, s). |
| 194 | B | 36 | mp 136.5-137.6° C.; IR ν$_{max}$(Nujol)/cm$^{-1}$ 3489, 3311, 3195, 2954, 1774 and 1613; NMR δ$_H$(400MHz, DMSO) 8.24(1H, s), 8.04(1H, d, J2.0Hz), 8.00(1H, d, J3.5Hz), 7.96(1H, dd, J8.5, 2.0Hz), 7.52-7.44(2H, s), 7.40(1H, d, J 8.5Hz), 6.99-6.95(1H, m), 5.83(2H, s), 5.54(2H, s), 3.66(2H, t, J8.0Hz), 0.93(2H, t, J8.0Hz) and 0.00(9H, s); Anal. Calcd for C$_{21}$H$_{25}$N$_7$O$_5$Si•0.1 H$_2$O: C, 51.97; H, 5.23, N, 20.20. Found: C, 51.97; H, 5.19; N, 19.86. |
| 195 | B | 12 | IR ν$_{max}$(Nujol)/cm$^{-1}$ 3652, 3506, 3307, 3196, 2990, 2878, 1633, 1521 and 1344; NMR δ$_H$(400MHz, DMSO) 8.14(1H, s), 7.94-7.88(2H, m), 7.46(1H, s), 7.40(2H, s), 7.23(1H, dd, J8.5, 2.0Hz), 6.88-6.85(1H, m), 5.78(2H, s), 2.80(2H, |

TABLE 2-continued

| Example | Method | Yield(%) | Physical Data |
|---|---|---|---|
| | | | q, 7.5Hz) and 1.17(3H, t, J7.5Hz); Anal. Calcd for $C_{17}H_{15}N_7O_3 \cdot 0.25\, H_2O$: C, 55.21; H, 4.22, N, 26.51. Found: C, 55.47; H, 4.12; N, 26.25. |
| 196 | B | 23 | mp 178.4-179.0° C.; IR $v_{max}$(Nujol)/cm$^{-1}$ 3469 and 3311; NMR $\delta_H$(400MHz, DMSO) 8.13-8.11(1H, m), 7.90-7.88(1H, dd, J1.0, 3.5Hz), 7.37-7.32(2H, s), 7.32-7.29(1H, dd, J1.5, 5.5Hz), 6.92-6.89(1H, dd, J3.5, 5.5Hz), 6.87-6.84(2H, m), 4.70-4.64(2H, t, J7.0Hz), and 3.53-3.48(2H, t, J7.0Hz); Anal. Calcd for $C_{14}H_{12}N_6OS$: C, 53.84; H, 3.87; N, 26.89. Found: C, 53.98; H, 3.87; N, 26.50. |
| 197 | B | 22 | mp 188.3-188.5° C.; IR $v_{max}$(DR)/cm$^{-1}$ 3324, 3189, 2964, 1649, 1513; NMR $\delta_H$(400MHz, DMSO) 8.14-8.13(1H, m), 7.93(1H, d, J3.5Hz), 7.67(1H, t, J7.5Hz), 7.34(2H, br s), 7.20(1H, d, J7.5Hz), 6.89(1H, d, J7.5Hz), 6.87-6.86(1H, m), 5.75(2H, s), 2.93(1H, sept, J7.0Hz), 1.12(6H, d, J7.0Hz); Anal. Calcd for $C_{17}H_{17}N_7O$: C, 60.88; H, 5.11, N, 29.22. Found: C, 61.03; H, 5.13; N, 28.95. |
| 198 | B | 27 | IR $v_{max}$(DR)/cm$^{-1}$ 3466, 3312, 3187, 2958, 2850, 1639, 1511, 1221, 1047, 756 and 599; NMR $\delta_H$(400MHz, DMSO) 8.13(1H, s), 8.09(1H, s), 7.91(1H, d, J 3.0Hz), 7.72(1H, d, J8.5Hz), 7.68(1H, s), 7.42(1H, d, J8.5Hz), 7.37(2H, br s), 6.88-6.83(1H, m), 5.82(1H, d, J9.5Hz), 5.77(2H, s), 3.90-3.80(1H, m), 3.77-3.64(1H, m), 2.45-2.30(1H, m), 2.10-1.88(2H, m), 1.80-1.63(1H, m), 1.62-1.49(2H, m). |
| 199 | B | 7 | mp 226.5-227.9° C.; IR $v_{max}$(DR)/cm$^{-1}$ 3466, 3316, 3182, 2962, 1645, 1606, 1546, 1514, 1473; NMR $\delta_H$(400MHz, DMSO) 8.14-8.13(1H, m), 7.92(1H, d, J3.0Hz), 7.33(2H, br s), 7.07-7.06(1H, m), 6.88-6.86(2H, m), 5.71(2H, s), 2.88(1H, sept, J7.0Hz), 2.82(1H, sept, J7.0Hz), 1.14(6H, d, J7.0Hz), 1.09(6H, d, J7.0Hz). |
| 200 | K | 99 | mp >300° C. dec; IR $v_{max}$(DR)/cm$^{-1}$ 3100, 1662, 1465, 1281, 1032, 782 and 592; NMR $\delta_H$(400MHz, DMSO) 8.16-8.13(1H, m), 8.07(1H, s), 7.92(1H, d, J3.5Hz), 7.68(1H, s), 7.54(1H, d, J8.5Hz), 7.35(1H, dd, 8.5, 1.5Hz), 6.87(1H, dd, J3.5, 2.0Hz) and 5.76(1H, s) |
| 201 | K | 99 | IR $v_{max}$(Nujol)cm$^{-1}$ 2999, 1656, 1530 and 1461; NMR $\delta_H$(400MHz, DMSO) 11.10(1H, s), 8.14(1H, d, J1.0Hz), 7.92(1H, d, J3.5Hz), 7.72(1H, d, J2.5Hz), 7.61(1H, dd, J8.5, 2.5Hz), 7.0(1H, d, J8.5Hz), 6.86-6.88(1H, m), 5.67(2H, s) and 5.11-5.16(3H, s). |
| 202 | B | 32 | mp 210.5-211.6° C.; IR $v_{max}$(FILM)/cm$^{-1}$ 3352, 3204, 3001, 1659, 1569, 1510, 1440; NMR $\delta_H$(400MHz, DMSO) 8.14(1H, m), 7.93(1H, d, J3.5Hz), 7.76(1H, t, J7.5Hz), 7.43(1H, d, J7.5Hz), 7.36(2H, br s), 7.03(1H, d, J7.5Hz), 6.87(1H, dd, J2.0, 3.5Hz), 6.75(1H, dd, J10.5, 17.5Hz), 6.09(1H, dd, J2.0, 17.5Hz), 5.78(2H, s), 5.43(1H, dd, J1.5, 10.5Hz); Anal. Calcd for $C_{16}H_{13}N_7O$: C, 60.18; H, 4.10, N, 30.69. Found: C, 60.14; H, 4.20; N, 30.39. |
| 203 | AS | 12 | IR $v_{max}$(Nujol)/cm$^{-1}$ 3514, 3298 and 1761; NMR $\delta_H$(400MHz, DMSO) 8.16-8.15(1H, m), 7.89-7.86(1H, dd, J1.0, 3.5Hz), 7.80-7.40(2H, s), 6.89-6.86(1H, dd, J1.5, 3.5Hz), and 1.66-1.64(9H, s). |
| 204 | B | 16 | mp 143.6-144.5° C.; IR $v_{max}$(DR)/cm$^{-1}$ 3644, 3315, 3195, 2978, 1743, 1608, 1163, 1086 and 746; NMR $\delta_H$(400MHz, DMSO) 8.14-8.10(1H, m), 8.05(1H, d, J8.0Hz), 7.88(1H, d, J3.5Hz), 7.81(1H, s), 7.66(1H, d, J7.5Hz), 7.42(2H, br s), 7.34(1H, t, J8.0Hz), 7.23(1H, t, J8.0Hz), 6.85(1H, dd, J3.5, 2.0Hz), 5.78(2H, s) and 1.63(9H, s) |
| 205 | B | 19 | IR $v_{max}$(DR)/cm$^{-1}$ 3431, 3325, 3217, 1646, 1504, 1431; NMR $\delta_H$(400MHz, DMSO) 9.87-9.86(1H, m), 8.14(1H, m), 8.05(1H, t, J8.0Hz), 7.94-7.92(1H, m), 7.88(1H, d, J8.0Hz), 7.52(1H, d, J8.0Hz), 7.38(2H, br s), 6.88-6.87(1H, m), 5.91(2H, s); Anal. Calcd for $C_{15}H_{11}N_7O_2 \cdot 0.3\, H_2O$: C, 55.15; H, 3.58, N, 30.01. Found: C, 55.33; H, 3.35; N, 29.64. |
| 206 | B | 30 | IR $v_{max}$(film)/cm$^{-1}$ 3327, 3209, 2987, 1730, 1664, 1390, 1168, 959, 745 and 664; NMR $\delta_H$(400MHz, DMSO) 8.16(1H, s), 8.09(1H, d, J8.0Hz), 7.97-7.92(2H, m), 7.47(1H, d, J7.5Hz), 7.44-7.35(2H, br s), 7.31(1H, t, J7.5Hz), 7.20(1H, t, J7.0Hz), 6.89(1H, dd, J3.5, 1.5Hz), 6.03-5.96(3H, m) and 1.64(9H, s) |
| 207 | AF | 71 | mp 289.1-289.3° C.; IR $v_{max}$(DR)/cm$^{-1}$ 3442, 3317, 3189, 1649, 1607, 1519, 1332, 1118, 1023 and 763; NMR $\delta_H$(400MHz, DMSO) 11.21(1H, br s), 8.13(1H, s), 7.91(1H, d, J3.5Hz), 7.46(1H, d, J8.0Hz), 7.38(2H, br s), 7.33(1H, d, J8.0Hz), 7.06(1H, t, J8.0Hz), 6.96(1H, t, J7.0Hz), 6.86(1H, dd, J3.5, 1.5Hz), 6.31(1H, s) and 5.79(2H, s) |
| 208 | B | 4 | NMR $\delta_H$(400MHz, DMSO) 8.13-8.12(1H, m), 7.91-7.88(1H, dd, J1.5, 3.5Hz), 7.46-7.36(2H, s), 6.98-6.96(1H, d, J3.5Hz), 6.87-6.84(1H, dd, J1.5, 3.5Hz), 6.72-6.69(1H, d, J3.5Hz), 5.76-5.74(2H, s), 2.52-2.48(2H, h, J 2.0, 3.5Hz) and 1.20-1.14(3H, t, J7.5Hz); M/Z 327(M+H)$^+$. |
| 209 | B | 17 | mp >250° C. dec; IR $v_{max}$(DR)/cm$^{-1}$ 3489, 3316, 2919, 1610, 1326, 1037, 862, 760 and 593; NMR $\delta_H$(400MHz, DMSO) 8.13-8.11(1H, m), 7.90(1H, d, J2.5Hz), 7.38(2H, br s), 6.92(1H, d, J2.0Hz), 6.88(1H, d, J8.0Hz), 6.86(1H, dd, J3.5, 2.0Hz), 6.79(1H, dd, J8.0, 1.5Hz), 6.00(2H, s) and 5.56(2H, s). |
| 210 | C | 36 | IR $v_{max}$(DR)/cm$^{-1}$ 3427, 3318, 3201, 2966, 1605, 1503, 1415, 1281, 1027 and 762; NMR $\delta_H$(400MHz, DMSO) 1.08(3H, t, J7.0Hz), 2.39(2H, q, J7.0Hz), 4.91(2H, s), 5.44(2H, s), 6.54(1H, d, J8.0Hz), 6.80-9.62(1H, m), 6.97(1H, s), 7.34(2H, s), 7.89(1H, s), 8.12(1H, s). Anal. Calcd for $C_{17}H_{17}N_7O \cdot 0.6\, H_2O$: C, 58.98; H, 5.30; N, 28.32. Found: C, 59.37; H, 5.02; N, 28.05. |
| 211 | AT | 13 | mp 257.1-257.3° C.; IR $v_{max}$(DR)/cm$^{-1}$ 3491, 3343, 3205, 3131, 2971, 1973, 1691, 1626, 1499, 1437, 1239, 1030 and 764; NMR $\delta_H$(400MHz, DMSO) |

TABLE 2-continued

| Example | Method | Yield(%) | Physical Data |
|---|---|---|---|
| | | | 6.26(2H, s), 6.86-6.91(1H, m), 7.33(2H, s), 7.63(2H, t, J7.5Hz), 7.77(1H, t, J 7.5Hz), 7.94(1H, d, J3.0Hz), 8.11-8.16(3H, m). |
| 212 | R | 58 | IR $\nu_{max}$(DR)/cm$^{-1}$ 3321, 1608, 1438, 1304, 1025 and 757; NMR $\delta_H$(400MHz, DMSO) 5.67(2H, s), 6.86-6.88(1H, m), 7.05(1H, d, J7.5Hz), 7.20(1H, dd, J 5.0, 3.5Hz), 7.35(1H, t, J8.0Hz), 7.39(2H, s), 7.55-7.58(1H, m), 7.72(1H, d, J7.5Hz), 7.85(1H, dd, J5.0, 1.0Hz), 7.92(1H, d, J3.5Hz), 7.98(1H, dd, J 3.5, 1.0Hz), 8.12-8.15(1H, m), 10.24(1H, s). |
| 213 | AU | 29 | IR $\nu_{max}$(DR)/cm$^{-1}$ 3285, 1975, 1625, 1461; NMR $\delta_H$(400MHz, DMSO) 8.14(1H, m), 7.92(1H, d, J3.0Hz), 7.80(1H, t, J7.5Hz), 7.44(1H, d, J7.5Hz), 6.98(1H, d, J7.5Hz), 6.87(1H, dd, J1.5, 3.5Hz), 5.75(2H, s), 4.52(2H, s). |
| 214 | R | 43 | IR $\nu_{max}$(DR)/cm$^{-1}$ 3321, 2956, 1610, 1234, 1027 and 757; NMR $\delta_H$(400MHz, DMSO) 0.99(9H, s), 2.14(2H, s), 5.63(2H, s), 6.85-6.89(1H, m), 6.94(1H, d, J8.0Hz), 7.27(1H, t, J7.5Hz), 7.33-7.45(3H, m), 7.59(1H, d, J9.0Hz), 7.92(1H, d, J3.5Hz), 8.12-8.15(1H, m). |
| 215 | R | 52 | IR $\nu_{max}$(DR)/cm$^{-1}$ 3510, 3278, 1631, 1425, 1293, 1217, 1024 and 757; NMR $\delta_H$(400MHz, DMSO) 0.71-0.79(4H, m), 1.72(1H, tt, J5.5, 7.0Hz), 5.63(2H, s), 6.85-6.89(1H, m), 6.96(1H, d, J8.0Hz), 7.27(1H, t, J7.5Hz), 7.32-7.45(3H, m), 7.55(1H, d, J8.0Hz), 7.92(1H, dd, J3.5, 1.0Hz), 8.12-8.15(1H, m), 10.19(1H, s). Anal. Calcd for $C_{19}H_{17}N_7O_2 \cdot 0.15 H_2O$: C, 60.36; H, 4.61; N, 25.93. Found: C, 60.89; H, 4.62; N, 25.54. |
| 216 | B | 15 | mp 178.3-178.5° C.; IR $\nu_{max}$(DR)/cm$^{-1}$ 3472, 3324, 3194, 2964, 1641, 1598, 1510; NMR $\delta_H$(400MHz, DMSO) 8.14(1H, m), 7.92(1H, dd, J1.0, 3.5Hz), 7.66(1H, t, J8.0Hz), 7.35(2H, br s), 7.17(1H, d, J8.0Hz), 6.90(1H, d, J8.0Hz), 6.87(1H, dd, J2.0, 3.5Hz), 5.73(2H, s), 2.63(2H, t, J7.5Hz), 1.59(2H, sext, J7.5Hz), 0.83(3H, t, J7.5Hz); Anal. Calcd for $C_{17}H_{17}N_7O \cdot 0.1 C_4H_8O_2$: C, 60.72; H, 5.21, N, 28.49. Found: C, 60.85; H, 5.22; N, 28.29. |
| 217 | B | 16 | mp 146.7-149.3° C.; IR $\nu_{max}$(DR)/cm$^{-1}$ 3518, 3323, 2955, 1605, 1511; NMR $\delta_H$(400MHz, DMSO) 8.14-8.13(1H, m), 7.92(1H, d, J3.5Hz), 7.79(1H, t, J7.5Hz), 7.35(2H, br s), 7.35(1H, d, J7.5Hz), 7.05(1H, d, J7.5Hz), 6.87(1H, dd, J1.5, 3.5Hz), 5.75(2H, s), 4.46(2H, s), 3.22(2H, d, J6.5Hz), 1.77-1.87(1H, m), 0.85(6H, d, J6.5Hz); Anal. Calcd for $C_{19}H_{21}N_7O_2 0.5 H_2O$: C, 58.75; H, 5.71, N, 25.24. Found: C, 58.87; H, 5.49; N, 24.92. |
| 218 | B | 14 | mp 196.0-196.1° C.; IR $\nu_{max}$(DR)/cm$^{-1}$ 3481, 3325, 3203, 1646, 1607, 1518, 1488; NMR $\delta_H$(400MHz, DMSO) 8.14(1H, m), 7.92(1H, d, J3.5Hz), 7.80(1H, t, J7.5Hz), 7.50(1H, d, J7.5Hz), 7.38(2H, br s), 7.04(1H, d, J7.5Hz), 6.87(1H, dd, J1.5, 3.5Hz), 5.77(2H, s), 4.64(2H, s). |
| 219 | C | 37 | IR $\nu_{max}$(DR)/cm$^{-1}$ 3480, 3379, 3199, 2958, 2761, 2104, 1879, 1776, 1659, 1516, 1439, 1334, 1024, 762 and 575; NMR $\delta_H$(400MHz, DMSO) 1.10(6H, d, J7.0Hz), 2.92(1H, sept, J6.5Hz), 4.93(2H, s), 5.44(2H, s), 6.54(1H, d, J8.0Hz), 6.80-6.88(2H, m), 7.09(1H, d, J2.0Hz), 7.34(2H, s), 7.88(1H, d, J3.5Hz), 8.10-8.13(1H, m). Anal. Calcd for $C_{18}H_{19}N_7O \cdot 0.3 H_2O$: C, 60.93; H, 5.57; N, 27.63. Found: C, 60.77; H, 5.50; N, 27.42. |
| 220 | AV | 26 | mp 223.3-223.4° C.; NMR $\delta_H$(400MHz, DMSO) 8.14(1H, m), 7.92(1H, dd, J 1.0, 3.5Hz), 7.82(1H, t, J7.5Hz), 7.37(1H, d, J7.5Hz), 7.36(2H, br s), 7.07(1H, d, J7.5Hz), 6.87(1H, dd, J1.5, 3.5Hz), 5.78(2H, s), 4.18(2H, s). |
| 221 | AW | 7 | NMR $\delta_H$(400MHz, DMSO) 9.48-9.45(1H, s), 8.12-8.10(1H, m), 7.90-7.88(1H, dd, J1.0, 3.5Hz), 7.36-7.30(2H, s), 7.17-7.12(2H, dd, J2.0, 8.5Hz), 6.86-6.84(1H, dd, J2.0, 3.5Hz), 6.74-6.70(2H, dd, J2.0, 8.5Hz) and 5.53-5.51(2H, s); M/Z 309(M+H)$^+$. |
| 222 | B | 18 | IR $\nu_{max}$(DR)/cm$^{-1}$ 3483, 3319, 3200, 2961, 1953, 1709, 1612, 1439, 1343, 1220, 995 and 761; NMR $\delta_H$(400MHz, DMSO) 6.37(2H, s), 6.86-6.91(1H, m), 7.35(2H, s), 7.94(1H, d, J3.0Hz), 8.15(1H, s), 8.37(2H, d, J8.5Hz), 8.43(2H, d, J8.5Hz). Anal. Calcd for $C_{16}H_{11}N_7O_4 \cdot 0.2 H_2O$: C, 52.09; H, 3.11; N, 26.58. Found: C, 51.94; H, 3.05; N, 26.27. |
| 223 | B | 41 | IR $\nu_{max}$(DR)/cm$^{-1}$ 4013, 3601, 3456, 3209, 2959, 2237, 1938, 1708, 1625, 1505, 1171, 1002, 827 and 733; NMR $\delta_H$(400MHz, DMSO) 6.33(2H, s), 6.84-6.91(1H, m), 7.34(2H, s), 7.94(1H, d, J3.5Hz), 8.09-8.18(3H, m), 8.28(2H, d, J 8.0Hz). Anal. Calcd for $C_{17}H_{11}N_7O_2 \cdot 0.7 H_2O$: C, 57.05; H, 3.49; N, 27.39. Found: C, 56.97; H, 3.12; N, 27.37. |
| 224 | AX | 54 | IR $\nu_{max}$(DR)/cm$^{-1}$ 3423, 3321, 3212, 1641, 1511, 1420, 1316, 1136 and 780; NMR $\delta_H$(400MHz, DMSO) 0.87(3H, t, J7.5Hz), 1.54-1.66(2H, m), 2.96-3.04(2H, m), 5.65(2H, s), 6.85-6.88(1H, m), 7.00-7.03(2H, m), 7.10-7.16(1H, m), 7.30(1H, t, J7.5Hz), 7.36(2H, s), 7.91(1H, dd, J3.5, 1.0Hz), 8.12-8.15(1H, m), 9.79(1H, s). Anal. Calcd for $C_{18}H_{19}N_7O_3S$: C, 52.29; H, 4.63; N, 23.70. Found: C, 52.22; H, 4.70; N, 23.36. |
| 225 | AX | 47 | IR $\nu_{max}$(DR)/cm$^{-1}$ 3477, 3319, 3114, 1609, 1479, 1414, 1349, 1162, 956 and 763; NMR $\delta_H$(400MHz, DMSO) 5.63(2H, s), 5.85-6.89(1H, m), 6.92(1H, t, J1.5Hz), 7.02-7.11(3H, m), 7.26-7.33(2H, m), 7.37(2H, s), 7.93(1H, dd, J3.5, 1.0Hz), 8.12-8.15(1H, m), 10.62(1H, s). |
| 226 | AY | 58 | mp 221.4-221.5° C.; IR $\nu_{max}$(DR)/cm$^{-1}$ 3569, 3134, 2701, 2421, 1656, 1460; NMR $\delta_H$(400MHz, DMSO) 8.14(1H, m), 7.92(1H, dd, J1.0, 3.5Hz), 7.88(1H, t, J7.5Hz), 7.48(1H, d, J7.5Hz), 7.16(1H, d, J7.5Hz), 6.88-6.87(1H, m), 5.80(2H, s), 4.27-4.24(2H, m), 2.60-2.56(3H, m). |
| 227 | B | 24 | IR $\nu_{max}$(DR)/cm$^{-1}$ 4011, 3491, 3377, 3210, 3125, 2975, 2663, 2106, 1924, 1740, 1618, 1438, 1201, 1004, 796 and 752; NMR $\delta_H$(400MHz, DMSO) 1.14(6H, t, J 6.5Hz), 3.46(4H, q, J6.5Hz), 6.00(2H, s), 6.76(2H, d, J9.0Hz), 6.87(1H, s), |

TABLE 2-continued

| Example | Method | Yield(%) | Physical Data |
|---|---|---|---|
| | | | 7.26(2H, s), 7.85-7.97(3H, m), 8.13(1H, s), Anal. Calcd for $C_{20}H_{21}N_7O_2 \cdot 0.6\ H_2O$: C, 59.72; H, 5.56; N, 24.38. Found: C, 60.00; H, 5.40; N, 24.03. |
| 228 | B | 26 | mp 164.3-169.3° C.; IR $\nu_{max}$(DR)/cm$^{-1}$ 3376, 3199, 2964, 1659, 1613, 1516, 1441; NMR $\delta_H$(400MHz, DMSO) 8.53(1H, d, J2.0Hz), 8.12-8.11(1H, m), 7.89(1H, d, J3.5Hz), 7.62(1H, dd, J2.5, 8.0Hz), 7.35(2H, br s), 7.26(1H, d, J 7.5Hz), 6.85(1H, dd, J1.5, 3.5Hz), 5.67(2H, s), 2.99(1H, sept, J7.0Hz), 1.20(6H, d, J7.0Hz); Anal. Calcd for $C_{17}H_{17}N_7O \cdot 0.5\ H_2O$: C, 59.29; H, 5.27, N, 28.47. Found: C, 59.28; H, 5.16; N, 28.23. |
| 229 | B | 40 | mp 258.2-258.4° C.; IR $\nu_{max}$(DR)/cm$^{-1}$ 3367, 3200, 2932, 1671, 1243, 1178, 1033, 797 and 610; NMR $\delta_H$(400MHz, DMSO) 8.12-8.07(3H, m), 7.91(1H, d, J3.5Hz), 7.15-7.09(4H, m), 6.85(1H, dd, J3.5, 1.5Hz), 6.10(2H, s) and 3.89(3H, s). |
| 230 | B | 25 | IR $\nu_{max}$(DR)/cm$^{-1}$ 3436, 3320, 3208, 2977, 1609, 1370, 1323, 1155, 1025, 840 and 768; NMR $\delta_H$(400MHz, DMSO) 8.12-8.10(1H, m), 7.89(1H, d, J3.5Hz), 7.78(1H, d, J4.0Hz), 7.73(1H, d, J2.5Hz), 7.33(2H, br s), 6.88-6.84(2H, m), 6.76(1H, d, J4.0Hz), 6.07(2H, s) and 1.50(9H, s). |
| 231 | AF | 76 | mp 321.8-322.2° C.; IR $\nu_{max}$(DR)/cm$^{-1}$ 3993, 3233, 1645, 1515, 1437, 1336, 1102, 854 and 759; NMR $\delta_H$(400MHz, DMSO) 11.56(1H, br s), 8.13-8.11(1H, m), 7.91(1H, d, J3.5Hz), 7.58(1H, d, J2.0Hz), 7.55(1H, t, J3.5Hz), 7.42(2H, br s), 6.86(1H, dd, J3.5, 2.0Hz), 6.73(1H, d, J2.0Hz), 6.52(1H, dd, J3.0, 2.0Hz) and 5.94(2H, s). |
| 232 | AX | 20 | IR $\nu_{max}$(DR)/cm$^{-1}$ 3216, 1713, 1610, 1505, 1421, 1185, 1124, 1026, 886 and 763; NMR $\delta_H$(400MHz, DMSO) 2.13(3H, s), 2.35(3H, s), 5.62(2H, s), 6.85-6.88(1H, m), 6.90-6.94(1H, m), 6.98-7.03(1H, m), 7.11(1H, d, J8.0Hz), 7.30(1H, t, J7.5Hz), 7.31(2H, s), 7.91(1H, d, J3.5Hz), 8.11-8.14(1H, m), 10.46(1H, s). |
| 233 | AV | 40 | mp 219.7-222.3° C.; IR $\nu_{max}$(DR)/cm$^{-1}$ 3326, 3191, 2821, 2772, 1595, 1504, 1432; NMR $\delta_H$(400MHz, DMSO) 8.13-8.12(1H, m), 7.91(1H, dd, J1.0, 3.5Hz), 7.74(1H, t, J7.5Hz), 7.35(1H, d, J7.5Hz), 7.31(2H, br s), 6.98(1H, d, J 7.5Hz), 6.86(1H, dd, J2.0, 3.5Hz), 5.74(2H, s), 3.46(2H, s), 2.15(6H, s); Anal. Calcd for $C_{17}H_{18}N_8O$: C, 58.28; H, 5.18, N, 31.97. Found: C, 57.94; H, 5.17; N, 31.70. |
| 234 | AV | 55 | mp 168.3-168.5° C.; IR $\nu_{max}$(DR)/cm$^{-1}$ 3416, 3322, 3180, 2911, 1646, 1612, 1509, 1436; NMR $\delta_H$(400MHz, DMSO) 8.13-8.12(1H, m), 7.91(1H, dd, J1.0, 3.5Hz), 7.74(1H, t, J7.5Hz), 7.32(1H, d, J7.5Hz), 7.31(2H, br s), 7.02(1H, d, J7.5Hz), 6.87-6.86(1H, m), 5.75(2H, s), 3.69(2H, s), 1.92(3H, s); Anal. Calcd for $C_{16}H_{15}N_7OS \cdot 0.2\ H_2O$: C, 53.83; H, 4.35, N, 27.46. Found: C, 53.74; H, 4.29; N, 27.13. |
| 235 | B | 3 | mp 231.6-231.7° C.; IR $\nu_{max}$(DR)/cm$^{-1}$ 3642, 3320, 3198, 1727, 1533, 1437, 1223, 1029, 842 and 639; NMR $\delta_H$(400MHz, DMSO) 8.18(1H, d, J7.5Hz), 8.13(1H, s), 8.00-7.93(2H, m), 7.91(1H, d, J3.5Hz), 7.89-7.82(1H, m), 7.34(2H, br s), 6.87(1H, dd, J3.5, 1.5Hz) and 6.01(2H, s). |
| 236 | AX | 32 | NMR $\delta_H$(400MHz, DMSO) 2.19(3H, s), 3.50(3H, s), 5.58(2H, s), 6.84-6.97(3H, m), 7.08(1H, d, J8.0Hz), 7.20(1H, t, J7.5Hz), 7.35(2H, s), 7.58(1H, s), 7.91(1H, d, J3.0Hz), 8.13(1H, s) and 10.14(1H, s); retention time 0.97 min. |
| 237 | AV | 40 | mp 259.3-259.4° C.; IR $\nu_{max}$(DR)/cm$^{-1}$ 3323, 3202, 1607, 1511; NMR $\delta_H$(400MHz, DMSO) 8.12-8.11(2H, m), 7.91(2H, dd, J1.0, 3.5Hz), 7.70-7.66(2H, m), 7.30(4H, br s), 7.10(4H, d, J8.0Hz), 6.85(2H, dd, J1.5, 3.5Hz), 5.73(4H, s), 4.23(4H, s), 2.78(3H, s). |
| 238 | AV | 17 | mp 238.2-238.6° C.; IR $\nu_{max}$(DR)/cm$^{-1}$ 3189, 2908, 1653, 1592, 1470; NMR $\delta_H$(400MHz, DMSO) 8.13-8.12(1H, m), 7.91(1H, d, J3.0Hz), 7.85(1H, t, J7.5Hz), 7.43(1H, d, J7.5Hz), 7.30(2H, br s), 7.23(1H, d, J7.5Hz), 6.87-6.85(1H, m), 5.81(2H, s), 4.56(2H, s), 2.87(3H, s). |
| 239 | AV | 71 | mp 205.8-206.0° C.; IR $\nu_{max}$(Nujol)/cm$^{-1}$ 3502, 3304, 3185, 2923, 1628, 1510; NMR $\delta_H$(400MHz, DMSO) 8.13-8.12(1H, m), 7.92(1H, d, J3.0Hz), 7.83(1H, t, J8.0Hz), 7.33(1H, d, J8.0Hz), 7.30(2H, br s), 7.17(1H, d, J8.0Hz), 6.87-6.86(1H, m), 5.79(2H, s), 4.31(2H, s), 2.84(3H, s), 2.67(3H, s); Anal. Calcd for $C_{17}H_{18}N_8O_3S$: C, 49.27; H, 4.38, N, 27.02. Found: C, 49.14; H, 4.49; N, 26.74. |
| 240 | C | 24 | mp 254.3-254.5.° C.; IR $\nu_{max}$(DR)/cm$^{-1}$ 3443, 3342, 3187, 1647, 1593, 1513, 1414, 1300, 1268 and 1225; NMR $\delta_H$(400MHz, DMSO) 7.37(2H, s), 6.96(1H, t, J7.8Hz), 6.46(1H, dd, J1.0, J8.0Hz), 6.40(2H, d, J7.5Hz), 6.33(1H, s), 5.56(2H, s), 5.2(2H, s), 2.5(3H, s) and 2.44(3H, s). |
| 241 | C | 17 | NMR $\delta_H$(400MHz, DMSO) 8.11-8.09(1H, m, J1.0, 3.5Hz), 7.89-7.86(1H, dd, J1.0, 3.5Hz), 7.32-7.27(2H, s), 7.22-6.95(1H, t, J9.0Hz), 6.85-6.83(1H, dd, J2.0, 3.5Hz), 6.35-6.29(2H, m), 5.48-5.46(2H, s) and 5.46-5.44(2H, s); Retention time 1.18 min. |
| 242 | B | 15 | IR $\nu_{max}$(DR)/cm$^{-1}$ 3850, 3667, 2923, 1730, 1601, 1464, 1023, 751 and 593; NMR $\delta_H$(400MHz, DMSO) 3.68(1H, dd, J16.0, 5.5Hz), 3.88(1H, dd, J16.0, 9.0Hz), 6.05(1H, dd, J8.5, 5.5Hz), 6.84-6.89(1H, m), 7.29(2H, s), 7.57(1H, t, J 7.0Hz), 7.72(1H, d, J7.5Hz), 7.78-7.87(2H, m), 7.91(1H, d, J3.5Hz), 8.13(1H, s). Anal. Calcd for $C_{17}H_{12}N_6O_2 \cdot 0.2\ H_2O$: C, 60.87; H, 3.72; N, 25.02. Found: C, 60.89; H, 3.68; N, 24.85. |
| 243 | AF | 53 | mp >300° C. dec; IR $\nu_{max}$(DR)/cm$^{-1}$ 3212, 2923, 1642, 1605, 1510, 1461, 1377, 1023 and 757; NMR $\delta_H$(400MHz, DMSO) 11.16(1H, br s), 8.12(1H, s), 7.91(1H, d, J3.5Hz), 7.44-7.36(3H, m), 7.29(1H, s), 6.86(1H, dd, J3.5, 1.5Hz), 6.58(1H, s), 6.42-6.38(1H, m), 5.87(2H, s) and 2.27(3H, s). |

TABLE 2-continued

| Example | Method | Yield(%) | Physical Data |
|---|---|---|---|
| 244 | BB | 7 | IR $\nu_{max}$(Nujol)/cm$^{-1}$ 3319, 2924, 1646, 1606, 1462; NMR $\delta_H$(400MHz, DMSO) 9.54(1H, s), 8.27-8.26(1H, m), 8.12-8.11(1H, m), 7.90(1H, d, J3.5Hz), 7.71(1H, d, J8.0Hz), 7.32(2H, br s), 7.17-7.15(1H, m), 7.11-7.09(1H, m), 6.86-6.85(1H, m), 5.59(2H, s), 2.18(3H, s). |
| 245 | B | 22 | IR $\nu_{max}$(Nujol)/cm$^{-1}$ 3849, 3500, 3298, 3174, 2924, 1698, 1631, 1604, 1456, 1379, 1226, 1027, 953 and 753; NMR $\delta_H$(400MHz, DMSO) 1.91(3H, d, J7.0Hz), 6.63(1H, q, J7.0Hz), 6.84-6.87(1H, m), 7.32(2H, s), 7.54(2H, t, J8.0Hz), 7.66(1H, tt, J7.5, 2.0Hz), 7.88(1H, d, J3.5Hz), 7.98-8.03(2H, m), 8.11-8.12(1H, m). Anal. Calcd for C$_{17}$H$_{14}$N$_6$O$_2$: C, 61.07; H, 4.22; N, 25.12. Found: C, 60.72; H, 4.27; N, 24.75. |
| 246 | BE | 81 | IR $\nu_{max}$(Nujol;)/cm$^{-1}$ 3313, 3189, 2924, 1605, 1461, 1377, 1236, 1026 and 762; NMR $\delta_H$(400MHz, DMSO) 11.62(1H, br s), 8.11(1H, dd, J2.0, 1.0Hz), 7.90(1H, d, J3.5Hz), 7.41(1H, t, J2.5Hz), 7.37-7.29(3H, m), 6.94(1H, d, J11.0Hz), 6.85(1H, dd, J3.5, 2.0Hz) 6.52-6.47(1H, m) and 5.71(2H, s). |
| 247 | B | 28 | mp 134.5-134.6° C.; IR $\nu_{max}$(Nujol)/cm$^{-1}$ 3306, 3189, 2924, 1635, 1610, 1580; NMR $\delta_H$(400MHz, DMSO) 8.13-8.12(1H, m), 7.92-7.91(1H, m), 7.79-7.75(1H, m), 7.35(1H, d, J8.0Hz), 7.31(2H, br s), 7.03(1H, d, J7.5Hz), 6.86(1H, dd, J3.5, 1.5Hz), 5.74(2H, s), 4.46(2H, s), 3.65(1H, sept, J6.0Hz), 1.12(6H, d, J6.0Hz); Anal. Calcd for C$_{18}$H$_{19}$N$_7$O$_2$•1.2 H$_2$O: C, 55.86; H, 5.57, N, 25.33. Found: C, 55.80; H, 5.41; N, 25.05. |
| 248 | B | 11 | mp 158.9.-161.3° C.; IR $\nu_{max}$(Nujol)/cm$^{-1}$ 3301, 3185, 2923, 1636, 1611, 1570, 1536, 1501, 1324 and 1210; NMR $\delta_H$(400MHz, DMSO) 7.88(1H, d, J3.0Hz), 7.66(1H, t, J7.5Hz) 7.18(1H, br s) 6.89(1H, d, J7.5Hz), 6.51(1H, dd, J1.0, J3.5Hz), 5.71(2H, s), 2.69(2H, q, J7.5Hz), 2.46(3H, s) and 1.15(3H, J7.5Hz). |
| 249 | BE | 76 | IR $\nu_{max}$(DR;)/cm$^{-1}$ 3319, 2928, 1605, 1334, 1226, 1027, 737 and 528; NMR $\delta_H$(400MHz, DMSO) 11.47(1H, s), 8.14-8.09(1H, m) 7.89(1H, d, J3.5Hz), 7.48(1H, d, J3.0Hz), 7.38-7.27(3H, m), 6.94(1H, d, J13.0Hz), 6.85(1H, dd, J3.5, 2.0Hz), 6.52-6.47(1H, m) and 5.81(2H, s). |
| 250 | BE | 68 | IR $\nu_{max}$(DR)/cm$^{-1}$ 3318, 2923, 1640, 1579, 1455, 1377, 1079, 1022, 750 and 588; NMR $\delta_H$(400MHz, DMSO) 11.13(1H, br s), 8.23(1H, s), 8.05-8.04(1H, m), 7.43(1H, d, J3.5Hz), 7.30(2H, s), 7.00(1H, t, J7.0Hz), 6.90(2H, s), 6.80-6.77(1H, m), 6.73(1H, d, J6.5Hz), 6.51(1H, s)and 5.63(2H, s). |
| 251 | BE | 42 | mp 294.0-294.2° C.; IR $\nu_{max}$(DR)/cm$^{-1}$ 3498, 3414, 1612, 1318, 1235, 102, 765 and 589; NMR $\delta_H$(400MHz, DMSO) 11.24(1H, br s), 8.12(1H, s), 7.91(1H, d, J3.5Hz), 7.53(1H, s), 7.39(1H, t, J2.5Hz) 7.36-7.26(3H, m), 6.88-6.82(1H, m), 6.43-6.38(1H, m) and 5.76(2H, s) |
| 252 | BF | 44 | mp 200.2.-201.2° C. IR $\nu_{max}$(DR)/cm$^{-1}$ 3390, 3205, 2924, 1725, 1648, 1603, 1508, 1423, 1332, 1277 and 1158; NMR $\delta_H$(400MHz, DMSO) 8.12(1H, s), 7.90(1H, d, J3.5Hz), 7.35-7.25(4H, m), 7.07-6.97(3H, m), 6.86(1H, dd, J 1.5, J3.5Hz), 6.45(2H, t, J7.5Hz), 6.37(1H, s), 6.32(1H, t, J6.0Hz), 5.49(2H, s) and 4.16(2H, s, J6.0Hz). |
| 253 | B | 18 | mp 181.8-182.1° C.; IR $\nu_{max}$(DR)/cm$^{-1}$ 3362, 3208, 2988, 1654, 1601, 1513; NMR $\delta_H$(400MHz, DMSO) 8.13-8.12(1H, m), 7.91(1H, d, J3.5Hz), 7.68(1H, m), 7.29(2H, br s), 6.87-6.85(1H, m), 6.74(1H, d, J7.5Hz), 6.68(1H, d, J8.0Hz), 5.69(2H, s), 4.07(2H, q, J7.0Hz), 1.12(3H, t, J7.0Hz). |
| 254 | B | 14 | mp 190.8-190.9° C.; IR $\nu_{max}$(DR)/cm$^{-1}$ 3514, 3292, 3158, 2984, 1615, 1500; NMR $\delta_H$(400MHz, DMSO) 7.88(1H, d, J3.5Hz), 7.65(1H, dd, J7.0, 8.0Hz), 7.25(2H, br s), 6.72(1H, d, J7.0Hz), 6.68(1H, d, J8.0Hz), 6.52-6.50(1H, m), 5.67(2H, s), 4.08(2H, q, J7.0Hz), 2.46(3H, s), 1.12(3H, t, J7.0Hz). |
| 255 | BF | 20 | mp 184.5-184.6° C.; IR $\nu_{max}$(DR)/cm$^{-1}$ 3202, 1649, 1601, 1509, 1436, 1331, 1277 and 1221; NMR $\delta_H$(400MHz, DMSO) 8.43(1H, d, J4.89Hz), 8.12(1H, dd, J0.8, 3.5Hz), 7.91(1H, dd, J0.9, 3.5Hz), 7.65(1H, td, J1.7, 7.7Hz), 7.30(2H, br s), 7.25(1H, d, J7.9Hz), 7.15(1H, dd, J4.9, 7.5Hz), 7.0(1H, t, J7.8Hz), 6.86(1H, dd, J1.7, 3.5Hz), 6.48-6.36(4H, m), 5.49(2H, s), 4.27(2H, s); Anal. Calcd for C$_{21}$H$_{18}$N$_8$O•0.3 H$_2$O: C, 62.46; H, 4.64, N, 27.75. Found: C, 62.66; H, 4.57; N, 27.36. |
| 256 | B | 6 | Mp 167.6-168.1° C. IR $\nu_{max}$(DR)/cm$^{-1}$ 3509, 3304, 3178, 1609, 1494, 1421, 1325, 1127, 839 and 752. NMR $\delta_H$(400MHz, DMSO) 2.05(3H, d, J7.0Hz), 6.14(1H, q, J7.0Hz), 6.84-6.88(1H, m), 7.30(2H, s), 7.52(2H, d, J8.5Hz), 7.73(2H, d, J8.0Hz), 7.91(1H, dd, J3.5, 1.0Hz), 8.11-8.13(1H, m). Anal. Calcd for C$_{17}$H$_{13}$N$_6$F$_3$O: C, 54.55; H, 3.50; N, 22.44. Found: C, 54.52; H, 3.65; N, 22.06. |
| 257 | BE | 75 | IR $\nu_{max}$(DR)/cm$^{-1}$ 3459, 3348, 3187, 2960, 1648, 1513, 1351, 1244, 1011, 837 and 759; NMR $\delta_H$(400MHz, DMSO) 11.18(1H, br s), 8.11(1H, s), 7.89(1H, d, J3.0Hz), 7.42(1H, d, J7.5Hz), 7.37-7.26(3H, m), 7.21(1H, d, J11.0Hz), 6.89-6.81(1H, m), 6.43-6.37(1H, s) and 5.72(2H, s). |
| 258 | BE | 94 | mp >300° C. dec; IR $\nu_{max}$(DR)/cm$^{-1}$ 3441, 3318, 2990, 1612, 1285, 1083, 839 and 593; NMR $\delta_H$(400MHz, DMSO) 11.29(1H, br s), 8.12(1H, s), 7.91(1H, d, J3.5Hz), 7.41-7.29(3H, m), 7.22(1H, dd, J10.0, 2.5Hz), 6.90(1H, dd, J9.5, 2.5Hz), 6.86(1H, dd, J3.5, 1.5Hz), 6.30(1H, s) and 5.79(2H, s). |
| 259 | B | 50 | mp 228.4-228.5° C.; NMR $\delta_H$(400MHz, DMSO) 8.13-8.12(1H, m), 7.91(1H, d, J3.5Hz), 7.34(2H, br s), 7.18(2H, s), 6.87-6.85(1H, m), 5.67(2H, s), 2.22(6H, s). |
| 260 | B | 8 | mp 150.3-151.0° C. IR $\nu_{max}$(DR)/cm$^{-1}$ 3510, 3306, 3183, 1633, 1495, 1423, 1240, 1029 and 753; NMR $\delta_H$(400MHz, DMSO) 2.02(3H, d, J7.0Hz), 6.05(1H, q, J7.0Hz), 6.83-6.88(1H, m), 7.10-7.22(3H, m), 7.30(2H, s), |

TABLE 2-continued

| Example | Method | Yield(%) | Physical Data |
|---|---|---|---|
|  |  |  | 7.40(1H, dt, J8.0, 6.5Hz), 7.91(1H, dd, J3.5, 1.0Hz), 8.10-8.13(1H, m). Anal. Calcd for $C_{16}H_{13}N_6OF \cdot 0.25\ H_2O$: C, 58.44; H, 4.14; N, 25.56. Found: C, 58.48; H, 3.98; N, 25.40. |
| 261 | BE | 91 | IR $\nu_{max}$(DR)/cm$^{-1}$ 3472, 3318, 3184, 2922, 1651, 1595, 1478, 1417, 1329, 1218, 1097, 1015, 870, 767 and 545; NMR $\delta_H$(400MHz, DMSO) 11.50(1H, s), 8.11(1H, s), 7.90(1H, d, J3.5Hz), 7.47(1H, t, J3.0Hz), 7.33(2H, s), 7.19(1H, s), 6.86-6.84(1H, m), 6.53-6.51(1H, m), 5.71(2H, s). |
| 262 | C | 34 | mp 250.1-261.3° C.; IR $\nu_{max}$(DR)/cm$^{-1}$ 3325, 3205, 2968, 1603, 1488; NMR $\delta_H$(400MHz, DMSO) 8.11-8.10(1H, m), 7.89-7.87(1H, m), 7.28(2H, br s), 6.85-6.83(1H, m), 6.81(2H, s), 5.40(2H, s), 4.56(2H, br s), 2.03(6H, s). |
| 263 | K | 72 | IR $\nu_{max}$(DR)/cm$^{-1}$ 2825, 2021, 1645, 1453, 1394, 1286, 1171, 1030, 779 and 619; NMR $\delta_H$(400MHz, DMSO) 2.02(3H, d, J7.0Hz), 6.07(1H, q, J7.0Hz), 6.85-6.88(1H, m), 7.13-7.18(1H, m), 7.25(1H, d, J8.5Hz), 7.36(1H, d, J 8.0Hz), 7.47(1H, t, J7.5Hz), 7.92(1H, d, J3.5Hz), 8.12-8.14(1H, m). Anal. Calcd for $C_{16}H_{15}N_7O \cdot 2HCl \cdot 0.8\ H_2O$: C, 47.02; H, 4.59; N, 23.99. Found: C, 46.87; H, 4.43; N, 23.71. |
| 264 | B | 26 | mp 162.0-162.6° C.; IR $\nu_{max}$(DR)/cm$^{-1}$ 3319, 3206, 2932, 1644, 1505; NMR $\delta_H$(400MHz, DMSO) 8.13-8.12(1H, m), 7.92-7.91(1H, m), 7.68-7.64(1H, m), 7.31(2H, br s), 7.21(1H, d, J7.5Hz), 6.92(1H, d, J8.0Hz), 6.86(1H, dd, J3.5, 1.5Hz), 5.74(2H, s), 3.58(2H, t, J6.5Hz), 3.16(3H, s), 2.84(2H, t, J6.5Hz); M/Z 352(M+H)$^+$. |
| 265 | B | 15 | NMR $\delta_H$(400MHz, DMSO) 8.12-8.11(1H, m), 7.92-7.90(1H, m), 7.47(1H, d, J8.0Hz), 7.28(2H, br s), 6.91(1H, d, J8.0Hz), 6.86(1H, dd, J2.0, 3.5Hz), 5.73-5.69(1H, m), 2.60-2.46(2H, m), 2.39(3H, s), 2.20(3H, s), 0.87(3H, t, J 7.0Hz); M/Z 350(M+H)$^+$. |
| 266 | AK | 99 | NMR $\delta_H$(400MHz, DMSO) 8.22-8.17(2H, m), 7.94(1H, d, J2.01Hz), 7.73-7.63(2H, m), 7.37(1H, d, J2.5Hz) and 5.86(2H, s); M/Z 338(M+H)$^+$; Retention time 1.74 min. |
| 267 | B | 58 | mp 255.6-255.7° C.; IR $\nu_{max}$(DR)/cm$^{-1}$ 3512, 3294, 3179, 2960, 2692, 1745, 1638, 1432 and 1371; NMR $\delta_H$(400MHz, DMSO) 7.88(1H, d, J3.51Hz), 7.81(1H, dd, J1.0, J8.0Hz), 7.46-7.29(2H, br s), 7.40(1H, t, J7.8Hz), 7.23(1H, d, J8.0Hz), 6.51(1H, dd, J1.0, 3.5Hz), 5.78(2H, s) and 2.46(6H, s). |
| 268 | B | 40 | mp 248.1-249.0° C. IR $\nu_{max}$(DR)/cm$^{-1}$ 3507, 3308, 3190, 2952, 1626, 1571, 1519, 1434, 1348 and 1291; NMR $\delta_H$(400MHz, DMSO) 8.22(2H, d, J8.5Hz), 7.89(1H, d, J3.5Hz), 7.49(2H, d, J9.0Hz), 7.36(2H, br s), 6.52(1H, dd, J1.0, 3.5Hz), 5.83(2H, s) and 2.46(3H, s). |
| 269 | B | 18 | NMR $\delta_H$(400MHz, DMSO) 8.14-8.12(1H, m), 7.92-7.90(1H, dd, J1.0, 3.5Hz), 7.42-7.34(2H, s), 7.26-7.25(4H, s), 6.87-6.85(1H, dd, J1.5, 3.5Hz), 5.66-5.64(2H, s), 3.15-3.13(3H, s) and 1.38-1.36(9H, s). |
| 270 | H | 46 | NMR $\delta_H$(400MHz, DMSO) 8.22-8.13(2H, m), 7.75-7.65(3H, m), 7.59(1H, dd, J1.5, J3.0Hz), 7.34(2H, br s), 6.96(1H, dd, J1.5, J3.5Hz), 6.45(1H, t, J 3.2Hz), 5.85(2H, s) and 1.22(9H, s); M/Z 437(M+H)$^+$; Retention time 4.36 min. |
| 271 | Q | 40 | NMR $\delta_H$(400MHz, DMSO) 8.21-8.17(2H, m), 7.71-7.63(2H, m), 7.48(2H, br s), 5.87(2H, s), 2.50(3H, s) and 2.44(3H, s); M/Z 383(M+H)$^+$; Retention time 3.69 min. |
| 272 | B |  | NMR $\delta_H$(400MHz, DMSO) 8.18(1H, dd, J9.6, 2.0Hz), 8.13(1H, d, J1.6Hz), 8.05(1H, dd, J8.4, 2.4Hz), 7.90(1H, d, J3.2Hz), 7.45(1H, t, J8.0Hz), 7.38(2H, br s), 6.86(1H, dd, J3.6, 2.0Hz) and 5.84(2H, s). |
| 273 | B |  | NMR $\delta_H$(400MHz, DMSO) 8.13-8.09(1H, m), 7.89(1H, d, J3.5Hz), 7.66(1H, d, J3.5Hz), 7.39(1H, s), 7.29(2H, br s), 6.85(1H, dd, J3.5, 2.0Hz), 6.68(1H, d, J3.5Hz), 6.65(1H, s), 2.27(3H, s) and 1.52(9H, s). |
| 274 | BA | 99 | IR $\nu_{max}$(Nujol)/cm$^{-1}$ 3313, 2923, 1693, 1603; NMR $\delta_H$(400MHz, DMSO) 8.78(1H, br s), 8.12-8.11(1H, m), 7.90(1H, d, J3.5Hz), 7.34-7.31(3H, m), 7.13-7.12(1H, m), 7.08-7.05(1H, m), 6.86-6.85(1H, m), 5.58(2H, s), 4.08(2H, q, J7.0Hz), 2.16(3H, s), 1.21(3H, t, J7.0Hz). |

Adenosine Receptor Binding

Binding Affinities at hA$_{2A}$ Receptors

The compounds were examined in an assay measuring in vitro binding to human adenosine A$_{2A}$ receptors by determining the displacement of the adenosine A$_{2A}$ receptor selective radioligand [$^3$H]-CGS 21680 using standard techniques. The results are summarised in Table 3.

TABLE 3

| Example | K$_i$ (nM) |
|---|---|
| Example 3 | 3 |
| Example 4 | 4 |
| Example 5 | 3 |
| Example 8 | 3 |
| Example 11 | 2 |
| Example 12 | 7 |
| Example 13 | 2 |
| Example 15 | 4 |
| Example 41 | 2 |
| Example 57 | 2 |
| Example 78 | 3 |
| Example 92 | 2 |
| Example 107 | 2 |
| Example 120 | 1 |
| Example 149 | 1 |
| Example 156 | 2 |
| Example 169 | 2 |

TABLE 3-continued

| Example | $K_i$ (nM) |
| --- | --- |
| Example 188 | 1 |
| Example 202 | 1 |
| Example 209 | 1 |
| Example 221 | 2 |
| Example 233 | 4 |
| Example 255 | 4 |

Evaluation of Potential Anti-Parkinsonian Activity In Vivo

Haloperidol-induced Hypolocomotion Model

It has previously been demonstrated that adenosine antagonists, such as theophylline, can reverse the behavioural depressant effects of dopamine antagonists, such as haloperidol, in rodents (Mandhane S. N. et al., *Adenosine $A_2$ receptors modulate haloperidol-induced catalepsy in rats. Eur. J. Pharmacol.* 1997, 328, 135-141). This approach is also considered a valid method for screening drugs with potential antiparkinsonian effects. Thus, the ability of novel adenosine antagonists to block haloperidol-induced deficits in locomotor activity in mice can be used to assess both in vivo and potential antiparkinsonian efficacy.

Method

Female TO mice (25-30 g) obtained from TUCK, UK, are used for all experiments. Animals are housed in groups of 8 [cage size–40 (width)×40 (length)×20 (height)cm] under 12 hr light/dark cycle (lights on 08:00 hr), in a temperature (20±2° C.) and humidity (55±15%) controlled environment. Animals have free access to food and water, and are allowed at least 7 days to acclimatize after delivery before experimental use.

Drugs

Liquid injectable haloperidol (1 ml Serenance ampoules from Baker Norton, Harlow, Essex, each containing haloperidol BP 5 mg, batch # P424) are diluted to a final concentration of 0.02 mg/ml using saline. Test compounds are typically prepared as aqueous suspensions in 8% Tween. All compounds are administered intraperitoneally in a volume of 10 ml/kg.

Procedure 1.5 hours before testing, mice are administered 0.2 mg/kg haloperidol, a dose that reduces baseline locomotor activity by at least 50%. Test substances are typically administered 5-60 minutes prior to testing. The animals are then placed individually into clean, clear polycarbonate cages [20 (width)×40 (length)×20 (height) cm, with a flat perforated, Perspex lid]. Horizontal locomotor activity is determined by placing the cages within a frame containing a 3×6 array of photocells linked to a computer, which tabulates beam breaks. Mice are left undisturbed to explore for 1 hour, and the number of beams breaks made during this period serves as a record of locomotor activity which is compared with data for control animals for statistically significant differences.

6-OHDA Model

Parkinson's disease is a progressive neurodegenerative disorder characterised by symptoms of muscle rigidity, tremor, paucity of movement (hypokinesia), and postural instability. It has been established for some time that the primary deficit in PD is a loss of dopaminergic neurones in the substantia nigra which project to the striatum, and indeed a substantial proportion of striatal dopamine is lost (ca 80-85%) before symptoms are observed. The loss of striatal dopamine results in abnormal activity of the basal ganglia, a series of nuclei which regulate smooth and well co-ordinated movement (Blandini F. et al., Glutamate and Parkinson's Disease. *Mol. Neurobiol.* 1996, 12, 73-94). The neurochemical deficits seen in Parkinson's disease can be reproduced by local injection of the dopaminergic neurotoxin 6-hydroxydopamine into brain regions containing either the cell bodies or axonal fibres of the nigrostriatal neurones.

By unilaterally lesioning the nigrostriatal pathway on only one-side of the brain, a behavioural asymmetry in movement inhibition is observed. Although unilaterally-lesioned animals are still mobile and capable of self maintenance, the remaining dopamine-sensitive neurones on the lesioned side become supersensitive to stimulation. This is demonstrated by the observation that following systemic administration of dopamine agonists, such as apomorphine, animals show a pronounced rotation in a direction contralateral to the side of lesioning. The ability of compounds to induce contralateral rotations in 6-OHDA lesioned rats has proven to be a sensitive model to predict drug efficacy in the treatment of Parkinson's Disease.

Animals

Male Sprague-Dawley rats, obtained from Charles River, are used for all experiments. Animals are housed in groups of 5 under 12 hr light/dark cycle (lights on 08:00 hr), in a temperature (20±2° C.) and humidity (55±15%) controlled environment. Animals have free access to food and water, and are allowed at least 7 days to acclimatize after delivery before experimental use.

Drugs

Ascorbic acid, desipramine, 6-OHDA and apomorphine (Sigma-Aldrich, Poole, UK). 6-OHDA is freshly prepared as a solution in 0.2% ascorbate at a concentration of 4 mg/mL prior to surgery. Desipramine is dissolved in warm saline, and administered in a volume of 1 ml/kg. Apomorphine is dissolved in 0.02% ascorbate and administered in a volume of 2 mL/kg. Test compounds are suspended in 8% Tween and injected in a volume of 2 mL/kg.

Surgery 15 minutes prior to surgery, animals are given an intraperitoneal injection of the noradrenergic uptake inhibitor desipramine (25 mg/kg) to prevent damage to non-dopamine neurones. Animals are then placed in an anaesthetic chamber and anaesthetised using a mixture of oxygen and isoflurane. Once unconscious, the animals are transferred to a stereotaxic frame, where anaesthesia is maintained through a mask. The top of the animal's head is shaved and sterilised using an iodine solution. Once dry, a 2 cm long incision is made along the midline of the scalp and the skin retracted and clipped back to expose the skull. A small hole is then drilled through the skill above the injection site. In order to lesion the nigrostriatal pathway, the injection cannula is slowly lowered to position above the right medial forebrain bundle at −3.2 mm anterior posterior, −1.5 mm medial lateral from bregma, and to a depth of 7.2 mm below the duramater. 2 minutes after lowing the cannula, 2 μL of 6-OHDA is infused at a rate of 0.5 μL/min over 4 minutes, yielding a final dose of 8 μg. The cannula is then left in place for a further 5 minutes to facilitate diffusion before being slowly withdrawn. The skin is then sutured shut using Ethicon W501 Mersilk, and the animal removed from the strereotaxic frame and returned to its homecage. The rats are allowed 2 weeks to recover from surgery before behavioural testing.

Apparatus

Rotational behaviour is measured using an eight station rotameter system provided by Med Associates, San Diego, USA. Each station is comprised of a stainless steel bowl (45 cm diameter×15 cm high) enclosed in a transparent Plexiglas cover running around the edge of the bowl, and extending to a height of 29 cm. To assess rotation, rats are placed in cloth jacket attached to a spring tether connected to optical rotameter positioned above the bowl, which assesses movement to the left or right either as partial (45°) or full (360°) rotations. All eight stations are interfaced to a computer that tabulated data.

Procedure

To reduce stress during drug testing, rats are initially habituated to the apparatus for 15 minutes on four consecutive days. On the test day, rats are given an intraperitoneal injection of test compound 30 minutes prior to testing. Immediately prior to testing, animals are given a subcutaneous injection of a subthreshold dose of apomorphine, then placed in the harness and the number of rotations recorded for one hour. The total number of full contralatral rotations during the hour test period serves as an index of antiparkinsonian drug efficacy.

The invention claimed is:

1. A method of treating a disorder selected from a group consisting of:
   acute pain; chronic pain; cerebral ischaemia; myocardial ischaemia; muscle ischaemia; retinal ischaemia-reperfusion injury; diabetic neuropathy; and depression;
   the method comprising administering to a subject in need of such treatment an effective dose of a pharmaceutical composition comprising a compound of formula (I) or a pharmaceutically acceptable salt thereof, and at least one pharmaceutically acceptable carrier:

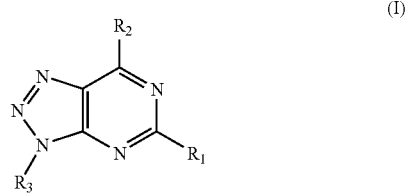

wherein
   $R_1$ is selected from the group consisting of H, alkyl, aryl, alkoxy, aryloxy, alkylthio, arylthio, halogen, CN, $NR_5R_6$, $NR_4COR_5$, $NR_4CONR_5R_6$, $NR_4CO_2R_7$ and $NR_4SO_2R_7$;
   $R_2$ is an aryl attached via an unsaturated ring carbon of said aryl group;
   $R_3$ is selected from the group consisting of H, alkyl, $COR_5$, $CO_2R_7$, $CONR_5R_6$, $CONR_4NR_5R_6$ and $SO_2R_7$;
   $R_4$, $R_5$ and $R_6$ are independently selected from the group consisting of H, alkyl and aryl, or where $R_5$ and $R_6$ are in an $NR_5R_6$ group, $R_5$ and $R_6$ may be linked to form a heterocyclic group, or where $R_4$, $R_5$ and $R_6$ are in a ($CONR_4NR_5R_6$) group, $R_4$ and $R_5$ may be linked to form a heterocyclic group; and
   $R_7$ is selected from the group consisting of alkyl and aryl.

2. The method according to claim 1 wherein the subject has cerebral ischaemia.

3. The method according to claim 1 wherein the subject has myocardial ischaemia.

4. The method according to claim 1 the subject has muscle ischaemia.

5. The method according to claim 1 wherein the subject has retinal ischaemia-reperfusion injury or diabetic neuropathy.

6. The method according to claim 1 wherein the subject has acute pain.

7. The method according to claim 1 wherein the subject has chronic pain.

8. The method according to claim 1 wherein the subject has depression.

9. The method according to claim 1 wherein the subject has a disorder selected from the group consisting of depression, acute pain and chronic pain.

10. The method according to claim 1 wherein the subject is human.

11. The method of claim 1 wherein the compound of formula (I) is 3-(4-amino-3-methylbenzyl)-7-(2-furyl)-3H-[1,2,3]triazolo[4,5-d]pyrimidine-5-amine, or a pharmaceutically acceptable salt thereof.

12. The method of claim 2 wherein the compound of formula (I) is 3-(4-amino-3-methylbenzyl)-7-(2-furyl)-3H-[1,2,3]triazolo[4,5-d]pyrimidine-5-amine, or a pharmaceutically acceptable salt thereof.

13. The method of claim 3 wherein the compound of formula (I) is 3-(4-amino-3-methylbenzyl)-7-(2-furyl)-3H-[1,2,3]triazolo[4,5-d]pyrimidine-5-amine, or a pharmaceutically acceptable salt thereof.

14. The method of claim 7, wherein the compound of formula (I) is 3-(4-amino-3-methylbenzyl)-7-(2-furyl)-3H-[1,2,3]triazolo[4,5-d]pyrimidine-5-amine, or a pharmaceutically acceptable salt thereof.

15. The method of claim 8, wherein the compound of formula (I) is 3-(4-amino-3-methylbenzyl)-7-(2-furyl)-3H-[1,2,3]triazolo[4,5-d]pyrimidine-5-amine, or a pharmaceutically acceptable salt thereof.

16. The method of claim 9 wherein the compound of formula (I) is 3-(4-amino-3-methylbenzyl)-7-(2-furyl)-3H-[1,2,3]triazolo[4,5-d]pyrimidine-5-amine, or a pharmaceutically acceptable salt thereof.

17. The method of claim 6, wherein the compound of formula (I) is 3-(4-amino-3-methylbenzyl)-7-(2-furyl)-3H-[1,2,3]triazolo[4,5-d]pyrimidine-5-amine, or a pharmaceutically acceptable salt thereof.

18. A method of treating a disorder in which blocking of adenosine $A_{2A}$ receptors is beneficial, wherein the disorders are selected from a group consisting of: acute pain; chronic pain; cerebral ischaemia; myocardial ischaemia; muscle ischaemia; retinal ischaemia-reperfusion injury; diabetic neuropathy; and depression
   the method comprising administering to a subject in need of such treatment an effective dose of a pharmaceutical composition comprising a compound of formula (I) or a pharmaceutically acceptable salt thereof, and at least one pharmaceutically acceptable carrier:

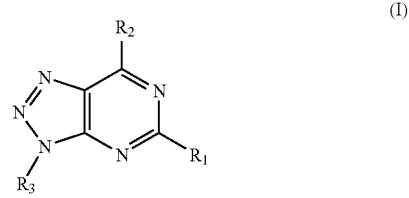

wherein
R₁ is selected from the group consisting of H, alkyl, aryl, alkoxy, aryloxy, alkylthio, arylthio, halogen, CN, NR₅R₆, NR₄COR₅, NR₄CONR₅R₆, NR₄CO₂R₇ and NR₄SO₂R₇;

R₂ is an aryl attached via an unsaturated ring carbon of said aryl group;

R₃ is selected from the group consisting of H, alkyl, COR₅, CO₂R₇, CONR₅R₆, CONR₄NR₅R₆ and SO₂R₇;

R₄, R₅ and R₆ are independently selected from the group consisting of H, alkyl and aryl, or where R₅ and R₆ are in an NR₅R₆ group, R₅ and R₆ may be linked to form a heterocyclic group, or where R₄, R₅ and R₆ are in a (CONR₄NR₅R₆) group, R₄ and R₅ may be linked to form a heterocyclic group; and R₇ is selected from the group consisting of alkyl and aryl.

19. The method according to claim 18 wherein the subject has a disorder caused by hyperfunctioning of the receptors.

20. A method of treating a patient suffering from Parkinson's disease comprising administering to the patient an effective dose of a pharmaceutical composition comprising a compound of formula (I) or a pharmaceutically acceptable salt thereof, and at least one pharmaceutically acceptable carrier:

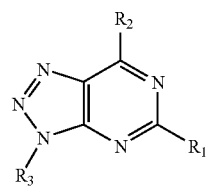

(I)

wherein
R₁ is selected from the group consisting of H, alkyl, aryl, alkoxy, aryloxy, alkylthio, arylthio, halogen, CN, NR₅R₆, NR₄COR₅, NR₄CONR₅R₆, NR₄CO₂R₇ and NR₄SO₂R₇;

R₂ is an aryl attached via an unsaturated ring carbon of said aryl group;

R₃ is selected from the group consisting of H, alkyl, COR₅, CO₂R₇, CONR₅R₆, CONR₄NR₅R₆ and SO₂R₇;

R₄, R₅ and R₆ are independently selected from the group consisting of H, alkyl and aryl, or where R₅ and R₆ are in an NR₅R₆ group, R₅ and R₆ may be linked to form a heterocyclic group, or where R₄, R₅ and R₆ are in a (CONR₄NR₅R₆) group, R₄ and R₅ may be linked to form a heterocyclic group; and R₇ is selected from the group consisting of alkyl and aryl.

21. A method of treating a patient suffering from drug-induced Parkinsonism, or Parkinsonism induced by poisoning comprising administering to the patient an effective dose of a pharmaceutical composition comprising a compound of formula (I) or a pharmaceutically acceptable salt thereof, and at least one pharmaceutically acceptable carrier:

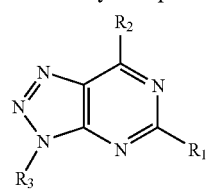

(I)

wherein
R₁ is selected from the group consisting of H, alkyl, aryl, alkoxy, aryloxy, alkylthio, arylthio, halogen, CN, NR₅R₆, NR₄COR₅, NR₄CONR₅R₆, NR₄CO₂R₇ and NR₄SO₂R₇;

R₂ is an aryl attached via an unsaturated ring carbon of said aryl group;

R₃ is selected from the group consisting of H, alkyl, COR₅, CO₂R₇, CONR₅R₆, CONR₄NR₅R₆ and SO₂R₇;

R₄, R₅ and R₆ are independently selected from the group consisting of H, alkyl and aryl, or where R₅ and R₆ are in an NR₅R₆ group, R₅ and R₆ may be linked to form a heterocyclic group, or where R₄, R₅ and R₆ are in a (CONR₄NR₅R₆) group, R₄ and R₅ may be linked to form a heterocyclic group; and R₇ is selected from the group consisting of alkyl and aryl.

22. A method of treating a patient suffering from post-encephalitic Parkinsonism or post-traumatic Parkinson's disease comprising administering to the patient an effective dose of a pharmaceutical composition comprising a compound of formula (I) or a pharmaceutically acceptable salt thereof, and at least one pharmaceutically acceptable carrier:

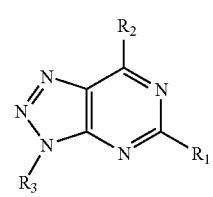

(I)

wherein
R₁ is selected from the group consisting of H, alkyl, aryl, alkoxy, aryloxy, alkylthio, arylthio, halogen, CN, NR₅R₆, NR₄COR₅, NR₄CONR₅R₆, NR₄CO₂R₇ and NR₄SO₂R₇;

R₂ is an aryl attached via an unsaturated ring carbon of said aryl group;

R₃ is selected from the group consisting of H, alkyl, COR₅, CO₂R₇, CONR₅R₆, CONR₄NR₅R₆ and SO₂R₇;

R₄, R₅ and R₆ are independently selected from the group consisting of H, alkyl and aryl, or where R₅ and R₆ are in an NR₅R₆ group, R₅ and R₆ may be linked to form a heterocyclic group, or where R₄, R₅ and R₆ are in a (CONR₄NR₅R₆) group, R₄ and R₅ may be linked to form a heterocyclic group; and R₇ is selected from the group consisting of alkyl and aryl.

23. A method of treating a patient suffering from Dopa-responsive dystonia-Parkinsonism comprising administering to the patient an effective dose of a pharmaceutical composition comprising a compound of formula (B or a pharmaceutically acceptable salt thereof, and at least one pharmaceutically acceptable carrier:

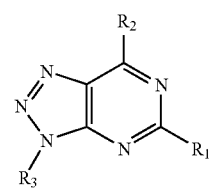

(I)

wherein

R$_1$ is selected from the group consisting of H, alkyl, aryl, alkoxy, aryloxy, alkylthio, arylthio, halogen, CN, NR$_5$R$_6$, NR$_4$COR$_5$, NR$_4$CONR$_5$R$_6$, NR$_4$CO$_2$R$_7$ and NR$_4$SO$_2$R$_7$;

R$_2$ is an aryl attached via an unsaturated ring carbon of said aryl group;

R$_3$ is selected from the group consisting of H, alkyl, COR$_5$, CO$_2$R$_7$, CONR$_5$R$_6$, CONR$_4$NR$_5$R$_6$ and SO$_2$R$_7$;

R$_4$, R$_5$ and R$_6$ are independently selected from the group consisting of H, alkyl and aryl, or where R$_5$ and R$_6$ are in an NR$_5$R$_6$ group, R$_5$ and R$_6$ may be linked to form a heterocyclic group, or where R$_4$, R$_5$ and R$_6$ are in a (CONR$_4$NR$_5$R$_6$) group, R$_4$ and R$_5$ may be linked to form a heterocyclic group; and R$_7$ is selected from the group consisting of alkyl and aryl.

24. The method of claim 20 wherein the compound of formula (I) is 3-(4-amino-3-methylbenzyl)-7-(2-furyl)-3H-[1,2,3]triazolo[4,5-d]pyrimidine-5-amine, or a pharmaceutically acceptable salt thereof.

25. A method of treating a patient suffering from Huntington's disease comprising administering to a subject in need of such treatment an effective dose of a pharmaceutical composition comprising a compound of formula (I) or a pharmaceutically acceptable salt thereof, and at least one pharmaceutically acceptable carrier:

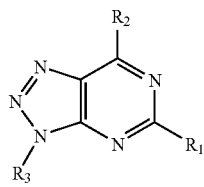
(I)

wherein

R$_1$ is selected from the group consisting of H, alkyl, aryl, alkoxy, aryloxy, alkylthio, arylthio, halogen, CN, NR$_5$R$_6$, NR$_4$COR$_5$, NR$_4$CONR$_5$R$_6$, NR$_4$CO$_2$R$_7$ and NR$_4$SO$_2$R$_7$;

R$_2$ is an aryl attached via an unsaturated ring carbon of said aryl group;

R$_3$ is selected from the group consisting of H, alkyl, COR$_5$, CO$_2$R$_7$, CONR$_5$R$_6$, CONR$_4$NR$_5$R$_6$ and SO$_2$R$_7$;

R$_4$, R$_5$ and R$_6$ are independently selected from the group consisting of H, alkyl and aryl, or where R$_5$ and R$_6$ are in an NR$_5$R$_6$ group, R$_5$ and R$_6$ may be linked to form a heterocyclic group, or where R$_4$, R$_5$ and R$_6$ are in a (CONR$_4$NR$_5$R$_6$) group, R$_4$ and R$_5$ may be linked to form a heterocyclic group; and R$_7$ is selected from the group consisting of alkyl and aryl.

26. The method of claim 25 wherein the compound of formula (I) is 3-(4-amino-3-methylbenzyl)-7-(2-furyl)-3H-[1,2,3]triazolo[4,5-d]pyrimidine-5-amine, or a pharmaceutically acceptable salt thereof.

* * * * *